(12) United States Patent
Markosyan et al.

(10) Patent No.: US 11,993,779 B2
(45) Date of Patent: May 28, 2024

(54) SINGLE NUCLEOTIDE POLYMORPHISM (SNP) MARKERS FOR STEVIA

(71) Applicant: PureCircle SDN BHD, Kuala Lumpur (MY)

(72) Inventors: Avetik Markosyan, Yerevan (AM); Seong Siang Ong, Selangor (MY); Yeen Yee Wong, Kuala Lumpur (MY); Yu Cheng Bu, Shanghai (CN); Jian Ning Chen, Ganzhou (CN)

(73) Assignee: PureCircle SDN BHD, Kuala Lumpur (MY)

( * ) Notice: Subject to any disclaimer, the term of this patent is extended or adjusted under 35 U.S.C. 154(b) by 428 days.

(21) Appl. No.: 17/205,889

(22) Filed: Mar. 18, 2021

(65) Prior Publication Data

US 2021/0207159 A1    Jul. 8, 2021

Related U.S. Application Data

(62) Division of application No. 16/418,640, filed on May 21, 2019, now Pat. No. 10,975,381, which is a division of application No. 15/512,271, filed as application No. PCT/US2015/052366 on Sep. 25, 2015, now Pat. No. 10,370,673.

(60) Provisional application No. 62/116,893, filed on Feb. 16, 2015, provisional application No. 62/064,601, filed on Oct. 16, 2014, provisional application No. 62/071,567, filed on Sep. 26, 2014, provisional application No. 62/071,568, filed on Sep. 26, 2014, provisional application No. 62/071,566, filed on Sep. 26, 2014.

(30) Foreign Application Priority Data

Jan. 23, 2015  (CN) .......................... 201510036580.4
Jan. 23, 2015  (CN) .......................... 201510036668.6
Jan. 23, 2015  (CN) .......................... 201510037435.8

(51) Int. Cl.
| | | |
|---|---|---|
| C12N 15/82 | (2006.01) | |
| A01H 5/12 | (2018.01) | |
| A23L 27/30 | (2016.01) | |
| C07H 21/04 | (2006.01) | |
| C12N 5/00 | (2006.01) | |
| C12N 5/04 | (2006.01) | |
| C12N 15/00 | (2006.01) | |
| C12N 15/52 | (2006.01) | |
| C12Q 1/68 | (2018.01) | |
| C12Q 1/6895 | (2018.01) | |

(52) U.S. Cl.
CPC ........... *C12N 15/8245* (2013.01); *A01H 5/12* (2013.01); *A23L 27/36* (2016.08); *C07H 21/04* (2013.01); *C12N 5/04* (2013.01); *C12N 15/52* (2013.01); *C12Q 1/68* (2013.01); *C12Q 1/6895* (2013.01); *C12N 5/00* (2013.01); *C12N 15/00* (2013.01)

(58) Field of Classification Search
None
See application file for complete search history.

(56) References Cited

U.S. PATENT DOCUMENTS

| | | |
|---|---|---|
| 9,668,450 B2 | 6/2017 | Li et al. |
| 9,668,451 B2 | 6/2017 | Li et al. |
| 9,675,015 B2 | 6/2017 | Li et al. |
| 10,370,673 B2 | 8/2019 | Markoysan et al. |
| 10,975,381 B2 | 4/2021 | Markosyan et al. |

FOREIGN PATENT DOCUMENTS

| | | | |
|---|---|---|---|
| CN | 107205353 A1 | 9/2017 | |
| CN | 4306173 A | 3/2021 | |
| CN | 113016623 A | 6/2021 | |
| EP | 3197269 A1 | 8/2017 | |
| IN | 201717014065 A1 | 9/2017 | |
| WO | 2011153378 A1 | 12/2011 | |
| WO | WO-2011153378 A1 * | 12/2011 | ............... A23L 2/60 |
| WO | 2012088612 A1 | 7/2012 | |
| WO | 2016049531 A1 | 3/2016 | |

OTHER PUBLICATIONS

Ashok Kumar Yadav et al., "A review on the improvement of stevia," Canadian Journal of Plant Science, Jan. 1, 2011, vol. 91, No. 1, p. 1-27.
Yao, Y., et al., "A genetic linkage map for stevia rebaudiana," Genome, Aug. 1999, vol. 42, No. 4, pp. 657-661.
Allen, Alissa L., et al., Rebaudioside A and Rebaudioside D Bitterness do not Covary with Acesulfame-K Bitterness or Polymorphisms in TAS2R9 and TAS2R31, Chemosensory Perception, Springer N.Y. LLC, Jul. 2, 2013, vol. 6, No. 3, pp. 109-117.

(Continued)

*Primary Examiner* — Mykola V. Kovalenko
*Assistant Examiner* — Aleksander Radosavljevic
(74) *Attorney, Agent, or Firm* — Weatherly IP Solutions, LLC; James M. Weatherly

(57) ABSTRACT

*Stevia* varieties with high a content of RebD, a high content of RebM, and a high content of RebD and RebM containing various SNP markers and UGT isoforms, are disclosed. Methods of screening for the SNPs are also disclosed as well as for using the SNPs in marker assisted breeding. Further provided are methods for introgressing the disclosed SNPs associated with high RebD and high RebM into *Stevia* plants by selecting plants comprising for one or more SNPs and breeding with such plants to confer such desirable agronomic phenotypes to plant progeny.

2 Claims, 51 Drawing Sheets
Specification includes a Sequence Listing.

(56) References Cited

OTHER PUBLICATIONS

Swati, Madan, et al., "*Stevia rebaudiana* (Bert) Bertoni—A Review," Indian Journal of National Products and Resources, Indian Society of Pharmacognosy, IN, Sep. 1, 2010, vol. 1, No. 3, pp. 267-286.
International Search Report and Written Opinion for Application No. PCT/US2015/052366, dated Jan. 12, 2016, 14 pages.
European Examination Report for Application No. 15782122.4, dated Oct. 1, 2018, 4 pages.
Response to European Examination Report for Application No. 15782122.4, dated Apr. 19, 2019, 40 pages.
U.S. Office Action received for U.S. Appl. No. 15/512,271 (now U.S. Pat. No. 10370673), dated Sep. 17, 2018, 41 pages.
Response to U.S. Office Action for U.S. Appl. No. 15/512,271 (now U.S. Pat. No. 10370673), filed Jan. 17, 2019, 15 pages.
Notice of Allowance and Interview Summary for U.S. Appl. No. 15/512,271 (now U.S. Pat. No. 10370673), dated Jun. 24, 2019, 22 pages.
First Office Action for China application No. 201580051948.2, dated Oct. 10, 2018, 8 pages.
Second Office Action for China application No. 201580051948.2, dated Jun. 5, 2019, 6 pages.
Third Office Action for China application No. 201580051948.2, dated Feb. 3, 2020, 8 pages.
First Examination Report for India application No. 201717014065, dated Feb. 21, 2020, 6 pages.
Response to First Examination Report for India application No. 201717014065, filed Aug. 11, 2020, 10 pages.
Restriction Requirement received for U.S. Appl. No. 17/205,889 (now U.S. Pat. No. 10,975,381), dated Jan. 24, 2020, 9 pages.
Response to Restriction Requirement for U.S. Appl. No. 17/205,889 (now U.S. Pat. No. 10,975,381), filed on Mar. 23, 2021, 2 pages.
Non-final Office Action received for U.S. Appl. No. 17/205,889 (now U.S. Pat. No. 10,975,381), dated May 5, 2020, 21 pages.
Response to Non-final Office Action, including Terminal Disclaimer filed, for U.S. Appl. No. 17/205,889 (now U.S. Pat. No. 10,975,381), filed on Sep. 4, 2020, 7 pages.
Notice of Allowance and Interview Summary received for U.S. Appl. No. 17/205,889 (now U.S. Pat. No. 10,975,381), dated Dec. 3, 2020, 24 pages.
Response to Interview Summary or U.S. Appl. No. 17/205,889 (now U.S. Pat. No. 10,975,381), filed on Dec. 30, 2020, 2 pages.
Notice of Allowance received for China application No. 201580051948.2, dated Dec. 15, 2020, 4 pages.
Patent Certificate for China application No. 201580051948.2, now Patent No. 4306173, granted Mar. 19, 2021, 4 pages.
Filing Receipt for China Divisional Application 202110226481.8 (from China Patent No. 4306173), dated Mar. 3, 2021, 2 pages.
First Action received for China Divisional Application 202110226481.8 (from China Patent No. 4306173), dated Jun. 30, 2022, English Translation, 8 pages.

\* cited by examiner

Figure 3

SNP2 (SEQ ID NO:1)

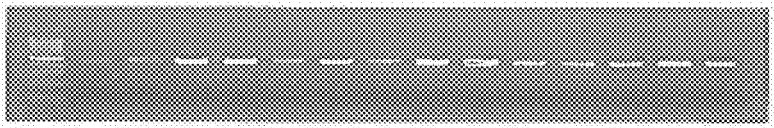

stv_snp_5090958 (SNP 2)

```
TCAGCCACCTTTCTATCTTGCAAAAGAACCAAAAAAAGATGAAAAATATTGTGCTTTTTAAA
CTCATGTAAGTTAAAAAGCAAAAGAAACAAAAATCAAGAAAATCTTTGATCTTGATGAAGAG
TGTACTTGCCTTTTCTTGGAAACTTGAATATCTTCCATTTTGATGTTGTTTATATGATGAAG
AAACTGAAAAAAGTGTTGTTGAATGAGTAAGTATGGAACTAGGAAGAGGATGAAAGTATTAA
AGAAGGACAATTGATTAAGAGGGAAAGAAAGGGAAATAAAGCAATAGGTGACAAGATCCCCA
TCATGCACTTCACCACTTCCATCCATGTGCTAATTACTTCAATACCCTTGTTCCCATGGATA
TAGTTTTTTATCCAAAAATTAATTAAATATACAAGTGGCCGATTTTTATTATTATTTCTATT
ATGTAGTAGTTGGGTGAGGTTAAATCCTCTAACTAACACATTGCAGT
```

SNP: CC genotype (homozygous recessive) for all RebD, RebM lines
See underline where a G to a C substitution is identified

Figure 4

SNP10 (SEQ ID NO:2)

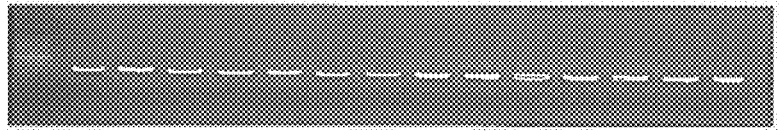

stv_snp_3488333 (SNP 10)

TCGTATACTGCTTTGGGTTGCCGGAAGTTGCCGTGTTAAGGGAAGAAGCCACGTCTGGTTGT
CTCTCTTAGGTACTCAGCGGCTCCGAAAAAGGTTCGGTCGATTTAGGTTTAATCGTGACCGA
AGACAAGGTTTTGGGTCGCCATTGATGTTTCACGAAGGAATTTAGTTTCTGCCTACTGGTTT
ATTTTTTATTGAACAGGGAAAAAGGATTTTTCAATTCCTGACTTGGAATAGGTAGATCTTCT
AATCTAACTTTGACTTCATGACCTTGATTCTCCAAGAACTCCTTTCGATCTCTAGTAGTGTT
GTTTCGGCTCCTCATAGCTCGAACAATCTTGTGACCCTGTTCTTGACCA

SNP: AA genotype (homozygous recessive) for all RebD, RebM lines
    See underline where a G to a A substitution is identified

Figure 5

SNP12 (SEQ ID NO:3)

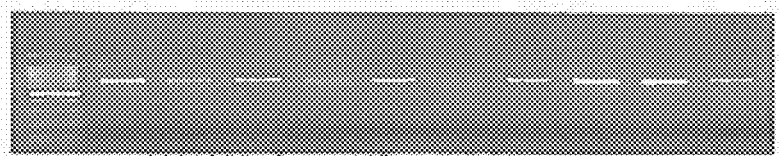

stv_snp_4414800 (SNP 12)

TTACATTTCATTTTGATACACAAACATATGTTTATGTGTGTCAATCAAAGTAGAAGAACTTA
CTTACCAAGTGGATTTGATTGATTTTAGCATCATTAATCTTGATTACACCAACATACACCTA
AATATAGATGAGATGTGTGTGTGGAGAATGATAGAGAGAGAGAACTATAAGCTAGAAGGAAA
AGGCTTGATCTTTATGAATGATATACACATGTGTATATGTGTATATATATATAGAGAGAGAG
AGAGACTTCAAGAAATATATGGTTTAATCTTTCTGGGTTATATGGTTTAATCTTTATGGGTG
CACATGGGATGACCTCATGTATCTTGGATTTACATATTAGTGGGAGTTGGTTTCTTCATTTA
ATTCAATAATTAATTTACTCAATTTGAAATCACATACTTAAATATTGCCATCTTGATTTATT
TATAAACAAAGCTTTTACACCTATTTTTTATTGCGCGGAGCTTGAATCCATGATTTTAAGAA
GAGTAATACATTTACTCTTTGTAAAATCAACAAATATTGAATGCCTCGTATACCATTTAAAT
AAAAATCAACATTTTTAATCCCAAACGTTGAATATAATTATTTATAAATAATATCTTAAGGCA
CAAAGATACAAACGACGACAAAGTTTATAATATGATACACGTTCCAAATAACTAGGAATCT

SNP: TT genotype (homozygous recessive) for all RebD, RebM lines
See underline where an C to a T substitution is identified

*Figure 6*

SNP17 (SEQ ID NO:4)

stv_snp_6262256 (SNP17)

CTTTCTTTGAGTCGGCGGAGATCAGATTGTAACTTCGTTTTTCTGTTTGGTGAACAAGCAAA
CTTATTTTTTTCTTGGTATTTTAATCTTTTATGATTCTTGTAGTGTTTTGTTTTTTGTCTT
GATACGATGGCTAGCTTAAGTTCCCATTCGTGTTTTTTGATGCTCGATTTTACGAATGAGCG
TTTATTTTGCATTCGTGTTCTTTTATGCTCGTTTTTATAGATTCGCCCAGTCATAAAACAAA
AGGGATAAAACTTGTTGCAACGTACGTAGTAAACCCC

SNP: CC genotype (homozygous recessive) for all RebD, RebM
lines See underline where a A to a C substitution is identified

Figure 7

SNP19 (SEQ ID NO:5)

stv_snp_6645712 (SNP 19)

TCGCACCTTACAAAAACAAAGAGTGTACAATTGTACATAATCATTTCATCTCCAAAAGCCCC
AAATAATTTCCATAGTTTCCTGGCGGGAACCATCATTTTCACACACTACACACAGTGACGCG
ATGGAAGATGAACCTGATGTTCCTGAACAACTCGTTCGCCGATCGGTTTGTCTCGAAATCCA
TTCACAAGTTCTTTTATATTGCACTGATTTGATACTTAGGGTTTTAATTTTGTTATACTGTA
TAATTGTGTATATTTGAGTGAGTGTATGTGTAATTGCTGTGTTTATGATCGATAGAAAAGGC
CTAGGGTTCCGACGAAGAACTTTGACGGGGAACCTAGTAGGAATCGAGATGTTTTTGAGTCC
GAGGAGGAGTCCGGTGATGAATTG

SNP: TT genotype (homozygous recessive) for all RebD, RebM
lines See underline where an A to a T substitution is
identified

Figure 8

SNP20 (SEQ ID NO:6)

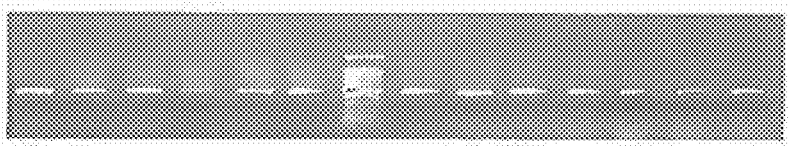

stv_snp_6647386 (SNP 20)

TTTGGATGGACTTGGTTTGAACTTGTGTTATGTTAAACTTACTTTTCATATGTTTTTATCAT
ATTATAATTTACGCTGTTTAATATTATGTGTATTTTAATTTATTCATTGAATTGAGTCAAAA
ACAAATTGAGCCGAACTCGAGCTCAGATTGTAAGCTCAGTTTAAAATCAAGTCGAGTCCGAG
CTTTGCCTGGCTTAATTAGCTCGGCTCATGAACAACCCTAACCGTGAGTCGTTTGACCGGAT
TTATCTGTTTCCTTCTTAGTTATTTCTTTTGCTCTTCTTGTTTGACTTGGCGGTTGTTTGAT
ACCAAATTAATTAATTACCTCGTTAAAATGCTACCTCGAATCGGCCAGAGGTATAGTCTGTT
TGGTTCACTATAATAATGACTATGAATCGATCAACAAGTTTCTTACCCATTCAACTTTAAAC
ACATAATGAATCATTTAGACCTTTACCCATCAAGCCTTTTACACGTCAAGCTCCACCAAACA
ACCT

SNP: AA genotype (homozygous recessive) for all RebD, RebM lines
    See underline where a G to an A substitution is identified

Figure 9

SNP22 (SEQ ID NO:7)

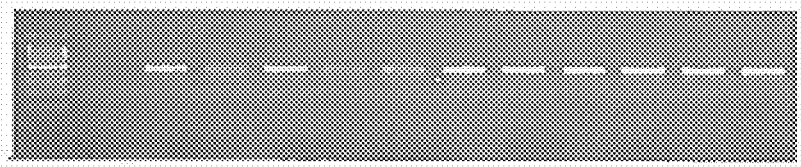

stv_snp_4704641 (SNP 22)

```
AACCTGTCTCAATGGGACCTAAAAGTTATTATGTATAACTATTATTATATACTTGAAATATT
GACAATCACTAAGTGTCTATTTCATTATCTGCAAGCATATATTTTAATGTTGCATGGCTTTA
GCTGATGCTTCTTGAATTATTTACTGATCTAACTTGTTTCTTATTTTTCGTCAGTTGATGGC
AGTTAAATCCTGTCATGACCGTAACATCACCCACAGGGATATTAAACCAGGTGAGAATATTA
TTGTCTTCTAACCAAAAGTGCAACTGTTTCTTGTTTTCATCTATAAAAGCATTCGTTCTTTT
TTAAATGGAAAATTGGATTTTAAGAATCCCAACTTTGACCTATTGGCCTGTAATAATCCCAA
TTCTGGAAATTGTTACCACCAATCCGAACTTTTATATCATTTACCTATGACAGTCTCCAGCC
AACAGAACCTAACTCCGTTAGCATTTTGTTAACGTGGCATGGCTAGCAATAT
```

SNP: GG genotype (homozygous recessive) for all RebD, RebM lines
See underline where a T to an G substitution is identified

Figure 10

SNP24 (SEQ ID NO:8)

stv_snp_5387123 (SNP 24)

TGGGGAATTGTGTTGACTGTTGACACAAACACTTTTTTTTGACCATTTTCCGAATCTTTAATA
TAAATAATTAATGTGCCAATTATGATTAGATGACAAATGATTTAAATCTTGACTATAATGAT
TTTGGAGGTTGGATGAAATATAGACATTGTTGACTTTCAACCTGTTTGACTTTCTTTTTTAT
CTAACTTTTTTCTTATTTGACCAGTTTCAGATAAAACACAACCCAAATTGACATGTAACTAA
ATGCGTCAAAATTACAACCTCTACTATTTTTATAGTTAAAGAAAGTCAAACATGTCAAAGAC
TGTTTCTTTTGATTATGAATCTGATTTTAGGGTTTTTGTTGTATTTTAGGGGTTGTTACTTT
CAAGAAGCAGATGATGTGAAAATGAATATGAGTATTGCAACTGCATACCAGAAATCAGTTGA
TACACTTTTGAATTGGATAAATAAAGAAGTAAATATAAATAAAACACAAGTTATTTTCCGAA
GCTT

SNP: AA genotype (homozygous recessive) for all RebD, RebM lines
    See underline where a G to an A substitution is identified Figure 14
Sequence alignment of S UGT76G1 isoforms of stevia variety '814011' corresponding to SEQ ID NOs: 9-13

```
1    cgtgggttggcgagtgaagataataacaataataataatattaagggagagtgaacgtgg
2    cgtgggttggcgagtgaagataataacaataataataatattaagggagagtgaacgtgg
3    ------------------------------------------------------------
4    ------------------------------------------------------------
5    ------------------------------------------------------------

1    tgctctaattcacctaagaaatttgcaggaattgaggacaattatgaaaaatgatgaatt
2    tgctctaattcacctaagaaatttgcaggaattgaggacaattatgaaaaatgatgaatt
3    ------------------------------------------------------------
4    ------------------------------------------------------------
5    ------------------------------------------------------------

1    aaacaacactaagttacaactcaactgtcggtgatcaaatgctattattattcaaagaga
2    aaacaacactaagttacaactcaactgtcggtgatcaaatgctattattattcaaagaga
3    ------------------------------------------------------------
4    ------------------------------------------------------------
5    ------------------------------------------------------------

1    atgaagatcgatcagaaagctttcgttttattggttgcataaacagaaacaataagaaac
2    atgaagatcgatcagaaagctttcgttttattggttgcataaacagaaacaataagaaac
3    ------------------------------------------------------------
4    ------------------------------------------------------------
5    ------------------------------------------------------------

1    atatgaaggcttttatagcctacaaaaacataacatataaactagctcacataaccaacaacc
2    atatgaaggcttttatagcctacaaaaacataacatataaactagctcacataaccaacaacc
3    ------------------------------------------------------------
4    ------------------------------------------------------------
5    ------------------------------------------------------------

1    atcctttatttaatttaaaccaagtagtctttgcttctaataactcaaattaccagctac
2    atcctttatttaatttaaaccaagtagtctttgcttctaataactcaaattaccagctac
3    ------------------------------------------------------------
4    ------------------------------------------------------------
5    ------------------------------------------------------------

1    tcagctagcatgcaatccaagtgcttgattaatcatcgtgttatttacaacgatgaaatg
2    tcagctagcatgcaatccaagtgcttgattaatcatcgtgttatttacaacgatgaaatg
3    ------------------------------------------------------------
4    ------------------------------------------------------------
5    ------------------------------------------------------------

1    taagaaactagagactctaatgattcgtaagatgaaccacccttcatcaaagaaacatct
2    taagaaactagagactctaatgattcgtaagatgaaccacccttcatcaaagaaacatct
3    ------------------------------------------------------------
4    ------------------------------------------------------------
5    ------------------------------------------------------------

1    gcctttgtttcaaaactcttgcattctgtctaatgtattctccttcttcatccaccata
2    gcctttgtttcaaaactcttgcattctgtctaatgtattctccttcttcatccaccata
3    ------------------------------------------------------------
4    ------------------------------------------------------------
5    ------------------------------------------------------------
```

Figure 14 continued

```
1  actcttcttattgcatttgctatctctcctctttcccacccatttctccaaatacacccct
2  actcttcttattgcatttgctatctctcctctttcccacccatttctccaaatacacccct
3  ------------------------------------------------------------
4  ------------------------------------------------------------
5  ------------------------------------------------------------

1  accttcaaaacatcactcatgtatctagcattcaacggttgatcgagcccaaaatccgag
2  accttcaaaacatcactcatgtatctagcattcaacggttgatcgagcccaaaatccgag
3  ------------------------------------------------------------
4  ------------------------------------------------------------
5  ------------------------------------------------------------

1  aaaatcataggaacaccttcacaaacgctttccaacgtagagttccatccgctatgagtc
2  aaaatcataggaacaccttcacaaacgctttccaacgtagagttccatccgctatgagtc
3  ---------------------------------------------catccgctatgagtc
4  ----------------------------------------------actctgagtg
5  ---------------------------------------------catccgctatgagtc
                                                 **  *****

1  cagaatgcgcctattgctccatgagctagcacttcttgctgcggaacccatttcacaata
2  cagaatgcgcctattgctccatgagctagcacttcttgctgcggaacccatttcacaata
3  cagaatgcgcctattgctccatgagctagcacttcttgctgcggaacccatttcacaata
4  cagaatgcacgattgctccatgagctagcacttcttgctgcggaacccatttcacaata
5  cagaatgcgcctattgctccatgagctagcacttcttgctgcggaacccatttcacaata
   ******** **  ***********************************************

1  cgtcctctttcacccaagaacccatctggcaacggttcgacccacgtcgaacccttgaca
2  cgtcctctttcacccaagaacccatctggcaacggttcgacccacgtcgaacccttgaca
3  cgtcctctttcacccaagaacccatctggcaacggttcgacccacgtcgaacccttgaca
4  cgtcctctttcacccaagaacccatctggcaacggttcgacccacgtcgaacccttgaca
5  cgtcctctttcacccaagaacccatctggcaacggttcgacccacgtcgaacccttgaca
   ************************************************************

1  aacccaggtcgaaccacccataaaaacgactgcttgctatcaaccaacccacgagctatt
2  aacccaggtcgaaccacccataaaaacgactgcttgctatcaaccaacccacgagctatt
3  aacccaggtcgaaccacccataaaaacgactgcttgctatcaaccaacccacgagctatt
4  aacccaggtcgaaccacccataaaaacgactgcttgctatcaaccaacccacgagctatt
5  aacccaggtcgaaccacccataaaaacgactgcttgctatcaaccaacccacgagctatt
   ************************************************************

1  tccaagaaatctttctcatccagtacttcagtaccactaccaaaactaacatacagtacc
2  tccaagaaatctttctcatccagtacttcagtaccactaccaaaactaacatacagtacc
3  tccaagaaatctttctcatccact---tcactagtactaccaaaactaacatacagtacc
4  tccaagaaatctttctcatcca---cttcagtaccactaccaaaactaacatacagtacc
5  tccaagaaatctttctcatccact---tcactagtactaccaaaactaacatacagtacc
   *********************        *** **  ***********************

1  gaacgtgacggttgttggtctaaccatggaaaaacggttcgatcgtggtctagtaagctg
2  gaacgtgacggttgttggtctaaccatggaaaaacggttcgatcgtggtctagtaagctg
3  gaacttgcggttgttggtctaaccatggaaaaacggttcgatcgtggtctagtaagctg
4  gaacgtgacggttgttggtctaaccatggaaaaacggttcgatcgtggtctagtaagctg
5  gaacgtgcggttgttggtctaaccatggaaaaacggttcgatcgtggtctagtaagctg
   **** ** *****************************************************
```

Figure 14 continued

```
1  ctggaagaggctgtcaaatgcttggggagtggtatcaagaaacttggagccggga---tc
2  ctggaagaggctgtcaaatgcttggggagtggtatcaagaaacttggagccggga---tc
3  ctggaagaggctgtcaaatgcttggggagtggtatcaagaaacttggagccgggaggaag
4  ctggaagaggctgtcaaatgcttggggagtggtatcaagaaacttggagccggga---tc
5  ctggaagaggctgtcaaatgcttggggagtggtatcaagaaacttggagccgggaggaag
   ********************************************************

1  tcacggataacagtttcgagctcagactcttcgagttccttaaatgagttccagatgact
2  tcacggataacagtttcgagctcagactcttcgagttccttaaatgagttccagatgact
3  tcacgggtaatcgtttcgacctcgggctcttcgagttccttaaatgagttccagatgact
4  tcacggataacagtttcgagctcagactcttcgagttccttaaatgagttccagatgact
5  tcacgggtaatcgtttcgacctcgggctcttcgagttccttaaatgagttccagatgact
   ******  ***  ******* ***  * ********************************

1  cctgaagatgcttttgtttgtttcgtaatgttctcgaaatactctttgtattttttccac
2  cctgaagatgcttttgtttgtttcgtaatgttctcgaaatactctttgtattttttccac
3  cctgaagatgcttttgtttgtttcgtaatgttctcgaaatactctttgtattttttccac
4  cctgaagatgcttttgtttgtttcgtaatgttctcgaaatactctttgtattttttccac
5  cctgaagatgcttttgtttgtttcgtaatgttctcgaaatactctttgtattttttccac
   ************************************************************

1  atcgaaaaactacacttgatatctttcactttcagcataggaaacccactcgcttgttct
2  atcgaaaaactacacttgatatctttcactttcagcataggaaacccactcgcttgttct
3  atcgaaaaactacacttgatatctttcactttcagcataggaaacccactcgcttgttct
4  atcgaaaaactacacttgatatctttcactttcagcataggaaacccactcgcttgttct
5  atcgaaaaactacacttgatatctttcactttcagcataggaaacccactcgcttgttct
   ************************************************************

1  tccaa-------------------------------------------------------
2  tccaaaccttaaatcaaataattcacaacgtaactgaaacataaaaacgagaaactaaat
3  tccaa-------------------------------------------------------
4  tccaa-------------------------------------------------------
5  tccaaaccttaaatcaaataattcacaacgtaactgaaacataaaaacgagaaactaaat
   *****

1  -------------acgggttttgtcatcaggatcgaggtaaccaagctcatcaaactgag
2  taattaatgactcacgggttttgtcatcaggatcgaggtaaccaagctcatcaaactgag
3  -------------acgggttttgtcatcaggatcgaggtaaccaagctcatcaaactgag
4  -------------acgggttttgtcatcaggatcgaggtaaccaagctcatcaaactgag
5  taattaatgactcacgggttttgtcatcaggatcgaggtaaccaagctcatcaaactgag
                ***********************************************

1  gaagtgaaacatgtgcatgaaaattaaacaagctgcttgtcaccaaaacaagccgtcgga
2  gaagtgaaacatgtgcatgaaaattaaacaagctgcttgtcaccaaaacaagccgtcgga
3  gaagtgaaacatgtgcatgaaaattaaacaagctgcttgtcaccaaaacaagccgtcgga
4  gaagtgaaacatgtgcatgaaaattaaacaagctgcttgtcaccaaaacaagccgtcgga
5  gaagtgaaacatgtgcatgaaaattaaacaagctgcttgtcaccaaaacaagccgtcgga
   ************************************************************

1  ggttaagactgtcagcaacagattgcgtgaagtaccaaatctgatcggcgattaaacacg
2  ggttaagactgtcagcaacagattgcgtgaagtaccaaatctgatcggcgattaaacacg
3  ggttaagactgtcagcaacagattgcgtgaagtaccaaatctgatcggcgattaaacacg
4  ggttaagactgtcagcaacagattgcgtgaagtaccaaatctgatcggcgattaaacacg
5  ggttaagactgtcagcaacagattgcgtgaagtaccaaatctgatcggcgattaaacacg
   ************************************************************

1  atacctctccatcttcttcagaagctaacatcaacagttccagttcgcgtcgtaattcgt
2  atacctctccatcttcttcagaagctaacatcaacagttccagttcgcgtcgtaattcgt
3  atacctctccatcttcttcagaagctaacatcaacagttccagttcgcgtcgtaattcgt
4  atacctctccatcttcttcagaagctaacatcaacagttccagttcgcgtcgtaattcgt
5  atacctctccatcttcttcagaagctaacatcaacagttccagttcgcgtcgtaattcgt
   ************************************************************
```

Figure 14 continued

```
1  cagctccgtgttcgttgataatcagaatccgcataacagcgagcggaccatgagtcggta
2  cagctccgtgttcgttgataatcagaatccgcataacagcgagcggaccatgagtcggta
3  cagctccgtgttcgttgataatc-------------------------------------
4  cagctccgtgttcgttgataatc-------------------------------------
5  cagctccgtgttcgttgataatc-------------------------------------
   ***********************

1  gattggaaatgcgtacgtcttgtgggtcgttgtcgaggatgaatctgaaagtgaagtgag
2  gattggaaatgcgtacgtcttgtgggtcgttgtcgaggatgaatctgaaagtgaagtgag
3  ------------------------------------------------------------
4  ------------------------------------------------------------
5  ------------------------------------------------------------

1  ggtaattagatgttttgggtttgttgaagttggtgtgaaagatggtgatactgaatcctt
2  ggtaattagatgttttgggtttgttgaagttggtgtgaaagatggtgatactgaatcctt
3  ------------------------------------------------------------
4  ------------------------------------------------------------
5  ------------------------------------------------------------

1  tggagtacaacacattggctagctgaagcattgggtttatgtgaccttgaaatggtaccg
2  tggagtacaacacattggctagctgaagcattgggtttatgtgaccttgaaatggtaccg
3  ------------------------------------------------------------
4  ------------------------------------------------------------
5  ------------------------------------------------------------

1  ggaataatattattctccggcgccggcgaacggtggtctccgttttatttttccattggt
2  ggaataatattattctccggcgccggcgaacggtggtctccgttttatttttccattggt
3  ------------------------------------------------------------
4  ------------------------------------------------------------
5  ------------------------------------------------------------

1  ttgactgatgtttacacacaagaattattaaaatatataacaataaaatagtgtcggcaa
2  ttgactgatgtttacacacaagaattattaaaatatataacaataaaatagtgtcggcaa
3  ------------------------------------------------------------
4  ------------------------------------------------------------
5  ------------------------------------------------------------

1  gcaattcatttaatttacagaggttaggtagctgagatctgcatgtggaaaatgcacatc
2  gcaattcatttaatttacagaggttaggtagctgagatctgcatgtggaaaatgcacatc
3  ------------------------------------------------------------
4  ------------------------------------------------------------
5  ------------------------------------------------------------

1  ttgtgtggtccaggttgttattgccgatccttatccttattatacagatgattggtcctg
2  ttgtgtggtccaggttgttattgccgatccttatccttattatacagatgattggtcctg
3  ------------------------------------------------------------
4  ------------------------------------------------------------
5  ------------------------------------------------------------

1  aagatcttgtgttgtatctatgtatttgtcaaattaataataaaagacaaagattccaat
2  aagatcttgtgttgtatctatgtatttgtcaaattaataataaaagacaaagattccaat
3  ------------------------------------------------------------
4  ------------------------------------------------------------
5  ------------------------------------------------------------
```

Figure 14 continued

```
1   aattctgcaaccatgcaaaaaagttccccataattttaaatttttttatatataatttg
2   aattctgcaaccatgcaaaaaagttccccataattttaaatttttttatatataatttg
3   ------------------------------------------------------------
4   ------------------------------------------------------------
5   ------------------------------------------------------------

1   tatgcaaaaatatttatataaaggtttatttattta
2   tatgcaaaaatattatataaaggtttatttattta
3   ----------------------------------
4   ----------------------------------
5   ----------------------------------
```

Figure 15
Sequence alignment of UGT76G1 isoforms corresponding to SEQ ID NO: 9, SEQ ID NO: 14 and SEQ ID NO: 19

```
9    cgtgggttggcgagtgaagataataacaataataataatattaagggagagtgaacgtgg
14   cgtgggttggcgagtgaagataataacaataataataatattaagggagagtgaacgtgg
19   cgtgggttggcgagtgaagataataacaataataataatattaagggagagtgaacgtgg
     ************************************************************

9    tgctctaattcacctaagaaatttgcaggaattgaggacaattatgaaaaatgatgaatt
14   tgctctaattcacctaagaaatttgcaggaattgaggacaattatgaaaaatgatgaatt
19   tgctctaattcacctaagaaatttgcaggaattgaggacaattatgaaaaatgatgaatt
     ************************************************************

9    aaacaacactaagttacaactcaactgtcggtgatcaaatgctattattattcaaagaga
14   aaacaacactaagttacaactcaactgtcggtgatcaaatgctattattattcaaagaga
19   aaacaacactaagttacaactcaactgtcggtgatcaaatgctattattattcaaagaga
     ************************************************************

9    atgaagatcgatcagaaagctttcgtttttattggttgcataaacagaaacaataagaaac
14   atgaagatcgatcagaaagctttcgtttttattggttgcataaacagaaacaataagaaac
19   atgaagatcgatcagaaagctttcgtttttattggttgcataaacagaaacaataagaaac
     ************************************************************

9    atatgaaggcttttatagcctacaaaacataacataaactagctcacataaccaacaacc
14   atatgaaggcttttatagcctacaaaacataacataaactagctcacataaccaacaacc
19   atatgaaggcttttatagcctacaaaacataacataaactagctcacataaccaacaacc
     ************************************************************

9    atcctttatttaatttaaaccaagtagtctttgcttctaataactcaaattaccagctac
14   atcctttatttaatttaaaccaagtagtctttgcttctaataactcaaattaccagctac
19   atcctttatttaatttaaaccaagtagtctttgcttctaataactcaaattaccagctac
     ************************************************************

9    tcagctagcatgcaatccaagtgcttgattaatcatcgtgttatttacaacgatgaaatg
14   tcagctagcatgcaatccaagtgcttgattaatcatcgtgttatttacaacgatgaaatg
19   tcagctagcatgcaatccaagtgcttgattaatcatcgtgttatttacaacgatgaaatg
     ************************************************************

9    taagaaactagagactctaatgattcgtaagatgaaccacccttcatcaaagaaacatct
14   taagaaactagagactctaatgattcgtaagatgaaccacccttcatcaaagaaacatct
19   taagaaactagagactctaatgattcgtaagacgaaccacccttcatcaaagaaacatct
     ******************************** ***************************

9    gccttttgtttcaaaactcttgcattctgtctaatgtattctccttcttcatccaccata
14   gccttttgtttcaaaactcttgcattctgtctaatgtattctccttcttcatccaccata
19   gccttttgtttcaaaactcttgcattctgtctaatgtattctccttcttcatccaccata
     ************************************************************

9    actcttcttattgcatttgctatctctcctctttcccacccatttccaaatacacccct
14   actcttcttattgcatttgctatctctcctctttcccacccatttccaaatacacccct
19   actcttcttattgcatttgctatctctcctctttcccacccatttccaaatacacccct
     ************************************************************

9    accttcaaaacatcactcatgtatctagcattcaacggttgatcgagcccaaaatccgag
14   accttcaaaacatcactcatgtatctagcattcaacggttgatcgagcccaaaatccgag
19   accttcaaaacatcactcatgtatctagcattcaacggttgatcgagcccaaaatccgag
     ************************************************************

9    aaaatcataggaacaccttcacaaacgctttccaacgtagagttccatccgctatgagtc
14   aaaatcataggaacaccttcacaaacgctttccaacgtagagttccatccgctatgagtc
19   aaaatcataggaacaccttcacaaacgctttccaacgtagagttccatccgctatgagtc
     ************************************************************

9    cagaatgcgcctattgctccatgagctagcacttcttgctgcggaacccatttcacaata
14   cagaatgcgcctattgctccatgagctagcacttcttgctgcggaacccatttcacaata
19   cagaatgcgcctattgctccatgagctagcacttcttgctgcggaacccatttcacaata
     ************************************************************
```

Figure 15 continued

```
9    cgtcctctttcacccaagaacccatctggcaacggttcgacccacgtcgaacccttgaca
14   cgtcctctttcacccaagaacccatctggcaacggttcgacccacgtcgaacccttgaca
19   cgtcctctttcacccaagaacccatctggcaacggttcgacccacgtcgaacccttgaca
     ************************************************************

9    aacccaggtcgaaccacccataaaaacgactgcttgctatcaaccaacccacgagctatt
14   aacccaggtcgaaccacccataaaaacgactgcttgctatcaaccaacccacgagctatt
19   aacccaggtcgaaccacccataaaaacgactgcttgctatcaaccaacccacgagctatt
     ************************************************************

9    tccaagaaatctttctcatccagtacttcagtaccactaccaaaactaacatacagtacc
14   tccaagaaatctttctcatccagtacttcagtaccactaccaaaactaacatacagtacc
19   tccaagaaatctttctcatccagtacttcagtaccactaccaaaactaacatacagtacc
     ************************************************************

9    gaacgtgacggttgttggtctaaccatggaaaaacggttcgatcgtggtctagtaagctg
14   gaacgtgacggttgttggtctaaccatggaaaaacggttcgatcgtggtctagtaagctg
19   gaacgtgacggttgttggtctaaccatggaaaaacggttcgatcgtggtctagtaagctg
     ************************************************************

9    ctggaagaggctgtcaaatgcttggggagtggtatcaagaaacttggagccgggatctca
14   ctggaagaggctgtcaaatgcttggggagtggtatcaagaaacttggagccgggatctca
19   ctggaagaggctgtcaaatgcttggggagtggtatcaagaaacttggagccgggatctca
     ************************************************************

9    cggataacagtttcgagctcagactcttcgagttccttaaatgagttccagatgactcct
14   cggataacagtttcgagctcagactcttcgagttccttaaatgagttccagatgactcct
19   cggataacagtttcgagctcagactcttcgagttccttaaatgagttccagatgactcct
     ************************************************************

9    gaagatgcttttgtttgtttcgtaatgttctcgaaatactctttgtattttttccacatc
14   gaagatgcttttgtttgtttcgtaatgttctcgaattactctttgtattttttccacatc
19   gaagatgcttttgtttgtttcgtaatgttctcgaatatctctttgccttgtttccacatc
     **********************************     ******  ** **********

9    gaaaaactacacttgatatctttcactttcagcataggaaacccactcgcttgttcttcc
14   gaaaaactacacttgatatctttcactttcagcataggaaacccactcgcttgttcttcc
19   gaaaaaccacacttgatatctttcactttcagcataggaaacccactcgcttgttcttcc
     ******  ****************************************************

9    aaacgggttttgtcatcaggatcgaggtaaccaagctcatcaaactgaggaagtgaaaca
14   aaacgggttttgtcatcaggatcgaggtaaccaagctcatcaaactgaggaagtgaaaca
19   aaacgggttttgtcatcaggatcgaggtaaccaagctcatcaaactgaggaagtgaaaca
     ************************************************************

9    tgtgcatgaaaattaaacaagctgcttgtcaccaaaacaagccgtcggaggttaagactg
14   tgtgcatgaaaattaaacaagctgcttgtcaccaaaacaagccgtcggaggttaagactg
19   tgtgcatgaaaattaaacaagctgcttgtcatcaaaacaagccgtcggaggttaagactg
     *******************************  ***************************

9    tcagcaacagattgcgtgaagtaccaaatctgatcggcgattaaacacgatacctctcca
14   tcagcaacagattgcgtgaagtaccaaatctgatcggcgattaaacacgatacctctcca
19   tcagcaacagattgcgtgaagtaccaaatctgatcggcgattaaacacgatacctctcca
     ************************************************************

9    tcttcttcagaagctaacatcaacagttccagttcgcgtcgtaattcgtcagctccgtgt
14   tcttcttcagaagctaacatcaacagttccagttcgcgtcgtaattcgtcagctccgtgt
19   tcttcttcagaagctaacatcaacagttccagttcgcgtcgtaattcgtcagctccgtgt
     ************************************************************

9    tcgttgataatcagaatccgcataacagcgagcggaccatgagtcggtagattggaaatg
14   tcgttgataatcagaatccgcataacagcgagcggaccatgagtcggtagattggaaatg
19   tcgttgataatcagaatccgcataacagcgagcggaccatgagtcggtagattggaaatg
     ************************************************************
```

Figure 15 continued

```
9    cgtacgtcttgtgggtcgttgtcgaggatgaatctgaaagtgaagtgagggtaattagat
14   cgtacgtcttgtgggtcgttgtcgaggatgaatctgaaagtgaagtgagggtaattagat
19   cgttcgtcttgtgggtcgttgtcgaggatgaatctgaaagtgaagtgagggtaattagat
     ************************************************************

9    gttttgggtttgttgaagttggtgtgaaagatggtgatactgaatcctttggagtacaac
14   gttttgggtttgttgaagttggtgtgaaagatggtgatactgaatcctttggagtacaac
19   gttttgggtttgttgaagttggtgtgaaagatggtgatactgaatcctttggagtacaac
     ************************************************************

9    acattggctagctgaagcattgggtttatgtgaccttgaaatggtaccgggaataatatt
14   acattggctagctgaagcattgggtttatgtgaccttgaaatggtaccgggaataatatt
19   acattggctagctgaagcattgggtttatgtgaccttgaaatggtaccgggaataatatt
     ************************************************************

9    attctccggcgccggcgaacggtggtctccgtttta ttttccattgggtttgactgatgt
14   attctccggcgccggcgaacggtggtctccgttttattttccattgggtttgactgatgt
19   attctccggcgccggcgaacggtggtctccgttttattttccattgggtttgactgatgt
     ************************************************************

9    ttacacacaagaattattaaaatatataacaataaaatagtgtcggcaagcaattcattt
14   ttacacacaagaattattaaaatatataacaataaaatagtgtcggcaagcaattcattt
19   ttacacacaagaattattaaaatatataacaataaaatagtgtcggcaagcaattcattt
     ************************************************************

9    aatttacagaggttaggtagctgagatctgcatgtggaaaatgcacatcttgtgtggtcc
14   aatttacagaggttaggtagctgagatctgcatgtggaaaatgcacatcttgtgtggtcc
19   aatttacagaggttaggtagctgagatctgcatgtggaaaatgcacatcttgtgtggtcc
     ************************************************************

9    aggttgttattgccgatccttatccttattatacagatgattggtcctgaagatcttgtg
14   aggttgttattgccgatccttatccttattatacagatgattggtcctgaagatcttgtg
19   aggttgttattgccgatccttatccttattatacagatgattggtcctgaagatcttgtg
     ************************************************************

9    ttgtatctatgtatttgtcaaattaataataaaagacaaagattccaataattctgcaac
14   ttgtatctatgtatttgtcaaattaataataaaagacaaagattccaataattctgcaac
19   ttgtatctatgtatttgtcaaattaataataaaagacaaagattccaataattctgcaac
     ************************************************************

9    catgcaaaaaagttccccataatttttaaatttttttatatataatttgtatgcaaaaat
14   catgcaaaaaagttccccataatttttaaatttttttatatataatttgtatgcaaaaat
19   catgcaaaaaagttccccataatttttaaatttttttatatataatttgtatgcaaaaat
     ************************************************************

9    attttatataaaggtttatttta ttta
14   attttatataaaggtttatttta ttta
19   attttatataaaggtttatttta ttta
     ***************************
```

Figure 16
Sequence alignment of UGT76G1 isoform sequences corresponding to SEQ ID
NO: 10, SEQ ID NO: 15, and SEQ ID NO: 20

```
10    cgtgggttggcgagtgaagataataacaataataataatattaagggagagtgaacgtgg
15    cgtgggttggcgagtgaagataataacaataataataatattaagggagagtgaacgtgg
20    cgtgggttggcgagtgaagataataacaataataataatattaagggagagtgaacgtgg
      ************************************************************

10    tgctctaattcacctaagaaatttgcaggaattgaggacaattatgaaaaatgatgaatt
15    tgctctaattcacctaagaaatttgcaggaattgaggacaattatgaaaaatgatgaatt
20    tgctctaattcacctaagaaatttgcaggaattgaggacaattatgaaaaatgatgaatt
      ************************************************************

10    aaacaacactaagttacaactcaactgtcggtgatcaaatgctattattattcaaagaga
15    aaacaacactaagttacaactcaactgtcggtgatcaaatgctattattattcaaagaga
20    aaacaacactaagttacaactcaactgtcggtgatcaaatgctattattattcaaagaga
      ************************************************************

10    atgaagatcgatcagaaagctttcgttttattggttgcataaacagaaacaataagaaac
15    atgaagatcgatcagaaagctttcgttttattggttgcataaacagaaacaataagaaac
20    atgaagatcgatcagaaagctttcgttttattggttgcataaacagaaacaataagaaac
      ************************************************************

10    atatgaaggcttttatagcctacaaaacataacataaactagctcacataaccaacaacc
15    atatgaaggcttttatagcctacaaaacataacataaactagctcacataaccaacaacc
20    atatgaaggcttttatagcctacaaaacataacataaactagctcacataaccaacaacc
      ************************************************************

10    atcctttatttaatttaaaccaagtagtctttgcttctaataactcaaattaccagctac
15    atcctttatttaatttaaaccaagtagtctttgcttctaataactcaaattaccagctac
20    atcctttatttaatttaaaccaagtagtctttgcttctaataactcaaattaccagctac
      ************************************************************

10    tcagctagcatgcaatccaagtgcttgattaatcatcgtgttatttacaacgatgaaatg
15    tcagctagcatgcaatccaagtgcttgattaatcatcgtgttatttacaacgatgaaatg
20    tcagctagcatgcaatccaagtgcttgattaatcatcgtgttatttacaacgatgaaatg
      ************************************************************

10    taagaaactagagactctaatgattcgtaagatgaaccacccttcatcaaagaaacatct
15    taagaaactagagactctaatgattcgtaagatgaaccacccttcatcaaagaaacatct
20    taagaaactagagactctaatgattcgtaagatgaaccacccttcatcaaagaaacatct
      ************************************************************

10    gccttttgtttcaaaactcttgcattctgtctaatgtattctccttcttcatccaccata
15    gccttttgtttcaaaactcttgcattctgtctaatgtattctccttcttcatccaccata
20    gccttttgtttcaaaactcttgcattctgtctaatgtattctccttcttcatccaccata
      ************************************************************

10    actcttcttattgcatttgctatctctcctctttcccacccattttccaaatacacccct
15    actcttcttattgcatttgctatctctcctctttcccacccattttccaaatacacccct
20    actcttcttattgcatttgctatctctcctctttcccacccattttccaaatacacccct
      ************************************************************

10    accttcaaaacatcactcatgtatctagcattcaacggttgatcgagcccaaaatccgag
15    accttcaaaacatcactcatgtatctagcattcaacggttgatcgagcccaaaatccgag
20    accttcaaaacatcactcatgtatctagcattcaacggttgatcgagcccaaaatccgag
      ************************************************************

10    aaaatcataggaacaccttcacaaacgctttccaacgtagagttccatccgctatgagtc
15    aaaatcataggaacaccttcacaaacgctttccaacgtagagttccatccgctatgagtc
20    aaaatcataggaacaccttcacaaacgctttccaacgtagagttccatccgctatgagtc
      ************************************************************

10    cagaatgcgcctattgctccatgagctagcacttcttgctgcggaacccatttcacaata
15    cagaatgcgcctattgctccatgagctagcacttcttgctgcggaacccatttcacaata
20    cagaatgcgcctattgctccatgagctagcacttcttgctgcggaacccatttcacaata
      ************************************************************
```

Figure 16 continued

```
10    cgtcctcttttcacccaagaacccatctggcaacggttcgacccacgtcgaacccttgaca
15    cgtcctcttttcacccaagaacccatctggcaacggttcgacccacgtcgaacccttgaca
20    cgtcctctttcacccaagaacccatctggcaacggttcgacccacgtcgaacccttgaca
      ************************************************************

10    aacccaggtcgaaccacccataaaaacgactgcttgctatcaaccaacccacgagctatt
15    aacccaggtcgaaccacccataaaaacgactgcttgctatcaaccaacccacgagctatt
20    aacccaggtcgaaccacccataaaaacgactgcttgctatcaaccaacccacgagctatt
      ************************************************************

10    tccaagaaatctttctcatccagtacttcagtaccactaccaaaactaacatacagtacc
15    tccaagaaatctttctcatccagtacttcagtaccactaccaaaactaacatacagtacc
20    tccaagaaatctttctcatccagtacttcagtaccactaccaaaactaacatacagtacc
      ************************************************************

20    gaacgtgacggttgttggtctaaccatggaaaaacggttcgatcgtggtctagtaagctg
15    gaacgtgacggttgttggtctaaccatggaaaaacggttcgatcgtggtctagtaagctg
10    gaacgtgacggttgttggtctaaccatggaaaaacggttcgatcgtggtctagtaagctg
      ************************************************************

10    ctggaagaggctgtcaaatgcttggggagtggtatcaagaaacttggagccgggatctca
15    ctggaagaggctgtcaaatgcttggggagtggtatcaagaaacttggagccgggatctca
20    ctggaagaggctgtcaaatgcttggggagtggtatcaagaaacttggagccgggatctca
      ************************************************************

10    cggataacagtttcgagctcagactcttcgagttccttaaatgagttccagatgactcct
15    cggataacagtttcgagctcagactcttcgagttccttaaatgagttccagatgactcct
20    cggataacagtttcgagctcagactcttcgagttccttaaatgagttccagatgactcct
      ************************************************************

10    gaagatgcttttgtttgtttcgtaatgttctcgaaatactctttgtatttttccacatc
15    gaagatgcttttgtttgtttcgtaatgttctcgaattactctttgtatttttccacatc
20    gaagatgcttttgtttgtttcgtaatgttctcgaatatctctttgcttgtttccacatc
      ***********************************   ******  ** **********

10    gaaaaactacacttgatatctttcactttcagcataggaaacccactcgcttgttcttcc
15    gaaaaactacacttgatatctttcactttcagcataggaaacccactcgcttgttcttcc
20    gaaaaaccacacttgatatctttcactttcagcataggaaacccactcgcttgttcttcc
      ****** *****************************************************

10    aaaccttaaatcaaataattcacaacgtaactgaaacataaaaacgagaaactaaattaa
15    aaaccttaaatcaaataattcacaacgtaactgaaacataaaaacgagaaactaaattaa
20    aaaccttaaatcaaataattcacaacgtaactgaaacataaaaacgagaaactaaattaa
      ************************************************************

10    ttaatgactcacgggttttgtcatcaggatcgaggtaaccaagctcatcaaactgaggaa
15    ttaatgactcacgggttttgtcatcaggatcgaggtaaccaagctcatcaaactgaggaa
20    ttaatgactcacgggttttgtcatcaggatcgaggtaaccaagctcatcaaactgaggaa
      ************************************************************

10    gtgaaacatgtgcatgaaaattaaacaagctgcttgtcaccaaaacaagccgtcggaggt
15    gtgaaacatgtgcatgaaaattaaacaagctgcttgtcaccaaaacaagccgtcggaggt
20    gtgaaacatgtgcatgaaaattaaacaagctgcttgtcatcaaaacaagccgtcggaggt
      *************************************** ********************

10    taagactgtcagcaacagattgcgtgaagtaccaaatctgatcggcgattaaacacgata
15    taagactgtcagcaacagattgcgtgaagtaccaaatctgatcggcgattaaacacgata
20    taagactgtcagcaacagattgcgtgaagtaccaaatctgatcggtgattaaacacgata
      *********************************************  *************

10    cctctccatcttcttcagaagctaacatcaacagttccagttcgcgtcgtaattcgtcag
15    cctctccatcttcttcagaagctaacatcaacagttccagttcgcgtcgtaattcgtcag
20    cctcttcatcttcttcagaagctaacatcaacagttccagttcgcgtcgtaattcgtcag
      **** *******************************************************
```

Figure 16 continued

```
10   ctccgtgttcgttgataatcagaatccgcataacagcgagcggaccatgagtcggtagat
15   ctccgtgttcgttgataatcagaatccgcataacagcgagcggaccatgagtcggtagat
20   ctccgtgttcgttgataatcagaatccgcataacagcgagcggaccatgagtcggtagat
     ************************************************************

10   tggaaatgcgtacgtcttgtgggtcgttgtcgaggatgaatctgaaagtgaagtgagggt
15   tggaaatgcgtacgtcttgtgggtcgttgtcgaggatgaatctgaaagtgaagtgagggt
20   tggaaatgcgttcgtcttgtgggtcgttgtcgaggatgaatctgaaagtgaagtgagggt
     *********** ************************************************

10   aattagatgttttgggtttgttgaagttggtgtgaaagatggtgatactgaatcctttgg
15   aattagatgttttgggtttgttgaagttggtgtgaaagatggtgatactgaatcctttgg
20   aattagatgttttgggtttgttgaagttggtgtgaaagatggtgatactgaatcctttgg
     ************************************************************

10   agtacaacacattggctagctgaagcattgggtttatgtgaccttgaaatggtaccggga
15   agtacaacacattggctagctgaagcattgggtttatgtgaccttgaaatggtaccggga
20   agtacaacacattggctagctgaagcattgggtttaatgtggccttgaaatggtaccggga
     ************************************    ****  **************

10   ataatattattctccggcgccggcgaacggtggtctccgttttattttccattgggtttg
15   ataatattattctccggcgccggcgaacggtggtctccgttttattttccattgggtttg
20   ataatattattctccggcgccggcgaacggtggtctccgttttattttccattgggtttg
     ************************************************************

10   actgatgtttacacacaagaattattaaaatatataacaataaaatagtgtcggcaagca
15   actgatgtttacacacaagaattattaaaatatataacaataaaatagtgtcggcaagca
20   actgatgtttacacacaagaattattaaaatatataacaataaaatagtgtcggcaagca
     ************************************************************

10   attcatttaatttacagaggttaggtagctgagatctgcatgtggaaaatgcacatcttg
15   attcatttaatttacagaggttaggtagctgagatctgcatgtggaaaatgcacatcttg
20   attcatttaatttacagaggttaggtagctgagatctgcatgtggaaaatgcacatcttg
     ************************************************************

10   tgtggtccaggttgttattgccgatccttatccttattatacagatgattggtcctgaag
15   tgtggtccaggttgttattgccgatccttatccttattatacagatgattggtcctgaag
20   tgtggtccaggttgttattgccgatccttatccttattatacagatgattggtcctgaag
     ************************************************************

10   atcttgtgttgtatctatgtatttgtcaaattaataataaaagacaaagattccaataat
15   atcttgtgttgtatctatgtatttgtcaaattaataataaaagacaaagattccaataat
20   atcttgtgttgtatctatgtatttgtcaaattaataataaaagacaaagattccaataat
     ************************************************************

10   tctgcaaccatgcaaaaaagttccccataatttttaaatttttttatatataatttgtat
15   tctgcaaccatgcaaaaaagttccccataatttttaaatttttttatatataatttgtat
20   tctgcaaccatgcaaaaaagttccccataatttttaaatttttttatatataatttgtat
     ************************************************************

10   gcaaaaatatttatataaaggtttatttatta
15   gcaaaaatatttatataaaggtttatttatta
20   gcaaaaatatttatataaaggtttatttatta
     ********************************
```

Figure 17
Sequence alignment of UGT76G1 isoform sequences corresponding to SEQ ID
NO: 11, SEQ ID NO: 16, and SEQ ID NO: 21

```
1    CATCCGCTATGAGTCCAGAATGCGCCTATTGCTCCATGAGCTAGCACTTCTTGCTGCGGA
2    CATCCGCTATGAGTCCAGAATGCGCCTATTGCTCCATGAGCTAGCACTTCTTGCTGCGGA
3    CATCCGCTATGAGTCCAGAATGCGCCTATTGCTCCATGAGCTAGCACTTCTTGCTGCGGA
     ************************************************************

1    ACCCATTTCACAATACGTCCTCTTTCACCCAAGAACCCATCTGGCAACGGTTCGACCCAC
2    ACCCATTTCACAATACGTCCTCTTTCACCCAAGAACCCATCTGGCAACGGTTCGACCCAC
3    ACCCATTTCACAATACGTCCTCTTTCACCCAAGAACCCATCTGGCAACGGTTCGACCCAC
     ************************************************************

1    GTCGAACCCTTGACAAACCCAGGTCGAACCACCCATAAAAACGACTGCTTGCTATCAACC
2    GTCGAACCCTTGACAAACCCAGGTCGAACCACCCATAAAAACGACTGCTTGCTATCAACC
3    GTCGAACCCTTGACAAACCCAGGTCGAACCACCCATAAAAACGACTGCTTGCTATCAACC
     ************************************************************

1    AACCCACGAGCTATTTCCAAGAAATCTTTCTCATCCACTTCACTAGTACTACCAAAACTA
2    AACCCACGAGCTATTTCCAAGAAATCTTTCTCATCCACTTCACTAGTACTACCAAAACTA
3    AACCCACGAGCTATTTCCAAGAAATCTTTCTCATCCACTTCACTAGTACTACCAAAACTA
     ************************************************************

1    ACATACAGTACCGAACTTGGCGGTTGTTGGTCTAACCATGGAAAAACGGTTCGATCGTGG
2    ACATACAGTACCGAACTTGGCGGTTGTTGGTCTAACCATGGAAAAACGGTTCGATCGTGG
3    ACATACAGTACCGAACTTGGCGGTTGTTGGTCTAACCATGGAAAAACGGTTCGATCTTCG
     ******************************************************* * *

1    TCTAGTAAGCTGCTGGAAGAGGCTGTCAAATGCTTGGGGAGTGGTATCAAGAAACTTGGA
2    TCTAGTAAGCTGCTGGAAGAGGCTGTCAAATGTTTGGGTAATGGTATCAGGAAACTTGGT
3    TCTAGTAAGCTGCTTGATGAGGCTGTCAAATGTTTGGGTAATGGTATCAGGAAACTTGGT
     ************** ** **************** ***** * ******** **********

1    GCCGGGAGGAAGTCACGGGTAATCGTTTCGACCTCGGGCTCTTCGAGTTCCTTAAATGAG
2    GTCGGGAGGAAGTCACGGGTAATCGTTTCGACCTCGGGCTCTTGGAGTTCCTTAAACGAG
3    GTCGGGAGGAAGTCACGGGTAATCGTTTCGACCTCGGGCTCTTGGAGTTCCTTAAACGAG
     * ****************************************** ************ ***

1    TTCCAGATGACTCCTGAAGATGCTTTTGTTTGTTTCGTAATGTTCTCGAAATACTCTTTG
2    TTCCAGATGACTCCTGAAGATGCTTTTGTTTGTTTCGTAATGTTCTCGAAATACTCTTTG
3    TTCCATATGATTCCTGAAGATGCTTTTGTTTGTTTATCATCTTCCCGAATATCTCTTTG
     ***** **** *********************** * ** *** **** *******

1    TATTTTTTCCACATCGAAAAACTACACTTGATATCTTTCACTTTCAGCATAGGAAACCCA
2    TATTTTTTCCACATCGAAAAACTACACTTGATATCTTTCACTTTCAGCATAGGAAACCCA
3    ACTACTTGCCAGTTCGAATACGCAGACTTGATGTCTTTCACTTTCAGCATAGGAAACCCA
     * ** *** ***** *   * ******* *****************************
```

Figure 17 continued

```
1    CTCGCTTGTTCTTCCAAACGGGTTTTGTCATCAGGATCGAGGTAACCAAGCTCATCAAAC
2    CTCGCTTGTTCTTCCAAACGGGTTTTGTCATCAGGATCGAGGTAACCAAGCTCATCAAAC
3    CTCGCTTGTTCTTCCAAACGGGTTTTGTCATCAGGATCGAGGTAACCAAGCTCATCAAAC
     ************************************************************

1    TGAGGAAGTGAAACATGTGCATGAAAATTAAACAAGCTGCTTGTCACCAAAACAAGCCGT
2    TGAGGAAGTGAAACATGTGCATGAAAATTAAACAAGCTGCTTGTCACCAAAACAAGCCGT
3    TGAGGAAGTGAAACATGTGCATGAAAATTAAACAAGCTGCTTGTCATCAAAACAAGCCGT
     **********************************************  ************

1    CGGAGGTTAAGACTGTCAGCAACAGATTGCGTGAAGTACCAAATCTGATCGGCGATTAAA
2    CGGAGGTTAAGACTGTCAGCAACAGATTGCGTGAAGTACCAAATCTGATCGGCGATTAAA
3    CGGAGGTTAAGACTGTCAGCAACAGATTGCGTGAAGTACCAAATCTGATCGGTGATTAAA
     ****************************************************  ******

1    CACGATACCTCTCCATCTTCTTCAGAAGCTAACATCAACAGTTCCAGTTCGCGTCGTAAT
2    CACGATACCTCTCCATCTTCTTCAGAAGCTAACATCAACAGTTCCAGTTCGCGTCGTAAT
3    CACGATACCTCTTCATCTTCTTCAGAAGCTAACATCAACAGTTCCAGTTCGCGTCGTAAT
     ***********  ***********************************************

1    TCGTCAGCTCCGTGTTCGTTGATAATC
2    TCGTCAGCTCCGTGTTCGTTGATAATC
3    TCGTCAGCTCCGTGTTCGTTGATAATC
     ***************************
```

Figure 18

Sequence alignment of UGT76G1 isoform sequences corresponding to SEQ ID NO: 12, SEQ ID NO: 17, and SEQ ID NO: 22

```
1    ACTCTGAGTGCAGAATGCACCGATTGCTCCATGAGCTAGCACTTCTTGCTGCGGAACCCA
2    ACTCTGAGTGCAAAATGCACCGATTGCTCCATGAGCTATCACTTCTTGCTGCGGAACCCA
3    ACTCTGAGTGCAGAATGCACCGATTGCTCCATGAGCTATCACTTCTTGCTGCGGAACCCA
     **********  ************************ *********************

1    TTTCACAATACGTCCTCTTTCACCCAAGAACCCATCTGGCAACGGTTCGACCCACGTCGA
2    TTTCACAATACGTCCTCTTTCACCCAAGAACCCATCTGGCAACGGTTCGACCCACGTCGA
3    TTTCACAATACGTCCTCTTTCACCCAAGAACCCATCTGGCAACGGTTCGACCCACGTCGA
     ************************************************************

1    ACCCTTGACAAACCCAGGTCGAACCACCCATAAAAACGACTGCTTGCTATCAACCAACCC
2    ACCCTTGACAAACCCAGGTCGAACCACCCATAAAAACGACTGCTTGCTATCAACCAACCC
3    ACCCTTGACAAACCCAGGTCGAACCACCCATAAAAACGACTGCTTGCTATCAACCAACCC
     ************************************************************

1    ACGAGCTATTTCCAAGAAATCTTTCTCATCCACTTCAGTACCACTACCAAAACTAACATA
2    ACGAGCTATTTCCAAGAAATCTTTCTCATCCACTTCACTACTACTACCAAAACTAACATA
3    ACGAGCTATTTCCAAGAAATCTTTCTCATCCACTTCACTAGCACTACCAAAACTAACATA
     ************************************* **  ******************

1    CAGTACCGAACGTGACGGTTGTTGGTCTAACCATGGAAAAACGGTTCGATCGTGGTCTAG
2    CAGTACCGAACTTGGCGGTTGTTGGTCTAACCATGGAAAAACGGTTCGATCGTGGTCTAG
3    CAGTACCGAACGTGACGGTTGTTGGTCTAACCATGGAAAAACGGTTCGATCGTGGTCTAG
     ***********  ** ********************************************

1    TAAGCTGCTGGAAGAGGCTGTCAAATGCTTGGGGAGTGGTATCAAGAAACTTGGAGCCGG
2    TAAGCTGCTGGAAGAGGCTGTCAAATGCTTGGGGAGTGGTATCAAGAAACTTGGAGCCGG
3    TAAGCTGCTGGAAGAGGCTGTCAAATGCTTGGGGAGTGGTATCAAGAAACTTGGAGCCGG
     ************************************************************

1    GATCTCACGGATAACAGTTTCGAGCTCAGACTCTTCGAGTTCCTTAAATGAGTTCCAGAT
2    GATCTCACGGATAACAGTTTCGAGCTCAGACTCTTCGAGTTCCTTAAATGAGTTCCAGAT
3    GATCTCACGGATAACAGTTTCGAGCTCAGACTCTTCGAGTTCCTTAAATGAGTTCCAGAT
     ************************************************************

1    GACTCCTGAAGATGCTTTTGTTTGTTTCGTAATGTTCTCGAAATACTCTTTGTATTTTTT
2    GACTCCTGAAGATGCTTTTGTTTGTTTCGTAATGTTCTCGAAATACTCTTTGTATTTTTT
3    GACTCCTGAAGATGCTTTTGTTTGTTTTGTAATGTTCTCGAATATCTCTTTGGCTTCTTT
     ***************************  *************  ********    * ***

1    CCACATCGAAAAACTACACTTGATATCTTTCACTTTCAGCATAGGAAACCCACTCGCTTG
2    CCACATCGAAAAACTACACTTGATATCTTTCACTTTCAGCATAGGAAACCCACTCGCTTG
3    CCAGTTCGAAAAACCAGACTTGATGTCTTTCACTTTCAGCATAGGAAACCCACTCGCTTG
     ***  ******** * ******** ***********************************
```

Figure 18 continued

```
1    TTCTTCCAAACGGGTTTTGTCATCAGGATCGAGGTAACCAAGCTCATCAAACTGAGGAAG
2    TTCTTCCAAACGGGTTTTGTCATCAGGATCGAGGTAACCAAGCTCATCAAACTGAGGAAG
3    TTCTTCCAAACGGGTTTTGTCATCAGGATCGAGGTAACCAAGCTCATCAAACTGAGGAAG
     ************************************************************

1    TGAAACATGTGCATGAAAATTAAACAAGCTGCTTGTCACCAAAACAAGCCGTCGGAGGTT
2    TGAAACATGTGCATGAAAATTAAACAAGCTGCTTGTCACCAAAACAAGCCGTCGGAGGTT
3    TGAAACATGTGCATGAAAATTAAACAAGCTGCTTGTCATCAAAACAAGCCGTCGGAGGTT
     ************************************** *********************

1    AAGACTGTCAGCAACAGATTGCGTGAAGTACCAAATCTGATCGGCGATTAAACACGATAC
2    AAGACTGTCAGCAACAGATTGCGTGAAGTACCAAATCTGATCGGCGATTAAACACGATAC
3    AAGACTGTCAGCAACAGATTGCGTGAAGTACCAAATCTGATCGGTGATTAAACACGATAC
     ******************************************* ****************

1    CTCTCCATCTTCTTCAGAAGCTAACATCAACAGTTCCAGTTCGCGTCGTAATTCGTCAGC
2    CTCTCCATCTTCTTCAGAAGCTAACATCAACAGTTCCAGTTCGCGTCGTAATTCGTCAGC
3    CTCTTCATCTTCTTCAGAAGCTAACATCAACAGTTCCAGTTCGCGTCGTAATTCGTCAGC
     **** *******************************************************

1    TCCGTGTTCGTTGATAATC
2    TCCGTGTTCGTTGATAATC
3    TCCGTGTTCGTTGATAATC
     *******************
```

Figure 19

Sequence alignment of UGT76G1 isoform sequences corresponding to SEQ ID NO: 13, SEQ ID NO: 18, and SEQ ID NO: 23

```
1    CATCCGCTATGAGTCCAGAATGCGCCTATTGCTCCATGAGCTAGCACTTCTTGCTGCGGA
2    CATCCGCTATGAGTCCAGAATGCGCCTATTGCTCCATGAGCTAGCACTTCTTGCTGCGGA
3    CATCCGCTATGAGTCCAGAATGCGCCTATTGCTCCATGAGCTAGCACTTCTTGCTGCGGA
     ************************************************************

1    ACCCATTTCACAATACGTCCTCTTTCACCCAAGAACCCATCTGGCAACGGTTCGACCCAC
2    ACCCATTTCACAATACGTCCTCTTTCACCCAAGAACCCATCTGGCAACGGTTCGACCCAC
3    ACCCATTTCACAATACGTCCTCTTTCACCCAAGAACCCATCTGGCAACGGTTCGACCCAC
     ************************************************************

1    GTCGAACCCTTGACAAACCCAGGTCGAACCACCCATAAAAACGACTGCTTGCTATCAACC
2    GTCGAACCCTTGACAAACCCAGGTCGAACCACCCATAAAAACGACTGCTTGCTATCAACC
3    GTCGAACCCTTGACAAACCCAGGTCGAACCACCCATAAAAACGACTGCTTGCTATCAACC
     ************************************************************

1    AACCCACGAGCTATTTCCAAGAAATCTTTCTCATCCACTTCACTAGTACTACCAAAACTA
2    AACCCACGAGCTATTTCCAAGAAATCTTTCTCATCCACTTCACTAGTACTACCAAAACTA
3    AACCCACGAGCTATTTCCAAGAAATCTTTCTCATCCACTTCACTAGTACTACCAAAACTA
     ************************************************************

1    ACATACAGTACCGAACGTGGCGGTTGTTGGTCTAACCATGGAAAAACGGTTCGATCGTGG
2    ACATACAGTACCGAACTTGGCGGTTGTTGGTCTAACCATGGAAAAACGGTTCGATCGTGG
3    ACATACAGTACCGAACTTGGCGGTTGTTGGTCTAACCATGGAAAAACGGTTCGATCTTCG
     **************** *******************************************  * *

1    TCTAGTAAGCTGCTGGAAGAGGCTGTCAAATGCTTGGGGAGTGGTATCAAGAAACTTGGA
2    TCTAGTAAGCTGCTGGAAGAGGCTGTCAAATGTTTGGGTAATGGTATCAGGAAACTTGGT
3    TCTAGTAAGCTGCTTGATGAGGCTGTCAAATGTTTGGGTAATGGTATCAGGAAACTTGGT
     ************** ** *************** *****   * ********* **********

1    GCCGGGAGGAAGTCACGGGTAATCGTTTCGACCTCGGGCTCTTCGAGTTCCTTAAATGAG
2    GTCGGGAGGAAGTCACGGGTAATCGTTTCGACCTCGGGCTCTTGGAGTTCCTTAAACGAG
3    GTCGGGAGGAAGTCACGGGTAATCGTTTCGACCTCGGGCTCTTGGAGTTCCTTAAACGAG
     *  ******************************************** ************* ***

1    TTCCAGATGACTCCTGAAGATGCTTTTGTTTGTTTCGTAATGTTCTCGAAATACTCTTTG
2    TTCCAGATGACTCCTGAAGATGCTTTTGTTTGTTTCGTAATGTTCTCGAAATACTCTTTG
3    TTCCATATGATTCCTGAAGATGCTTTTGTTTGTTTTATCATCTTCCCGAATATCTCTTTG
     ***** **** *********************** * ** *** ****  *******

1    TATTTTTTCCACATCGAAAAACTACACTTGATATCTTTCACTTTCAGCATAGGAAACCCA
2    TATTTTTTCCACATCGAAAAACTACACTTGATATCTTTCACTTTCAGCATAGGAAACCCA
3    ACTACTTGCCAGTTCGAATACGCAGACTTGATGTCTTTCACTTTTAGCATAGGAAACCCA
     *  ** ***  *****  *  *   * ******************** ******* ******* ********
```

Figure 19 continued

```
1   CTCGCTTGTTCTTCCAAACCTTAAATCAAATAATTCACAACGTAACTGAAACATAAAAAC
2   CTCGCTTGTTCTTCCAAACCTTAAATCAAATAATTCACAACGTAACTGAAACATAAAAAC
3   CTCGCTTGTTCTTCCAAACCTTAAATCAAATAATTCACAACGTAACTGAAACATAAAAAC
    ************************************************************

1   GAGAAACTAAATTAATTAATGACTCACGGGTTTTGTCATCAGGATCGAGGTAACCAAGCT
2   GAGAAACTAAATTAATTAATGACTCACGGGTTTTGTCATCAGGATCGAGGTAACCAAGCT
3   GAGAAACTAAATTAATTAATGACTCACGGGTTTTGTCATCAGGATCGAGGTAACCAAGCT
    ************************************************************

1   CATCAAACTGAGGAAGTGAAACATGTGCATGAAAATTAAACAAGCTGCTTGTCACCAAAA
2   CATCAAACTGAGGAAGTGAAACATGTGCATGAAAATTAAACAAGCTGCTTGTCACCAAAA
3   CATCAAACTGAGGAAGTGAAACATGTGCATGAAAATTAAACAAGCTGCTTGTCATCAAAA
    ******************************************************* *****

1   CAAGCCGTCGGAGGTTAAGACTGTCAGCAACAGATTGCGTGAAGTACCAAATCTGATCGG
2   CAAGCCGTCGGAGGTTAAGACTGTCAGCAACAGATTGCGTGAAGTACCAAATCTGATCGG
3   CAAGCCGTCGGAGGTTAAGACTGTCAGCAACAGATTGCGTGAAGTACCAAATCTGATCGG
    ************************************************************

1   CGATTAAACACGATACCTCTCCATCTTCTTCAGAAGCTAACATCAACAGTTCCAGTTCGC
2   CGATTAAACACGATACCTCTCCATCTTCTTCAGAAGCTAACATCAACAGTTCCAGTTCGC
3   TGATTAAACACGATACCTCTTCATCTTCTTCAGAAGCTAACATCAACAGTTCCAGTTCGC
     ******************* ****************************************

1   GTCGTAATTCGTCAGCTCCGTGTTCGTTGATAATC
2   GTCGTAATTCGTCAGCTCCGTGTTCGTTGATAATC
3   GTCGTAATTCGTCAGCTCCGTGTTCGTTGATAATC
    ***********************************
```

Figure 20 Sequence alignment of UGT91D2 isoform sequences of '817096' corresponding to SEQ ID NOs: 24-54

```
1     ggctggagtcaattgttttatacaatacataatatagcgttaaatggctttataataac
7     ---------------ttttttttttttta------cggctgga---------------
3     ---------------ttttttttttttta------cggctgga---------------
6     ---------------ttttttttttttta------cggctgga---------------
8     ---------------ttttttttttttta------cggctgga---------------
4     ------cacaat-actactctttagttaccaatataccataac---------------
2     ----------------------------------------------------------
5     ----------------------------------------------------------

1     gacggaaaagttaatgactcgattctaccaacgacttagcaattccaacatgtgattaaa
7     ---------atcaattgctttattc---------------atcacataatttggcttta
3     ---------atcaattgctttattc---------------atcacataatttggcttta
6     ---------atcaattgctttattc---------------atcacataatttggcttta
8     ---------atcaattgctttattc---------------atcacataatttggcttta
4     ---------caaaattgtttgatag---------------ataagattatcctatatta
2     ----------------------------------------------tag----tga
5     ----------------------------------------------tag----tga
                                                    *       *

1     aaagaagtgtaacaaggacaatcataacatcatatgaatcattccaaagaaacccaacaa
7     aatagccttacaataacaac--ttat-ta----atatagtagcttaaaa----caattaa
3     aatagccttacaataacaac--ttat-ta----atatagtagcttaaaa----caattaa
6     aatagccttacaataacaac--ttat-ta----atatagtagcttaaaa----caattaa
8     aatagccttacaataacaac--ttat-ta----atatagtagcttaaaa----caattaa
4     aaattgatgaaacccagtcgatttat-caataaaagaaatagatcaatg----aaattat
2     atgtatataacataaatgatatgttt-caacctaacaaacggt----------------
5     atgtatataacataaatgatatgttt-caacctaacaaacggt----------------
         *     *                      *   *    *

1     ctaacttacttatagtctgtgaaacgactt-atatattctttttggttaactctcatggt
7     ctaggacacct----------cctaagactc---------gatcgattctaccaacatatt
3     ctaggacacct----------cctaagactc---------gatcgattctaccaacatatt
6     ctaggacacct----------cctaagactc---------gatcgattctaccaacatatt
8     ctaggacacct----------cctaagactc---------gatcgattctaccaacatatt
4     ctagtttgtgaatttatcacattgatgtttctaccttatttcaaacaaaccagatactt
2     ----tatttca-------------------------tacacggaaaacaaaaattta
5     ----tatttca-------------------------tacacggaaaacaaaaattta
                                                          **

1     t---gttggcaaccacacgtacgttc----ttttccatatagtctgtgaaacgacttata
7     tagcaattccaacatttcatttgaatc-tttccaaaagaaacccaacaactcacacatac
3     tagcaattccaacatttcatttgaatc-tttccaaaagaaacccaacaactcacacatac
6     tagcaattccaacatttcatttgaatc-tttccaaaagaaacccaacaactcacacatac
8     tagcaattccaacatttcatttgaatc-tttccaaaagaaacccaacaactcacacatac
4     caattaattcaag-caacatttgatcatgaaga---------------------------
2     tgattattcaaag-aaacatttgatcatctagctagacaaaccaataacacatatattc
5     tgattattcaaag-aaacatttgatcatctagctagacaaaccaataacacatatattc
          **      *  *  *

1     tattcttttttggttaactctcatggttgttggcaaccacacgtacgttcttttccatata
7     ttgatgatatagttaactctcatgatcgatggcaaccgcacgcgcattctttccaaata
3     ttgatgatatagttaactctcatgatcgatggcaaccgcacgcgcattctttccaaata
6     ttgatgatatagttaactctcatgatcgatggcaaccgcacgcgcattctttccaaata
8     ttgatgatatagttaactctcatgatcgatggcaaccgcacgcgcattctttccaaata
4     -caaa-ccaacaacgcacattcttcatacggttaacgtacgtcgtgtcttctccaaata
2     ttcat-acgatcaaagctcatg--ctcaatagcaaccacacgacctttttgttccaaata
5     ttcat-acgatcaaagctcatg--ctcaatagcaaccacacgacctttttgttccaaata
           *  *                 *  *  *  **           *   *   ****  ***
```

Figure 20 continued

```
1  gtctgtgaaacgacttatatattccttttgcagcttagtgtcgctgaatattttactcat
7  gtctacgaattggcttacatattcttttcaaccttagtgtcgttatagattttactcag
3  gtctacgaattggcttacatattcttttcaaccttagtgtcgttatagattttactcag
6  gtctacgaattggcttacatattcttttcaaccttagtgtcgttatagattttactcag
8  gtctacgaattggcttacatattcttttcaaccttagtgtcgttatagattttactcag
4  atctatgaaatggtttatatacttctttcccatcttagtgtctccgaacaatctacttaa
2  gtctataaaagggtttatatacttattttccggcttactatcccgaatcgttgactcaa
5  gtctataaaagggtttatatacttattttccggcttactatcccgaatcgttgactcaa 1  ctctctcgcattcgccttgtagatctctccttcatcgtctacaacaaccgacctcagtga
7  ctccctcgcgttcgccttgtagatctcccttcttttttccacaacaacggacctcagtga
3  ctccctcgcgttcgccttgtagatctcccttcttttttccacaacaacggacctcagtga
6  ctccctcgcgttcgccttgtagatctcccttcttttttccacaacaacggacctcagtga
8  ctccctcgcgttcgccttgtagatctcccttcttttttccacaacaacggacctcagtga
4  ctccatcgcattttccttgtaaatcttcatcatcagctcgtacaaccgaccgcactga
2  ctccatcgccttcgccttgtagatcttccttcatcatcgactaaaaccaacctcaatga
5  ctccatcgccttcgccttgtagatcttcccttcatcatcgactacaaccaacctcaatga 1  cgtggcaaccgactccttggtgaagtagccatcttcctcatttcttggtatctcgatccc
7  tctagcaaccgactccttggtcaagcaaccatcttcctcatttcttggtatctcgattcc
3  tctagcaaccgactccttggtcaagcaaccatcttcctcatttcttggtatctcgattcc
6  tctagcaaccgactccttggtcaagcaaccatcttcctcatttcttggtatctcgattcc
8  tctagcaaccgactccttggtcaagcaaccatcttcctcatttcttggtatctcgattcc
4  tcttgccactgactccttgttgaaggagccatcttcgtcatttcttggtatctcgaattcc
2  tctggccaccgactccttggtgaatgaaccatcttcctcatttcttggtatctcgattcc
5  tctggccaccgactccttggtgaatgaacatcttcctcatttcttggtatctcgattcc 1  cacctgtttgtccgctaatagtcgagcattcagacattggtccccgaaaatcggtagcat
7  cacctgtttgtcctccagtaatcgagcattcagaggttggtccccaaaaatcggtagcat
3  cacctgtttgtcctccagtaatcgagcattcagaggttggtccccaaaaatcggtagcat
6  cacctgtttgtcctccagtaatcgagcattcagaggttggtccccaaaaatcggtagcat
8  cacctgtttgtcctccagtaatcgagcattcagaggttggtccccaaaaatcggtagcat
4  cacctgattatccgccattactcgagcatttagaccttgatccaccgaaagcggtagcat
2  cacctgtttatccgccattactcgagcatttagaccttggtccccaaaaatcggtagcat
5  cacctgtttatccgccattactcgagcatttagaccttggtccaccaaaatcggtagcat 1  gattaaagggtgaccgaacattaacccttccaccactgaactccaaccacagtgagtcaa
7  gattagagggtgaccaaacattagcccttccacaattgatccagaaccacaatgagtcaa
3  gattagagggtgaccaaacattagcccttccacaattgatccagaaccacaatgagtcaa
6  gattagagggtgaccaaacattagcccttccacaattgatccagaaccacaatgagtcaa
8  gattagagggtgaccaaacattagcccttccacaattgatccagaaccacaatgagtcaa
4  tattaaagggtgaccgaacatcatcgcttccacaattgaactccaaccacaatgagtcaa
2  gattagagggtgaccgaacatcatcgcttccacaattgaactccaaccacaatgagtcaa
5  gattagagggtgaccgaacatcatcgcttccacaattgaactccaaccacaatgagtcaa 1  gaaaccacacaccgactcatggctcagtattcgtaactgaggtgcccaactcgtccaaac
7  gaaaccacacaccgactcatggctcagtattcgtaactgaggtgcccaactcgtccagac
3  gaaaccacaaaccgactcatggctcagtattcgtaactgaggtgcccaactcgtccagac
6  gaaaccacaaaccgactcatggctcagtattcgtaactgaggtgcccaactcgtccagac
8  gaaaccacaaaccgactcatggctcagtattcgtaactgaggtgcccaactcgtccagac
4  gaaaccacaaaccgactcatggctcagtattcgtaactgaggtgcccaactcgtccagac
2  gaaaccacaaaccgactcatggctcagtattcgtaactgaggtgcccaactcgtccagac
5  gaaaccacaaaccgactcatggctcagtattcgtaactgaggtgcccaactcgtccagac
```

Figure 20 continued

```
1  catcccacggttactagttcgttccaagaacccgttaggcaactccaccgagtctgactc
7  caacccacggtcacgagttcgttccacgaacccgtctggcaactccaccgagttac----
3  caacccacggtcacgagttcgttccacgaacccgtctggcaactccaccgagttac----
6  caacccacggtcacgagttcgttccacgaacccgtctggcaactccaccgagttac----
8  caacccacggtcacgagttcgttccacgaacccgtctggcaactccaccgagttac----
4  caacccacggtcacgagttcgttccacgaacccgtctggcaactccaccgagttac----
2  caacccacggtcacgagttcgttccacgaacccgtctggcaactccaccgagttac----
5  caacccacggtcacgagttcgttccacgaacccgtctggcaactccaccgagttac----
    ** ******** ** ********** ******** ***************

1  ggtggaacctgcgggttttctgagaacccacaaaaatggcaacccagagagctcgagacc
7  --cagagccaaccggttttctaagaacccacaaaaatggcaacccagagagctcgagacc
3  --cagagccaaccggttttctaagaacccacaagaatggcaacccagagagctcgagacc
6  --cagagccaaccggttttctaagaacccacaaaaatggcaacccagagagctcgagacc
8  --cagagccaaccggttttctaagaacccaaaagaatggcaacccggagagctcgagacc
4  --cagagccaaccggtttttctaagaaccccaaaagaatggcaacccggagagctcgagacc
2  --cagagccaaccggttttctaagaacccaaaagaatggcaaccc ggagagctcgagacc
5  --cagagccaaccggttttctaagaacccaaaagaatggcaacccggagagctcgagacc
    ** ** * ******** ********* ** ************* **************

1  tagcgctaactcagccagctcgcttttggtcaccgtaacttcacttcctaatgcgacgta
7  taacgctaactcagccagctcgcttttggtcaccgtaacttcacttcctaatgcgacgta
3  taacgctaactcagccagctcgcttttggtcaccgtaacttcacttcctaatgcgacgta
6  taacgctaactcagccagctcgcttttggtcaccgtaacttcacttcctaatgcgacgta
8  cagagctaactcagccagctcgcttttgctcaccgtaacttcacttcctaatgcgacgta
4  cagagctaactcagccagctcgcttttgctcaccgtaacttcacttcctaatgcgacgta
2  cagagctaactcagccagctcgctttggctcatcgtaccttcacttccaaatgccacgta
5  cagagctaactcagccagctcgctttggctcatcgtaccttcacttccaaatgccacgta
    *  ************************ *  ***  ****  ******** ***** ******

1  caccacatgcccta ttggttgaccatcgagccacttcttgattgacacccatgggt----
7  caccacatggttaacttgctgaccatcgagccacttcttgactgtcacccacgtctcatc
3  caccacatggttaacttgctgaccatcgagccacttcttgattgtcacccatgggtctcc
6  caccacatggttaacttgctgaccatcgagccacttcttgattgtcacccatgggtctcc
8  caccacatggttaacttgctgaccatcgagccacttcttgattgacacccatgtatcatc
4  caccacatggttaacttgctgaccatcgagccacttcttgactgacacccatgtatcatc
2  caccacatgcccta ttggttgaccatcgagccacttcttgattgtcacccatgggt----
5  caccacatgcccta ttggttgaccatcgagccacttcttgactgtgacccatgtctcatc
   ********  *  * * ***************** ** ***** *  *

1  --------ctccggtgctggtgggtggttcgggtggcaataatcccacgggaaccaccgg
7  attcccgtctccgatgttggtgggttttctggtggcaataatccgacaggaaccaccgg
3  ggtgc------------tggtgggtggttcgggtggcaataatcccacgggaaccaccgg
6  ggtgc------------tggtgggtggttcgggtggcaataatcccacgggaaccaccgg
8  tttctcgt---------ctccgtatgtttcaggtggcattaatccaaccggaactaccgg
4  tttctcgtctccgta---------tgtttcaggtggcattaatccaaccggaactaccgg
2  --------ctccggtgctggtgggtggttcgggtggcaataatcccacgggaaccaccgg
5  tttcccgtctccgatgttggtgggttttctggtggcaataatccgacaggaaccaccgg
    *  *** ******  ****** ****** ***** ****

1  tagctgatgcagcttttctaaaagggttagccattggggttcgaactcatggcaatgtct
7  taggtgatggagcttctctaaaagggttaaccattgaggttcgaactcataactatgtct
3  taggtgatgcagcttttccaaaagggttagccattggggttcgacctcataacaacttct
6  taggtgatgcagcttttctaaaagggttagccattggggttcgaactcatggcaatgtct
8  tatacggtatagcttccccaaaagggttagccattggggttcgaactcatggcaatgtct
4  tatacggtatagcttcccaaaagggttagccattggggttcgaactcatggcaatgtct
2  tagctgatgcagcttttctaaaagggttagccattggggttcgaactcatggcaatgtct
5  taggtgatggagcttctctaaaagggttaaccattgaggttcgaactcataactatgtct
    ** * *  * *****  * ********* ****** ** ******* ***** * * ***
```

Figure 20 continued

```
1   tataaacatacaatctgatcccttataaccattcctaaacgatataaatctgatacacc
7   tataaacatacagtcagatcctttcaaaatcattcccacacgatacacacttgatattcc
3   tataaacagacaatcagattccttcaaaaccgtcatcattctgtgctttaga------cc
6   tataaacatacaatctgatcccttataaccattcctaaacgatataaatctgatacacc
8   tataaacatacaatctgatcccttataaccattcctaaacgatataaatctgatacacc
4   tataaacatacaatctgatcccttataaccattcctaaacgatataaatctgatacacc
2   tataaacatacaatctgatcccttataaccattcctaaacgatataaatctgatacacc
5   tataaacatacagtcagatcctttcaaaatcattcccacacgatacacacttgatattcc
    ********  ***  **  ***  *  **  *  **  *  *    *     *    **

1   agaagaattaacagaaatattatcagcaaatatcaaattggcctcatgcttccggtagca
7   agaagcattagccgaagta---ttccctaccatccgaaccgcctcatacttccggtagca
3   tgaaatcacaggattattagcagcagacatcttgcgcacaaactcatgcttccggtagca
6   agaagaattaacagaaatattatcagcaaatatcaaattggcctcatgcttccggtagca
8   agaagaattaacagaaatattatcagcaaatatcaaattggcctcatgcttccggtagca
4   agaagaattaacagaaatattatcagcaaatatcaaattggcctcatgcttccggtagca
2   agaagaattaacagaaatattatcagcaaatatcaaattggcctcatgcttccggtagca
5   agaagcattagccgaagtattccc---taccatccgaaccgcctcatacttccggtagca
    ***    *  *  **    *           *      *     *****  *********

1   tactttgctcggaaacggaatccacttcggcggtgtcataaaattctcaaccctcgttcg
7   cacgtttgtcggaaacggaacccacttcggcggtgtcataaaattctcaaccctcgttcg
3   tactttgctcggaaacggaatccacttgggcggtgtcatgaaatcctcaactgtcgttcg
6   tactttacttgggaacggaaaccacttcggcggtgtcaggaaatcgtcggctgtgttccg
8   tactttgcttgggaacggaaaccacttcggcggtgtcaggaaatcgtcggctgtgttccg
4   tactttgctcgggaacggaaaccacttcggcggtgtcaggaaatcgtcggctgtgttccg
2   tactttacttgggaacggaaaccacttcggcggtgtcaggaaatcgtcggctgtgttccg
5   cacgtttgtcggaaacggaacccacttcggcggtgtcataaaattctcaaccctcgttcg
    **  **   *  **  *******  ******  *********  ****  **  *  *  **

1   atgatcataaccggaaccacttatcaagtcgtcagccgacgctccgagaaaagcaatgaa
7   atgatcataaccggaaccacttatcaagtcgtcagccgacgctccgagaaaagcaatgaa
3   actctcgaaa-------ctattttttcatgtcatcgggtaacggtcccacgtgcgccatgaa
6   atcgtctgta-------ccgtttatgatgtcatcgggagaagatccgaaaaagagacggt
8   atcgtctgta-------ccgtttatgatgtcatcgggagaagatccgaaaaagagacggt
4   atcgtct--------gtaccgtttatgatgtcatcgggagaagatccgaaaaagagacggt
2   atcgtct--------gtaccgtttatgatgtcatcgggagaagatccgaaaaagagacggt
5   atgatcataaccggaaccacttatcaagtcgtcagccgacgctccgagaaaagcaatgaa
    *   **          *    **  *  ***  **    *  *  ***  *     *  *

1   ccatgcgttaaaattcgagtaaaaggctcgcgaggtccgtagtccagctgcgacggacgg
7   ccatgcgttaaaattcgagtaaaaggctcgcgaggtccgtagtccagctgcgacggacgg
3   ccatggtgaggcagtgataaaaaggctcgcgagatcccaaggtccgccgcgacggatgg
6   ccatgcgttaaaattgagaaaaaacctcgtgaaattccaaggctagtggctaccgccgg
8   ccatgcgttaaaattgagaaaaaacctcgtgaaattccaaggctagtggctaccgccgg
4   ccatgcgttaaaattgagaaaaaacctcgtgaaattccaaggctagtggctaccgccgg
2   ccatgcgttaaaattgagaaaaaacctcgtgaaattccaaggctagtggctaccgccgg
5   ccatgcgttaaaattcgagtaaaaggctcgcgaggtccgtagtccagctgcgacggacgg
    *****     *  *   ****   ****  **   *    **    *    **  *  **

1   caaccaatac----------
7   caaccaatac----------
3   caaccagtg-----------
6   caaccaatagggagcaa
8   caaccaatagggagcaa
4   caaccaatagggagcaa
2   caaccaatagggagcaa
5   caaccaatac----------
    ****** *
```

Figure 20 continued

```
9    ggctggagtcaattgtttttatacaatacataatatagcgttaaatggctttataataac
16   ------------------------------------tttataataacgacggaaaagt
13   ------------------------------------------------------------
14   ------------------------------------------------------------
10   ------------------------------------------------------------
15   ------------------------------------------------------------
11   ------------------------------------------------------------
12   ------------------------------------------------------------

9    gacggaaaagttaatgactcgattctaccaacgacttagcaattccaacatgtgattaaa
16   agcgcaccacttaatgactcgattctaccaacgacttagcaattccaacatgtgattaaa
13   ------------------tttttttttttttac------ggctggaatcaattgctttat
14   ------------------tttttttttttttac------ggctggaatcaattgctttat
10   ---------------------------------------------------------tagt
15   ---------------------------------------------------------tagt
11   ------cacaat----actactctttagttaccaatataccataaccaaaattgtttgat
12   ------cacaat----actactctttagttaccaatataccataaccaaaattgtttgat
                                                              *

9    aaag----aagtgtaacaaggacaatcataacatcatgaatcattccaaagaaaccca
16   aaag----aagtgtaacaaggacaatcataacatcatgaatcattccaaagaaaccca
13   tcatcacataatttggctttaaatagccttacaataacaacttattaatatagtagctta
14   tcatcacataatttggctttaaatagcctcacaataacacttattaatatagtagctta
10   --------------------gaatgtataacataaatgatatgtttcaacctaacaaac
15   --------------------gaatgtatataacataaatgatatgtttcaacctaacaaac
11   agataagattatcctatattaaaattgatgaaaccagtcgattatcaataaaagaaat
12   agataagattatcctatattaaaattgatgaaaccagtcgattatcaataaaagaaat
            * * *                  *              *      *

9    aca--acta-acttacttatagtctgtgaaacgacttatatattctttttggttaactct
16   aca--acta-acttacttatagtctgtgaaacgacttatatattctttttggttaactct
13   aaacaatta-actaggacacctcctaagactcgatcgatctaccaacatatt------t
14   aaacaatta-actaggacacctcctaagactcgatcgatctaccaacatatt------t
10   ggttatttcatacacggaaaacaaaaattatgattattcaaagaaaca--tt------t
15   ggttatttcatacacggaaaacaaaaattatgattattcaaagaaaca--tt------t
11   aga-------tcaatgaaattatctagtttgtgaattttatcacattgatgtt------t
12   aga-------tcaatgaaattatctagtttgtgaattttatcacattgatgtt------t
         *                 **        *                   *

9    catggttgttggcaaccacacgtacgttcttttccatatagtctgtgaaacgacttatat
16   catggttgttggcaaccacacgtacgttcttttccatatagtctgtgaaacgacttatat
13   agcaattccaacatttcatttgaatc-ttccaaaagaaacccaacaactcacacatact
14   agcaattccaacatttcatttgaatc-ttccaaaagaaacccaacaactcacacatact
10   gatcatctagctagacaaaccca-----------ataacacatatattc---------
15   gatcatctagctagacaaaccca-----------ataacacatatattc---------
11   ctaccttatttcaaacaaaccagatacttcaattaattcaagcaacatttgatcatgaag
12   ctaccttatttcaaacaaaccagatacttcaattaattcaagcaacatttgatcatgaag
         *                *                 *   *

9    attctttttggttaactctcatggttgttggcaaccacacgtacgttcttttccatatag
16   attctttttggttaactctcatggttgttggcaaccacacgtacgttcttttccatatag
13   tgatgatatagttaactctcatgatcgatggcaaccgcacgtgcattcttttccaaatag
14   tgatgatatagttaactctcatgatcgatggcaaccgcacgcgcattcttttccaaatag
10   ttcatacgatcaaagctcat--gctcaatagcaaccacacgaccttttgttccaaatag
15   ttcatacgatcaaagctcat--gctcaatagcaaccacacgaccttttgttccaaatag
11   acaaacccaacaacgcacattcttcatacggttaacgtacgtcgtgtcttctccaaataa
12   acaaacccaacaacgcacattcttcatacggttaacgtacgtcgtgtcttctccaaataa
              *        *   *    *  **   *  *  ****  ***
```

Figure 20 continued

```
9     tctgtgaaacgacttatatattccttttgcagcttagtgtcgctgaatatttactcatc
16    tctgtgaaacgacttatatattccttttgcagcttagtgtcgctgaatatttactcatc
13    tctacgaattggcttacatattctttttcaaccttagtgtcgttatagattttactcagc
14    tctacgaattggcttacatattctttttcaaccttagtgtcgttatagattttactcagc
10    tctataaaagggtttatatacttattttccggcttactatccccgaatcgttgactcaac
15    tctataaaagggtttatatacttattttccggcttactatccccgaatcgttgactcaac
11    tctatgaaatggtttatatacttctttcccatcttagtgtctccgaacaatctacttaac
12    tctatgaaatggtttatatacttctttcccatcttagtgtctccgaacaatctacttaac
      ***   **  *  *** ***  *  ***    **** * **    *   *  *** * *

9     tctctcgcattcgccttgtagatctctccttcatcgtctacaacaaccgacctcagtgac
16    tctctcgcattcgccttgtagatctctccttcatcgtctacaacaaccgacctcagtgac
13    tccctcgcgttcgccttgtagatctcccctctttttccacaacaacggacctcagtgat
14    tccctcgcgttcgccttgtagatctcccctctttttccacaacaacggacctcagtgat
10    tccatcgccttcgccttgtagatcttcccttcatcatcgactaaaaccaacctcaatgat
15    tccatcgccttcgccttgtagatctcccttcatcatcgactaaaaccaacctcaatgat
11    tccatcggtaggaaccaccggtaggtgatggagc-ttctctaaaagggttaaccattgag
12    tccatcgcattttcttgtaaatcttcccttcatcatcagctacaaccgaccgcactgat
      **  ***      *          **       **    *  *         **  ***

9     gtggcaaccgactccttggtgaagtagccatcttcctcatttcttggtatctcgatcccc
16    gtggcaaccgactccttggtgaagtagccatcttcctcatttcttggtatctcgatcccc
13    ctagcaaccgactccttggtcaagcaaccatcttcctcatttcttggtatctcgattccc
14    ctagcaaccgactccttggtcaagcaaccatcttcctcatttcttggtatctcgattccc
10    ctggccaccgactccttggtgaatgaaccatcttccatttcttggtatctcgattccc
15    ctggccaccgactccttggtgaatgaaccatcttcctcatttcttggtatctcgattccc
11    gttcgaactcataactatgtcttataaacatacag-tcagatcctttcaaaatcattccc
12    cttgccactgactccttgttgaaggagccatcttcgtcatttcttggtatctcaattccc
       *   **   * **   *    *   ***  ***   ** *  *       ** ***

9     acctgtttgtccgctaatagtcgagcattcagacattggtccccgaaaatcggtagcatg
16    acctgtttgtccgctaatagtcgagcattcagacattggtccccgaaaatcggtagcatg
13    acctgtttgtcctccagtaatcgagcattcagaggttggtccccaaaaatcggtagcatg
14    acctgtttgtcctccagtaatcgagcattcagaggttggtccccaaaaatcggtagcatg
10    acctgattatccgccattactcgagcattagaccttggtccaccgaaaatcggtagcatg
15    acctgattatccgccattactcgagcatttagaccttggtccaccgaaaatcggtagcatg
11    acacgatac-----------------------acactgatattccagaagcattagccga
12    acctgattatccgccattactcgagcatttagacccttgatccaccgaaagcggtagcatt
      ** * *                          ***  *  *    ** * ****

9     attaa---agggtggccgaacattaacccttccaccattgaactccaaccacagtgagtc
16    attaa---agggtggccgaacattaacccttccaccactgaactccaaccacagtgagtc
13    attag---agggtgaccaaacattagcccttccacaattgatccagaaccacaatgagtc
14    attag---agggtgaccgaacattagcccttccacaattgatccagaaccacaatgagtc
10    attag---agggtgaccgaacatcatcgcttccacaattgaactccaaccacaatgagtc
15    attag---agggtgaccgaacatcatcgcttccacaattgaactccaaccacaatgagtc
11    agtattccctaccatccgaaccgcctcatacttcggtagcac--------acgtttgtc
12    attaa---agggtgaccgaacatcatcgcttccacaattgaactccaaccacaatgagtc
      *  **       **   ***         *   *   *   *           *  ***

9     aagaaaccacacaccgactcatggctcagtattcgtaactgaggtgcccaactcgtccaa
16    aagaaaccacacaccgactcatgactcagtattcgtaactgaggtgcccaactcgtccaa
13    aagaaaccacaaaccgactcatggctcagtattcgtaactgaggtgcccaactcgtccag
14    aagaaaccacaaaccgactcatggctcagtattcgtaactgaggtgcccaactcgtccag
10    aagaaaccacaaaccgactcatggctcagtattcgtaactgaggtgcccaactcgtccag
15    aagaaaccacaaaccgactcatggctcagtattcgtaactgaggtgcccaactcgtccag
11    --ggaaacggaacccacttcggcggtgtca------------------------------
12    aagaaaccacaaaccgactcatggctcagtattcgtaactgaggtgcccaactcgtccag
        * **  * **   *   **  **
```

Figure 20 continued

```
9   accatcccacggttactagttcgttccaagaacccgttaggcaactccaccgagtctgac
16  accatcccacggttactagttcgttccaagaacccgttaggcaactccaccgagtctgac
13  accaacccacggtcacgagttcgttccacgaacccgtctggcaactccaccgagttacca
14  accaacccacggtcacgagttcgttccacgaacccgtctggcaactccaccgagtctgac
10  accaacccacggtcacgagttcgttccacgaaccctctggcaactccaccgagttacca
15  accaacccacggtcacgagttcgttccacgaacccgtctggcaactccaccgagttacca
11  ------------------------------------------------------------
12  accaacccacggtcacgagttcgttccacgaacccctctggcaactccaccgagttacca 9   tcggtggaacctgcgggttttctgagaacccacaaaaatggcaacccagagagctcgaga
16  tcggtggaacctgcgggttttctgagaacccacaaaaatggcaacccagagagctcgaga
13  ------gagccaaccggttttctaagaacccaaaagaatggcaacccggagagctcgaga
14  ttcgcgggaccttttggttttctataagaaacaagatggcaacccagagaagctcgaga
10  ------gagccaaccggttttctaagaacccaaaagaatggcaacccggagagctcgaga
15  ------gagccaaccggttttctaagaacccaaaagaatggcaacccggagagctcgaga
11  ------------------------------------------------------------
12  ------gagccaaccggttttctaagaacccaaaagaatggcaaccggagagctcgaga 9   cctagagctaactcagccagctcgcttttggtcaccgtaacttcacttcctaatgccacg
16  cctagcgctaactcagccagctcgcttttggtcaccgtaacttcacttcctaatgccacg
13  cccagagctaactcagccagctcgctttggctcaccgtaacttcacttcctaatgcgacg
14  cccaatgctaactcaacaacctcggtttggctcaccaaaacctcgcttcctaatgcaacg
10  cccagagctaactcagccagctcgctttggctcatcgtaccttcacttccaaatgccacg
15  cccagagctaactcagccagctcgctttggctcaccgtaacttcacttcctaatgcgacg
11  ------------------------------------------------------------
12  cccagagctaactcagccagctcgctttggctcatcgtaccttcacttccaaatgccacg 9   tacaccacatgccctattggttgaccatcgagccacttcttgactgtgacccatgtctca
16  tacaccacatgccctattggttgaccatcgagccacttcttgactgtgacccatgtctca
13  tacaccacatggttaacttgctgaccatcgagccacttcttgactgtgacccatgtatca
14  tacaccacatgccttttttgtttaccatcgagccacatttcttgattgacacccatgtttca
10  tacaccacatgccctattggttgaccatcgagccacttcttgattgtcacccatgggtct
15  tacaccacatggtcaacttgctgaccatcgagccacttcttgactgacacccatgtatca
11  ------------------------------------------------------------
12  tacaccacatgccctattggttgaccatcgagccacttcttgattgtcacccatgggtct 9   tctttcccgtctccgatgttggtgggttttctggtggcaataatccgacaggaaccacc
16  tctttcccgtctccgatgttggtgggttttctggtggcaataatccgacaggaaccacc
13  tctttctcgtctc---------cgtatgtttcaggtggcattaatccaaccggaactacc
14  tctttctcgtctc---------cgggtatttccggcggcagtaatcccaccggaaccacc
10  ccggtg---ctgg---------tgggtggttcgggtggcaataatcccacgggaaccacc
15  tctttctcgtctc---------cgtatgtttcaggtggcattaatccaaccggaactacc
11  ------------------------------------------------------------
12  ccggtg---ctgg---------tgggtggttcgggtggcaataatcccacgggaaccacc 9   ggtaggtgatggagcttctctaaaagggttaaccattgaggttcgaactcataactatgt
16  ggtaggtgatggagcttctctaaaagggttaaccattgaggttcgaactcataactatgt
13  ggtatacggtatagcttccccaaaagggttagccattggggttcgaactcatggcaatgt
14  ggtacttggtgtagtgtctccaaaagaggtagccattgagttccaaactcatggtaacat
10  ggtagctgatgcagcttttctaaaagggttagccattggggttcgaactcatggcaatgt
15  ggtatacggtatagcttccccaaaagggttagccattggggttcgaactcatggcaatgt
11  ------------------------------------------------------------
12  ggtaggtgatgcagcttttctaaaagggttagccattggggttcgaactcatggcaatgt
```

Figure 20 continued

```
9   cttataaacatacagtcagatcctttcaaaatcattcccacacgatacacacttgatatt
16  cttataaacatacagtcagatcctttcaaaatcattcccacacgatacacacttgatatt
13  cttataaacatacaatctgatccctttataaccattcctaaacgatataaatctgataca
14  ttggaaagcaaacaatcagatcccttaaaaaccagcccccatacggtatccatcagatatc
10  cttataaacatacaatctgatccctttataaccattcctaaacgatataaatctgataca
15  cttataaacatacaatctgatccctttataaccattcctaaacgatataaatctgataca
11  ------------------------------------------------------------
12  cttataaacatacaatctgatccctttataaccattcctaaacgatataaatctgataca 9   ccagaagcattagccgaagtattcc---ctaccatccgaaccgcctcatacttccggtag
16  ccagaagcattagccgaagtattcc---ctaccatccgaaccgcctcatacttccggtag
13  ccagaagaattaacagaaatattatcagcaaatatcaaattggcctcatgcttccggtag
14  cccggagctttg-----------taaggaccagtcgggcaagatcatgcttccgccag
10  ccagaagaattaacagaaatattatcagcaaatatcaaattggcctcatgcttccggtag
15  ccagaagaattaacagaaatattatcagcaaatatcaaattggcctcatgcttccggtag
11  ------------------------------------------------------------
12  ccagaagaattaacagaaatattatcagcaaatatcaaattggcctcatgcttccggtag 9   cacacgtttgtcggaaacggaacccacttcggcggtgtcataaaattctcaaccctcgtt
16  cacacgtttgtcggaaacggaacccacttcggcggtgtcataaaattctcaaccctgtcgt
13  catactttgctcggaaacggaatccacttgggcggtgtcatgaaatcctcaactgtcgtt
14  catactttggtcggaaagggaaaccacttgggcggtgtcgtgagatcctcaaccgtggtt
10  catactttgctcggaaacggaatccacttgggcggtgtcatgaaatcctcaactgtcgtt
15  catactttgcttgggaacggaaaccacttcggcggtgtcaggaaatcgtcggctgttttc
11  ------------------------------------------------------------
12  catactttgctcggaaacggaatccacttgggcggtgtcatgaaatcctcaactgtcgtt 9   cgatgatcataaccggaaccacttatcaagtcgtcagccgacgctccgagaaaagcaatg
16  cgatgatcataaccggaaccacttatcaagtcgtcagccgacgctccgagaaaagcaatg
13  cgactctcgaaac-------tattttcatgtcatcggtaacggtccacgtgcgccatg
14  cgaccatctgaac-------catttatcatggcgtcagctgagggtcccatataagcaatg
10  cgactctcgaaac-------tattttcatgtcatcgggtaacggtcccacgtgcgccatg
15  cgatcgtctgtac-------cgtttatgatgtcatcgggagaagatccgaaaaagagacg
11  ------------------------------------------------------------
12  cgactctcgaaac-------tattttcatgtcatcgggtaacggtcccacgtgcgccatg 9   aaccatgcgttaaaattcgagtaaaaggctcgcgaggtccgtagtccagctgcgacggac
16  aaccatgcgttaaaattcgagtaaaaggctcgcgaggtccgtagtccagctgcgacggac
13  aaccatggtgaggcagtgataaaaaggctcgcgagatcccaaggtccgccgcgacggat
14  gcccatggagtggtgacgagaagtgggctcgtgagataccgaggctagccgcgatggat
10  aaccatggtgaggcagtgataaaaaaggctcgcgagatcccaaggtccgccgcgacggat
15  gtccatgcgttaaaaattgagaaaaaacctcgtgaaattccaaggctagtggctaccgcc
11  ------------------------------------------------------------
12  aaccatggtgaggcagtgataaaaaaggctcgcgagatcccaaggtccgccgcgacggat 9   ggcaaccaatac------------------------------------------------
16  ggcaaccaatac------------------------------------------------
13  ggcaaccagtg-------------------------------------------------
14  ggcaaccagtagtgagtataatcataaataatccagtccggagactctt
10  ggcaaccagtg-------------------------------------------------
15  ggcaaccaatagggagcaa-----------------------------------------
11  ------------------------------------------------------------
12  ggcaaccagtg-------------------------------------------------

18  ------------------------------------------------------------
17  ------------------------------------------------------------
20  ------------------------------------------------------------
19  ---------------------------------------tttataataacgacggaaaagt
21  ggctggagtcaattgttttttatacaatacataatatagcgttaaatggctttataataac
22  ------------------------------------------------------------
23  ---------------------------------------tttataataacgacggaaaagt
```

Figure 20 continued

```
18    ------------------ttttttttttttttacgg--------ctggaatcaattgctttat
17    --------------cacaatactactctttagttaccaatataccataaccaaaattgtttgat
20    
19    agcgcaccacttaatgactcgattctaccaacgacttagcaattccaacatgtgattaaa
21    gacggaaaagttaatgactcgattctaccaacgacttagcaattccaacatgtgattaaa
22    
23    agcgcaccacttaatgactcgattctaccaacgacttagcaattccaacatgtgattaaa 18    tcatcacataatttggctttaaatagccttacaataacaacttattaatatagtagctta
17    agataagattatcc---tatattaaaattgatgaaacccagtcgatttatcaataaaaga
20    
19    aaagaagtgtaaca---a----ggacaatcataacatcatatgaatcattcca----aaga
21    aaagaagtgtaaca---a----ggacaatcataacatcatatgaatcattcca----aaga
22    
23    aaagaagtgtaaca---a----ggacaatcataacatcatatgaatcattcca----aaga 18    aaacaattaactaggacacctcctaagactcgatcgattctaccaacatatt---------
17    aatagatcaatgaaattatct--agtttgtga------attttatcacattgatgtttc--
20    
19    aacccaacaactaacttacttatagtctgtgaaacgacttatatattcttttttggttaac
21    aacccaacaactaacttacttatagtctgtgaaacgacttatatattcttttttggttaac
22    
23    aacccaacaactaacttacttatagtctgtgaaacgacttatatattcttttttggttaac 18    ------tagcaattccaacatttcatttgaatctttc--caaaagaaaccaacaactca
17    ----taccttatttcaaacaaaccaga-----tacttcaattaattcaagcaacatttga
20    
19    tctcatggttgttggcaaccacacgtacgttcttttccatatagtctgtgaaacgact--
21    tctcatggttgttggcaaccacacgtacgttcttttccatatagtctgtgaaacgact--
22    
23    tctcatggttgttggcaaccacacgtacgttcttttccatatagtctgtgaaacgact--

18    cacatactgatgatatagttaactctcatgatcgatggcaacgcacgcgcattctttt
17    tcatgaagacaaacccaacaacgcacattcttcatacggttaacgtacgtcgtgtcttct
20    
19    -tatatattcttttttggtt--aactctcatggttgttggcaaccacacgtacgttctttt
21    -tatatattcttttttggtt--aactctcatggttgttggcaaccacacgtacgttctttt
22    
23    -tatatattcttttttggtt--aactctcatggttgttggcaaccacacgtacgttctttt 18    ccaaatagtctacgaattggcttacatattcttttcaaccttagtgtcgttatagattt
17    ccaaataatctatgaaatggtttatatacttctttcccatcttagtgtctccgaacaatc
20    
19    ccatatagtctgtgaaacgacttatatattccttttgcagcttagtgtcgctgaatattt
21    ccatatagtctgtgaaacgacttatatattccttttgcagcttagtgtcgctgaatattt
22    
23    ccatatagtctgtgaaacgacttatatattccttttgcagcttagtgtcgctgaatattt 18    tactcagctccctcgcgttcgccttgtagatctcccttctttttccacaacaacggacc
17    tacttaactccatcgcgcattttccttgtaaatcttccttcatcatcagctacaaccgacc
20    
19    tactcatctctctcgcattcgccttgtagatctctccttcatcgtctacaacaaccgacc
21    tactcatctctctcgcattcgccttgtagatctctccttcatcgtctacaacaaccgacc
22    
23    tactcatctctctcgcattcgccttgtagatctctccttcatcgtctacaacaaccgacc
```

Figure 20 continued

```
18  tcagtgatctagcaaccgactccttggtcaagcaaccatcttcctcatttcttggtatct
17  gcactgatcttgccactgactccttgttgaaggagccatcttcgtcatttcttggtatct
20  ------------------------------------tcctcatttcttggtatct
19  tcagtgacgtggcaaccgactccttggtgaagtagccatcttcctcatttcttggtatct
21  tcagtgacgtggcaaccgactccttggtgaagtagccatcttcctcatttcttggtatct
22  ------------------------------------------------------------
23  tcagtgacgtggcaaccgactccttggtgaagtagccatcttcctcatttcttggtatct 18  cgattcccacctgtttgtcctccagtaatcgagcattcagaggttggtccccaaaaatcg
17  caattcccacctgattatccgccattactcgagcatttagaccttgatccaccgaaagcg
20  cgatccccacctgtttgtccgctaatagtcgagcattcagacattggtccccgaaaatcg
19  cgatccccacctgtttgtccgctaatagtcgagcattcagacattggtccccgaaaatcg
21  cgatccccacctgtttgtccgctaatagtcgagcattcagacattggtccccgaaaatcg
22  ------------------------------------------------------------
23  cgatccccacctgtttgtccgctaatagtcgagcattcagacattggtccccgaaaatcg 18  gtagcatgattagagggtgaccaaacattagcccttccacaattgatccagaaccacaat
17  gtagcattattaaagggtgaccgaacatcatcgcttccacaattgaactccaaccacaat
20  gtagcatgattaaagggtggccgaacattaacccttccaccactgaactccaaccacagt
19  gtagcatgattaaagggtggccgaacattaacccttccaccactgaactccaaccacagt
21  gtagcatgattaaagggtgaccgaacattaacccttccaccactgaactccaaccacagt
22  -----------------------------------------actgaactccaaccacagt
23  gtagcatgattaaagggtggccgaacattaacccttccaccactgaactccaaccacagt 18  gagtcaagaaaccacaaaccgactcatggctcagtattcgtaactgaggtgcccaactcg
17  gagtcaagaaaccacaaaccgactcatggctcagtattcgtaactgaggtgcccaactcg
20  gagttaagaaaccacacaccgactcatgactcagtattcgtaactgaggtgcccaactcg
19  gagtcaagaaaccacacaccgactcatggctcagtattcgtaactgaggtgcccaactcg
21  gagtcaagaaaccacacaccgactcatggctcagtattcgtaactgaggtgcccaactcg
22  gagttaagaaaccacacaccgactcatgactcagtattcgtaactgaggtgcccaactcg
23  gagtcaagaaaccacacaccgactcatggctcagtattcgtaactgaggtgcccaactcg 18  tccagaccaacccacggtcacgagttcgttccacgaacccgtctggcaactccaccgagt
17  tccagaccaacccacggtcacgagttcgttccacgaacccgtctggcaactccaccgagt
20  tccaaaccatcccacggttactagttcgttccaagaacccgttaggcaactccaccgagt
19  tccaaaccatcccacggttactagttcgttccaagaacccgttaggcaactccaccgagt
21  tccaaaccatcccacggttactagttcgttccaagaacccgttaggcaactccaccgagt
22  tccaaaccatcccacggttactagttcgttccaagaacccgttaggcaactccaccgagt
23  tccaaaccatcccacggttactagttcgttccaagaacccgttaggcaactccaccgagt 18  tac-------cagagccaaccggttttctaagaacccaaaagaatggcaacccggagagct
17  tac-------cagagccaaccggttttctaagaacccaaaagaatggcaacccggagagct
20  ctgactcggtggaacctgcgggttttctgagaacccacaaaaatggcaacccagagagct
19  ctgactcggtggaacctgcgggttttctgagaacccacaaaaatggcaacccagagagct
21  ctgactcggtggaacctgcgggttttctgagaacccacaaaaatggcaacccagagagct
22  ctgactcggtggaacctgcgggttttctgagaacccacaaaaatggcaacccagagagct
23  ctgactcggtggaacctgcgggttttctgagaacccacaaaaatggcaacccagagagct 18  cgagacccagagctaactcagccagctcgctttggctcatcgtaccttcacttccaaatg
17  cgagacccagagctaactcagccagctcgctttggctcatcgtaccttcacttccaaatg
20  cgagacctagagctaactcagccagctcgctttggtcacgtaacttcacttcctaatg
19  cgagacctaacgctaactcagccagctcgcttttggtcacgtaacttcacttcctaatg
21  cgagacctagagctaactcagccagctcgctttggtcacgtaacttcacttcctaatg
22  cgagacctagagctaactcagccagctcgctttggtcacgtaacttcacttcctaatg
23  cgagacctagcgctaactcagccagctcgctttggtcacgtaacttcacttcctaatg
```

Figure 20 continued

```
18    ccacgtacaccacatgccctattggttgaccatcgagccacttcttgattgacacccatg
17    ccacgtacaccacatgccctattggttgaccatcgagccacttcttgattgacacccatg
20    cgacgtacaccacatgccctattggttgaccatcgagccacttcttgattgacacccatg
19    cgacgtacaccacatggttaacttgctgaccatcgagccacttcttgactgacacccatg
21    cgacgtacaccacatggttaacttgctgaccatcgagccacttcttgactgacacccatg
22    cgacgtacaccacatggttaacttgctgaccatcgagccacttcttgactgacacccatg
23    cgacgtacaccacatgccctattggttgaccatcgagccacttcttgattgtcacccatg 18    ggtctccggtg---ctggtgggtggttcgggtggcaataatcccacgggaaccaccggta
17    ggtctccggtg---ctggtgggtggttcgggtggcaataatcccacgggaaccaccggta
20    ggtctccggtg---ctggtgggtggttcgggtggcaataatcccacgggaaccaccggta
19    tatcatctttctcgtctccgtatgtttcaggtggcattaatccaaccggaactaccggta
21    tatcatctttctcgtctccgtatgtttcaggtggcattaatccaaccggaactaccggta
22    tatcatctttctcgtctccgtatgtttcaggtggcattaatccaaccggaactaccggta
23    ggtctccggtg---ctggtgggtggttcgggtggcaataatcccacgggaaccaccggta 18    ggtgatgcagcttttctaaaagggttagccattggggttcgaactcatggcaatgtctta
17    ggtgatgcagcttttctaaaagggttagccattggggttcgaactcatggcaatgtctta
20    gctggtgtagcttctccaaaagggttagccattggggttcgacctcataacaacttctta
19    tacggtatagcttcccaaaagggttagccattggggttcgacctcataacaacttctta
21    tacggtatagcttcccaaaagggttagccattggggttcgacctcataacaacttctta
22    tacggtatagcttcccaaaagggttagccattggggttcgaactcatggcaatgtctta
23    gctgatgcagcttttctaaaagggttagccattggggttcgaactcatggcaatgtctta 18    taaacatacaatctgatccctttataaccattcctaaacgatataaatctgatacaccag
17    taaacatacaatctgatccctttataaccattcctaaacgatataaatctgatacaccag
20    taaacagacaatcagattccttcaaaaccgtcatcattctgtgctttaga------cctg
19    taaacagacaatcagattccttcaaaaccgtcatcattctgtgctttaga------cctg
21    taaacagacaatcagattccttcaaaaccgtcatcattctgtgctttaga------cctg
22    taaacatacaatctgatccctttataaccattcctaaacgatataaatctgatacaccag
23    taaacatacaatctgatccctttataaccattcctaaacgatataaatctgatacaccag 18    aagaattaacagaaatattatcagcaaatatcaaattggcctcatgcttccggtagcata
17    aagaattaacagaaatattatcagcaaatatcaaattggcctcatgcttccggtagcata
20    aaatcacaggattattagcagcagacatcttgcgcacaaactcatgcttccggtagcata
19    aaatcacaggattattagcagcagacatcttgcgcacaaactcatgcttccggtagcata
21    aaatcacaggattattagcagcagacatcttgcgcacaaactcatgcttccggtagcata
22    aagaattaacagaaatattatcagcaaatatcaaattggc--------------------
23    aagaattaacagaaatattatcagcaaatatcaaattggcctcatgcttccggtagcata 18    ctttgctcggaaacggaatccacttcggcggtgtcataaaattctcaaccctcgttcgat
17    ctttacttgggaacggaaaccacttcggcggtgtcaggaaatcgtcggctgttttccgat
20    cttt--------------------------------------------------------
19    ctttgctcggaaacggaatccacttgggcggtgtcatgaaatcctcaactgtcgttcgac
21    ctttgctcggaaacggaatccacttgggcggtgtcatgaaatcctcaactgtcgttcgac
22    ------------------------------------------------------------
23    ctttgctcggaaacggaatccacttcggcggtgtcataaaattctcaaccctcgttcgat 18    gatcataaccggaaccacttatcaagtcgtcagccgacgctccgagaaaagcaatgaacc
17    cgtctgtaccgt------ttatgatgtcatcgggagaagatccgaaaaagagacggtcc
20    ------------------------------------------------------------
19    tctcgaaactat------ttttcatgtcatcgggtaacggtcccacgtgcgccatgaacc
21    tctcgaaactat------ttttcatgtcatcgggtaacggtcccacgtgcgccatgaacc
22    ------------------------------------------------------------
23    gatcataaccggaaccacttatcaagtcgtcagccgacgctccgagaaaagcaatgaacc
```

Figure 20 continued

```
18  atgcgttaaaattcgagtaaaaggctcgcgaggtccgtagtccagctgcgacggacggca
17  atgcgttaaaaattgagaaaaaacctcgtgaaattccaaggctagtggctaccgccggca
20  ------------------------------------------------------------
19  atggtgaggcagtgataaaaaaggctcgcgagatcccaaggtccgccgcgacggatggca
21  atggtgaggcagtgataaaaaaggctcgcgagatcccaaggtccgccgcgacggatggca
22  ------------------------------------------------------------
23  atgcgttaaaattcgagtaaaaggctcgcgaggtccgtagtccagctgcgacggacggca 18  accaatac-------
17  accaatagggagcaa
20  ---------------
19  accagtg--------
21  accagtg--------
22  ---------------
23  accaatac-------

28  ------------------------------------------------------------
30  ------------------------------------------------------------
26  ------------------------------------------------------------
29  ggctggagtcaattgttttttatacaatacataatatagcgttaaatggctttataataac
31  -----------------------------------------tttataataacgacggaaaagt
24  ------------------------------------------------------------
27  ------------------------------------------------------------

28  ----------------------------------------------------------tagt
30  -----------cacaatactactctttagttaccaatataccataaccaaaattgtttgat
26  ------------------------------------------------------------
29  gacggaaaagttaatgactcgattctaccaacgacttagcaattccaacatgtgattaaa
31  agcgcaccacttaatgactcgattctaccaacgacttagcaattccaacatgtgattaaa
24  -----------cacaatactactctttagttaccaatataccataaccaaaattgtttgat
27  ------------------------------------------------------------

28  g--------------aatgtatataacataaatgatatgtttcaacctaacaaac
30  agataagactatcctatattaaaattgatgaaacccagtcgatttatcaataaaagaaat
26  ---------------------------------tagtgaatg-----------------t
29  aaagaagtgtaacaa----ggacaatcataacatcatatgaatcattcca---aagaaac
31  aaagaagtgtaacaa----ggacaatcataacatcatatgaatcattcca---aagaaac
24  agataagattatcctatattaaaattgatgaaacccagtcgatttatcaataaaagaaat
27  ------------------------------------------------------------

28  ggttatttcatacacggaaaacaaaaatttatgattattcaaagaaac-----------
30  aga------tcaatgaaattatctagtttgtgaattttatcacattgat---------
26  atataacataaatgatatgtttcaacctaacaaacggttatttcatacacggaaaacaaa
29  ccaacaactaacttacttatagtctgtgaaacgacttatatattcttttttggttaactct
31  ccaacaactaacttacttatagtctgtgaaacgacttatatattcttttttggttaactct
24  agatcaatgaaattatc--tagtttgtgaa-----ttttatcacattgatgttc-----
27  ------------------------------------------------------------

28  -atttgatcatctagctagacaaacccaa-------------taacacatatattctt--
30  -gttctaccttatttcaaacaaaccagatacttcaattaattcaagcaacattgatca
26  aattatgattattcaaagagaaca--aacccaataacaca
29  catggttgttggcaaccacacgtacgttcttttccatatagtctgtgaaacgact---ta
31  catggttgttggcaaccacacgtacgttcttttccatatagtctgtgaaacgact---ta
24  -tacctatttcaaacaaaccaga-----tacttcaattaattcaagcaacattgatca
27  ------------------------------------------------------------

28  --------catacgatcaaagctcatg--ctcaatagcaaccacacgacctttttgttcca
30  tgaagacaaacccaacaacgcacattcttcatacggttaacgtacgtcgtgtcttctcca
26  tatattcttcatacgatcaaagctcatgctcaataagcaaccacacgacctttttgttcca
29  tatattctttttggttaa--ctctcatggttgttggcaaccacacgtacgttcttttcca
31  tatattctttttggttaa--ctctcatggttgttggcaaccacacgtacgttcttttcca
24  tgaagacaaacccaacaacgcacattcttcatacggttaacgtacgtcgtgtcttctcca
27  ------------------------------------------------------------
```

Figure 20 continued

```
28  aatagtctataaaagggtttatatacttattttccggcttactatccccgaatcgttgac
30  aataatctatgaaatggtttatatacttctttcccatcttagtgtctccgaacaatctac
26  aatagtctataaaagggtttatatacttattttccggcttactatccccgaatcgttgac
29  tatagtctgtgaaacgacttatatattcctttttgcagcttagtgtcgctgaatattttac
31  tatagtctgtgaaacgacttatatattcctttttgcagcttagtgtcgctgaatattttac
24  aataatctatgaaatggtttatatacttctttcccatcttagtgtctccgaacaatctac
27  ------------------------------------------------------------

28  tcaactccatcgcctttcgccttgtagatcttcccttcatcatcgactaaaaccaacctca
30  ttaactccatcgcattttccttgtaaatcttcccttcatcatcagctacaaccgaccgca
26  tcaactccatcgcctttcgccttgtagatcttcccttcatcatcgactaaaaccaacctca
29  tcatctctctcgcattcgccttgtagatctctccttcatcgtctacaacaaccgacctca
31  tcatctctctcgcattcgccttgtagatctctccttcatcgtctacaacaaccgacctca
24  ttaactccatcgcattttccttgtaaatcttcccttcatcatcagctacaaccgaccgca
27  ------------------------------------------------------------

28  atgatctggccaccgactccttggtgaaggaaccatcttcctcatttcttggtatctcga
30  ctgatcttgccactgactccttgaaggagccatcttcgtcatttcttggtatctcaa
26  atgatctggccaccgactccttggtgaatgaaccatcttcctcatttcttggtatctcga
29  gtgacgtggcaaccgactccttggtgaagtagccatcttcctcatttcttggtatctcga
31  gtgacgtggcaaccgactccttggtgaagtagccatcttcctcatttcttggtatctcga
24  ctgatcttgccactgactccttgttgaaggagccatcttcgtcatttcttggtatctcaa
27  ------------------------------------------------------------

28  ttcccacctgtttatccgccattactcgagcatttagaccttgatccaccaaaatcggta
30  ttcccacctgattatccgccattactcgagcatttagaccttgatccaccgaaagcggta
26  ttcccacctgattatccgccattactcgagcatttagaccttggtccccaaaatcggta
29  tccccacctgtttgtccgctaatagtcgagcattcagacattggtccccgaaaatcggta
31  tccccacctgtttgtccgctaatagtcgagcattcagacattggtccccgaaaatcggta
24  ttcccacctgattatccgccattactcgagcatttagaccttgatccaccgaaagcggta
27  ----------------------------------------------------ggta
                                                        ****

28  gcatgattagagggtgaccgaacatcatcgcttccacaattgaactccaaccacaatgag
30  gcattattaaagggtgaccgaacatcatcgcttccacaattgaactccaaccacaatgag
26  gcatgattagagggtgaccgaacatcatcgcttccacaattgaactccaaccacaatgag
29  gcatgattaaagggtggccgaacattaaccccttccaccactgaactccaaccacagtgag
31  gcatgattaaagggtggccgaacattaaccccttccaccactgaactccaaccacagtgag
24  gcattattaaagggtgaccgaacatcatcgcttccacaattgaactccaaccacaatgag
27  gcatgattagagggtgaccaaacattagcccttccacaattgatccagaaccacaatgag
    **** **** ****** ** ***** * * ******* * *** *  ******* ****

28  tcaagaaaccacaaaccgactcatggctcagtattcgtaactgaggtgcccaactcgtcc
30  tcaagaaaccacaaaccgactcatggctcagtattcgtaactgaggtgcccaactcgtcc
26  tcaagaaaccacaaaccgactcatggctcagtattcgtaactgaggtgcccaactcgtcc
29  tcaagaaaccacacaccgactcatggctcagtattcgtaactgaggtgcccaactcgtcc
31  tcaagaaaccacaaaccgactcatggctcagtattcgtaactgaggtgcccaactcgtcc
24  tcaagaaaccacaaaccgactcatggctcagtattcgtaactgaggtgcccaactcgtcc
27  tcaagaaaccacaaaccgactcatggctcagtattcgtaactgaggtgcccaactcgtcc
    ************* ********************************************

28  agaccaacccacggtcacgagttcgttccacgaacccgtctggcaactccaccgagtctg
30  agaccaacccacggtcacgagttcgttccacgaacccgtctggcaactccaccgagtctg
26  agaccaacccacggtcacgagttcgttccacgaacccgtctggcaactccaccgagttac
29  aaaccaacccacggttactagttcgttccaagaacccgttaggcaactccaccgagtctg
31  aaaccatcccacggttactagttcgttccacgaacccgttaggcaactccaccgagtctg
24  agaccaacccacggtcacgagttcgttccacgaacccgtctggcaactccaccgagttac
27  agaccaacccacggtcacgagttcgttccacgaacccgtctggcaactccaccgagttac
    * **** ******* **  ********* ********  * ***************
```

Figure 20 continued

```
28  acttcgcgggacctttggttttctataagcccaaacaaatggcaacccagaaagctcga
30  acttcgcgggacctttggttttctataagcccaaacaaatggcaacccagaaagctcga
26  ------cagagccaaccggttttctaagaacccaaaagaatggcaacccggagagctcga
29  actcggtggaacctgcgggttttctgagaacccacaaaaatggcaacccagagagctcga
31  actcggtggaacctgcgggttttctgagaacccacaaaaatggcaacccagagagctcga
24  ------cagagccaaccggttttctaagaacccaaaagaatggcaaccggagagctcga
27  ------cagagccaaccggttttctaagaacccacaaaaatggcaacccagagagctcga
         **  ********  * **** * ************ ** ********

28  gacccaatgctaactcaacaacctcggtttggctcaccaaagcctcgcttcctaatgcaa
30  gacccaatgctaactcaacaaacctcggtttggctcaccaaagcctcgcttcctaatgcaa
26  gaccagagctaactcagccagctcgcttttggctcacgtaacttcacttcctaatgcga
29  gacctaacgctaactcagccagctcgcttttggtcaccgtaacttcacttcctaatgcga
31  gacctaacgctaactcagccagctcgcttttggtcaccgtaacttcacttcctaatgcga
24  gacccagagctaactcagccagctcgctttggctcaccgtaccttcacttcctaatgcga
27  gacctaacgctaactcagccagctcgctttggtcaccgtaacttcacttcctaatgcga
    ****  * ********* * **** *** * ***** * * ** ************* *

28  cgtacaccacactgcctttttgtttaccatcgagccatttcttgattgacacccatgttt
30  cgtacaccacactgcctttttgtttaccatcgagccatttcttgattgacacccatgttt
26  cgtacaccacatggttaacttgctgaccatcgagccacttcttgactgacacccatgtat
29  cgtacaccacatggttaacttgctgaccatcgagccacttcttgactgacacccatgtat
31  cgtacaccacatggttaacttgctgaccatcgagccacttcttgactgacacccatgtat
24  cgtacaccacatggttaacttgctgaccatcgagccacttcttgactgacacccatgtat
27  cgtacaccacatggttaacttgctgaccatcgagccacttcttgactgacacccatgtat
    ***********  *  * ******** ******** * ****** ************ *

28  catctttctcgtctccgggtatttccggtggcagtaatcccaccggaaccaccggtactt
30  catctttctcgtctccgggtatttccggtggcagtaatcccaccggaaccaccggtactt
26  catctttctcgtctccgtatgtttcaggtggcattaatccaaccggaactaccggtatac
29  catctttctcgtctccgtatgtttcaggtggcattaatccaaccggaactaccggtatac
31  catctttctcgtctccgtatgtttcaggtggcattaatccaaccggaactaccggtatac
24  catctttctcgtctccgtatgtttcaggtggcattaatccaaccggaactaccggtatac
27  catctttctcgtctccgtatgtttcaggtggcattaatccaaccggaactaccggtatac
    *****************  *  **** ****** ****** ******** *******

28  ggtgtagtgtctccaaaagaggtagccattgagttccaaactcatggtaacatttgaaaa
30  ggtgtagtgtctccaaaagaggtagccattgagttccaaactcatggtaacatttgaaaa
26  ggtatagcttccccaaaagggttagccattggggttcgacctcataacaacttcttataa
29  ggtatagcttccccaaaagggttagccattggggttcgaactcatggcaatgtcttataa
31  ggtatagcttccccaaaagggttagccattggggttcgaactcatggcaatgtcttataa
24  ggtatagcttccccaaaagggttagccattggggttcgaactcatggcaatgtcttataa
27  ggtatagcttccccaaaagggttagccattggggttcgaactcatggcaatgtcttataa
    ***  ***  ** *********  ********  *   **** *    **  *  * **

28  gcaaacaatcagatcccttaaaaaccagccccatacggtatccatcagatatcccggag
30  gcaaacaatcagatcccttaagaaccagccccatacggtatccatcagatatcccggag
26  acagacaatcagattccttcaaaaccgtcattctctgtgtctttaga------cctgaaa
29  acatacaatctgatcccttataaccattcctaaacgatataaatctgatacaccagaag
31  acatacaatctgatcccttataaccattcctaaacgatataaatctgatacaccagaag
24  acatacaatctgatcccttataaccattcctaaacgatataaatctgatacaccagaag
27  acatacaatctgatcccttataaccattcctaaacgatataaatctgatacaccagaag
    ** ****** *** ****  * ****      *  *   *            ** * *

28  ct-------------ttgtaaggcaccagtcgggcaagatcatgcttccgccagcatactt
30  ct-------------ttgtaaggcaccagtcgggcaagatcatgcttccgccagcatactt
26  tcacaggattattagcagcagacatctgcgcaaaatcatgcttccggtagcatactt
29  aattaacagaaatattatcagcaaatatcaaattggcctcatgcttccggtagcatactt
31  aattaacagaaatattatcagcaaatatcaaattggcctcatgcttccggtagcatactt
24  aattaacagaaatattatcagcaaatatcaaattggcctcatgcttccggtagcatactt
27  aattaacagaaatattatcagcaaatatcaaattggc--------------------
                                **  *
```

Figure 20 continued

```
28  tggtcggaaagggaaaccacttgggcggtgtcgtgagatcctcaaccgtggttcgaccat
30  tggtcggaaagggaaaccacttgggcggtgtcgtgagatcctcaaccgtggttcgaccat
26  tgctcggaaacggaatccacttggcggtgtcatgaaatcctcaactgtcgttcgactct
29  tgctcggaaacggaaaccacttcggcggtgtcaggaaatcgtcgggtgttttccgattgt
31  tgctcggaaacggaaaccacttcggcggtgtcaggaaatcgtcgggtgttttccgattgt
24  tgctcggaaacggaatccacttgggcggtgtcatgaaatcctcaactgtcgttcgactct
27  ------------------------------------------------------------

28  ctgaaccatttatcatggcgtcagctgagggtcccatataagcaatggcccatggagtgg
30  ctgaaccatttatcatggcgtcagctgagggtcccatataagcaatggcccatggagtgg
26  cgaaactattttcatgtcatcgggtaacggtcccacgtgcgccatgaaccatggtgagg
29  ctgtaccgtttatcatgttatcgggagacgatccgaaaaaagagacggtccatgcgttat
31  ctgtaccgtttatcatgttatcgggagacgatccgaaaaaagagacggtccatgcgttat
24  cgaaactattttcatgtcatcgggtaacggtcccacgtgcgccatgaaccatggtgagg
27  ------------------------------------------------------------

28  tgacggagaagtaggctcgtgagataccgaggctagccgcgatggatggcaaccagtagt
30  tgacggagaagtgggctcgtgagataccgaggctagccgcgatggatggcaaccagtagt
26  cagtgataaaaaaggctcgcgagatcccaaggtccgccgcgacggatggcaaccagtg--
29  ag----------------------------------------------------------
31  ag----------------------------------------------------------
24  cagtgataaaaaaggctcgcgagatcccaaggtccgccgcgacggatggcaaccagtgca
27  ------------------------------------------------------------

28  gagtataatcataaataatccagtccggagactctt------------------------
30  gagtataatcataaataatccagtccggagactctt------------------------
26  ------------------------------------------------------------
29  ------------------------------------------------------------
31  ------------------------------------------------------------
24  caatactactctttagttaccaatataccataaccaaaattgtttgatagataagattat
27  ------------------------------------------------------------

28  ------------------------------------------------------------
30  ------------------------------------------------------------
26  ------------------------------------------------------------
29  ------------------------------------------------------------
31  ------------------------------------------------------------
24  cctatattaaaattgatgaaacccagtcgatttatcaataaaagaaatagatcaatgaaa
27  ------------------------------------------------------------

28  ------------------------------------------------------------
30  ------------------------------------------------------------
26  ------------------------------------------------------------
29  ------------------------------------------------------------
31  ------------------------------------------------------------
24  ttatctagtttgtgaattttatcacattgatgtttctaccttatttcaaacaaaccagat
27  ------------------------------------------------------------

28  ------------------------------------------------------------
30  ------------------------------------------------------------
26  ------------------------------------------------------------
29  ------------------------------------------------------------
31  ------------------------------------------------------------
24  acttcaattaattcaagcaacatttgatcatgaagacaaaccaacaacgcacattcttc
27  ------------------------------------------------------------
```

Figure 20 continued

```
28
30
26
29
31
24  atacggttaacgtacgtcgtgtcttctccaaataatctatgaaatggtttatatacttct
27

28
30
26
29
31
24  ttccatcttagtgtctccgaacaatctacttaactccatcgcattttccttgtaaatct
27

28
30
26
29
31
24  tcccttcatcatcagctacaaccgaccgcactgatcttgccactgactccttgttgaagg
27

28
30
26
29
31
24  agccatcttcgtcatttcttggtatctcaattcccacctgattatccgccattactcgag
27

28
30
26
29
31
24  cattagaccttgatccaccgaaagcggtagcattattaaagggtgaccgaacatcatcg
27

28
30
26
29
31
24  cttccacaattgaactccaaccacaatgagtcaagaaaccacaaaccgactcatggctca
27

28
30
26
29
31
24  gtattcgtaactgaggtgcccaactcgtccagaccaacccacggtcacgagttcgttcca
27
```

Figure 20 continued

```
28
30
26
29
31
24  cgaacccctctggcaactccaccgagttaccagagccaaccggttttctaagaacccaaa
27

28
30
26
29
31
24  agaatggcaacccggagagctcgagacccagagctaactcagccagctcgctttggctca
27

28
30
26
29
31
24  tcgtaccttcacttccaaatgccacgtacaccacatgccctattggttgaccatcgagcc
27

28
30
26
29
31
24  acttcttgactgtgacccatgtctcatctttcccgtctccgatgttggtgggttttctg
27

28
30
26
29
31
24  gtggcaataatccgacaggaaccaccggtaggtgatggagcttctctaaaagggttaacc
27

28
30
26
29
31
24  attgaggttcgaactcataactatgtcttataaacatacagtcagatcctttcaaaatca
27

28
30
26
29
31
24  ttcccacacgatacacacttgatattccagaagcattagccgaagtattccctaccatcc
27
```

Figure 20 continued

```
28
30
26
29
31
24   gaaccgcctcatacttccggtagcacacgtttgtcggaaacggaacccacttcggcggtg
27

28
30
26
29
31
24   tcataaaattctcaaccctcgttcgatgatcataaccggaaccacttatcaagtcgtcag
27

28
30
26
29
31
24   ccgacgctccgagaaaagcaatgaaccatgcgttaaaattcgagtaaaaggctcgcgagg
27

28
30
26
29
31
24   tccgtagtccagctgcgacggacggcaaccaatac
27
```

Figure 21
Sequence alignment of UGT91D2 isoforms corresponding to SEQ ID NO: 24, SEQ ID NO: 55 and SEQ ID NO: 86

```
817096    GGCTGGAGTCAATTGTTTTTATACAATACATAATATAGCGTTAAATGGCTTTATAATAAC
807086    GGCTGGAGTCAATTGTTTTTATACAATACATAATATAGCGTTAAATGGCTTTATAATAAC
814011    GGCTGGAGTCAATTGTTTTTATACAATACATAATATAGCGTTAAATGGCTTTATAATAAC
          ************************************************************

817096    GACGGAAAAGTTAATGACTCGATTCTACCAACGACTTAGCAATTCCAACATGTGATTAAA
807086    GACGGAAAAGTTAATGACTCGATTCTACCAACGACTTAGCAATTCCAACATGTGATTAAA
814011    GACGGAAAAGTTAATGACTCGATTCTACCAACGACTTAGCAATTCCAACATGTGATTAAA
          ************************************************************

817096    AAAGAAGTGTAACAAGGACAATCATAACATCATATGAATCATTCCAAAGAAACCCAACAA
807086    AAAGAAGTGTAACAAGGACAATCATAACATCATATGAATCATTCCAAAGAAACCCAACAA
814011    AAAGAAGTGTAACAAGGACAATCATAACATCATATGAATCATTCCAAAGAAACCCAACAA
          ************************************************************

817096    CTAACTTACTTATAGTCTGTGAAACGACTTATATATTCTTTTTGGTTAACTCTCATGGTT
807086    CTAACTTACTTATAGTCTGTGAAACGACTTATATATTCTTTTTGGTTAACTCTCATGGTT
814011    CTAACTTACTTATAGTCTGTGAAACGACTTATATATTCTTTTTGGTTAACTCTCATGGTT
          ************************************************************

817096    GTTGGCAACCACACGTACGTTCTTTTCCATATAGTCTGTGAAACGACTTATATATTCTTT
807086    GTTGGCAACCACACGTACGTTCTTTTCCATATAGTCTGTGAAACGACTTATATATTCTTT
814011    GTTGGCAACCACACGTACGTTCTTTTCCATATAGTCTGTGAAACGACTTATATATTCTTT
          ************************************************************

817096    TTGGTTAACTCTCATGGTTGTTGGCAACCACACGTACGTTCTTTTCCATATAGTCTGTGA
807086    TTGGTTAACTCTCATGGTTGTTGGCAACCACACGTACGTTCTTTTCCATATAGTCTGTGA
814011    TTGGTTAACTCTCATGGTTGTTGGCAACCACACGTACGTTCTTTTCCATATAGTCTGTGA
          ************************************************************

817096    AACGACTTATATATTCCTTTTGCAGCTTAGTGTCGCTGAATATTTTACTCATCTCTCTCG
807086    AACGACTTATATATTCCTTTTGCAGCTTAGTGTCGCTGAATATTTTACTCATCTCTCTCG
814011    AACGACTTATATATTCCTTTTGCAGCTTAGTGTCGCTGAATATTTTACTCATCTCTCTCG
          ************************************************************

817096    CATTCGCCTTGTAGATCTCTCCTTCATCGTCTACAACAACCGACCTCAGTGACGTGGCAA
807086    CATTCGCCTTGTAGATCTCCCCTTCATTTTCCGCAACAACGGACCTCAGTGATCTAGCAA
814011    CATTCGCCTTGTAGATCTCCCCTTCTTTTTCCACAACAACGGACCTCAGTGATCTAGCAA
          ******************* *****  *  ******* ***********  *  ****

817096    CCGACTCCTTGGTGAAGTAGCCATCTTCCTCATTTCTTGGTATCTCGATCCCCACCTGTT
807086    CCGACTCCTTGGTCAAGCAACCATCTTCCTCATTTCTTGGTATCTCGATTCCCACCTGTT
814011    CCGACTCCTTGGTCAAGCAACCATCTTCCTCATTTCTTGGTATCTCGATTCCCACCTGTT
          ************* ***  *  * ****************************  **********

817096    TGTCCGCTAATAGTCGAGCATTCAGACATTGGTCCCCGAAAATCGGTAGCATGATTAAAG
807086    TGTCCTCCAGTAATCGAGCATTCAGACGTTGGTCCCCAAAAATCGGTAGCATGATTAGAG
814011    TGTCCTCCAGTAATCGAGCATTCAGAGGTTGGTCCCCGAAAATCGGTAGCATGATTAGAG
          ***** * * ** **************  ******** ********************** **
```

Figure 21 continued

```
817096   GGTGACCGAACATTAACCCTTCCACCACTGAACTCCAACCACAGTGAGTCAAGAAACCAC
807086   GGTGACCGAACATTAACCCTTCCACAATTGAACTCCAACCACAATGAGTCAAGAAACCAC
814011   GGTGACCAAACATTAGCCCTTCCACAATTGATCCAGAACCACAATGAGTCAAGAAACCAC
         ******* ******** ********* * *** *      ******* ************

817096   ACACCGACTCATGGCTCAGTATTCGTAACTGAGGTGCCCAACTCGTCCAAACCATCCCAC
807086   ACACCGACTCATGGCTCAGTATTCGTAACTGAGGTGCCCAACTCGTCCAGACCAACCCAC
814011   AAACCGACTCATGGCTCAGTATTCGTAACTGAGGTGCCCAACTCGTCCAGACCATCCCAC
         *  ********************************************** **** *****

817096   GGTTACTAGTTCGTTCCAAGAACCCGTTAGGCAACTCCACCGAGTCTGACTCGGTGGAAC
807086   GGTCACGAGTTCGTTCCAAGAACCCGTCTGGCAAATCCACCGAGTCTGACTCGGTGGAGC
814011   GGTCAGTAGTTCGTTCCACGAACCCGTCTGGCAACTCCACCGAGTCTGACTCGGTGGAAC
         *** *  *********** ********  ****  ************************* *

817096   CTGCGGGTTTTCTGAGAACCCACAAAAATGGCAACCCAGAGAGCTCGAGACCTAGCGCTA
807086   CTGCGGGTTTTCTAAGAACCCAAAAGAATGGCAACCCGGAGAGCTCGAGACCCAGAGCTA
814011   CTGCGGGTTTTCTAAGAACCCAAAAGAATGGCAACCCGGAGAGCTCGAGACCCAGAGCTA
         ************* ******* ** *********** **************** ** ****

817096   ACTCAGCCAGCTCGCTTTTGGTCACCGTAACTTCACTTCCTAATGCGACGTACACCACAT
807086   ACTCAGCCAGCTCGCTTTGGCTCATCGTACCTTCACTTCCAAATGCCACGTACACCACAT
814011   ACTCAGCCAGCTCGCTTTGGCTCATCGTACCTTCACTTCCAAATGCCACGTACACCACAT
         ****************** * *** **** ********** ***** *************

817096   GCCCTATTGGTTGACCATCGAGCCACTTCTTGATTGACACCCATGGGTCTCCGGTGCTGG
807086   GCCCTATTGGTTGACCATCGAGCCACTTCTTGATTGTCACCCATGGGTCTCCGGTGCTGG
814011   GCCCTATTGGTTGACCATCGAGCCACTTCTTGATTGTCACCCATGGGTCTCCGGTGCTGG
         ************************************ ***********************

817096   TGGGTGGTTCGGGTGGCAATAATCCCACGGGAACCACCGGTAGCTGATGCAGCTTTTCTA
807086   TGGGTGGTTCGGGTGGCAATAATCCCACGGGAACCACTGGTAGGTGATGCAGCTTTTCTA
814011   TGGGTGGTTCGGGTGGCAATAATCCCACGGGAACCACTGGTAGGTGATGCAGCTTTTCTA
         ************************************ ***** *****************

817096   AAAGGGTTAGCCATTGGGGTTCGAACTCATGGCAATGTCTTATAAACATACAATCTGATC
807086   AAAGGGTTAGCCATTGGGGTTCGAACTCATGGCAATGTCTTATAAACATACAATCTGATC
814011   AAAGGGTTAGCCATTGGGGTTCGAACTCATGGCAATGTCTTATAAACATACAATCTGATC
         ************************************************************

817096   CCTTTATAACCATTCCTAAACGATATAAATCTGATACACCAGAAGAATTAACAGAAATAT
807086   CCTTTATAACCATTCCAGCACGATATATATCTGAAACCCAGAAGAATTAATAGAAAAAT
814011   CCTTTATAACCATTCCAGCACGATATATATCTGAAACCCAGAAGAATTAATAGAAAAAT
         ****************  *******   ******  ************* ***** **

817096   TATCAGCAAATATCAAATTGGCCTCATGCTTCCGGTAGCATACTTTGCTCGGAAACGGAA
807086   TATCAGCAAATATCGAATTGGCCTCATGCTTCCGGTAGCATACTTTGCTTGGAAACGGAA
814011   TATCAGCAAATATCGAATTGGCCTCATGCTTCCGGTAGCATACTTTGCTTGGAAACGGAA
         ************** ********************************* **********
```

Figure 21 continued

```
817096    TCCACTTCGGCGGTGTCATAAAATTCTCAACCCTCGTTCGATGATCATAACCGGAACCAC
807086    CCCACTTCGGCGGTGTCATAAAATCCTCAACCCTCGTTCGATGATCATAACCGGAACCAC
814011    CCCACTTCGGCGGTGTCATAAAATTCTCAACCCTCGTTCGATGATCATAACCGGAACCAC
           ********************** *************************************

817096    TTATCAAGTCGTCAGCCGACGCTCCGAGAAAAGCAATGAACCATGCGTTAAAATTCGAGT
807086    TTATCAAGTCGTCAGCCGACGCTCCGAGAAAAGCAATGAACCATGCGTTAAAATTCGAGT
814011    TTATCAAGTCGTCAGCCGACGCTCCGAGAAAAGCAATGAACCATGCGTTAAAATTCGAGT
          ************************************************************

817096    AAAAGGCTCGCGAGGTCCGTAGTCCAGCTGCGACGGACGGCAACCAATAC
807086    AAAAGGCTCGCGAGATCCGTAGTCCAGCTGCGACGGACGGCAACCAATAC
814011    AAAAGGCTCGCGAGGTCCGTAGTCCAGCTGCGACGGACGGCAACCAATAC
          *************** **********************************
```

SINGLE NUCLEOTIDE POLYMORPHISM (SNP) MARKERS FOR STEVIA

CROSS REFERENCE TO RELATED APPLICATION

This application is a divisional patent application and claims priority to a divisional U.S. application Ser. No. 16/418,640, as filed on May 21, 2019, which claims priority to U.S. application Ser. No. 15/512,271, as filed Mar. 17, 2017, which claims priority to PCT Application No. PCT/US2015/52366, as filed on Sep. 25, 2015; which claims priority to U.S. Provisional Application No. 62/116,893, filed Feb. 16, 2015; Chinese Patent Application No. 201510036580.4, filed on Jan. 23, 2015; Chinese Patent Application No. 201510037435.8, filed on Jan. 23, 2015; Chinese Patent Application No. 201510036668.6, filed on Jan. 23, 2015; U.S. Provisional Patent Application No. 62/064,601, filed on Oct. 16, 2014; U.S. Provisional Application No. 62/071,567, filed on Sep. 26, 2014; U.S. Provisional Application No. 62/071,566, filed on Sep. 26, 2014; and U.S. Provisional Application No. 62/071,568, filed on Sep. 26, 2014; the entire contents of which are incorporated herein by reference for all purposes.

SUBMISSION OF SEQUENCE LISTING

The Sequence Listing associated with this application is filed in electronic format via EFS-Web and is hereby incorporated by reference into the specification in its entirety.

BACKGROUND

*Stevia* is an important and valuable field crop for the production of sweeteners, sugar substitutes, and other consumable ingredients. Thus, a continuing goal of *Stevia* plant breeders is to develop stable, high yielding *Stevia* cultivars of *Stevia* species that are agronomically sound. The reasons for this goal are to maximize the amount and quality of the sweeteners, sugar substitutes, and other consumable ingredients. To accomplish this goal, the *Stevia* breeder must select and develop plants that have the traits that result in superior cultivars.

The development of new *Stevia* cultivars requires the evaluation and selection of parents and the crossing of these parents. The lack of predictable success of a given cross requires that a breeder, in any given year, make several crosses with the same or different breeding objectives.

The foregoing examples of the related art and limitations related therewith are intended to be illustrative and not exclusive. Other limitations of the related art will become apparent to those of skill in the art upon a reading of the specification

SUMMARY

The following embodiments and aspects thereof are described and illustrated in conjunction with products and methods, which are meant to be exemplary and illustrative, not limiting in scope. In various embodiments, one or more of the above-described problems have been reduced or eliminated, while other embodiments are directed to other improvements.

The present disclosure provides a *Stevia* plant comprising the following single nucleotide polymorphisms (SNPs), wherein said SNPs are found in homozygous form: SNP2, which comprises a G to C nucleotide substitution at position number 225 in SEQ ID NO:1, SNP10, which comprises a G to A nucleotide substitution at position number 187 in SEQ ID NO:2, SNP12, which comprises an C to T nucleotide exchange at position number 345 in SEQ ID NO:3, SNP17, which comprises an A to C nucleotide substitution at position number 129 in SEQ ID NO:4, SNP19, which comprises an A to T nucleotide substitution at position number 173 in SEQ ID NO:5, SNP20, which comprises a G to A nucleotide substitution at position number 221 in SEQ ID NO:6, SNP22, which comprises a T to G nucleotide substitution at position number 160 in SEQ ID NO:7, and SNP24, which comprises a G to A nucleotide substitution at position number 325 in SEQ ID NO:8.

Another embodiment discloses a *Stevia* plant, wherein the leaves of said *Stevia* plant have a rebaudioside D/total steviol glycoside percentage between 8% and 38% and a rebaudioside M/total steviol glycoside percentage between 0% and 14% and further comprise the following SNPs in homozygous form: SNP17, which comprises an A to C nucleotide substitution at position number 129 in SEQ ID NO:4, SNP19, which comprises an A to T nucleotide substitution at position number 173 in SEQ ID NO:5, and SNP 20, which comprises a G to A nucleotide substitution at position number 221 in in SEQ ID NO:6.

Another embodiment discloses a method for producing a *Stevia* plant having a high rebaudioside D and high rebaudioside M content, said method comprising: (a) screening a population of *Stevia* plants for at least one of the following SNPs: SNP2, which comprises a G to C nucleotide substitution at position number 225 in SEQ ID NO:1, SNP10, which comprises a G to A nucleotide substitution at position number 187 in SEQ ID NO:2, SNP12, which comprises an C to T nucleotide exchange at position number 345 in SEQ ID NO:3, SNP17, which comprises an A to C nucleotide substitution at position number 129 in SEQ ID NO:4, SNP19, which comprises an A to T nucleotide substitution at position number 173 in SEQ ID NO:5, SNP20, which comprises a G to A nucleotide substitution at position number 221 in SEQ ID NO:6, SNP22, which comprises a T to G nucleotide substitution at position number 160 in SEQ ID NO:7, and SNP24, which comprises a G to A nucleotide substitution at position number 325 in SEQ ID NO:8; (b) selecting a first *Stevia* plant having at least one said SNP; (c) crossing said first selected *Stevia* plant having at least one said SNP with a second *Stevia* plant having at least one said SNP; (d) repeating steps (b) and (c) to obtain *Stevia* plants homozygous for all said SNPs; and (e) screening said *Stevia* plants homozygous for all said SNPs to confirm the presence of all said SNPs in homozygous form to produce a *Stevia* plant, wherein the leaves of said *Stevia* plant have a high rebaudioside D content, high rebaudioside M content, or a high rebaudioside D and high rebaudioside M content.

BRIEF DESCRIPTION OF THE SEQUENCE LISTINGS

SEQ ID NO: 1 discloses the CC genotype (homozygous recessive) for all RebD, and RebM lines (sty_snp_5090958) and identified as SNP2.

SEQ ID NO: 2 discloses the AA genotype (homozygous recessive) for all RebD, and RebM lines (sty_snp_3488333) and identified as SNP10.

SEQ ID NO: 3 discloses the TT genotype (homozygous recessive) for all RebD, and RebM lines (sty_snp_4414800) and identified as SNP12.

SEQ ID NO: 4 discloses the CC genotype (homozygous recessive) for all RebD, and RebM lines (sty_snp_6262256) and identified as SNP17.

SEQ ID NO: 5 discloses the TT genotype (homozygous recessive) for all RebD, and RebM lines (sty_snp_6645712) and identified as SNP19.

SEQ ID NO: 6 discloses the AA genotype (homozygous recessive) for all RebD, and RebM lines (sty_snp_6647386) and identified as SNP20.

SEQ ID NO: 7 discloses the GG genotype (homozygous recessive) for all RebD, and RebM lines (sty_snp_4704641) and identified as SNP22.

SEQ ID NO: 8 discloses the AA genotype (homozygous recessive) for all RebD, and RebM lines (sty_snp_5387123) and identified as SNP24.

SEQ ID NO: 9 discloses UGT76G1 isoform sequence for 814011 (Ref_*Stevia*_Transcript_185827_2127).

SEQ ID NO: 10 discloses UGT76G1 isoform sequence for 814011 (Ref_*Stevia*_Transcript_185828_2195).

SEQ ID NO: 11 discloses UGT76G1 isoform sequence for 814011 (Ref_*Stevia*_Transcript_185829_807).

SEQ ID NO: 12 discloses UGT76G1 isoform sequence for 814011 (Ref_*Stevia*_Transcript_185830_799).

SEQ ID NO: 13 discloses UGT76G1 isoform sequence for 814011 (Ref_*Stevia*_Transcript_185831_875).

SEQ ID NO: 14 discloses UGT76G1 isoform sequence for 807086 (Ref_*Stevia*_Transcript_185827_2127).

SEQ ID NO: 15 discloses UGT76G1 isoform sequence for 807086 (Ref_*Stevia*_Transcript_185828_2195).

SEQ ID NO: 16 discloses UGT76G1 isoform sequence for 807086 (Ref_*Stevia*_Transcript_185829_807).

SEQ ID NO: 17 discloses UGT76G1 isoform sequence for 807086 (Ref_*Stevia*_Transcript_185830_799).

SEQ ID NO: 18 discloses UGT76G1 isoform sequence for 807086 (Ref_*Stevia*_Transcript_185831_875).

SEQ ID NO: 19 discloses UGT76G1 isoform sequence for 817096 (Ref_*Stevia*_Transcript_185827_2127).

SEQ ID NO: 20 discloses UGT76G1 isoform sequence for 817096 (Ref_*Stevia*_Transcript_185828_2195).

SEQ ID NO: 21 discloses UGT76G1 isoform sequence for 817096 (Ref_*Stevia*_Transcript_185829_807).

SEQ ID NO: 22 discloses UGT76G1 isoform sequence for 817096 (Ref_*Stevia*_Transcript_185830_799).

SEQ ID NO: 23 discloses UGT76G1 isoform sequence for 817096 (Ref_*Stevia*_Transcript_185831_875).

SEQ ID NO: 24 discloses UGT91D2 isoform sequence for 817096 (Ref_*Stevia*_Transcript_203252_1370).

SEQ ID NO: 25 discloses UGT91D2 isoform sequence for 817096 (Ref_*Stevia*_Transcript_203253_1205).

SEQ ID NO: 26 discloses UGT91D2 isoform sequence for 817096 (Ref_*Stevia*_Transcript_203254_1266).

SEQ ID NO: 27 discloses UGT91D2 isoform sequence for 817096 (Ref_*Stevia*_Transcript_203255_1292).

SEQ ID NO: 28 discloses UGT91D2 isoform sequence for 817096 (Ref_*Stevia*_Transcript_203256_1213).

SEQ ID NO: 29 discloses UGT91D2 isoform sequence for 817096 (Ref_*Stevia*_Transcript_203257_1280).

SEQ ID NO: 30 discloses UGT91D2 isoform sequence for 817096 (Ref_*Stevia*_Transcript_203258_1288).

SEQ ID NO: 31 discloses UGT91D2 isoform sequence for 817096 (Ref_*Stevia*_Transcript_203259_1283).

SEQ ID NO: 32 discloses UGT91D2 isoform sequence for 817096 (Ref_*Stevia*_Transcript_203260_1379).

SEQ ID NO: 33 discloses UGT91D2 isoform sequence for 817096 (Ref_*Stevia*_Transcript_203261_1197).

SEQ ID NO: 34 discloses UGT91D2 isoform sequence for 817096 (Ref_*Stevia*_Transcript_203262_573).

SEQ ID NO: 35 discloses UGT91D2 isoform sequence for 817096 (Ref_*Stevia*_Transcript_203263_1281).

SEQ ID NO: 36 discloses UGT91D2 isoform sequence for 817096 (Ref_*Stevia*_Transcript_203264_1275).

SEQ ID NO: 37 discloses UGT91D2 isoform sequence for 817096 (Ref_*Stevia*_Transcript_203265_1307).

SEQ ID NO: 38 discloses UGT91D2 isoform sequence for 817096 (Ref_*Stevia*_Transcript_203266_1208).

SEQ ID NO: 39 discloses UGT91D2 isoform sequence for 817096 (Ref_*Stevia*_Transcript_203267_1341).

SEQ ID NO: 40 discloses UGT91D2 isoform sequence for 817096 (Ref_*Stevia*_Transcript_203268_1289).

SEQ ID NO: 41 discloses UGT91D2 isoform sequence for 817096 (Ref_*Stevia*_Transcript_203269_1279).

SEQ ID NO: 42 discloses UGT91D2 isoform sequence for 817096 (Ref_*Stevia*_Transcript_203270_1322).

SEQ ID NO: 43 discloses UGT91D2 isoform sequence for 817096 (Ref_*Stevia*_Transcript_203271_674).

SEQ ID NO: 44 discloses UGT91D2 isoform sequence for 817096 (Ref_*Stevia*_Transcript_203272_1360).

SEQ ID NO: 45 discloses UGT91D2 isoform sequence for 817096 (Ref_*Stevia*_Transcript_203273_539).

SEQ ID NO: 46 discloses UGT91D2 isoform sequence for 817096 (Ref_*Stevia*_Transcript_203274_1332).

SEQ ID NO: 47 discloses UGT91D2 isoform sequence for 817096 (Ref_*Stevia*_Transcript_203275_1284).

SEQ ID NO: 48 discloses UGT91D2 isoform sequence for 817096 (Ref_*Stevia*_Transcript_203276_1297).

SEQ ID NO: 49 discloses UGT91D2 isoform sequence for 817096 (Ref_*Stevia*_Transcript_203277_1194).

SEQ ID NO: 50 discloses UGT91D2 isoform sequence for 817096 (Ref_*Stevia*_Transcript_203278_575).

SEQ ID NO: 51 discloses UGT91D2 isoform sequence for 817096 (Ref_*Stevia*_Transcript_203279_1232).

SEQ ID NO: 52 discloses UGT91D2 isoform sequence for 817096 (Ref_*Stevia*_Transcript_203280_1310).

SEQ ID NO: 53 discloses UGT91D2 isoform sequence for 817096 (Ref_*Stevia*_Transcript_203281_1316).

SEQ ID NO: 54 discloses UGT91D2 isoform sequence for 817096 (Ref_*Stevia*_Transcript_203282_1272).

SEQ ID NO: 55 discloses UGT91D2 isoform sequence for 807086 (Ref_*Stevia*_Transcript_203252_1370).

SEQ ID NO: 56 discloses UGT91D2 isoform sequence for 807086 (Ref_*Stevia*_Transcript_203253_1205).

SEQ ID NO: 57 discloses UGT91D2 isoform sequence for 807086 (Ref_*Stevia*_Transcript_203254_1266).

SEQ ID NO: 58 discloses UGT91D2 isoform sequence for 807086 (Ref_*Stevia*_Transcript_203255_1292).

SEQ ID NO: 59 discloses UGT91D2 isoform sequence for 807086 (Ref_*Stevia*_Transcript_203256_1213).

SEQ ID NO: 60 discloses UGT91D2 isoform sequence for 807086 (Ref_*Stevia*_Transcript_203257_1280).

SEQ ID NO: 61 discloses UGT91D2 isoform sequence for 807086 (Ref_*Stevia*_Transcript_203258_1288).

SEQ ID NO: 62 discloses UGT91D2 isoform sequence for 807086 (Ref_*Stevia*_Transcript_203259_1283).

SEQ ID NO: 63 discloses UGT91D2 isoform sequence for 807086 (Ref_*Stevia*_Transcript_203260_1379).

SEQ ID NO: 64 discloses UGT91D2 isoform sequence for 807086 (Ref_*Stevia*_Transcript_203261_1197).

SEQ ID NO: 65 discloses UGT91D2 isoform sequence for 807086 (Ref_*Stevia*_Transcript_203262_573).

SEQ ID NO: 66 discloses UGT91D2 isoform sequence for 807086 (Ref_*Stevia*_Transcript_203263_1281).

SEQ ID NO: 67 discloses UGT91D2 isoform sequence for 807086 (Ref_*Stevia*_Transcript_203264_1275).

SEQ ID NO: 68 discloses UGT91D2 isoform sequence for 807086 (Ref_*Stevia*_Transcript_203265_1307).
SEQ ID NO: 69 discloses UGT91D2 isoform sequence for 807086 (Ref_*Stevia*_Transcript_203266_1208).
SEQ ID NO: 70 discloses UGT91D2 isoform sequence for 807086 (Ref_*Stevia*_Transcript_203267_1341).
SEQ ID NO: 71 discloses UGT91D2 isoform sequence for 807086 (Ref_*Stevia*_Transcript_203268_1289).
SEQ ID NO: 72 discloses UGT91D2 isoform sequence for 807086 (Ref_*Stevia*_Transcript_203269_1279).
SEQ ID NO: 73 discloses UGT91D2 isoform sequence for 807086 (Ref_*Stevia*_Transcript_203270_1322).
SEQ ID NO: 74 discloses UGT91D2 isoform sequence for 807086 (Ref_*Stevia*_Transcript_203271_674).
SEQ ID NO: 75 discloses UGT91D2 isoform sequence for 807086 (Ref_*Stevia*_Transcript_203272_1360).
SEQ ID NO: 76 discloses UGT91D2 isoform sequence for 807086 (Ref_*Stevia*_Transcript_203273_539).
SEQ ID NO: 77 discloses UGT91D2 isoform sequence for 807086 (Ref_*Stevia*_Transcript_203274_1332).
SEQ ID NO: 78 discloses UGT91D2 isoform sequence for 807086 (Ref_*Stevia*_Transcript_203275_1284).
SEQ ID NO: 79 discloses UGT91D2 isoform sequence for 807086 (Ref_*Stevia*_Transcript_203276_1297).
SEQ ID NO: 80 discloses UGT91D2 isoform sequence for 807086 (Ref_*Stevia*_Transcript_203277_1194).
SEQ ID NO: 81 discloses UGT91D2 isoform sequence for 807086 (Ref_*Stevia*_Transcript_203278_575).
SEQ ID NO: 82 discloses UGT91D2 isoform sequence for 807086 (Ref_*Stevia*_Transcript_203279_1232).
SEQ ID NO: 83 discloses UGT91D2 isoform sequence for 807086 (Ref_*Stevia*_Transcript_203280_1310).
SEQ ID NO: 84 discloses UGT91D2 isoform sequence for 807086 (Ref_*Stevia*_Transcript_203281_1316).
SEQ ID NO: 85 discloses UGT91D2 isoform sequence for 807086 (Ref_*Stevia*_Transcript_203282_1272).
SEQ ID NO: 86 discloses UGT91D2 isoform sequence for 814011 (Ref_*Stevia*_Transcript_203252_1370).
SEQ ID NO: 87 discloses UGT91D2 isoform sequence for 814011 (Ref_*Stevia*_Transcript_203253_1205).
SEQ ID NO: 88 discloses UGT91D2 isoform sequence for 814011 (Ref_*Stevia*_Transcript_203254_1266).
SEQ ID NO: 89 discloses UGT91D2 isoform sequence for 814011 (Ref_*Stevia*_Transcript_203255_1292).
SEQ ID NO: 90 discloses UGT91D2 isoform sequence for 814011 (Ref_*Stevia*_Transcript_203256_1213).
SEQ ID NO: 91 discloses UGT91D2 isoform sequence for 814011 (Ref_*Stevia*_Transcript_203257_1280).
SEQ ID NO: 92 discloses UGT91D2 isoform sequence for 814011 (Ref_*Stevia*_Transcript_203258_1288).
SEQ ID NO: 93 discloses UGT91D2 isoform sequence for 814011 (Ref_*Stevia*_Transcript_203259_1283).
SEQ ID NO: 94 discloses UGT91D2 isoform sequence for 814011 (Ref_*Stevia*_Transcript_203260_1379).
SEQ ID NO: 95 discloses UGT91D2 isoform sequence for 814011 (Ref_*Stevia*_Transcript_203261_1197).
SEQ ID NO: 96 discloses UGT91D2 isoform sequence for 814011 (Ref_*Stevia*_Transcript_203262_573).
SEQ ID NO: 97 discloses UGT91D2 isoform sequence for 814011 (Ref_*Stevia*_Transcript_203263_1281).
SEQ ID NO: 98 discloses UGT91D2 isoform sequence for 814011 (Ref_*Stevia*_Transcript_203264_1275).
SEQ ID NO: 99 discloses UGT91D2 isoform sequence for 814011 (Ref_*Stevia*_Transcript_203265_1307).
SEQ ID NO: 100 discloses UGT91D2 isoform sequence for 814011 (Ref_*Stevia*_Transcript_203266_1208).
SEQ ID NO: 101 discloses UGT91D2 isoform sequence for 814011 (Ref_*Stevia*_Transcript_203267_1341).
SEQ ID NO: 102 discloses UGT91D2 isoform sequence for 814011 (Ref_*Stevia*_Transcript_203268_1289).
SEQ ID NO: 103 discloses UGT91D2 isoform sequence for 814011 (Ref_*Stevia*_Transcript_203269_1279).
SEQ ID NO: 104 discloses UGT91D2 isoform sequence for 814011 (Ref_*Stevia*_Transcript_203270_1322).
SEQ ID NO: 105 discloses UGT91D2 isoform sequence for 814011 (Ref_*Stevia*_Transcript_203271_674).
SEQ ID NO: 106 discloses UGT91D2 isoform sequence for 814011 (Ref_*Stevia*_Transcript_203272_1360).
SEQ ID NO: 107 discloses UGT91D2 isoform sequence for 814011 (Ref_*Stevia*_Transcript_203273_539).
SEQ ID NO: 108 discloses UGT91D2 isoform sequence for 814011 (Ref_*Stevia*_Transcript_203274_1332).
SEQ ID NO: 109 discloses UGT91D2 isoform sequence for 814011 (Ref_*Stevia*_Transcript_203275_1284).
SEQ ID NO: 110 discloses UGT91D2 isoform sequence for 814011 (Ref_*Stevia*_Transcript_203276_1297).
SEQ ID NO: 111 discloses UGT91D2 isoform sequence for 814011 (Ref_*Stevia*_Transcript_203277_1194).
SEQ ID NO: 112 discloses UGT91D2 isoform sequence for 814011 (Ref_*Stevia*_Transcript_203278_575).
SEQ ID NO: 113 discloses UGT91D2 isoform sequence for 814011 (Ref_*Stevia*_Transcript_203279_1232).
SEQ ID NO: 114 discloses UGT91D2 isoform sequence for 814011 (Ref_*Stevia*_Transcript_203280_1310).
SEQ ID NO: 115 discloses UGT91D2 isoform sequence for 814011 (Ref_*Stevia*_Transcript_203281_1316).
SEQ ID NO: 116 discloses UGT91D2 isoform sequence for 814011 (Ref_*Stevia*_Transcript_203282_1272).
SEQ ID NO: 117 discloses the forward primer for SNP2.
SEQ ID NO: 118 discloses the reverse primer for SNP2.
SEQ ID NO: 119 discloses the forward primer for SNP10.
SEQ ID NO: 120 discloses the reverse primer for SNP10.
SEQ ID NO: 121 discloses the forward primer for SNP12.
SEQ ID NO: 122 discloses the reverse primer for SNP12.
SEQ ID NO: 123 discloses the forward primer for SNP17.
SEQ ID NO: 124 discloses the reverse primer for SNP17.
SEQ ID NO: 125 discloses the forward primer for SNP19.
SEQ ID NO: 126 discloses the reverse primer for SNP19.
SEQ ID NO: 127 discloses the forward primer for SNP20.
SEQ ID NO: 128 discloses the reverse primer for SNP20.
SEQ ID NO: 129 discloses the forward primer for SNP22.
SEQ ID NO: 130 discloses the reverse primer for SNP22.
SEQ ID NO: 131 discloses the forward primer for SNP24.
SEQ ID NO: 132 discloses the reverse primer for SNP24.
SEQ ID NO: 133 discloses the forward primer for the SNP17 probe.
SEQ ID NO: 134 discloses the reverse primer for the SNP17 probe.
SEQ ID NO: 135 discloses the forward primer for the SNP19 probe.
SEQ ID NO: 136 discloses the reverse primer for the SNP19 probe.
SEQ ID NO: 137 discloses the forward primer for the SNP20 probe.
SEQ ID NO: 138 discloses the reverse primer for the SNP20 probe.

BRIEF DESCRIPTION OF THE FIGURES

The accompanying figures, which are incorporated herein and form a part of the specification, illustrate some, but not the only or exclusive, example embodiments and/or features.

It is intended that the embodiments and figures disclosed herein are to be considered illustrative rather than limiting.

FIG. 3 shows PCR amplification of SNP2 as well as the location of the substitution of a G nucleotide to a C.

FIG. 4 shows PCR amplification of SNP10 as well as the location of the substitution of a G nucleotide to an A.

FIG. 5 shows PCR amplification of SNP12 as well as the location of the substitution of an C nucleotide to a T.

FIG. 6 shows PCR amplification of SNP17 as well as the location of the substitution of an A nucleotide to a C.

FIG. 7 shows PCR amplification of SNP19 as well as the location of the substitution of an A nucleotide to a T.

FIG. 8 shows PCR amplification of SNP20 as well as the location of the substitution of a G nucleotide to an A.

FIG. 9 shows PCR amplification of SNP22 as well as the location of the substitution of a T nucleotide to a G.

FIG. 10 shows PCR amplification of SNP24 as well as the location of the substitution of a G nucleotide to an A.

FIG. 14 discloses a multiple sequence alignment of various UGT76G1 isoforms from 814011 plants. (1=Ref_*Stevia*_Transcript_185827_2127), (2=Ref_*Stevia*_Transcript_185828_2195), (3=Ref_*Stevia*_Transcript_185829_807), (4=Ref_*Stevia*_Transcript_185830_799) and (5=Ref_*Stevia*_Transcript_185831_875).

FIG. 15 discloses a multiple sequence alignment of various UGT76G1 Ref_*Stevia*_Transcript_185827_2127 isoforms across (9)=814011, (14)=807086 and (19)=817096. All these isoforms shared 99% nucleotide identity with few SNPs.

FIG. 16 discloses a multiple sequence alignment of various UGT76G1 Ref_*Stevia*_Transcript_185828_2195 isoforms across (10)=814011, (15)=807086 and (20)=817096. All these isoforms shared 99% nucleotide identity with few SNPs.

FIG. 17 discloses a multiple sequence alignment of various UGT76G1 Ref_*Stevia*_Transcript_185829_807 isoforms across (1)=814011, (2)=807086 and (3)=817096. All these isoforms shared 99% nucleotide identity with few SNPs.

FIG. 18 discloses a multiple sequence alignment of various UGT76G1 Ref_*Stevia*_Transcript_185830_799 isoforms across (1)=814011, (2)=807086 and (3)=817096. All these isoforms shared 99% nucleotide identity with few SNPs.

FIG. 19 discloses a multiple sequence alignment of various UGT76G1 Ref_*Stevia*_Transcript_185831_875 isoforms across (1)=814011, (2)=807086 and (3)=817096. All these isoforms shared 99% nucleotide identity with few SNPs.

FIG. 20 discloses a multiple sequence alignment of various UGT91D2 isoforms from 817096. (1=>Ref_*Stevia*_Transcript_203252_1370), (2=>Ref_*Stevia*_Transcript_203253_1205), (3=>Ref_*Stevia*_Transcript_203254_1266), (4=>Ref_*Stevia*_Transcript_203255_1292), (5=>Ref_*Stevia*_Transcript_203256_1213), (6=>Ref_*Stevia*_Transcript_203257_1280), (7=>Ref_*Stevia*_Transcript_203258_1288), (8=>Ref_*Stevia*_Transcript_203259_1283), (9=>Ref_*Stevia*_Transcript_203260_1379), (10=>Ref_*Stevia*_Transcript_203261_1197), (11=>Ref_*Stevia*_Transcript_203262_573), (12=>Ref_*Stevia*_Transcript_203263_1281), (13=>Ref_*Stevia*_Transcript_203264_1275), (14=>Ref_*Stevia*_Transcript_203265_1307), (15=>Ref_*Stevia*_Transcript_203266_1208), (16=>Ref_*Stevia*_Transcript_203267_1341), (17=>Ref_*Stevia*_Transcript_203268_1289), (18=>Ref_*Stevia*_Transcript_203269_1279), (19=>Ref_*Stevia*_Transcript_203270_1322), (20=>Ref_*Stevia*_Transcript_203271_674), (21=>Ref_*Stevia*_Transcript_203272_1360), (22=>Ref_*Stevia*_Transcript_203273_539), (23=>Ref_*Stevia*_Transcript_203274_1332), (24=>Ref_*Stevia*_Transcript_203275_1284), (25=>Ref_*Stevia*_Transcript_203276_1297), (26=>Ref_*Stevia*_Transcript_203277_1194), (27=>Ref_*Stevia*_Transcript_203278_575), (28=>Ref_*Stevia*_Transcript_203279_1232), (29=>Ref_*Stevia*_Transcript_203280_1310), (30=>Ref_*Stevia*_Transcript_203281_1316), (31=>Ref_*Stevia*_Transcript_203282_1272).

FIG. 21 discloses a multiple sequence alignment of various UGT91D2>Ref_*Stevia*_Transcript_203252_1370 isoforms across 814011, 807086 and 817096. All these isoforms shared 99% nucleotide identity with few SNPs.

DEFINITIONS

Figure 1:
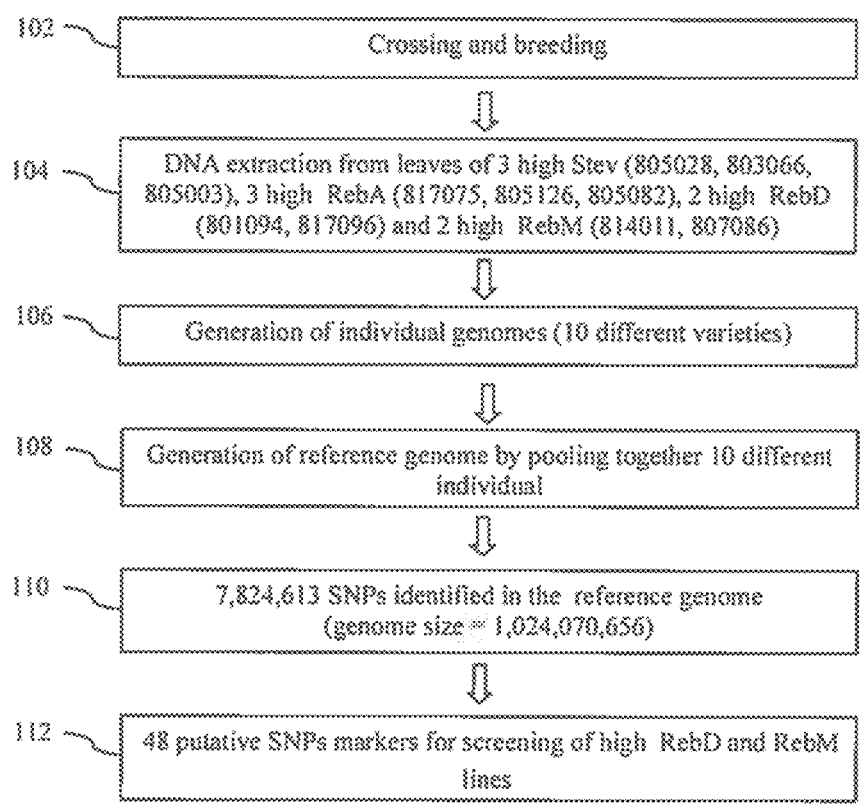
FIG. 1 shows a flow diagram showing the stage involved for the identification of putative SNPs markers.

In the description and tables, which follow, a number of terms are used. In order to provide a clear and consistent understanding of the specification and claims, including the scope to be given such terms, the following definitions are provided. All rebaudioside contents are represented as a percentage of the dry weight of leaves.

High rebaudioside A: As used herein, plants described as having high rebaudioside A have a rebaudioside A content of greater than or equal to 9%, a rebaudioside D content of less than or equal to 0.3%, and a rebaudioside M content of less than or equal to 0.2%.

High rebaudioside D: As used herein, plants described as having high rebaudioside D have a rebaudioside D content of greater than or equal to 0.6% and a rebaudioside D/total steviol glycoside greater than or equal to 8%.

High rebaudioside D and high rebaudioside M: As used herein, plants described as having rebaudioside D and high rebaudioside M content have a rebaudioside D content of greater than or equal to 0.6% and a rebaudioside D/total steviol glycoside greater than or equal to 8%, and a rebaudioside M content that is greater than or equal to 0.5%.

High rebaudioside M: As used herein, plants described as having high rebaudioside M have a rebaudioside M content that is greater than or equal to 0.5%.

High stevioside: As used herein, plants described as having high stevioside have a stevioside content of greater than or equal to 7%, a rebaudioside D content of less than or equal to 0.3%, and a rebaudioside M content of less than or equal to 0.2%.

High stevioside and high rebaudioside A: As used herein, plants described as having high stevioside and high rebaudioside A have a rebaudioside D/total steviol glycoside less than or equal to 7.60% and a rebaudioside M/total steviol glycoside less than or equal to 1.9%.

Marker: As used herein, a "marker" is an indicator for the presence of at least one polymorphism, thus a marker can be the nucleotide sequence itself, or a probe, for example.

Plant: As used herein, the term "plant" includes reference to an immature or mature whole plant, including a plant that has been processed for steviol glycosides. Seed or plant part that will produce the plant is also considered to be the plant.

Plant Part: As used herein, the term "plant part" includes leaves, stems, roots, seed, embryo, pollen, ovules, flowers, root tips, anthers, tissue, cells and the like.

Rebaudioside A (RebA): As used herein "Rebaudioside A" or "RebA" is a steviol glycoside that contains only glucose as its monosaccharide moieties. It contains four glucose molecules in total with the central glucose of the triplet connected to the main steviol structure at its hydroxyl group, and the remaining glucose at its carboxyl group forming an ester bond.

Rebaudioside D (RebD): As used herein, "Rebaudioside D" or "RebD" is an entkaurane diterpene glycoside isolated from *Stevia rebaudiana*.

Rebaudioside M (RebM): As used herein, "Rebaudioside M" or "RebM" is an entkaurane diterpene glycoside isolated from *Stevia rebaudiana*.

SNP: As used herein, the term "SNP" shall refer to a single nucleotide polymorphism.

Stevioside content: As used herein, stevioside is the percent glycoside derived from the *Stevia* plant.

DETAILED DESCRIPTION OF THE INVENTION

Embodiments described herein provide *Stevia* plants containing eight (8) SNP markers in homozygous form, SNP2, SNP12, SNP17, SNP19, SNP20, SNP22, and SNP24. As will be described in detail below, *Stevia* plants containing these eight SNPs are shown to express either high RebD, or high RebM or plants with all eight SNPs may express both high RebD and high RebM. Embodiments described herein also provide methods for screening for *Stevia* plants containing these eight SNPs as well as methods and steps for using these SNPs in marker assisted breeding to produce *Stevia* plants expressing either high RebD, or RebM or plants with all eight SNPs may express both high RebD and high RebM. Also described herein are methods for introgressing all eight SNPs associated with high RebD and high RebM into *Stevia* plants by selecting plants comprising for one or more SNPs and breeding with such plants to confer such desirable agronomic phenotypes to plant progeny.

*Stevia rebaudiana* (Bertoni) is a herbaceous perennial plant of family Asteraceae, which consists of approximately 230 species of herbaceous, shrub and sub-shrub plants. *Stevia rebaudiana* is known to yield diterpenoid steviol glycosides (SGs), which are about 300 times sweeter than sucrose. Twenty-one diterpene glycosides have been identified in leaf tissues of *Stevia* (US2011/0183056). Among these, four major steviol glycosides synthesized in the leaves of *Stevia* are stevioside (STEV), RebA, rebaudioside C (RebC) and rebaudioside F (RebF). STEV account for 5-10% of the dry weight of the leaves while RebA accounts for 2-4% (Pande and Priyanka 2013).

All *Stevia rebaudiana* planted across the whole world are 97-99% genetically identical with estimation of a 2 GB genome. Genetic differences comprise only 2-3% of this 2 GB genome among different *Stevia rebaudiana* plants and are the key attributes for *Stevia* adaptability, growth performance, leaves sizes, disease resistance, variation in steviol glycosides composition and so on.

The present disclosure relates generally to *Stevia* varieties, and more particularly to SNP markers and UGT isoforms for *Stevia* varieties with high content of RebD and Rebaudioside M.

Although pathway enzymes of SG biosynthesis have been documented, there are still many uncertainties on the regulatory network involved in this SG biosynthesis. Through successive selection and crossing, new varieties of *Stevia rebaudiana* having very low RebD and RebM were produced. After several cycles of selection and intercrossing of superior parents, new varieties, '817096', '814011' and '807086' with a higher amount of specific Reb D and RebM glycosides were obtained.

Discovery of SNPs Markers for High RebD and RebM Identification

Figure 11:
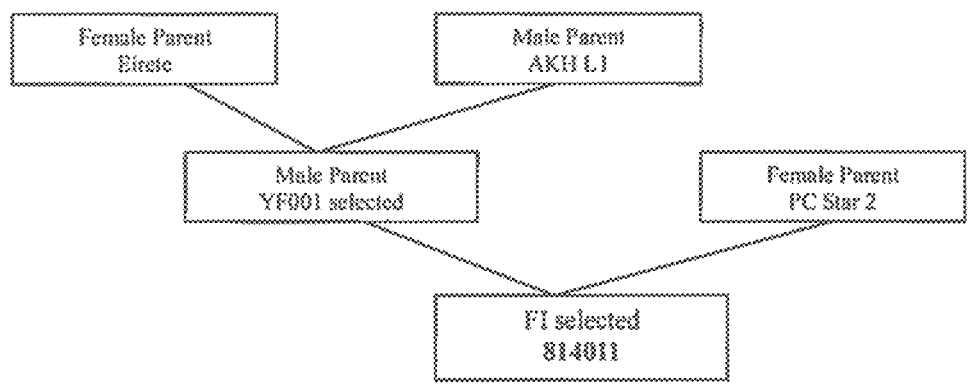
FIG. 11 shows the breeding scheme for variety '814011'. '814011' originated from a tri-cross conducted in Ganzhou, Jiangxi Province, the People's Republic of China in September 2013 between the proprietary male *Stevia* variety 'YF01' (unpatented) and an $F_1$ derived from a cross between the female *Stevia* variety 'Eirete' (unpatented) and the proprietary male *Stevia* variety 'AKHL1' (U.S. Plant Pat. No. 23,164) and the proprietary female variety 'PC Star 2' (unpatented).
Figure 12:
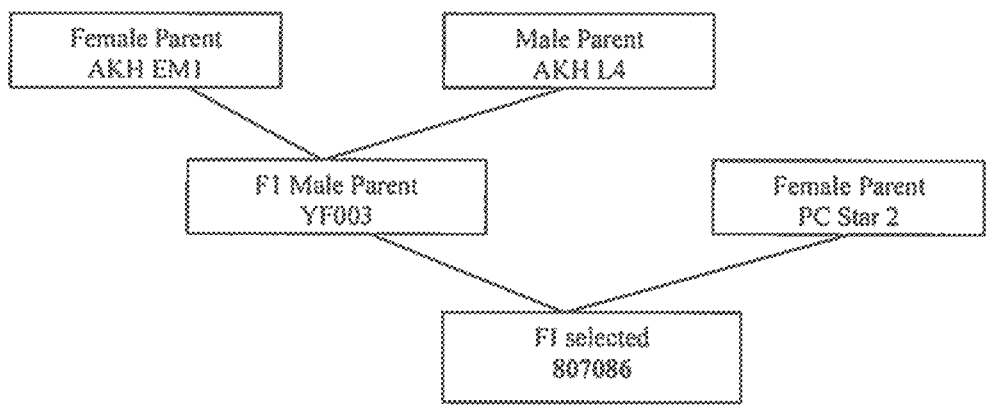
FIG. 12 shows the breeding scheme for variety '807086'. '807086' is a selection that results from a tri-cross conducted in Ganzhou, Jiangxi Province, the People's Republic of China of the proprietary Fi male *Stevia* line 'YF003' (unpatented) (from the cross of the female parent 'AKH EM1' (unpatented) and the male parent 'AKH L4' (U.S. Plant Pat. 23,728)) and the female *Stevia* line 'PC Star 2' (unpatented).
Figure 13:
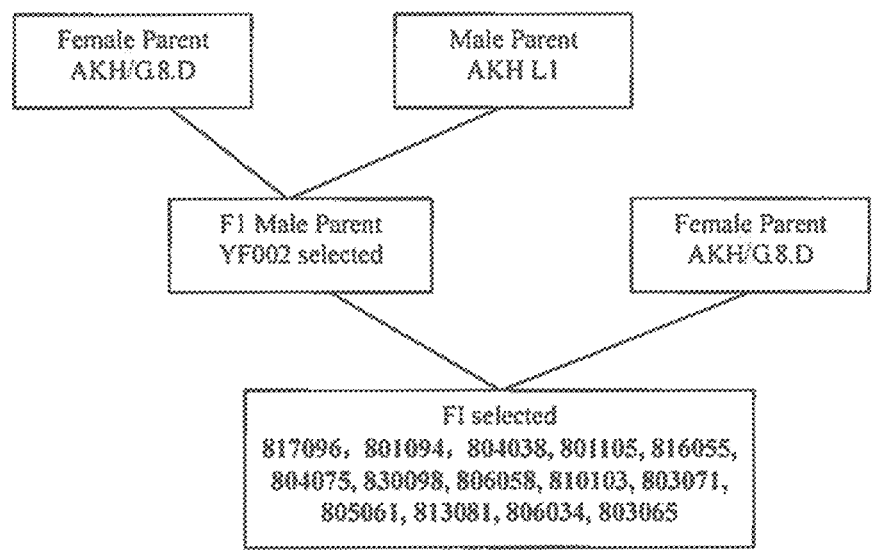
FIG. 13 shows the breeding scheme for varieties '817096', '801094', '804038', '801105', '816055', '804075', '830098', '806058', '810103', '803071', '805061', '813081', '806034' and '803065'. These varieties resulted from a backcross conducted in Ganzhou, Jiangxi Province, the People's Republic of China. The proprietary $F_1$ male *Stevia* line 'YFOO2' (unpatented) (derived from a cross between female parent 'AKH/G.8.D' (unpatented) and male parent 'AKH L1' (U.S. Plant Pat. No. 23,164)) was backcrossed to female parent 'AKH/G.8.D'.

As outlined in the flow diagram of FIG. 1, the present disclosure provides eight markers (the SNPs identified in SEQ ID NOs: 1-8) for the identification of *Stevia* varieties with high RebD content, high RebM content or varieties with both RebD and RebM content. Methods for breeding and selection of new *Stevia* varieties with high RebD and RebM contents are also described in further detail below. Briefly, as shown in step 102, through successive selection and crossing, new varieties of *Stevia rebaudiana* have been produced. In step 104, ten *Stevia* leaf samples with contrasting glycosides composition (three high Stevioside (805028', '803066', and '805003'), three high RebA (817075', '805126', and '805082'), two high RebD (801094' and '817096') and two high RebM (814011' and '807086') (104) were studied for their genetic background. The two high RebD lines were produced using the breeding flow diagram shown in FIG. 13, while the two high RebM lines were produced using the breeding flow diagrams shown in FIGS. 11 and 12. Briefly, as shown in FIG. 11, parental varieties 'Eirete' and 'AKHL1' were crossed to produce 'YFOO1'. This selection was outcrossed to 'PC Star 2' to produce high RebM line '814011'. As shown in FIG. 12, parental varieties 'AKH EM1' and 'AKHL4' were crossed to produce 'YF003'. This selection was outcrossed to 'PC Star 2' to produce high RebM line '807086'. As shown in FIG. 13, parental varieties 'AKH/G.8.D' and 'AKH L1' were crossed to produce 'YFOO2'. This selection was backcrossed to parental line 'AKH/G.8.D' to produce 14 high RebD lines, including '817096' and '801094'.

As shown in step 106 of FIG. 1, varieties reported to have high Stevioside and high rebaudioside A were randomly selected. Genome sequencing was employed in each of these varieties for an approximate target coverage of 10× each. Genomic DNAs were isolated from the leaves of each of these varieties/lines using Nucleospin Plant II kit (Macherey-Nagel) following manufacturer's protocol. Extracted DNA quality and quantity were measured using NanoDrop 2000 (Thermo Fisher Scientific Inc., USA) and Qubit 2.0 DNA Broad Range Assay (Invitrogen, USA). The samples were also run on 1% agarose gel to determine the integrity of genomic DNA. At least 1 μg of high quality DNA (as measured by Qubit) is required for TruSeq library preparation. The isolated genomic DNA samples were fragmented using Covaris S220 (Covaris Inc, USA) to a targeted size of 400-700 bp. The fragmented DNA was then end end-repaired, ligated to Illumina TruSeq adapters, and PCR enriched using TruSeq DNA Sample Preparation kit (Illumina, USA) according to manufacturer's protocol. The final sequencing libraries were quantified using KAPA kit (KAPA Biosystem, USA) on Agilent Strategene Mx-3005p quantitative PCR (Agilent, USA) and library size was confirmed using Agilent Bioanalyzer High Sensitivity DNA Chips (Agilent, USA). The resulting libraries were sequenced using an Illumina flow cell with 202 cycles of the Illumina HiSeq2000 platform (Illumina, USA). The sequencing run generated a total of 235.4 GB of raw data.

In step 108 of FIG. 1, all ten *Stevia* genomes from the ten *Stevia* plants were assembled separately using the "MGRC Assembler Pipeline" software (version 1.4). A pan genome pooled assembly methodology was also performed using in-house assembly pipeline tools. The merged sequence yielded a draft genome assembly of 1.02 Gbp. There was a total of 269,395 contigs with minimum contig size of 1 kbp.

In step 110, SNPs were identified using Samtools from individual sample reads mapping against a database of the draft genome assembly. Approximately 7.8 million SNPs were identified across the ten genomes. In step 112, of these 7.8 million SNPs, only 48 SNPs were putative SNPs for RebD and RebM identification. NCBI (National Centre of Biotechnological Information) BLAST® analysis indicated that these SNPs had not been reported in a public database.

Figure 2:
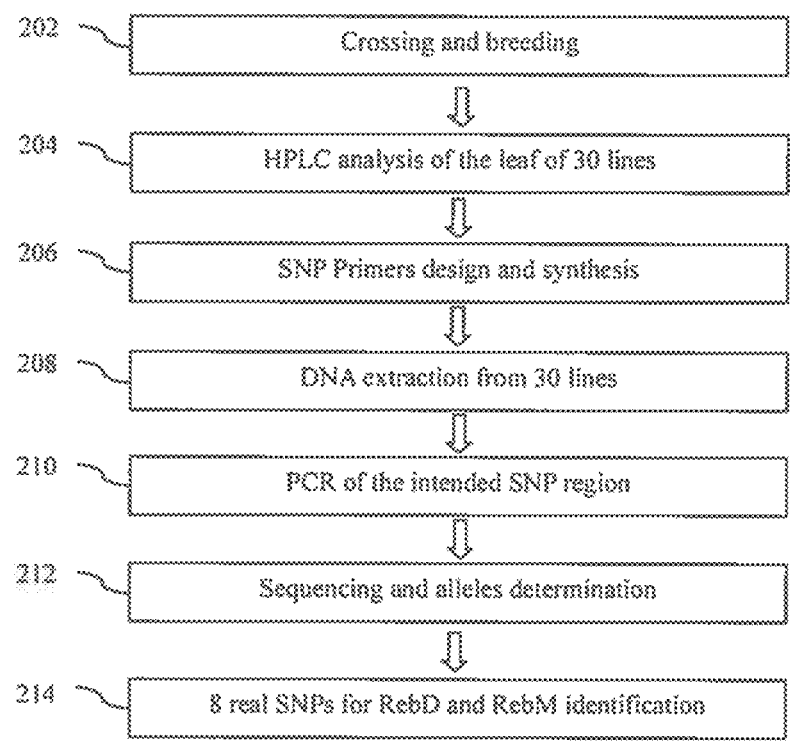
FIG. 2 shows a flow diagram showing the stage involved for these 48 putative SNPs markers verification across 30 *Stevia* plants with contrasting steviol glycoside composition.

The flow diagram of FIG. 2 outlines how the eight SNPs for high RebD and high RebM were identified. Briefly, following additional breeding (shown in step 202), in step 204 leaf samples with contrasting glycoside composition were analyzed via HPLC (High Performance Liquid Chromatography). SNP primers were designed in step 206 and DNA was extracted in step 208 for PCR amplification of the SNP region (shown in step 210). In step 212, PCR products were sequenced to determine alleles. In step, 214, eight SNPs for high RebD and high RebM were identified.

As shown in the flow diagram of FIG. 2, a total of 30 leaf samples with contrasting glycosides composition (9 high rebaudioside A, 5 high Stevioside, 14 high RebD and 2 high RebM) were selected for HPLC verification of the 48 putative SNP markers (204). *Stevia* varieties reported to have high Stevioside or high rebaudioside A were randomly selected. The 14 high RebD lines were produced using the breeding flow diagram shown in FIG. 13, while the two high RebM lines were produced using the breeding flow diagrams shown in FIGS. 11 and 12. Table 1 below shows the HPLC data of these 30 lines selected for SNP verification.

For HPLC analysis, the *Stevia* leaf samples were air-dried/oven-dried before grinding into fine powder using a pestle and mortar. For each sample, leaf powder (100 mg) was extracted with 15 ml of 60° C. distilled water for 18 hours. The mixture was centrifuged and the supernatant filtered and collected for steviol glycoside composition analysis by HPLC (Agilent, USA). The analysis of steviol glycosides was carried out using an Agilent Technologies 1200 Series (USA) HPLC equipped Agilent Poroshell 120 SB-C18 2.7 μm, 4.6×150 mm. A diode array set at 210 nm was used as the detector. The reference standards for all glycosides, including rebaudioside E, RebD, RebM, rebaudioside N, and rebaudioside O were purchased from ChromaDex Inc. (USA). The following method was used for analysis of Rebaudioside E (RebE), RebD, RebM, Rebaudioside N (RebN), and Rebaudioside O (RebO): column temperature: 40° C., mobile phase: Solvent A 10 mM Monosodium dihydrogen Phosphate pH2.6: Acetonitrile, 75%:25% (v/v), Solvent B Water: Acetonitrile, 50%:50% (v/v), Gradient program % v/v: at 0.0 and 14.0 minutes 100% A and 0% B, at 14.5 and 25.0 minutes 100% B and 0% A, flow rate: 0.5 mL/min, injection: 5 μL, autosampler temperature: ambient. To analyze Rebaudioside A (RebA), Stevioside (Stev), Rebaudioside F (RebF), Rebaudioside C (RebC), Dulcoside A (DulA), Rubusoside (Rub), Rebaudioside B (RebB), and Steviolbioside (Stev) the same method as described above was used except the mobile phase consisted of Isocratic 10 mM Monosodium dihydrogen Phosphate pH 2.6: Acetonitrile, 68%:32% (v/v) at a flow rate of 1.0 mL/min, with a run time of 20 minutes. 13 compounds, RebA, RebD, RebM, Rebaudioside E, Stevioside, Rebaudioside N, Rebaudioside O, Rebaudioside F, Rebaudioside C, Dulcoside A, Rubusoside, Rebaudioside B, and Steviolbioside were identified.

Table 1 provides an analysis of steviol glycosides in 30 *Stevia* varieties. The top row of Table 1 shows the various glycosides group, and the first column shows the *Stevia* variety and the classification as a high RebD, high RebM, high RebD/RebM, high RebA, high Stev or high RebA/Stev line. The numbers in Table 1 represent the percentage of a particular rebaudioside group in a specific *Stevia* variety. High RebD lines are defined as having a RebD content that is ≥0.6% and a RD/TSG ≥8%. High RebM lines are defined as having a RebM content that is ≥0.5%. High RebA lines are defined as having a RebA content that is ≥9%, a RebD content that is ≤0.3%, and a RebM content of ≤0.2%. High Stev lines are defined as having a Stev content of ≥7%, a RebD content of ≤0.3%, and a, RebM content of ≤0.2%. TSG=total steviol glycoside. Deposited varieties '817096', '814011', and '807086' are bolded.

Table 2 shows a descriptive statistical analysis of the first 16 varieties shown in Table 1, all designated as high RebD. The last two varieties of this group, '814011' and '807086' are also designated as high RebM. Min=minimum, Max=maximum, SV=sample variance, SD=standard deviation, SD=standard error.

TABLE 1

HPLC analysis of steviol glycosides in 30 stevia varieties

| | Variety | | | | | | | | | | |
|---|---|---|---|---|---|---|---|---|---|---|---|
| Sample ID | DA | Stev | RebC | RebF | RebA | RebD | RebM | TSG | RA/TSG | ST/TSG | RD/TSG | RM/TSG |
| 804038 (RebD) | 0.00 | 0.66 | 0.35 | 0.05 | 3.42 | 2.23 | 0.48 | 7.19 | 47.57 | 9.18 | 31.02 | 6.68 |
| 801105 (RebD) | 0.00 | 0.33 | 0.55 | 0.16 | 7.13 | 1.14 | 0.38 | 9.69 | 73.58 | 3.41 | 11.76 | 3.92 |

TABLE 1-continued

HPLC analysis of steviol glycosides in 30 stevia varieties

| Sample ID | Variety DA | Stev | RebC | RebF | RebA | RebD | RebM | TSG | RA/TSG | ST/TSG | RD/TSG | RM/TSG |
|---|---|---|---|---|---|---|---|---|---|---|---|---|
| 816055 (RebD) | 0.01 | 0.26 | 0.47 | 0.21 | 6.94 | 0.89 | 0.31 | 9.09 | 76.35 | 2.86 | 9.79 | 3.41 |
| 817096 (RebD) | 0.05 | 2.06 | 0.50 | 0.10 | 2.35 | 3.28 | 0.38 | 8.72 | 26.95 | 23.62 | 37.61 | 4.36 |
| 801094 (RebD) | 0.00 | 0.63 | 0.62 | 0.09 | 5.41 | 1.62 | 0.25 | 8.62 | 62.76 | 7.31 | 18.79 | 2.90 |
| 804075 (RebD) | 0.00 | 0.57 | 0.41 | 0.16 | 4.35 | 0.97 | 0.24 | 6.70 | 64.93 | 8.51 | 14.48 | 3.58 |
| 806058 (Reb D) | 0.02 | 0.42 | 0.38 | 0.13 | 5.32 | 0.83 | 0.00 | 7.10 | 74.93 | 5.92 | 11.69 | 0 |
| 810103 (Reb D) | 0.00 | 0.28 | 0.46 | 0.15 | 4.52 | 0.95 | 0.00 | 6.36 | 71.07 | 4.40 | 14.94 | 0 |
| 803071 (RebD) | 0.00 | 0.44 | 0.48 | 0.11 | 4.30 | 0.70 | 0.00 | 6.03 | 71.31 | 7.30 | 11.61 | 0 |
| 805061 (RebD) | 0.02 | 0.42 | 0.09 | 0.04 | 4.32 | 1.07 | 0.00 | 5.96 | 72.48 | 7.05 | 17.95 | 0 |
| 813081 (RebD) | 0.01 | 0.30 | 0.31 | 0.11 | 4.54 | 0.65 | 0.00 | 5.92 | 76.69 | 5.07 | 10.98 | 0 |
| 806034 (RebD) | 0.00 | 0.21 | 0.25 | 0.09 | 3.71 | 0.62 | 0.00 | 4.88 | 76.02 | 4.30 | 12.70 | 0 |
| 830098 (RebD) | 0.00 | 0.41 | 0.53 | 0.12 | 5.51 | 1.03 | 0.00 | 7.60 | 72.50 | 5.39 | 13.55 | 0 |
| 803065 (RebD) | 0.00 | 0.72 | 0.42 | 0.10 | 4.13 | 0.63 | 0.00 | 6.00 | 68.83 | 12 | 10.50 | 0 |
| 814011 (RebD/ RebM) | 0.02 | 0.38 | 0.76 | 0.21 | 8.45 | 1.11 | 1.12 | 12.05 | 70.12 | 3.15 | 9.21 | 9.29 |
| 807086 (RebD/ RebM) | 0.00 | 0.21 | 0.32 | 0.08 | 4.15 | 1.55 | 1.00 | 7.31 | 56.77 | 2.87 | 21.20 | 13.68 |
| 805082 (RebA) | 0.00 | 0.65 | 0.54 | 0.07 | 10.78 | 0.18 | 0.00 | 12.22 | 88.22 | 5.32 | 1.47 | 0 |
| 817075 (RebA) | 0.00 | 0.56 | 0.51 | 0.08 | 10.68 | 0.19 | 0.00 | 12.02 | 88.85 | 4.66 | 1.58 | 0 |
| 805126 (RebA) | 0.00 | 0.45 | 0.63 | 0.07 | 10.77 | 0.25 | 0.00 | 12.17 | 88.50 | 3.70 | 2.05 | 0 |
| 815034 (RebA) | 0.00 | 0.69 | 0.77 | 0.25 | 9.51 | 0.20 | 0.00 | 11.42 | 83.27 | 6.04 | 1.75 | 0 |
| 802057 (RebA) | 0.00 | 0.56 | 1.06 | 0.32 | 11.55 | 0.17 | 0.00 | 13.66 | 84.55 | 4.10 | 1.24 | 0 |
| 812051 (RebA) | 0.01 | 0.56 | 0.91 | 0.28 | 11.44 | 0.17 | 0.00 | 13.37 | 85.56 | 4.19 | 1.27 | 0 |
| 805068 (RebA) | 0.00 | 1.09 | 0.83 | 0.06 | 12.32 | 0.10 | 0.00 | 14.40 | 85.56 | 7.57 | 0.69 | 0 |
| 813057 (RebA) | 0.00 | 0.54 | 0.99 | 0.21 | 12.29 | 0.15 | 0.00 | 14.18 | 86.67 | 3.81 | 1.06 | 0 |
| 805000 3 (Stev) | 1.05 | 10.13 | 0.01 | 0.01 | 0.1 | 0.04 | 0.00 | 11.34 | 0.88 | 89.33 | 0.35 | 0 |
| 805028 (Stev) | 0.81 | 9.58 | 0.02 | 0.01 | 0.18 | 0.02 | 0.00 | 10.62 | 1.69 | 90.21 | 0.19 | 0 |
| 803066 (Stev) | 0.93 | 10.03 | 0.03 | 0.02 | 0.26 | 0.01 | 0.00 | 11.28 | 2.30 | 88.92 | 0.09 | 0 |
| 412-31 (Stev) | 0.44 | 8.57 | 0.02 | 0.00 | 0.13 | 0.08 | 0.00 | 9.24 | 1.41 | 92.75 | 0.87 | 0 |
| 43-2 (Stev) | 0.53 | 7.87 | 0.12 | 0.01 | 0.28 | 0.00 | 0.00 | 8.81 | 3.18 | 89.33 | 0.00 | 0 |
| 49-58 (Stev) | 0.05 | 11.36 | 0.02 | 0.00 | 0.43 | 0.02 | 0.00 | 11.88 | 3.62 | 95.62 | 0.17 | 0 |

TABLE 2

Analysis of steviol glycosides in lines designated as high RebD shown in Table 1

| | Min | Max | Range | SV | SD | SE | Mean |
|---|---|---|---|---|---|---|---|
| DA | 0 | 0.05 | 0.05 | 0 | 0.01 | 0 | 0 |
| Stev | 0.21 | 2.06 | 1.85 | 0.19 | 0.44 | 0.11 | 0.52 |
| RebC | 0.09 | 0.76 | 0.67 | 0.02 | 0.16 | 0.04 | 0.43 |
| RebF | 0.04 | 0.21 | 0.17 | 0 | 0.05 | 0.01 | 0.12 |
| RebA | 2.35 | 8.45 | 6.1 | 2.34 | 1.53 | 0.38 | 4.91 |
| RebD | 0.62 | 3.28 | 2.66 | 0.49 | 0.70 | 0.17 | 1.20 |
| RebM | 0 | 1.12 | 1.12 | 0.13 | 0.36 | 0.09 | 0.26 |
| TSG | 4.88 | 12.05 | 7.17 | 3.27 | 1.81 | 0.45 | 7.45 |

TABLE 2-continued

Analysis of steviol glycosides in lines designated as high RebD shown in Table 1

|  | Min | Max | Range | SV | SD | SE | Mean |
|---|---|---|---|---|---|---|---|
| RA/TSG | 26.95 | 76.69 | 49.74 | 172.04 | 13.12 | 3.28 | 66.43 |
| ST/TSG | 2.86 | 23.62 | 20.76 | 26.13 | 5.11 | 1.28 | 7.02 |
| RD/TSG | 9.21 | 37.61 | 28.4 | 63.15 | 7.95 | 1.99 | 16.11 |
| RM/TSG | 0 | 13.68 | 13.68 | 16.16 | 4.02 | 1.00 | 2.99 |

As shown in Table 1 and Table 2 above, the 16 *Stevia* varieties classified as high RebD had a RebD content that ranged between approximately 0.6% and 3.3% and a RD/TSG that ranged between approximately 9.2% and 38% (see Table 2). Within these 16 varieties, two were classified as also having high RebM (see Table 1, varieties labeled '814011' and '807086' in bold font). The RebM content ranged between approximately 0% and 1.15% and the RM/TSG ranged between approximately 0% and 14%. Other varieties having even higher contents of RebD, RebM, or RebD and RebM and SEQ ID NOs: 1-8 are contemplated by this invention.

As further outlined in the flow diagram of FIG. 2, primers were designed for each of the 48 putative SNP markers (shown in step 206) and were used for SNP amplification of extracted DNA (shown in step 208). The 48 SNPs markers identified from the SNPs discovery stage (FIG. 1) were selected for further verification using SNP gene amplification across the randomly selected 30 *Stevia* plants with contrasting steviol glycoside composition (see Table 1). These 30 plants were obtained through three different parental groups of crossing (FIGS. 11, 12, and 13) and hence, contain the best genetic materials for putative SNPs verification. A total of 48 pairs of SNPs primers were designed using primer 3 software and synthesized by Integrated DNA Technologies (IDT; Coralville, IA).

DNA was extracted (step 208) from the frozen leaves of 30 different *Stevia* plants with contrasting glycosides composition (see Table 1) using DNeasy Plant Mini kit (Qiagen, Germany) or Nucleospin Plant II kit (Macherey-Nagel). Extracted DNA quantity were measured using Fluorescence dsDNA Assay and quality were analyzed using agarose gel 1% (75 Volt, 60 minutes). Good quality DNA with a concentration around 10 ng was selected for PCR amplification using each SNP primer set (step 210).

PCR (step 210) was performed using the following 34 cycle protocol: an initial three minute denaturation at 94° C., with subsequent cycles having a denaturation of 30 seconds at 94° C.; annealing at 55° C. for 30 seconds; and an extension at 72° C. for one minute, with a final extension of ten minutes.

The PCR products obtained were run on 1.5% agarose gel (60 min, 75 volt) to check the specificity of the amplified products. The amplification products were purified and sequenced with an automatic ABI 3730 sequencer. SNP locations were analyzed across these 30 samples using Sequence Scanner v1.0 (Applied Biosystems) software (step 212) and sequencing verification indicated only eight SNPs (SNP2, SNP10, SNP12, SNP17, SNP19, SNP20, SNP22 & SNP24) are real SNP markers for high RebD and RebM identification (step 214). The PCR primers and product length in base pairs (bp) for each of the eight SNPs, as well as their location, is shown in Table 3.

TABLE 3

SNP locus and primers

| SNP | Forward primer | Reverse primer | Product Length (bp) and SEQ ID NO | SNP location |
|---|---|---|---|---|
| SNP2 | SEQ ID No: 117 | SEQ ID No: 118 | 481 bp SEQ ID NO: 1 | G to C at 225 |
| SNP10 | SEQ ID No: 119 | SEQ ID No: 120 | 359 bp SEQ ID NO: 2 | G to A at 187 |
| SNP12 | SEQ ID No: 121 | SEQ ID No: 122 | 681 bp SEQ ID NO: 3 | C to T at 345 |
| SNP17 | SEQ ID No: 123 | SEQ ID No: 124 | 285 bp SEQ ID NO: 4 | A to C at 129 |
| SNP19 | SEQ ID No: 125 | SEQ ID No: 126 | 396 bp SEQ ID NO: 5 | A to T at 173 |
| SNP20 | SEQ ID No: 127 | SEQ ID No: 128 | 500 bp SEQ ID NO: 6 | G to A at 221 |
| SNP22 | SEQ ID No: 129 | SEQ ID No: 130 | 486 bp SEQ ID NO: 7 | T to G at 160 |
| SNP24 | SEQ ID No: 131 | SEQ ID No: 132 | 500 bp SEQ ID NO: 8 | G to A at 325 |

As shown in FIG. 3, the genomic region containing SNP2 (SEQ ID NO:1) has been amplified using the primer sequences referenced above in Table 3. The PCR product is shown as 481 base pair length bands on the gel electrophoresis image, and the G to C SNP at base pair location 225 is underlined in the sequence below the gel image.

As shown in the data of Table 4 and in FIG. 3, any *Stevia* plants with high Stev and high RebA can be either homozygous dominant GG alleles or heterozygous GC alleles. Allele G is dominant to allele C and allele C is recessive to allele G. Any *Stevia* plants with this homozygous dominant GG allele combination are stable for high Stev and RebA variety. Since allele G is dominant to allele C, any individuals with GC genotype can be of high Stev or high RebA variety as the dominant allele G masks the effect of recessive allele C. Allele assortment among those high Stev and high RebA varieties or progeny after several generations results in the generation of progeny with recessive CC alleles (corresponding to SNP2). Any progeny with this CC genotype will be identified as high RebD and RebM lines.

As shown in FIG. 4, the genomic region containing SNP10 (SEQ ID NO:2) has been amplified using the primer sequences referenced above in Table 3. The PCR product is shown as 359 base pair length bands on the gel electrophoresis image, and the G to A SNP at base pair location 187 is underlined in the sequence below the gel image.

As shown in the data of Table 4 and in FIG. 4, any *Stevia* plants with high Stev and high RebA can be either homozygous dominant GG alleles or heterozygous AG alleles. Allele G is dominant to allele A and allele A is recessive to allele G. Any *Stevia* plants with this homozygous dominant GG allele combination are stable for high Stev and RebA variety. Since allele G is dominant to allele A, any individuals with AG genotype can be of high Stev or high RebA variety as the dominant allele G masks the effect of recessive allele A. Allele assortment among those high Stev and high RebA varieties or progeny after several generations results in the generation of progeny with recessive AA alleles (corresponding to SNP10). Any progeny with this AA genotype will be identified as high RebD and RebM lines.

As shown in FIG. 5, the genomic region containing SNP12 (SEQ ID NO:3) has been amplified using the primer sequences referenced above in Table 3. The PCR product is shown as 681 base pair length bands on the gel electrophoresis image, and the C to T SNP at base pair location 345 is underlined in the sequence below the gel image.

As shown in the data of Table 4 and in FIG. 5, any *Stevia* plants with high Stev and high RebA can be either homozygous dominant CC alleles or heterozygous CT alleles. Allele C is dominant to allele T and allele T is recessive to allele C. Any *Stevia* plants with this homozygous dominant CC allele combination are stable for high Stev and RebA variety. Since allele C is dominant to allele T, any individuals with CT genotype can be of high Stev or high RebA variety as the dominant allele C masks the effect of recessive allele T. Allele assortment among those high Stev and high RebA varieties or progeny after several generations results in the generation of progeny with recessive TT alleles (corresponding to SNP12). Any progeny with this TT genotype will be identified as high RebD and RebM lines.

As shown in FIG. 6, the genomic region containing SNP17 (SEQ ID NO:4) has been amplified using the primer sequences referenced above in Table 3. The PCR product is shown as 285 base pair length bands on the gel electrophoresis image, and the A to C SNP at base pair location 129 is underlined in the sequence below the gel image.

As shown in the data of Table 4 and in FIG. 6, any *Stevia* plants with high Stev and high RebA can be either homozygous dominant AA alleles or heterozygous AC alleles. Allele A is dominant to allele C and allele C is recessive to allele A. Any *Stevia* plants with this homozygous dominant AA allele combination are stable for high Stev and RebA variety. Since allele A is dominant to allele C, any individuals with AC genotype can be of high Stev or high RebA variety as the dominant allele A masks the effect of recessive allele C. Allele assortment among those high Stev and high RebA varieties or progeny after several generations results in the generation of progeny with recessive CC alleles (corresponding to SNP17). Any progeny with this CC genotype will be identified as high RebD and RebM lines.

As shown in FIG. 7, the genomic region containing SNP19 (SEQ ID NO:5) has been amplified using the primer sequences referenced above in Table 3. The PCR product is shown as 396 base pair length bands on the gel electrophoresis image, and the A to T SNP at base pair location 173 is underlined in the sequence below the gel image.

As shown in the data of Table 4 and in FIG. 7, any *Stevia* plants with high Stev and high RebA can be either homozygous dominant AA alleles or heterozygous AT alleles. Allele A is dominant to allele T and allele T is recessive to allele A. Any *Stevia* plants with this homozygous dominant AA allele combination are stable for high Stev and RebA variety. Since allele A is dominant to allele T, any individuals with AT genotype can be of high Stev or high RebA variety as the dominant allele A masks the effect of recessive allele T. Allele assortment among those high Stev and high RebA varieties or progeny after several generations results in the generation of progeny with recessive TT alleles (corresponding to SNP19). Any progeny with this TT genotype will be identified as high RebD and RebM lines.

As shown in FIG. 8, the genomic region containing SNP20 (SEQ ID NO:6) has been amplified using the primer sequences referenced above in Table 3. The PCR product is shown as 500 base pair length bands on the gel electrophoresis image, and the G to A SNP at base pair location 221 is underlined in the sequence below the gel image.

As shown in the data of Table 4 and in FIG. 8, any *Stevia* plants with high Stev and high RebA can be either homozygous dominant GG alleles or heterozygous GA alleles. Allele G is dominant to allele A and allele A is recessive to allele G. Any *Stevia* plants with this homozygous dominant GG allele combination are stable for high Stev and RebA variety. Since allele G is dominant to allele A, any individuals with GA genotype can be of high Stev or high RebA variety as the dominant allele G masks the effect of recessive allele A. Allele assortment among those high Stev and high RebA varieties or progeny after several generations results in the generation of progeny with recessive AA alleles (corresponding to SNP20). Any progeny with this AA genotype will be identified as high RebD and RebM lines.

As shown in FIG. 9, the genomic region containing SNP22 (SEQ ID NO:7) has been amplified using the primer sequences referenced above in Table 3. The PCR product is shown as 486 base pair length bands on the gel electrophoresis image, and the T to G SNP at base pair location 160 is underlined in the sequence below the gel image.

As shown in the data of Table 4 and in FIG. 9, any *Stevia* plants with high Stev and high RebA can be either homozygous dominant TT alleles or heterozygous TG alleles. Allele T is dominant to allele G and allele G is recessive to allele T. Any *Stevia* plants with this homozygous dominant TT allele combination are stable for high Stev and RebA variety. Since allele T is dominant to allele G, any individuals with TG genotype can be of high Stev or high RebA variety as the dominant allele T masks the effect of recessive allele G. Allele assortment among those high Stev and high RebA varieties or progeny after several generations results in the generation of progeny with recessive GG alleles (corresponding to SNP22). Any progeny with this GG genotype will be identified as high RebD and RebM lines.

As shown in FIG. 10, the genomic region containing SNP24 (SEQ ID NO:8) has been amplified using the primer sequences referenced above in Table 3. The PCR product is shown as 500 base pair length bands on the gel electrophoresis image, and the G to A SNP at base pair location 325 is underlined in the sequence below the gel image.

As shown in the data of Table 4 and in FIG. 10, any *Stevia* plants with high Stev and high RebA can be either homozygous dominant GG alleles or heterozygous GA alleles. Allele G is dominant to allele A and allele A is recessive to allele G. Any *Stevia* plants with this homozygous dominant GG allele combination are stable for high Stev and RebA variety. Since allele G is dominant to allele A, any individuals with GA genotype can be of high Stev or high RebA variety as the dominant allele G masks the effect of recessive allele A. Allele assortment among those high Stev and high RebA varieties or progeny after several generations results in the generation of progeny with recessive AA alleles (corresponding to SNP24). Any progeny with this AA genotype will be identified as high RebD and RebM lines.

As shown in FIGS. 3 through 10, and summarized below in Table 4, *Stevia* varieties with high content of RebD and RebM have SNP2 (CC genotype), SNP10 (AA genotype), SNP12 (TT genotype), SNP17 (CC genotype), SNP19 (TT genotype), SNP20 (AA genotype), SNP22 (GG genotype), and SNP24 (AA genotype).

TABLE 4

SNP markers and genotypes

| SNPs markers | Samples identification using Sanger Sequencer (first generation) and Illumina HiSeq 2000 Sequencer (second generation) | |
|---|---|---|
| | RebD, RebM lines | Stevioside, RebA lines |
| SNP2 | CC genotype | GG or GC genotype |
| SNP10 | AA genotype | GG or GA genotype |
| SNP12 | TT genotype | CC or CT genotype |
| SNP17 | CC genotype | AA or AC genotype |
| SNP19 | TT genotype | AA or AT genotype |
| SNP20 | AA genotype | GG or AG genotype |
| SNP22 | GG genotype | TT or TG genotype |
| SNP24 | AA genotype | GG or GA genotype |

One embodiment of the instant application discloses a *Stevia* plant comprising the following single nucleotide polymorphisms (SNPs), wherein said SNPs are found in homozygous form: SNP2, which comprises a G to C nucleotide substitution at position number 225 in SEQ ID NO:1, SNP10, which comprises a G to A nucleotide substitution at position number 187 in SEQ ID NO:2, SNP12, which comprises an C to T nucleotide exchange at position number 345 in SEQ ID NO:3, SNP17, which comprises an A to C nucleotide substitution at position number 129 in SEQ ID NO:4, SNP19, which comprises an A to T nucleotide substitution at position number 173 in SEQ ID NO:5, SNP20, which comprises a G to A nucleotide substitution at position number 221 in SEQ ID NO:6, SNP22, which comprises a T to G nucleotide substitution at position number 160 in SEQ ID NO:7, and SNP24, which comprises a G to A nucleotide substitution at position number 325 in SEQ ID NO:8.

Another embodiment discloses a *Stevia* plant, wherein the leaves of said *Stevia* plant have a RebD content of between 0.6% and 3.3% of dry weight.

Another embodiment discloses a *Stevia* plant, wherein the leaves of said *Stevia* plant have a RebM content of between 0.5% and 1.15% of dry weight.

Another embodiment discloses a *Stevia* plant, wherein the leaves of said *Stevia* plant have a RebD content of between 0.6% and 3.3% of dry weight and a RebM content of between 0.5% and 1.15% of dry weight.

Another embodiment discloses a method for producing a high RebD and high RebM *Stevia* plant comprising: (a) screening a population of *Stevia* plants for at least one of the following SNPs: SNP2, which comprises a G to C nucleotide substitution at position number 225 in SEQ ID NO:1, SNP10, which comprises a G to A nucleotide substitution at position number 187 in SEQ ID NO:2, SNP12, which comprises an C to T nucleotide exchange at position number 345 in SEQ ID NO:3, SNP17, which comprises an A to C nucleotide substitution at position number 129 in SEQ ID NO:4, SNP19, which comprises an A to T nucleotide substitution at position number 173 in SEQ ID NO:5, SNP20, which comprises a G to A nucleotide substitution at position number 221 in SEQ ID NO:6, SNP22, which comprises a T to G nucleotide substitution at position number 160 in SEQ ID NO:7, and SNP24, which comprises a G to A nucleotide substitution at position number 325 in SEQ ID NO:8; (b) selecting a first *Stevia* plant having at least one SNP; (c) crossing the first selected *Stevia* plant having at least one SNP with a second *Stevia* plant having at least one SNP; (d) repeating steps (b) and (c) to obtain *Stevia* plants homozygous for all the SNPs; and (e) screening the *Stevia* plants homozygous for all the SNPs to confirm the presence of all the SNPs in homozygous form to produce a *Stevia* plant, wherein the leaves of the *Stevia* plant have a high RebD content, high RebM content, or a high RebD and high RebM content.

Another embodiment provided herein discloses a *Stevia* plant produced by the breeding method above, wherein the RebD content of the leaves is at least 0.6% of dry weight.

Another embodiment provided herein discloses a *Stevia* plant produced by the breeding method above, wherein the RebM content of the leaves is at least 0.5% of dry weight.

Another embodiment provided herein discloses a *Stevia* plant produced by the breeding method above, wherein the RebD content of the leaves is at least 0.6% of dry weight and wherein the RebM content of the leaves is at least 0.5% of dry weight.

Another embodiment provided herein discloses a method of screening *Stevia* varieties comprising a PCR reaction followed by DNA sequencing, wherein the PCR reaction uses at least one of the following primer sequences: SEQ ID NO:117, SEQ, SEQ ID NO:118, SEQ ID NO:119, SEQ ID No:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:133, SEQ ID NO:134, SEQ ID NO:135, SEQ ID NO:136, SEQ ID NO:137, and SEQ ID NO:138.

UGT76G1 and UGT91D2 Isoforms Discovery from Transcriptome Sequencing of High RebD and RebM Varieties Several key UDP-glucosyltransferases (UGTs) are reported to play an important role in the biosynthesis of various steviol glycosides. For instance, UGT76G1 catalyzes the 1-3 β-glycosylation of C-13-O glucose of *Stevia* which results in RebA production. UGT91D2 catalyzes the conversion of RebA to RebD. From RebD, UGT76G1 catalyzes the conversion to RebM. Research by the Applicant has shown that UGT76G1 plays an important role in conversion of Stev to RebA and RebD to RebM. UGT91D2 was reported to convert RebA into RebD.

RNA-Seq (transcriptome sequencing) was employed to discover the various UGT76G1 and UGT91D2 isoforms belonging to high RebD and RebM *Stevia rebaudiana* leaves. Total RNA was isolated from the leaves of '814011', '807086' and '817096'. Messenger RNA were isolated and cDNA libraries were synthesized. Two extraction methods, Trizol or MRIP buffer was used to produce good quality and yield of RNA. Extracted RNA was check using NanoDrop 2000 (Thermo Fisher Scientific Inc., USA), Qubit 2.0 RNA Broad Range Assay (Invitrogen, USA) and Agilent Bioanalyzer RNA Nano chip. RNA samples with RIN 7 and above were selected for library preparation. Messenger RNA isolation and cDNA synthesis was conducted using TruSeq RNA Sample Preparation Kit (Illumina, USA) and SuperScript II Reverse Transcriptase (Invitrogen, USA) according to the manufacturer's protocol. The synthesized cDNA was quantified using Qubit 2.0 DNA Broad Range Assay (Invitrogen, USA). A minimum 20 ng of cDNA was fragmented using Covaris 5220 (Covaris Inc, USA) to a targeted size of 200 to 300 base pairs. The fragmented cDNA were then end-repaired, ligated to Illumina TruSeq adapters, and PCR-enriched using TruSeq RNA Sample Preparation Kit (Illumina, USA) according to manufacturer's protocol. The final sequencing libraries were quantified using KAPA kits (KAPA Biosystem, USA) on Agilent Stratagene Mx-3005p quantitative PCR (Agilent, USA) and sizes were confirmed using Agilent Bioanalyzer High Sensitivity DNA Chips (Agilent, USA). Resulting sequencing libraries were sequenced using an Illumina flow cell, and 209 cycles on the Illumina HiSeq 2000 platform (Illumina, USA). The sequencing run generated a total of 128 GB of raw data. Sequences obtained were searched for identity using NCBI (National Centre of Biotechnological Information) BLAST® analysis tool.

Bioinformatics pipeline analysis reveal there are 5 different UGT76G1 isoforms and 31 different UGT91D2 isoforms. Multiple sequence alignment using CLUSTAL W (1.83) software revealed the isolated UGT76G1 and UGT91D2 isoforms are of various lengths and were differentiated among each other by sequence insertion, deletion and mutation. Single Nucleotide Polymorphism (SNPs) and alternative splicing play an important role in generating these variants. Similar isoforms family are identical (99%) across various investigated lines.

For UGT76G1, a total of 5 main isoform families were isolated from each RebD ('817096') and RebM lines ('807086', '814011'). For '814011' these correspond to SEQ ID NO: 9, SEQ ID NO: 10, SEQ ID NO: 11, SEQ ID NO: 12, and SEQ ID NO: 13. For '807086' these correspond to SEQ ID NO: 14, SEQ ID NO: 15, SEQ ID NO: 16, SEQ ID NO: 17, and SEQ ID NO: 18. For '817096' these correspond to SEQ ID NO: 19, SEQ ID NO: 20, SEQ ID NO: 21, SEQ ID NO: 22, and SEQ ID NO: 23.

Multiple sequence alignment of the 5 main UGT76G1 isoforms obtained from '814011' (FIG. 14) revealed that these 5 main different isoforms are differentiated by sequence deletion, insertion and mutation. However, multiple sequence alignments of each of these same isoforms across '814011', '807086' and '817096' (FIG. 15 through FIG. 19) indicated only SNPs play a fundamental role in differentiating this isoforms. FIG. 15 shows the sequence alignment of UGT76G1 isoform sequences SEQ ID NO: 9, SEQ ID NO: 14, and SEQ ID NO: 19 (sequences labelled 1, 2, and 3, respectfully). FIG. 16 shows the sequence alignment of UGT76G1 isoform sequences SEQ ID NO: 10, SEQ ID NO: 15, and SEQ ID NO: 20 (sequences labelled 1, 2, and 3, respectfully). FIG. 17 shows the sequence alignment of UGT76G1 isoform sequences SEQ ID NO: 11, SEQ ID NO: 16, and SEQ ID NO: 21 (sequences labelled 1, 2, and 3, respectfully). FIG. 18 shows the sequence alignment of UGT76G1 isoform sequences SEQ ID NO: 12, SEQ ID NO: 17, and SEQ ID NO: 22 (sequences labelled 1, 2, and 3, respectfully). FIG. 19 shows the sequence alignment of UGT76G1 isoform sequences SEQ ID NO: 13, SEQ ID NO: 18, and SEQ ID NO: 23 (sequences labelled 1, 2, and 3, respectfully).

For UGT91D2, 31 main isoforms were isolated from each RebD ('817096') and RebM lines ('807086', '814011'). For Stevia variety '817096' these isoforms correspond to SEQ ID NOs: 24-54. For Stevia variety '807086' these isoforms correspond to SEQ ID NOs: 55-85. For Stevia variety '814011' these isoforms correspond to SEQ ID NOs: 86-116. A multiple sequence alignment of the 31 isoforms obtained from '817096' revealed some of these different isoforms are differentiated by sequence deletion, insertion and mutation (SNPs) (FIG. 20, SEQ ID NO's: 24-54 are labelled 1-31, respectively). However, multiple sequence alignment of each of these same isoforms across '814011', '807086' and '817096' indicated only SNPs play a fundamental roles in differentiating this isoforms (FIG. 21, alignment of SEQ ID NO: 24 from '817096', SEQ ID NO: 55 from '807086', and SEQ ID NO: 86 from '814011').

These UGT isoforms show variation to those known in public database (National Centre for Biotechnology Information). They are specific to high RebD and RebM lines. UGT isoforms sequences undergo some alternative splicing due to genome rearrangement after many generation of crossings of parental lines. UGT isoforms sequence also have some mutations in the respective nucleotides compare to published sequence.

Thus, another embodiment of the present disclosure is a Stevia plant further comprising isoforms of UDP-glucosyltransferase 76G1 (UGT76G1), wherein the isoforms correspond to SEQ ID NOs: 19-23, and wherein the Stevia plant further comprises isoforms of UDP-glucosyltransferase 91D2 (UGT91D2), wherein the isoforms correspond to SEQ ID NOs: 24-54, and wherein the Stevia plant has high RebD content.

Another embodiment discloses a Stevia plant further comprising isoforms of UDP-glucosyltransferase 76G1 (UGT76G1), wherein the isoforms correspond to SEQ ID NOs: 9-13, and wherein the Stevia plant further comprises isoforms of UDP-glucosyltransferase 91D2 (UGT91D2), wherein the isoforms correspond to SEQ ID NOs: 86-116, and wherein the Stevia plant has high RebM content.

Another embodiment discloses a Stevia plant further comprising isoforms of UDP-glucosyltransferase 76G1 (UGT76G1), wherein the isoforms correspond to SEQ ID NOs: 14-18, and wherein the Stevia plant further comprises isoforms of UDP-glucosyltransferase 91D2 (UGT91D2), wherein the isoforms correspond to SEQ ID NOs: 55-85, and wherein the Stevia plant has high RebM content.

Another embodiment discloses a Stevia plant further comprising isoforms of UDP-glucosyltransferase 76G1 (UGT76G1), wherein the isoforms correspond to SEQ ID NOs: 9-13, and wherein the Stevia plant further comprises isoforms of UDP-glucosyltransferase 91D2 (UGT91D2), wherein the isoforms correspond to SEQ ID NOs: 86-116, and wherein the Stevia plant has high RebD content.

Another embodiment discloses a Stevia plant further comprising isoforms of UDP-glucosyltransferase 76G1 (UGT76G1), wherein the isoforms correspond to SEQ ID NOs: 14-18, and wherein the Stevia plant further comprises isoforms of UDP-glucosyltransferase 91D2 (UGT91D2), wherein the isoforms correspond to SEQ ID NOs: 55-85, and wherein the Stevia plant has high RebD content.

Another embodiment discloses a method of producing a commodity plant product, comprising obtaining a plant having SNP2, SNP10, SNP12, SNP17, SNP19, SNP20, SNP22, and SNP24, or a part thereof, and producing the commodity plant product from the plant or part thereof, wherein the commodity plant product is a composition of glycosides.

EXAMPLES

The following examples are provided to illustrate further the various applications and are not intended to limit the invention beyond the limitations set forth in the appended claims.

Example 1—SNP17, SNP19, and SNP20 Successfully Predict High RebD and RebM Content Using probe based genotyping, SNP probes for SNP17, SNP19, and SNP20 were designed and used to screen 38 lines from different genetic backgrounds in 2014 and across 1,000 additional lines in 2015. Probes were designed and synthesized by Integrated DNA Technologies (IDT; Coralville, IA). Probes consisted of a fluorescent reporter attached to the 5' end and a non-fluorescent (quencher) attached to the 3' end (Table 5A). Primer sequences are referenced in Table 5B.

TABLE 5A

Probe designs for SNP17, SNP19, and SNP20 genotyping

| Probe | Probe allele | Probe sequence |
|---|---|---|
| SNP17 | SNP17-A | 5HEX/TGA + T + A + A + GAT + G + GCT/3IABkFQ |
|  | SNP17-C | 56-FAM/TGA + T + A + C + GAT + GGCT/3IABkFQ |
| SNP19 | SNP19-A | 56-FAM/TC + G + GT + T + A + GT + CTC/3IABkFQ |
|  | SNP19-T | 5HEX/TC + G + GT + T + T + G T + CT C/3IABkFQ |
| SNP20 | SNP20-A | 56-FAM/AA + CA + A + C + C + C + TAA C/3IABkFQ |
|  | SNP20-G | 5HEX/AC + A + A + G + CC + C + T + AAC/3IABkFQ |

TABLE 5B

Primer designs for SNP17, SNP19, and SNP20 genotyping

| Primers | Primer | Probe sequence |
|---|---|---|
| SNP17 | SNP17-Forward | SEQ ID NO: 133 |
|  | SNP17-Reverse | SEQ ID NO: 134 |
| SNP19 | SNP19-Forward | SEQ ID NO: 135 |
|  | SNP19-Reverse | SEQ ID NO: 136 |
| SNP20 | SNP20-Forward | SEQ ID NO: 137 |
|  | SNP20-Reverse | SEQ ID NO: 138 |

DNA was extracted from the frozen leaves of 1,000 different *Stevia* plants with contrasting glycoside compositions using DNeasy Plant Mini kit (Qiagen, Germany). Extracted DNA quantity were analyzed using agarose gel 1% (75 Volt, 60 minutes). Good quality DNA with a concentration around 2 ng was selected for genotyping using each SNP primer and probe set.

Genotyping was performed using the following 45 cycle protocol: (a) an initial 5 minute denaturation at 95° C., with subsequent cycles having a denaturation of 15 seconds at 95° C.; (b) annealing/extension at 60° C. for 30 seconds in Rotor-Gene Q 5 plex HRM system (Qiagen, Germany). For each reaction, the following were used: 10 µl of Type-it Fast SNP Probe PCR Master Mix, 2×; 1 µl of 20× primer-probe mix, 1 µl of genomic DNA and the volume was added with dH$_2$O until it reach 20 µl. Scatter graph analysis was performed using Rotor-Gene Q Series Software to group all the homozygous dominant, homozygous recessive and heterozygous lines.

From these 1,000 *Stevia* lines, 120 plants were randomly selected for HPLC analysis, along with the 38 lines from 2014 (Table 6). Based on the presence or absence of these SNPs, plants were predicted to be in one of two groups, either high RebA and/or high Stev, or high RebD and/or high RebM. Following HPLC analysis plants were assigned to one of the following groups based on steviol glycoside content: ST, RA, ST/RA, RD, RM, RD/RM (column 2, Table 6).

The plants were analyzed for rebaudioside content by HPLC as described above and the percent content for rebaudioside for each variety is shown in columns 3 through 15 of Table 6. Column 1 of Table 6 shows the variety, and column 2 of Table 6 shows the group based on steviol glycoside content. High RebD lines are defined as having a RebD content that is ≥0.6% and a RebD/TSG≥8%. High RebM lines are defined as having a RebM content that is ≥0.5%. High RebA lines are defined as having a RebA content that is ≥9%, a RebD content that is ≤0.3%, and a RebM content of ≤0.2%. High Stev lines are defined as having a Stev content of ≥7%, a RebD content of ≤0.3%, and a RebM content of ≤0.2%. Columns labelled RD and RM are in bold. Deposited varieties '817096', '814011', and '807086' are bolded and underlined. RE=rebaudioside E, RO=rebaudioside O, RD=RebD, RN=rebaudioside N, RM=RebM, RA=rebaudioside A, ST=stevioside, RF=rebaudioside F, RC=rebaudioside C, DA=Dulcoside A, RU=rebaudioside U, RB=rebaudioside B, and SB=Steviolbioside. ND=Not Determined.

TABLE 6

SNP genotyping predicts high RebD and RebM content

| Variety | Group | RE | RO | RD | RN | RM | RA | ST | RF | RC | DA | RU | RB | SB |
|---|---|---|---|---|---|---|---|---|---|---|---|---|---|---|
| 412-31 | ST | ND | ND | 0.08 | ND | ND | 0.13 | 8.57 | ND | 0.02 | 0.44 | ND | ND | ND |
| 43-2 | ST | ND | ND | 0.00 | ND | ND | 0.28 | 7.87 | 0.01 | 0.12 | 0.53 | ND | ND | ND |
| 49-58 | ST | ND | ND | 0.02 | ND | ND | 0.43 | 11.36 | ND | 0.02 | 0.05 | ND | ND | ND |
| 805028 | ST | ND | ND | 0.02 | ND | ND | 0.18 | 9.58 | 0.01 | 0.02 | 0.81 | ND | ND | ND |
| 805003 | ST | ND | ND | 0.04 | ND | ND | 0.10 | 10.13 | 0.01 | 0.01 | 1.05 | ND | ND | ND |
| 803066 | ST | ND | ND | 0.01 | ND | ND | 0.26 | 10.03 | 0.02 | 0.03 | 0.93 | ND | ND | ND |
| 813057 | RA | ND | ND | 0.15 | ND | ND | 12.29 | 0.54 | 0.21 | 0.99 | ND | ND | ND | ND |
| 812051 | RA | ND | ND | 0.17 | ND | ND | 11.44 | 0.56 | 0.28 | 0.91 | 0.01 | ND | ND | ND |
| 805068 | RA | ND | ND | 0.10 | ND | ND | 12.32 | 1.09 | 0.06 | 0.83 | ND | ND | ND | ND |
| 815034 | RA | ND | ND | 0.20 | ND | ND | 9.51 | 0.69 | 0.25 | 0.77 | ND | ND | ND | ND |
| 802057 | RA | ND | ND | 0.17 | ND | ND | 11.55 | 0.56 | 0.32 | 1.06 | ND | ND | ND | ND |
| 817075 | RA | ND | ND | 0.19 | ND | ND | 10.68 | 0.56 | 0.08 | 0.51 | ND | ND | ND | ND |
| PC star | RA/ST | ND | ND | 0.22 | ND | ND | 7.89 | 0.91 | 0.15 | 1.42 | 0.18 | 0.05 | ND | ND |
| PC1 | RA/ST | ND | ND | 0.13 | ND | ND | 5.83 | 1.82 | 0.17 | 0.74 | 0.03 | 0.05 | 0.15 | 0.07 |
| M3 | RA | ND | ND | 0.22 | ND | ND | 9.03 | 0.99 | 0.17 | 1.02 | 0.02 | 0.02 | ND | 0.06 |
| Hybrid | RA/ST | ND | ND | 0.16 | ND | ND | 6.81 | 3.77 | 0.21 | 0.96 | 0.06 | 0.04 | 0.04 | 0.03 |
| 805126 | RA | ND | ND | 0.25 | ND | ND | 10.77 | 0.45 | 0.07 | 0.63 | ND | ND | ND | ND |
| 805082 | RA | ND | ND | 0.18 | ND | ND | 10.78 | 0.65 | 0.07 | 0.54 | ND | ND | ND | ND |
| 803065 | RD/RM | ND | ND | 0.63 | ND | 0.00 | 4.13 | 0.72 | 0.10 | 0.42 | 1.00 | ND | ND | ND |
| 807086 | RD/RM | 0.04 | 0.90 | 1.55 | 0.36 | 1.00 | 4.15 | 0.21 | 0.08 | 0.32 | 0.00 | ND | ND | ND |
| 814011 | RD/RM | 0.07 | 0.88 | 1.11 | 0.24 | 1.12 | 8.45 | 0.38 | 0.21 | 0.76 | 0.02 | ND | ND | ND |

TABLE 6-continued

SNP genotyping predicts high RebD and RebM content

| Variety | Group | RE | RO | RD | RN | RM | RA | ST | RF | RC | DA | RU | RB | SB |
|---|---|---|---|---|---|---|---|---|---|---|---|---|---|---|
| 817096 | RD | 1.60 | 0.64 | 3.28 | 0.63 | 0.38 | 2.35 | 2.06 | 0.10 | 0.50 | 0.05 | ND | ND | ND |
| 806034 | RD | ND | ND | 0.62 | ND | ND | 3.71 | 0.21 | 0.09 | 0.25 | ND | ND | ND | ND |
| 830098 | RD | ND | ND | 1.03 | ND | ND | 5.51 | 0.41 | 0.12 | 0.53 | ND | ND | ND | ND |
| 803071 | RD | ND | ND | 0.70 | ND | ND | 4.30 | 0.44 | 0.11 | 0.48 | ND | ND | ND | ND |
| 805061 | RD | ND | ND | 1.07 | ND | ND | 4.32 | 0.42 | 0.04 | 0.09 | 0.02 | ND | ND | ND |
| 813081 | RD | ND | ND | 0.62 | ND | ND | 4.54 | 0.30 | 0.11 | 0.31 | 0.01 | ND | ND | ND |
| 806058 | RD | ND | ND | 0.83 | ND | ND | 5.32 | 0.42 | 0.13 | 0.38 | 0.02 | ND | ND | ND |
| 810103 | RD | ND | ND | 0.95 | ND | ND | 4.52 | 0.28 | 0.15 | 0.46 | ND | ND | ND | ND |
| 801094 | RD | ND | ND | 1.62 | ND | 0.25 | 5.41 | 0.63 | 0.09 | 0.62 | ND | ND | ND | ND |
| 804075 | RD | ND | ND | 0.97 | ND | 0.24 | 4.35 | 0.57 | 0.16 | 0.41 | ND | ND | ND | ND |
| 804038 | RD | ND | ND | 2.23 | ND | 0.48 | 3.42 | 0.66 | 0.05 | 0.35 | ND | ND | ND | ND |
| 801105 | RD | ND | ND | 1.14 | ND | 0.38 | 7.13 | 0.33 | 0.16 | 0.55 | ND | ND | ND | ND |
| 816055 | RD | ND | ND | 0.89 | ND | 0.31 | 6.94 | 0.26 | 0.10 | 0.47 | 0.01 | ND | ND | ND |
| 10-43 | RD/RM | ND | ND | 1.59 | ND | 0.68 | 6.81 | 1.11 | 0.16 | 0.89 | ND | 0.18 | ND | ND |
| 10-43-3 | RD/RM | ND | ND | 2.55 | ND | 0.81 | 5.73 | 0.93 | 0.13 | 0.67 | ND | 0.02 | 0.14 | 0.03 |
| 21-11 | RD | ND | ND | 0.66 | ND | 0.29 | 4.13 | 0.43 | 0.10 | 0.14 | ND | ND | 0.10 | 0.03 |
| 3-6 | RD/RM | ND | ND | 0.92 | ND | 0.63 | 6.40 | 0.22 | 0.14 | 0.26 | ND | ND | 0.11 | 0.04 |
| 15101060 | RA/ST | ND | ND | 0.59 | ND | ND | 8.88 | 1.86 | 0.18 | 0.93 | 0.01 | ND | 0.06 | 0.02 |
| 15103014 | RA/ST | 0.13 | 0.02 | 0.26 | 0.12 | 0.01 | 4.22 | 5.77 | 0.14 | 1.02 | 0.09 | 0.02 | 0.01 | 0.02 |
| 15103015 | ST | 0.38 | 0.01 | 0.01 | 0.01 | 0.00 | 0.07 | 7.13 | ND | 0.02 | 0.55 | 0.02 | ND | 0.02 |
| 15103018 | RA/ST | 0.30 | 0.02 | 0.67 | 0.23 | 0.03 | 5.43 | 5.59 | 0.15 | 0.94 | 0.06 | 0.01 | 0.02 | 0.03 |
| 15103025 | RA/ST | 0.08 | 0.01 | 0.23 | 0.11 | 0.05 | 6.00 | 2.98 | 0.13 | 0.83 | 0.02 | 0.01 | 0.01 | 0.01 |
| 15103045 | RA/ST | 0.08 | 0.10 | 0.32 | 0.12 | 0.08 | 5.51 | 2.40 | 0.12 | 0.73 | 0.02 | ND | 0.01 | ND |
| 15103052 | RA/ST | 0.18 | 0.01 | 0.25 | 0.13 | 0.05 | 4.14 | 4.22 | 0.12 | 0.73 | 0.05 | 0.01 | 0.02 | 0.01 |
| 15106002 | RA/ST | 0.19 | 0.10 | 0.77 | 0.26 | 0.06 | 5.72 | 4.28 | 0.14 | 0.83 | 0.04 | 0.01 | 0.01 | 0.02 |
| 15106018 | RA/ST | 0.13 | 0.09 | 0.50 | 0.16 | 0.12 | 7.57 | 1.87 | 0.16 | 0.85 | 0.02 | 0.01 | 0.02 | 0.01 |
| 15106021 | RA/ST | 0.07 | 0.72 | 0.34 | 0.12 | 0.11 | 8.59 | 1.84 | 0.14 | 1.00 | 0.02 | ND | ND | 0.01 |
| 15106038 | RA/ST | 0.21 | 0.19 | 0.44 | 0.13 | 0.11 | 1.74 | 2.54 | 0.06 | 0.34 | 0.05 | 0.01 | ND | 0.01 |
| 15106047 | RA/ST | 0.40 | 0.11 | 0.71 | 0.20 | 0.08 | 5.53 | 6.58 | 0.18 | 1.08 | 0.10 | 0.02 | 0.02 | 0.03 |
| 15106052 | RA | ND | ND | 0.93 | ND | 0.00 | 9.85 | 1.89 | 0.19 | 0.96 | 0.02 | ND | 0.06 | 0.02 |
| 15107001 | RA/ST | 0.28 | 0.15 | 0.35 | 0.10 | 0.13 | 8.79 | 3.66 | 0.19 | 1.12 | 0.02 | 0.02 | 0.02 | 0.01 |
| 15107005 | ST | 0.97 | 0.02 | 0.01 | ND | 0.01 | 0.13 | 9.82 | 0.00 | 0.02 | 0.70 | 0.02 | ND | 0.07 |
| 15108016 | RA/ST | 0.10 | 0.10 | 0.42 | 0.09 | 0.14 | 8.87 | 1.85 | 0.17 | 0.86 | 0.01 | 0.01 | 0.04 | ND |
| 15111055 | RA/ST | 0.07 | 0.10 | 0.56 | 0.30 | 0.17 | 7.99 | 2.10 | 0.13 | 0.90 | 0.01 | 0.13 | 0.07 | 0.01 |
| 15111074 | ST | 0.47 | 0.16 | 0.37 | 0.13 | 0.07 | 1.87 | 7.62 | 0.10 | 0.81 | 0.17 | 0.02 | 0.01 | 0.03 |
| 15111075 | RA | 0.08 | 0.33 | 0.54 | 0.19 | 0.16 | 9.65 | 2.09 | 0.20 | 1.07 | 0.01 | 0.06 | 0.06 | 0.01 |
| 15112004 | RA/ST | 0.13 | 0.16 | 0.67 | 0.18 | 0.16 | 6.97 | 1.76 | 0.14 | 0.79 | 0.01 | 0.01 | 0.01 | ND |
| 15112010 | RA/ST | 0.16 | 0.10 | 0.72 | 0.18 | 0.09 | 6.79 | 3.93 | 0.17 | 0.89 | 0.02 | 0.01 | 0.02 | 0.02 |
| 15112023 | RA | ND | ND | 0.75 | ND | 0.00 | 9.56 | 1.80 | 0.18 | 1.07 | 0.01 | ND | 0.08 | 0.02 |
| 15112046 | RA/ST | 0.10 | 0.49 | 0.51 | 0.15 | 0.18 | 8.31 | 1.13 | 0.14 | 0.77 | 0.01 | 0.01 | 0.02 | 0.00 |
| 15114004 | RA/ST | ND | ND | 0.50 | ND | 0.00 | 8.86 | 3.84 | 0.22 | 2.08 | 0.03 | 0.11 | 0.06 | 0.04 |
| 15114039 | RA | 0.31 | 0.16 | 0.58 | 0.17 | 0.22 | 10.80 | 1.91 | 0.21 | 1.10 | 0.01 | ND | 0.09 | 0.04 |
| 15115008 | RA | ND | ND | 0.36 | ND | 0.00 | 11.17 | 1.97 | 0.23 | 1.76 | 0.01 | 0.09 | 0.06 | 0.02 |
| 15101010 | ST | 0.48 | 0.12 | 0.53 | 0.11 | 0.00 | 2.33 | 8.79 | 0.11 | 1.03 | 0.33 | 0.07 | 0.03 | 0.10 |
| 15101015 | RA/ST | 0.13 | 0.11 | 0.79 | 0.26 | 0.02 | 5.44 | 3.21 | 0.14 | 0.96 | 0.03 | 0.11 | 0.05 | 0.08 |
| 15102028 | RA/ST | 0.12 | 0.02 | 0.43 | 0.07 | 0.01 | 4.92 | 3.06 | 0.14 | 0.85 | 0.03 | 0.07 | 0.04 | 0.04 |
| 15102057 | RA/ST | 0.11 | 0.02 | 0.34 | 0.09 | 0.05 | 6.86 | 2.03 | 0.17 | 0.85 | 0.02 | 0.04 | 0.04 | 0.04 |
| 15103021 | RA | 0.01 | 0.09 | 0.40 | 0.06 | 0.06 | 9.23 | 2.28 | 0.19 | 1.08 | 0.02 | 0.08 | 0.10 | 0.06 |
| 15103068 | RA | 0.01 | 0.06 | 0.46 | 0.15 | 0.06 | 9.04 | 1.62 | 0.18 | 1.13 | 0.01 | 0.07 | 0.10 | 0.06 |
| 15104003 | ST | 0.32 | 0.03 | 0.39 | 0.05 | 0.00 | 2.71 | 8.03 | 0.11 | 1.10 | 0.15 | 0.08 | 0.04 | 0.06 |
| 15104048 | RA/ST | 0.19 | 0.01 | 0.62 | 0.06 | 0.01 | 4.07 | 4.51 | 0.15 | 0.81 | 0.06 | 0.05 | 0.04 | 0.06 |
| 15105008 | RA/ST | 0.16 | 0.15 | 0.92 | 0.20 | 0.07 | 5.77 | 3.59 | 0.16 | 0.95 | 0.03 | 0.10 | 0.05 | 0.04 |
| 15105063 | RA/ST | 0.29 | 0.01 | 0.29 | 0.05 | 0.03 | 2.76 | 6.22 | 0.13 | 0.86 | 0.18 | 0.03 | 0.03 | 0.09 |
| 15106034 | RA/ST | 0.03 | ND | 0.31 | 0.06 | 0.03 | 5.63 | 1.81 | 0.15 | 0.73 | 0.01 | 0.06 | 0.04 | 0.02 |
| 15106067 | RA/ST | 0.02 | 0.16 | 0.68 | 0.19 | 0.08 | 8.33 | 2.11 | 0.18 | 1.00 | 0.01 | 0.08 | 0.06 | 0.03 |
| 15107013 | RA/ST | 0.15 | 0.03 | 0.48 | 0.13 | 0.02 | 3.42 | 4.50 | 0.12 | 0.83 | 0.09 | 0.07 | 0.04 | 0.05 |
| 15107054 | RA/ST | 0.04 | 0.01 | 0.39 | 0.05 | 0.05 | 6.55 | 2.45 | 0.18 | 0.87 | 0.03 | 0.04 | 0.06 | 0.04 |
| 15108012 | ST | 0.29 | 0.01 | 0.44 | 0.05 | 0.03 | 3.22 | 7.80 | 0.13 | 0.91 | 0.21 | 0.06 | 0.03 | 0.07 |
| 15108033 | RA/ST | 0.11 | 0.14 | 0.41 | 0.05 | 0.00 | 4.24 | 4.08 | 0.14 | 0.89 | 0.06 | 0.05 | 0.05 | 0.05 |
| 15109002 | ST | 0.29 | 0.06 | 0.36 | 0.19 | 0.01 | 3.00 | 7.53 | 0.12 | 1.13 | 0.14 | 0.07 | 0.02 | 0.07 |
| 15109008 | ST | 0.75 | 0.04 | 0.00 | 0.17 | 0.04 | 0.09 | 8.35 | 0.01 | 0.09 | 0.65 | 0.02 | ND | 0.08 |
| 15110059 | RA/ST | 0.23 | 0.01 | 0.60 | 0.20 | 0.00 | 4.24 | 3.58 | 0.14 | 0.82 | 0.04 | 0.02 | 0.03 | 0.05 |
| 15111007 | ST | 0.34 | 0.06 | 0.33 | 0.13 | 0.01 | 2.48 | 9.39 | 0.11 | 1.02 | 0.20 | 0.02 | 0.03 | 0.07 |
| 15111020 | RA/ST | 0.22 | 0.07 | 0.29 | 0.10 | 0.02 | 5.10 | 2.00 | 0.15 | 0.77 | 0.02 | 0.00 | 0.05 | 0.02 |
| 15112014 | RA/ST | 0.06 | 0.12 | 0.40 | 0.14 | 0.07 | 7.57 | 2.90 | 0.19 | 1.02 | 0.03 | 0.01 | 0.05 | 0.02 |
| 15112035 | RA/ST | 0.26 | 0.06 | 0.53 | 0.13 | 0.01 | 4.15 | 5.53 | 0.17 | 0.84 | 0.09 | 0.01 | 0.05 | 0.04 |
| 15113010 | RA/ST | 0.04 | 0.13 | 0.24 | 0.14 | 0.08 | 8.10 | 3.69 | 0.23 | 1.10 | 0.04 | 0.01 | 0.09 | 0.03 |
| 15113030 | RA/ST | 0.06 | 0.02 | 0.25 | 0.08 | 0.01 | 6.09 | 4.37 | 0.23 | 1.13 | 0.05 | 0.02 | 0.05 | 0.02 |
| 15114011 | RA/ST | 0.07 | 0.07 | 0.11 | 0.04 | 0.01 | 2.59 | 4.08 | 0.13 | 0.62 | 0.09 | 0.01 | 0.03 | 0.03 |
| 15114031 | ST | 0.71 | 0.03 | 0.01 | 0.01 | 0.01 | 0.07 | 7.43 | 0.01 | 0.05 | 0.48 | 0.02 | 0.00 | 0.04 |
| 15115017 | RA/ST | 0.12 | 0.14 | 0.82 | 0.33 | 0.06 | 6.52 | 3.59 | 0.17 | 1.05 | 0.04 | 0.01 | 0.06 | 0.02 |
| 15115037 | RA | 0.07 | 0.16 | 0.51 | 0.16 | 0.17 | 10.17 | 1.53 | 0.32 | 0.99 | 0.01 | 0.01 | 0.06 | 0.02 |
| 15101023 | RD | 0.66 | 0.60 | 3.01 | 0.65 | 0.31 | 2.71 | 1.06 | 0.08 | 0.33 | 0.01 | ND | 0.06 | 0.04 |
| 15101045 | RD | 0.67 | 0.08 | 2.23 | 0.75 | 0.16 | 2.07 | 1.32 | 0.08 | 0.33 | 0.01 | 0.01 | 0.06 | 0.07 |
| 15101057 | RD/RM | 0.17 | 0.34 | 1.83 | 0.46 | 0.50 | 4.15 | 0.50 | 0.12 | 0.32 | 0.01 | ND | 0.05 | 0.02 |
| 15102008 | RD | 0.42 | 0.05 | 2.27 | 0.84 | 0.25 | 2.64 | 1.04 | 0.07 | 0.29 | 0.01 | ND | 0.05 | 0.04 |

TABLE 6-continued

SNP genotyping predicts high RebD and RebM content

| Variety | Group | RE | RO | RD | RN | RM | RA | ST | RF | RC | DA | RU | RB | SB |
|---|---|---|---|---|---|---|---|---|---|---|---|---|---|---|
| 15102016 | RD | 0.08 | 0.30 | 1.05 | 0.37 | 0.35 | 4.15 | 0.38 | 0.07 | 0.34 | ND | ND | 0.04 | ND |
| 15102017 | RD | 0.07 | 0.33 | 0.62 | 0.36 | 0.36 | 3.02 | 0.39 | 0.05 | 0.27 | ND | 0.01 | 0.04 | 0.01 |
| 15102048 | RD | 0.06 | 0.87 | 1.09 | 0.42 | 0.30 | 4.09 | 0.39 | 0.08 | 0.33 | ND | 0.01 | 0.04 | ND |
| 15102049 | RD | 0.11 | 0.38 | 1.56 | 0.49 | 0.46 | 3.34 | 0.46 | 0.08 | 0.30 | ND | 0.03 | 0.03 | 0.01 |
| 15112062 | RD | 3.26 | 0.18 | 1.35 | 0.22 | 0.01 | 0.33 | 1.41 | 0.02 | 0.11 | 0.04 | 0.01 | 0.02 | 0.07 |
| 15102067 | RD | 1.08 | 0.01 | 1.23 | 0.36 | 0.03 | 0.79 | 2.31 | 0.03 | 0.26 | 0.03 | 0.01 | 0.01 | 0.06 |
| 15103002 | RD | 0.38 | 0.44 | 1.50 | 0.31 | 0.48 | 4.70 | 0.58 | 0.12 | 3.72 | ND | 0.25 | 0.09 | 0.06 |
| 15103003 | RD/RM | 0.40 | 0.51 | 1.75 | 0.38 | 0.52 | 3.50 | 0.31 | 0.09 | 1.78 | ND | 0.15 | 0.07 | 0.03 |
| 15103009 | RD | 0.63 | 0.39 | 2.42 | 0.45 | 0.24 | 2.38 | 0.99 | 0.07 | 0.29 | 0.01 | 0.01 | 0.04 | 0.03 |
| 15103010 | RD | 0.06 | 0.49 | 0.88 | 0.25 | 0.29 | 4.29 | 0.27 | 0.07 | 0.34 | ND | 0.00 | 0.04 | ND |
| 15104007 | RD | 0.27 | 0.31 | 0.94 | 0.25 | 0.41 | 3.76 | 0.39 | 0.10 | 3.13 | ND | 0.23 | 0.04 | 0.04 |
| 15104023 | RD | 0.33 | 0.37 | 1.11 | 0.27 | 0.38 | 3.34 | 0.33 | 0.09 | 1.70 | ND | 0.14 | 0.05 | 0.02 |
| 15104030 | RD | 0.51 | 0.07 | 2.59 | 0.98 | 0.31 | 1.96 | 0.95 | 0.05 | 0.29 | ND | ND | 0.04 | 0.03 |
| 15104054 | RD/RM | 0.49 | 0.46 | 1.95 | 0.51 | 0.51 | 3.99 | 0.46 | 0.10 | 1.29 | ND | 0.11 | 0.08 | 0.03 |
| 15104058 | RD | 0.10 | 0.21 | 0.71 | 0.24 | 0.28 | 4.14 | 0.48 | 0.08 | 0.35 | ND | 0.01 | 0.03 | ND |
| 15104059 | RD | 0.68 | 0.39 | 1.83 | 0.48 | 0.44 | 2.59 | 0.46 | 0.06 | 0.25 | ND | ND | 0.03 | 0.02 |
| 15104062 | RD | 0.45 | 0.69 | 2.06 | 0.53 | 0.30 | 3.33 | 1.20 | 0.08 | 0.40 | 0.01 | ND | 0.03 | 0.02 |
| 15105018 | RD | 0.92 | 0.37 | 2.52 | 0.51 | 0.16 | 2.17 | 1.08 | 0.08 | 0.28 | 0.01 | ND | 0.05 | 0.04 |
| 15105025 | RD | 0.11 | 0.43 | 1.71 | 0.43 | 0.47 | 3.81 | 0.52 | 0.09 | 0.37 | ND | ND | 0.07 | 0.02 |
| 15105031 | RD | 1.63 | 0.09 | 1.52 | 0.37 | 0.07 | 0.56 | 1.90 | 0.01 | 0.21 | 0.04 | ND | 0.02 | 0.06 |
| 15105048 | RD/RM | 0.04 | 0.52 | 1.51 | 0.43 | 0.58 | 4.95 | 0.50 | 0.10 | 0.43 | 0.01 | ND | 0.09 | 0.01 |
| 15105051 | RD | 0.07 | 0.28 | 1.05 | 0.27 | 0.39 | 2.93 | 0.28 | 0.06 | 0.23 | ND | 0.01 | 0.06 | 0.01 |
| 15105056 | RD | 0.04 | 0.38 | 1.23 | 0.35 | 0.43 | 3.75 | 0.52 | 0.07 | 0.33 | 0.01 | 0.01 | 0.06 | ND |
| 15105061 | RD | 1.18 | 0.54 | 2.98 | 0.59 | 0.27 | 2.39 | 1.55 | 0.08 | 0.34 | 0.01 | ND | 0.05 | 0.06 |
| 15105066 | RD | 0.38 | 0.42 | 1.26 | 0.29 | 0.43 | 4.14 | 0.29 | 0.10 | 2.27 | ND | 0.18 | 0.05 | 0.03 |
| 15106015 | RD | 0.44 | 0.31 | 1.03 | 0.25 | 0.31 | 3.64 | 0.38 | 0.09 | 2.64 | 0.00 | 0.21 | 0.05 | 0.04 |
| 15106017 | RD | 1.42 | 0.30 | 2.11 | 0.42 | 0.16 | 1.44 | 1.61 | 0.04 | 0.22 | 0.02 | 0.01 | 0.02 | 0.04 |
| 15106022 | RD | 0.35 | 0.38 | 1.65 | 0.37 | 0.20 | 2.29 | 0.97 | 0.06 | 0.30 | 0.01 | ND | 0.03 | 0.02 |
| 15106024 | RD | 1.31 | 0.15 | 1.86 | 0.52 | 0.11 | 1.17 | 1.75 | 0.03 | 0.30 | 0.02 | ND | 0.03 | 0.06 |
| 15106028 | RD/RM | 0.37 | 0.53 | 1.05 | 0.28 | 0.51 | 4.76 | 0.39 | 0.10 | 0.41 | ND | 0.01 | 0.07 | ND |
| 15106049 | RD | 0.25 | 0.15 | 0.82 | 0.30 | 0.30 | 3.35 | 0.44 | 0.09 | 2.82 | ND | 0.23 | 0.04 | 0.03 |
| 15106058 | RD | 0.31 | 0.35 | 0.98 | 0.26 | 0.37 | 4.90 | 0.57 | 0.10 | 0.41 | ND | 0.01 | 0.08 | 0.02 |
| 15106059 | RD | 0.22 | 0.40 | 1.00 | 0.24 | 0.41 | 4.04 | 0.29 | 0.08 | 0.30 | ND | ND | 0.06 | 0.01 |
| 15107009 | RD | 0.97 | 0.43 | 2.06 | 0.42 | 0.13 | 1.74 | 1.49 | 0.04 | 0.36 | 0.08 | 0.01 | 0.03 | 0.06 |
| 15107022 | RD | 2.04 | 0.34 | 2.87 | 0.60 | 0.11 | 1.80 | 1.73 | 0.08 | 0.43 | 0.01 | 0.03 | 0.09 | 0.00 |
| 15107060 | RD | 1.63 | 0.01 | 2.33 | 0.66 | 0.05 | 1.22 | 1.38 | 0.07 | 0.50 | 0.04 | 0.03 | 0.07 | 0.03 |
| 15107063 | RD | 1.44 | 0.01 | 1.45 | 0.44 | 0.03 | 1.08 | 2.11 | 0.05 | 0.37 | 0.09 | 0.01 | 0.02 | 0.04 |
| 15107066 | RD | 0.80 | 0.13 | 1.85 | 0.55 | 0.20 | 1.93 | 1.53 | 0.05 | 0.34 | 0.02 | ND | 0.03 | 0.04 |
| 15108006 | RD | 1.46 | 0.01 | 3.01 | 0.87 | 0.16 | 1.82 | 1.81 | 0.07 | 0.46 | 0.04 | 0.01 | 0.10 | 0.06 |
| 15108014 | RD | 2.05 | ND | 2.45 | 0.69 | 0.05 | 0.73 | 1.65 | 0.04 | 0.30 | 0.03 | 0.02 | 0.01 | 0.05 |
| 15108027 | RD | 1.97 | 0.26 | 1.91 | 0.39 | 0.04 | 0.96 | 1.48 | 0.06 | 0.32 | 0.05 | 0.01 | 0.03 | 0.07 |
| 15108043 | RD | 0.27 | 0.49 | 1.98 | 0.49 | 0.37 | 2.49 | 0.73 | 0.06 | 0.28 | 0.00 | 0.15 | 0.04 | 0.02 |
| 15108044 | RD | 0.23 | 0.42 | 1.80 | 0.47 | 0.30 | 4.14 | 1.26 | 0.10 | 0.42 | 0.01 | 0.18 | 0.10 | 0.05 |
| 15109003 | RD | 0.07 | 0.35 | 0.73 | 0.36 | 0.39 | 4.72 | 0.43 | 0.07 | 0.34 | ND | 0.17 | 0.10 | 0.01 |
| 15109004 | RD | 0.32 | 0.01 | 1.81 | 0.75 | 0.23 | 3.05 | 1.30 | 0.07 | 0.34 | ND | 0.19 | 0.07 | 0.04 |
| 15109018 | RD/RM | 0.07 | 0.50 | 1.28 | 0.48 | 0.52 | 4.02 | 0.42 | 0.07 | 0.27 | ND | 0.20 | 0.06 | 0.01 |
| 15110017 | RD | 0.35 | 0.04 | 1.14 | 0.28 | 0.03 | 5.83 | 4.42 | 0.19 | 1.06 | 0.06 | 0.06 | 0.04 | 0.04 |
| 15111003 | RD | 1.17 | 0.02 | 2.59 | 0.72 | 0.12 | 1.53 | 1.58 | 0.04 | 0.33 | 0.01 | ND | 0.05 | 0.07 |
| 15110023 | RD/RM | 0.53 | 0.57 | 1.82 | 0.50 | 0.57 | 3.85 | 0.55 | 0.08 | 0.36 | 0.09 | 0.01 | 0.03 | 0.01 |
| 15111050 | RD | 0.03 | 0.38 | 1.27 | 0.30 | 0.45 | 3.40 | 0.40 | 0.07 | 0.28 | ND | ND | 0.04 | 0.02 |
| 15111066 | RD | 0.31 | 0.57 | 2.56 | 0.59 | 0.36 | 2.56 | 0.80 | 0.07 | 0.30 | 0.01 | 0.01 | 0.04 | 0.03 |
| 15113035 | RD | 1.06 | 0.38 | 2.11 | 0.42 | 0.12 | 1.27 | 2.01 | 0.05 | 0.29 | 0.03 | ND | 0.01 | 0.04 |
| 15113056 | RD | 0.36 | 0.04 | 2.05 | 0.71 | 0.21 | 2.25 | 1.47 | 0.06 | 0.35 | 0.01 | 0.01 | 0.06 | 0.05 |
| 15113062 | RD | 0.06 | 0.27 | 1.34 | 0.34 | 0.34 | 3.68 | 0.72 | 0.09 | 0.39 | ND | 0.01 | 0.08 | 0.03 |
| 15114055 | RD | 0.26 | 0.00 | 2.04 | 0.82 | 0.25 | 3.09 | 1.26 | 0.16 | 1.41 | 0.01 | 0.15 | 0.05 | 0.05 |
| 15114067 | RD | 0.43 | 0.48 | 1.90 | 0.41 | 0.23 | 2.70 | 1.00 | 0.15 | 1.46 | 0.01 | 0.17 | 0.04 | 0.04 |
| 15115007 | RD | 0.09 | 0.26 | 0.97 | 0.27 | 0.28 | 4.89 | 0.86 | 0.19 | 3.26 | 0.01 | 0.23 | 0.07 | 0.05 |
| 15115021 | RD | 2.06 | 0.18 | 2.07 | 0.44 | 0.07 | 1.15 | 2.23 | 0.04 | 0.31 | 0.04 | 0.01 | 0.03 | 0.11 |
| 15115032 | RD | 0.67 | 0.03 | 2.35 | 0.80 | 0.18 | 2.23 | 1.43 | 0.06 | 0.36 | 0.01 | 0.01 | 0.04 | 0.06 |
| 15115067 | RD | 0.90 | 0.07 | 2.16 | 0.69 | 0.11 | 1.07 | 1.28 | 0.04 | 0.30 | 0.01 | ND | 0.02 | 0.03 |
| 15115070 | RD | 0.99 | 0.01 | 2.54 | 0.61 | 0.08 | 0.81 | 2.00 | 0.02 | 0.22 | 0.01 | 0.01 | 0.02 | 0.08 |

Table 7 below summarizes the HPLC data from Table 6. TSG=total steviol glycoside, RA/TSG is the percent of rebaudioside A out of the total steviol glycoside, RD/TSG is the percent of RebD out of the total steviol glycoside, RM/TSG is the percent of RebM out of the total steviol glycoside, and ST/TSG is the percent of stevioside out of the total steviol glycoside. Columns labelled RD/TSG and RM/TSG are in bold. Deposited varieties '817096', '814011', and '807086' are bolded and underlined.

TABLE 7

Summary of HPLC data from Table 6

| Variety | Group | TSG | RA/TSG | RD/TSG | RM/TSG | ST/TSG |
|---|---|---|---|---|---|---|
| 412-31 | ST | 9.24 | 1.41 | 0.87 | 0.00 | 92.75 |
| 43-2 | ST | 8.81 | 3.18 | 0.00 | 0.00 | 89.33 |
| 49-58 | ST | 11.88 | 3.62 | 0.17 | 0.00 | 95.62 |
| 805028 | ST | 10.62 | 1.69 | 0.19 | 0.00 | 90.21 |
| 805003 | ST | 11.34 | 0.88 | 0.35 | 0.00 | 89.33 |

TABLE 7-continued

Summary of HPLC data from Table 6

| Variety | Group | TSG | RA/TSG | RD/TSG | RM/TSG | ST/TSG |
|---|---|---|---|---|---|---|
| 803066 | ST | 11.28 | 2.30 | 0.09 | 0.00 | 88.92 |
| 813057 | RA | 14.18 | 86.67 | 1.06 | 0.00 | 3.81 |
| 812051 | RA | 13.37 | 85.56 | 1.27 | 0.00 | 4.19 |
| 805068 | RA | 14.40 | 85.56 | 0.69 | 0.00 | 7.57 |
| 815034 | RA | 11.42 | 83.27 | 1.75 | 0.00 | 6.04 |
| 802057 | RA | 13.66 | 84.55 | 1.24 | 0.00 | 4.10 |
| 817075 | RA | 12.02 | 88.85 | 1.58 | 0.00 | 4.66 |
| PC star | RA/ST | 10.95 | 72.05 | 2.01 | 1.19 | 8.31 |
| PC1 | RA/ST | 9.02 | 64.63 | 1.44 | 0.33 | 20.18 |
| M3 | RA | 11.65 | 77.51 | 1.89 | 1.03 | 8.50 |
| Hybrid | RA/ST | 12.08 | 56.37 | 1.32 | 0.00 | 31.21 |
| 805126 | RA | 12.17 | 88.50 | 2.05 | 0.00 | 3.70 |
| 805082 | RA | 12.22 | 88.22 | 1.47 | 0.00 | 5.32 |
| 807086 | RD/RM | 8.61 | 48.20 | 18.00 | 11.61 | 2.44 |
| 814011 | RD/RM | 13.24 | 63.82 | 8.38 | 8.46 | 2.87 |
| 817096 | RD | 11.59 | 20.28 | 28.30 | 3.28 | 17.77 |
| 806034 | RD | 4.88 | 76.02 | 12.70 | 0.00 | 4.30 |
| 830098 | RD | 7.60 | 72.50 | 13.55 | 0.00 | 5.39 |
| 803071 | RD | 6.03 | 71.31 | 11.61 | 0.00 | 7.30 |
| 805061 | RD | 5.96 | 72.48 | 17.95 | 0.00 | 7.05 |
| 813081 | RD | 5.89 | 77.08 | 10.53 | 0.00 | 5.09 |
| 806058 | RD | 7.10 | 74.93 | 11.69 | 0.00 | 5.92 |
| 810103 | RD | 6.36 | 71.07 | 14.94 | 0.00 | 4.40 |
| 801094 | RD | 8.62 | 62.76 | 18.79 | 2.90 | 7.31 |
| 804075 | RD | 6.70 | 64.93 | 14.48 | 3.58 | 8.51 |
| 804038 | RD | 7.19 | 47.57 | 31.02 | 6.68 | 9.18 |
| 801105 | RD | 9.69 | 73.58 | 11.76 | 3.92 | 3.41 |
| 816055 | RD | 8.98 | 77.28 | 9.91 | 3.45 | 2.90 |
| 10-43 | RD/RM | 11.59 | 58.76 | 13.72 | 5.87 | 9.58 |
| 10-43-3 | RD/RM | 10.97 | 52.23 | 23.25 | 7.38 | 8.48 |
| 21-11 | RD | 5.90 | 70.00 | 11.19 | 4.92 | 7.29 |
| 3-6 | RD/RM | 8.82 | 72.56 | 10.43 | 7.14 | 2.49 |
| 15101060 | RA/ST | 12.51 | 70.94 | 4.72 | 0.00 | 14.83 |
| 15103014 | RA/ST | 11.81 | 35.73 | 2.20 | 0.08 | 48.81 |
| 15103015 | ST | 8.21 | 0.87 | 0.12 | 0.00 | 86.85 |
| 15103018 | RA/ST | 13.48 | 40.28 | 4.97 | 0.22 | 41.47 |
| 15103025 | RA/ST | 10.46 | 57.36 | 2.20 | 0.48 | 28.49 |
| 15103045 | RA/ST | 9.48 | 58.15 | 3.38 | 0.84 | 25.33 |
| 15103052 | RA/ST | 9.90 | 41.77 | 2.53 | 0.51 | 42.58 |
| 15106002 | RA/ST | 12.42 | 46.05 | 6.20 | 0.48 | 34.42 |
| 15106018 | RA/ST | 11.48 | 65.94 | 4.36 | 1.05 | 16.25 |
| 15106021 | RA/ST | 12.95 | 66.32 | 2.63 | 0.85 | 14.21 |
| 15106038 | RA/ST | 5.82 | 29.84 | 7.57 | 1.89 | 43.68 |
| 15106047 | RA/ST | 15.02 | 36.78 | 4.73 | 0.53 | 43.77 |
| 15106052 | RA | 13.90 | 70.83 | 6.69 | 0.00 | 13.60 |
| 15107001 | RA/ST | 14.82 | 59.30 | 2.36 | 0.88 | 24.70 |
| 15107005 | ST | 11.75 | 1.06 | 0.09 | 0.09 | 83.53 |
| 15108016 | RA/ST | 12.65 | 70.08 | 3.32 | 1.11 | 14.58 |
| 15111055 | RA/ST | 12.52 | 63.78 | 4.47 | 1.36 | 16.73 |
| 15111074 | ST | 11.82 | 15.79 | 3.13 | 0.59 | 64.45 |
| 15111075 | RA | 14.45 | 66.81 | 3.74 | 1.11 | 14.47 |
| 15112004 | RA/ST | 10.99 | 63.45 | 6.10 | 1.46 | 16.02 |
| 15112010 | RA/ST | 13.08 | 51.93 | 5.51 | 0.69 | 30.02 |
| 15112023 | RA | 13.47 | 70.97 | 5.57 | 0.00 | 13.36 |
| 15112046 | RA/ST | 11.81 | 70.39 | 4.32 | 1.52 | 9.53 |
| 15114004 | RA/ST | 15.22 | 58.18 | 3.29 | 0.00 | 25.20 |
| 15114039 | RA | 15.59 | 69.28 | 3.72 | 1.41 | 12.22 |
| 15115008 | RA | 15.30 | 73.00 | 2.32 | 0.00 | 12.85 |
| 15101010 | ST | 14.03 | 16.61 | 3.78 | 0.00 | 62.65 |
| 15101015 | RA/ST | 11.33 | 48.01 | 6.97 | 0.18 | 28.33 |
| 15102028 | RA/ST | 9.80 | 50.20 | 4.39 | 0.10 | 31.22 |
| 15102057 | RA/ST | 10.66 | 64.35 | 3.19 | 0.47 | 19.04 |
| 15103021 | RA | 13.66 | 67.57 | 2.93 | 0.44 | 16.69 |
| 15103068 | RA | 12.95 | 69.81 | 3.55 | 0.46 | 12.51 |
| 15104003 | ST | 13.07 | 20.73 | 2.98 | 0.00 | 61.44 |
| 15104048 | RA/ST | 10.64 | 38.25 | 5.83 | 0.09 | 42.39 |
| 15105008 | RA/ST | 12.19 | 47.33 | 7.55 | 0.57 | 29.45 |
| 15105063 | RA/ST | 10.97 | 25.16 | 2.64 | 0.27 | 56.70 |
| 15106034 | RA/ST | 8.88 | 63.40 | 3.49 | 0.34 | 20.38 |
| 15106067 | RA/ST | 12.93 | 64.42 | 5.26 | 0.62 | 16.32 |
| 15107013 | RA/ST | 9.93 | 34.44 | 4.83 | 0.20 | 45.32 |
| 15107054 | RA/ST | 10.76 | 60.87 | 3.62 | 0.46 | 22.77 |
| 15108012 | ST | 13.25 | 24.30 | 3.32 | 0.23 | 58.87 |
| 15108033 | RA/ST | 10.27 | 41.29 | 3.99 | 0.00 | 39.73 |
| 15109002 | ST | 12.99 | 23.09 | 2.77 | 0.08 | 57.97 |
| 15109008 | ST | 10.29 | 0.87 | 0.00 | 0.39 | 81.15 |
| 15110059 | RA/ST | 9.96 | 42.57 | 6.02 | 0.00 | 35.94 |
| 15111007 | ST | 14.19 | 17.48 | 2.33 | 0.07 | 66.17 |
| 15111020 | RA/ST | 8.81 | 57.89 | 3.29 | 0.23 | 22.70 |
| 15112014 | RA/ST | 12.58 | 60.17 | 3.18 | 0.56 | 23.05 |
| 15112035 | RA/ST | 11.87 | 34.96 | 4.47 | 0.08 | 46.59 |
| 15113010 | RA/ST | 13.92 | 58.19 | 1.72 | 0.57 | 26.51 |
| 15113030 | RA/ST | 12.38 | 49.19 | 2.02 | 0.08 | 35.30 |
| 15114011 | RA/ST | 7.88 | 32.87 | 1.40 | 0.13 | 51.78 |
| 15114031 | ST | 8.87 | 0.89 | 0.13 | 0.13 | 83.77 |
| 15115017 | RA/ST | 12.95 | 50.35 | 6.33 | 0.46 | 27.72 |
| 15115037 | RA | 14.18 | 71.72 | 3.60 | 1.20 | 10.79 |
| 803065 | RD/RM | 7.00 | 59.00 | 9.00 | 0.00 | 10.29 |
| 15101023 | RD | 9.50 | 28.47 | 31.68 | 3.26 | 11.16 |
| 15101045 | RD | 7.81 | 26.52 | 28.57 | 2.05 | 16.85 |
| 15101057 | RD/RM | 8.46 | 49.02 | 21.64 | 5.91 | 5.85 |
| 15102008 | RD | 7.96 | 33.12 | 28.54 | 3.14 | 13.07 |
| 15102016 | RD | 7.12 | 58.22 | 14.75 | 4.92 | 5.34 |
| 15102017 | RD | 5.51 | 54.72 | 11.25 | 6.53 | 7.08 |
| 15102048 | RD | 7.68 | 53.22 | 14.20 | 3.91 | 5.08 |
| 15102049 | RD | 7.20 | 46.42 | 21.68 | 6.39 | 6.32 |
| 15112062 | RD | 7.02 | 4.70 | 19.24 | 0.14 | 20.03 |
| 15102067 | RD | 6.19 | 12.77 | 19.89 | 0.49 | 37.27 |
| 15103002 | RD | 12.62 | 37.22 | 11.89 | 3.80 | 4.60 |
| 15103003 | RD/RM | 9.47 | 36.91 | 18.48 | 5.49 | 3.27 |
| 15103009 | RD | 7.92 | 29.99 | 30.56 | 3.03 | 12.44 |
| 15103010 | RD | 6.97 | 61.52 | 12.63 | 4.16 | 3.88 |
| 15104007 | RD | 9.84 | 38.16 | 9.55 | 4.17 | 3.91 |
| 15104023 | RD | 8.11 | 41.21 | 13.70 | 4.69 | 4.01 |
| 15104030 | RD | 7.77 | 25.24 | 33.35 | 3.99 | 12.17 |
| 15104054 | RD/RM | 9.96 | 40.01 | 19.58 | 5.12 | 4.62 |
| 15104058 | RD | 6.61 | 62.60 | 10.75 | 4.24 | 7.19 |
| 15104059 | RD | 7.23 | 35.82 | 25.31 | 6.09 | 6.36 |
| 15104062 | RD | 9.07 | 36.66 | 22.71 | 3.31 | 13.18 |
| 15105018 | RD | 8.18 | 26.47 | 30.81 | 1.96 | 13.20 |
| 15105025 | RD | 8.02 | 47.47 | 21.33 | 5.86 | 6.49 |
| 15105031 | RD | 6.48 | 8.65 | 23.47 | 1.08 | 29.34 |
| 15105048 | RD/RM | 9.17 | 53.98 | 16.47 | 6.32 | 5.45 |
| 15105051 | RD | 5.62 | 52.05 | 18.68 | 6.94 | 4.98 |
| 15105056 | RD | 7.18 | 55.23 | 17.13 | 5.99 | 7.24 |
| 15105061 | RD | 10.02 | 23.80 | 29.74 | 2.69 | 15.47 |
| 15105066 | RD | 9.83 | 42.12 | 12.82 | 4.37 | 2.90 |
| 15106015 | RD | 9.38 | 38.77 | 10.99 | 3.31 | 4.05 |
| 15106017 | RD | 7.80 | 18.41 | 27.07 | 2.05 | 20.65 |
| 15106022 | RD | 6.61 | 34.57 | 24.96 | 3.03 | 14.60 |
| 15106024 | RD | 7.29 | 16.05 | 25.51 | 1.51 | 23.94 |
| 15106028 | RD/RM | 8.47 | 56.14 | 12.40 | 6.02 | 4.60 |
| 15106049 | RD | 8.79 | 38.05 | 9.33 | 3.41 | 4.95 |
| 15106058 | RD | 8.35 | 58.62 | 11.74 | 4.43 | 6.83 |
| 15106059 | RD | 7.03 | 57.47 | 14.22 | 5.83 | 4.05 |
| 15107009 | RD | 7.82 | 22.25 | 26.34 | 1.66 | 19.05 |
| 15107022 | RD | 10.13 | 17.77 | 28.33 | 1.09 | 17.08 |
| 15107060 | RD | 8.02 | 15.21 | 29.05 | 0.62 | 17.21 |
| 15107063 | RD | 7.14 | 15.13 | 20.31 | 0.42 | 29.55 |
| 15107066 | RD | 7.45 | 25.92 | 24.85 | 2.69 | 20.48 |
| 15108006 | RD | 9.88 | 18.42 | 30.47 | 1.62 | 18.32 |
| 15108014 | RD | 8.07 | 9.05 | 30.36 | 0.62 | 20.45 |
| 15108027 | RD | 7.55 | 12.72 | 25.30 | 0.53 | 19.60 |
| 15108043 | RD | 7.36 | 33.79 | 26.92 | 5.03 | 9.93 |
| 15108044 | RD | 9.46 | 43.73 | 19.04 | 3.17 | 13.27 |
| 15109003 | RD | 7.72 | 61.08 | 9.46 | 5.05 | 5.57 |
| 15109004 | RD | 8.17 | 37.35 | 22.17 | 2.82 | 15.92 |
| 15109018 | RD/RM | 7.90 | 50.92 | 16.21 | 6.59 | 5.32 |
| 15110017 | RD | 13.54 | 43.06 | 8.42 | 0.22 | 32.64 |
| 15111003 | RD | 8.21 | 18.59 | 31.57 | 1.46 | 19.20 |
| 15110023 | RD/RM | 8.97 | 42.92 | 20.29 | 6.35 | 6.13 |
| 15111050 | RD | 6.63 | 51.21 | 19.16 | 6.79 | 5.96 |
| 15111066 | RD | 8.19 | 31.28 | 31.28 | 4.40 | 9.71 |
| 15113035 | RD | 7.78 | 16.33 | 27.14 | 1.54 | 25.79 |
| 15113056 | RD | 7.62 | 29.55 | 26.92 | 2.76 | 19.24 |
| 15113062 | RD | 7.33 | 50.20 | 18.28 | 4.64 | 9.75 |
| 15114055 | RD | 9.55 | 32.36 | 21.36 | 2.62 | 13.19 |
| 15114067 | RD | 9.02 | 29.93 | 21.06 | 2.55 | 11.09 |
| 15115007 | RD | 11.43 | 42.78 | 8.49 | 2.45 | 7.52 |
| 15115021 | RD | 8.73 | 13.12 | 23.72 | 0.80 | 25.56 |
| 15115032 | RD | 8.22 | 27.08 | 28.61 | 2.19 | 17.41 |

TABLE 7-continued

Summary of HPLC data from Table 6

| Variety | Group | TSG | RA/TSG | RD/TSG | RM/TSG | ST/TSG |
|---|---|---|---|---|---|---|
| 15115067 | RD | 6.66 | 16.07 | 32.43 | 1.65 | 19.22 |
| 15115070 | RD | 7.39 | 10.96 | 34.37 | 1.08 | 27.06 |

SNP markers for SNP17, SNP19, and SNP20 successfully predict *Stevia* plants having high RebD and/or high RebM, as all plants placed into this grouping based on the presence of these SNPs show high RebD and/or high RebM based on HPLC analysis (Table 6 and Table 7 above). Additionally, this genotyping method can successfully screen out 100% of *Stevia* plants in the RA/ST group, thus facilitating the breeding of only plants having high RebD and RebM.

Shown below in Table 8, the data from Tables 7 and 6 are combined and summarized. Column 1 lists the average, minimum, and maximum values of RD/TSG and RM/TSG, and columns 2 and 3 list the group. For example, the average value of RD/TSG in the RA/ST group is 3.08%, compared to 19.89% in the RD/RM group. Additionally, RD/TSG exhibits a range of 8.38% to 34.37% in the RD/RM group, compared to a range of 0% to 7.57% in the RA/ST group. Similarly, RM/TSG exhibits a range of 0% to 11.61% in the RD/RM group, compared to a range of 0% to 1.89% in the RA/ST group.

TABLE 8

Average, minimum, and maximum values per group

|  | RA/ST group | RD/RM group |
|---|---|---|
| average value of RD/TSG | 3.08% | 19.89% |
| average value of RM/TSG | 0.38% | 3.44% |
| minimum value RD/TSG | 0% | 8.38% |
| maximum value RD/TSG | 7.57% | 34.37% |
| minimum value of RM/TSG | 0% | 0% |
| maximum value of RM/TSG | 1.89% | 11.61% |

As shown in Tables 6-8 above, SNP probe genotyping for SNP17, SNP19, and SNP20 shows that there is a correlation between specific SNPs and steviol glycosides composition. SNP17, SNP19, and SNP20 successfully predict *Stevia* plants having high RebD and high RebM. Additionally, this genotyping method can successfully screen out 100% of *Stevia* plants in the RA/ST group, thus facilitating the breeding of only plants having high RebD and RebM.

Thus, another embodiment of the instant application discloses *Stevia* plant, wherein the leaves of the *Stevia* plant have a RebD/total steviol glycoside percentage between 8% and 38% and a RebM/total steviol glycoside percentage between 0% and 14% and further comprise the following SNPs in homozygous form: SNP17, which comprises an A to C nucleotide substitution at position number 129 in SEQ ID NO:4, SNP19, which comprises an A to T nucleotide substitution at position number 173 in SEQ ID NO:5, and SNP 20, which comprises a G to A nucleotide substitution at position number 221 in in SEQ ID NO:6.

Another embodiment discloses a *Stevia* plant, wherein the RebD/total steviol glycoside percentage is between 8% and 17% of dry weight, and wherein the RebM/total steviol glycoside percentage is between 0% and 4% of dry weight.

Another embodiment discloses a *Stevia* plant, wherein the RebD/total steviol glycoside percentage is between 17.1% and 27% of dry weight, and wherein the RebM/total steviol glycoside percentage is between 4.1% and 8% of dry weight.

Another embodiment a *Stevia* plant, wherein the RebD/total steviol glycoside percentage is between 27.1% and 38% of dry weight, and wherein the RebM/total steviol glycoside percentage is between 8.1% and 14% of dry weight.

Additional Methods for Detecting SNPs for Marker Assisted Breeding

In addition to the direct or indirect sequencing of the site and the probes described above, the SNPs disclosed herein may also be detected by a variety of effective methods well known in the art including those disclosed in U.S. Pat. Nos. 5,468,613 and 5,217,863; 5,210,015; 5,876,930; 6,030,787 6,004,744; 6,013,431; 5,595,890; 5,762,876; 5,945,283; 5,468,613; 6,090,558; 5,800,944 and 5,616,464. In particular, polymorphisms in DNA sequences can be detected by hybridization to allele-specific oligonucleotide (ASO) probes as disclosed in U.S. Pat. Nos. 5,468,613 and 5,217,863. The nucleotide sequence of an ASO probe is designed to form either a perfectly matched hybrid or to contain a mismatched base pair at the site of the variable nucleotide residues. The distinction between a matched and a mismatched hybrid is based on differences in the thermal stability of the hybrids in the conditions used during hybridization or washing, differences in the stability of the hybrids analyzed by denaturing gradient electrophoresis or chemical cleavage at the site of the mismatch.

If a SNP creates or destroys a restriction endonuclease cleavage site, it will alter the size or profile of the DNA fragments that are generated by digestion with that restriction endonuclease. As such, plants that possess a variant sequence can be distinguished from those having the original sequence by restriction fragment analysis. SNPs that can be identified in this manner are termed "restriction fragment length polymorphisms" ("RFLPs"). RFLPs have been widely used in human and plant genetic analyses (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al., PCT Application WO 90/13668; Uhlen, PCT Application WO 90/11369.

An alternative method of determining SNPs is based on cleaved amplified polymorphic sequences (CAPS) (Konieczny, A. and F. M. Ausubel, *Plant J.* 4:403-410 (1993); Lyamichev et al., *Science* 260:778-783 (1993). A modified version of CAPs, known as dCAPs, is a technique for detection of Single Nucleotide Polymorphisms (SNPs). The dCAPS technique introduces or destroys a restriction enzyme recognition sites by using primers that containing one or more mismatches to the template DNA. The PCR product modified in this manner is then subjected to restriction enzyme digestion and the presence or absence of the SNP is determined by the resulting restriction pattern. This technique is useful for genotyping known mutations and genetic mapping of isolated DNAs (Neff M M, Neff J D, Chory J, Pepper A E. dCAPS, a simple technique for the genetic analysis of single nucleotide polymorphisms: experimental applications in *Arabidopsis thaliana* genetics. Plant J. 1998 May; 14(3):387-92).

SNPs can also be identified by single strand conformation polymorphism (SSCP) analysis. The SSCP technique is a method capable of identifying most sequence variations in a single strand of DNA, typically between 150 and 250 nucleotides in length (Elles, *Methods in Molecular Medicine: Molecular Diagnosis of Genetic Diseases*, Humana Press (1996); Orita et al., *Genomics* 5:874-879 (1989). Under denaturing conditions a single strand of DNA will adopt a conformation that is uniquely dependent on its sequence. This conformation usually will be different even if only a single base is changed. Most conformations have been reported to alter the physical configuration or size sufficiently to be detectable by electrophoresis. A number of protocols have been described for SSCP including, but not limited to Lee et al., *Anal. Biochem.* 205:289-293 (1992); Suzuki et al., *Anal. Biochem.* 192:82-84 (1991); Lo et al., *Nucleic Acids Research* 20:1005-1009 (1992); Sarkar et al., *Genomics* 13:441-443 (1992).

SNPs may also be detected using a DNA fingerprinting technique called amplified fragment length polymorphism (AFLP), which is based on the selective PCR amplification of restriction fragments from a total digest of genomic DNA to profile that DNA. Vos et al., *Nucleic Acids Res.* 23:4407-4414 (1995). This method allows for the specific co-amplification of many restriction fragments, which can be analyzed without knowledge of the nucleic acid sequence. AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel (Beismann et al., *Mol. Ecol.* 6:989-993 (1997); Janssen et al., *Int. J. Syst. Bacteriol* 47:1179-1187 (1997); Huys et al., *Int. J. Syst. Bacteriol.* 47:1165-1171 (1997); McCouch et al., *Plant Mol. Biol.* 35:89-99 (1997); Nandi et al., *Mol. Gen. Genet.* 255:1-8 (1997); Cho et al. *Genome* 39:373-378 (1996); Simons et al., *Genomics* 44:61-70 (1997); Cnops et al., *Mol. Gen. Genet.* 253:32-41 (1996); Thomas et al., *Plant J.* 8:785-794 (1995).

SNPs may also be detected using random amplified polymorphic DNA (RAPD) (Williams et al., *Nucl. Acids Res.* 18:6531-6535 (1990).

SNPs can be detected by methods as disclosed in U.S. Pat. Nos. 5,210,015; 5,876,930 and 6,030,787 in which an oligonucleotide probe having reporter and quencher molecules is hybridized to a target polynucleotide. The probe is degraded by 5'→3' exonuclease activity of a nucleic acid polymerase.

SNPs can also be detected by labelled base extension methods as disclosed in U.S. Pat. Nos. 6,004,744; 6,013,431; 5,595,890; 5,762,876; and 5,945,283. These methods are based on primer extension and incorporation of detectable nucleoside triphosphates. The primer is designed to anneal to the sequence immediately adjacent to the variable nucleotide which can be can be detected after incorporation of as few as one labelled nucleoside triphosphate. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labelled sequence-specific oligonucleotide probe Other methods for identifying and detecting SNPs in addition to those described above include the use of restriction enzymes (Botstein et al., *Am. J. Hum. Genet.* 32:314-331 (1980); and Konieczny and Ausubel, *Plant J.* 4:403-410 (1993)), enzymatic and chemical mismatch assays (Myers et al., *Nature* 313:495-498 (1985)), allele-specific PCR (Newton et al., *Nucl. Acids Res.* 17:2503-2516 (1989); and Wu et al., *Proc. Natl. Acad. Sci. USA* 86:2757-2760 (1989)), ligase chain reaction (Barany, *Proc. Natl. Acad. Sci. USA* 88:189-193 (1991)), single-strand conformation polymorphismanalysis (Labrune et al., *Am. J. Hum. Genet.* 48: 1115-1120 (1991)), single base primer extension (Kuppuswamy et al., *Proc. Natl. Acad. Sci. USA* 88:1143-1147 (1991); and Goelet, U.S. Pat. Nos. 6,004,744 and 5,888,819, solid-phase ELISA-based oligonucleotide ligation assays (Nikiforov et al., *Nucl. Acids Res.* 22:4167-4175 (1994)), dideoxy fingerprinting (Sarkar et al., *Genomics* 13:441-443 (1992)), oligonucleotide fluorescence-quenching assays (Livak et al., *PCR Methods Appl.* 4:357-362 (1995)), 5'-nuclease allele-specific hybridization TaqMan™ assay (Livak et al., *Nature Genet.* 9:341-342 (1995)), template-directed dye-terminator incorporation (TDI) assay (Chen and Kwok, *Nucl. Acids Res.* 25:347-353 (1997)), allele-specific molecular beacon assay (Tyagi et al., *Nature Biotech.* 16: 49-53 (1998)), PinPoint assay (Haff and Smirnov, *Genome Res.* 7: 378-388 (1997)), dCAPS analysis (Neffetal., *Plant J.* 14:387-392 (1998)), pyrosequencing (Ronaghi et al, *Analytical Biochemistry* 267:65-71 (1999); Ronaghi et al PCT application WO 98/13523; and Nyren et al PCT application WO 98/28440), using mass spectrometry e.g., the Masscode™ system (Howbert et al WO 99/05319; Howber et al WO 97/27331), mass spectroscopy (U.S. Pat. No. 5,965,363, invasive cleavage of oligonucleotide probes (Lyamichev et al *Nature Biotechnology* 17:292-296), and using high density oligonucleotide arrays (Hacia et al *Nature Genetics* 22:164-167).

While certain methods for detecting SNPs are described herein, other detection methodologies may be utilized. For example, additional methodologies are known and set forth, in Birren et. al., *Genome Analysis*, 4:135-186, *A Laboratory Manual. Mapping Genomes*, Cold Spring Harbor Laboratory Press, Cold Spring Harbor, N.Y. (1999); Maliga et al., *Methods in Plant Molecular Biology. A Laboratory Course Manual*, Cold Spring Harbor Laboratory Press, Cold Spring Harbor, N.Y. (1995); Paterson, *Biotechnology Intelligence Unit: Genome Mapping in Plants*, R. G. Landes Co., Georgetown, Tex., and Academic Press, San Diego, Calif. (1996); *The Maize Handbook*, Freeling and Walbot, eds., Springer-Verlag, New York, N.Y. (1994); *Methods in Molecular Medicine: Molecular Diagnosis of Genetic Diseases*, Elles, ed., Humana Press, Totowa, N. J. (1996); Clark, ed., *Plant Molecular Biology: A Laboratory Manual*, Clark, ed., Springer-Verlag, Berlin, Germany (1997).

Additional Methods for Detecting and Measuring Steviol Glycosides

In addition to HPLC, steviol glycosides may be detected and measured by a number of methods well known in the art.

Breeding for High RebD and High RebM Stevia Plants

Different parental lines, Eirete, AKHL1, AKH EM1, AKHL4, AKH/G.8.D and PC Star 2, were selected and grouped accordingly for the crossings conducted in Ganzhou, Jiangxi Province, the People's Republic of China. Three different sets of crossings were conducted. High RebA Stevia plants (817075', '805082', '805126', '815034', '802057', '801025', '813057', '812051' and '805068') and high Stev *Stevia* plants (805028', '803066', '805003', '43-2' and '49-58') were used for SNP genotyping and HPLC analysis. High RebD and high RebM lines '814011' and '807086' are derived from different sets of parental crossing (see FIGS. 11 and 12). Other high RebD lines (817096', '801094', '804038', '801105', '816055', '804075', '830098', '806058', '810103', '803071', '805061', '813081', '806034' and '803065') were all derived from the same parental crossings (FIG. 13).

Breeding Methods that May be Combined with SNP Marker Selection

There are numerous steps in the development of any desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. In *Stevia*, the important traits leaf yield, earlier maturity, improved leaf quality, rebaudioside content, stevioside content, resistance to diseases and insects, resistance to drought and heat, and improved agronomic traits. Choice of breeding or selection methods depends on the mode of plant reproduction, the heritability of the trait(s) being improved, and the type of cultivar used commercially (e.g., Fi hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to popular cultivars in environments representative of the commercial target area(s) for three or more years. The lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefore, development of new cultivars is a time-consuming process that requires precise forward planning, efficient use of resources, and a minimum of changes in direction.

A most difficult task is the identification of individuals that are genetically superior because for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The goal of a commercial *Stevia* breeding program is to develop new, unique, and superior *Stevia* cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic, and soil conditions and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new *Stevia* cultivars.

Pureline cultivars of *Stevia* are commonly bred by hybridization of two or more parents followed by selection. The complexity of inheritance, the breeding objectives, and the available resources influence the breeding method. Pedigree breeding, recurrent selection breeding, and backcross breeding are breeding methods commonly used in self-pollinated crops such as *Stevia*. These methods refer to the manner in which breeding pools or populations are made in order to combine desirable traits from two or more cultivars or various broad-based sources. The procedures commonly used for selection of desirable individuals or populations of individuals are called mass selection, plant-to-row selection, and single seed descent or modified single seed descent. One or a combination of these selection methods can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by selfing $F_2$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or to further select individual plants. Once a progeny row or progeny hill is selected as having desirable traits, it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

The single seed descent procedure in the strict sense refers to planting a segregating population, harvesting one seed from every plant, and combining these seeds into a bulk, which is planted as the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using winter nurseries.

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

In addition to phenotypic observations, the genotype of a plant can also be examined. There are many laboratory-based techniques available for the analysis, comparison, and characterization of plant genotype. Among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs—which are also referred to as Microsatellites), and Single Nucleotide Polymorphisms (SNPs).

Breeding with Molecular Techniques

Targeted genome editing may be achieved by using engineered nucleases. In bacteria, CRISPRs (clustered regularly interspaced short palindromic repeats) are segments of prokaryotic DNA containing short repetitions of base sequences. Each repetition is followed by short segments of "spacer DNA" from previous exposures to a bacterial virus or plasmid. It is pronounced "crisper". Upon subsequent exposure to the virus, the bacteria is able to recognize, target, and destroy the foreign DNA. The CRISPR system can be used for gene editing by using the Cas9 nuclease which uses a guide RNA molecule to home in on its target DNA, then induces double stranded breaks in the DNA to disrupt genes or desired sequences. The DNA is then repaired via the non-homologous repair system or the homologous dependent repair system. In the latter case, artificial oligos may be used to insert a new sequence into the cut site. See also US20100076057A1, WO2010075424A2, WO2013126794A1, WO2013142578, WO2013169398, WO2013176772A1, US2013181440A1, US20140017214A1, WO2014011237A1, WO2014022702A2, WO2014071219A1, U.S. Pat. No. 8,697,359B1, and WO2014018423A2.

Isozyme Electrophoresis and RFLPs have been widely used to determine genetic composition. Shoemaker and Olsen, (Molecular Linkage Map of Soybean (*Glycine max* L. *Merr.*) pp. 6.131-6.138 in S. J. O'Brien (Ed.) *Genetic Maps: Locus Maps of Complex Genomes*, Cold Spring Harbor Laboratory Press, Cold Spring Harbor, N.Y., (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (Eds.), *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). Additional SNPs to those described herein may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162,967. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation Breeding

Mutation breeding is another method of introducing new traits into *Stevia* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethylenamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

Production of Double Haploids

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., Allard (1960); Simmonds (1979); Sneep, et al. (1979); Fehr (1987)).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, and to the grower, processor, and consumer, for special advertising, marketing and commercial production practices, and new product utilization. The testing preceding the release of a new cultivar should take into consideration research and development costs as well as technical superiority of the final cultivar. For seed-propagated cultivars, it must be feasible to produce seed easily and economically.

The *Stevia* flower is monoecious in that the male and female structures are in the same flower. The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

FURTHER EMBODIMENTS

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, in particular embodiments, also relates to transformed versions of the claimed cultivar.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed *Stevia* plants, using transformation methods as described below to incorporate transgenes into the genetic material of the *Stevia* plant(s).

Expression Vectors for *Stevia* Transformation: Marker Genes

Expression vectors include at least one genetic marker operably linked to a regulatory element (for example, a promoter) that allows transformed cells containing the marker to be either recovered by negative selection (i.e., inhibiting growth of cells that do not contain the selectable marker gene), or by positive selection (i.e., screening for the product encoded by the genetic marker). Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals, confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Other selectable marker genes for plant transformation that are not of bacterial origin include, for example, mouse dihydrofolate reductase, plant 5-enolpyruvyl-shikimate-3-phosphate synthase and plant acetolactate synthase. Eichholtz, et al., *Somatic Cell Mol. Genet.*, 13:67 (1987); Shah, et al., *Science*, 233:478 (1986); Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase. Jefferson, R. A., *Plant Mol. Biol. Rep.*, 5:387 (1987); Teeri, et al., *EMBO J.*, 8:343 (1989); Koncz, et al., *PNAS*, 84:131 (1987); DeBlock, et al., *EMBO J.* 3:1681 (1984).

In-vivo methods for visualizing GUS activity that do not require destruction of plant tissue are available. Molecular Probes Publication 2908, IMAGENE GREEN, pp. 1-4 (1993) and Naleway, et al., *J. Cell Biol.*, 115:151a (1991). However, these in-vivo methods for visualizing GUS activity have not proven useful for recovery of transformed cells because of low sensitivity, high fluorescent backgrounds, and limitations associated with the use of luciferase genes as selectable markers. A gene encoding Green Fluorescent Protein (GFP) has been utilized as a marker for gene expression in prokaryotic and eukaryotic cells. Chalfie, et al., Science, 263:802 (1994). GFP and mutants of GFP may be used as screenable markers.

Expression Vectors for *Stevia* Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in *Stevia*. Optionally, the inducible promoter is operably linked to a nucleotide sequence encoding a signal sequence which is operably linked to a gene for expression in *Stevia*. With an inducible promoter the rate of transcription increases in response to an inducing agent.

Any inducible promoter can be used in the instant invention. See Ward, et al., *Plant Mol. Biol.*, 22:361-366 (1993). Exemplary inducible promoters include, but are not limited to, that from the ACEI system which responds to copper (Mett, et al., *PNAS,* 90:4567-4571 (1993)); In2 gene from maize which responds to benzenesulfonamide herbicide safeners (Hershey, et al., *Mol. Gen. Genet.*, 227:229-237 (1991) and Gatz, et al., *Mol. Gen. Genet.*, 243:32-38 (1994)); or Tet repressor from Tn10 (Gatz, et al., *Mol. Gen. Genet.*, 227:229-237 (1991)). An example inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *PNAS,* 88:0421 (1991)).

B. Constitutive Promoters:

A constitutive promoter is operably linked to a gene for expression in *Stevia* or the constitutive promoter is operably linked to a nucleotide sequence encoding a signal sequence which is operably linked to a gene for expression in *Stevia*.

Many different constitutive promoters can be utilized in the instant invention. Exemplary constitutive promoters include, but are not limited to, the promoters from plant viruses such as the 35S promoter from CaMV (Odell, et al., *Nature,* 313:810-812 (1985)) and the promoters from such genes as rice actin (McElroy, et al., *Plant Cell,* 2:163-171 (1990)); ubiquitin (Christensen, et al., *Plant Mol. Biol.,* 12:619-632 (1989) and Christensen, et al., *Plant Mol. Biol.,* 18:675-689 (1992)); pEMU (Last, et al., *Theor. Appl. Genet.,* 81:581-588 (1991)); MAS (Velten, et al., *EMBO J.,* 3:2723-2730 (1984)); and maize H3 histone (Lepetit, et al., *Mol. Gen. Genet.,* 231:276-285 (1992) and Atanassova, et al., *Plant Journal,* 2 (3): 291-300 (1992)).

The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a gene for expression in *Stevia*. Optionally, the tissue-specific promoter is operably linked to a nucleotide sequence encoding a signal sequence which is operably linked to a gene for expression in *Stevia*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science,* 23:476-482 (1983) and Sengupta-Gopalan, et al., *PNAS,* 82:3320-3324 (1985)); a leaf-specific and light-induced promoter, such as that from cab or rubisco (Simpson, et al., *EMBO J.,* 4(11):2723-2729 (1985) and Timko, et al., *Nature,* 318:579-582 (1985)); an anther-specific promoter, such as that from LAT52 (Twell, et al., *Mol. Gen. Genet.,* 217:240-245 (1989)); a pollen-specific promoter, such as that from Zm13 (Guerrero, et al., *Mol. Gen. Genet.,* 244:161-168 (1993)); or a microspore-preferred promoter, such as that from apg (Twell, et al., *Sex. Plant Reprod.,* 6:217-224 (1993)).

Signal Sequences for Targeting Proteins to Subcellular Compartments

Transport of protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Close, P. S., et al., Master's Thesis, Iowa State University (1993); Knox, C., et al., *Plant Mol. Biol.,* 9:3-17 (1987); Lerner, et al., *Plant Physiol.,* 91:124-129 (1989); Fontes, et al., *Plant Cell,* 3:483-496 (1991); Matsuoka, et al., *PNAS,* 88:834 (1991); Gould, et al., *J. Cell. Biol.,* 108:1657

(1989); Creissen, et al., *Plant J.*, 2:129 (1991); Kalderon, et al., *Cell*, 39:499-509 (1984); Steifel, et al., *Plant Cell*, 2:785-793 (1990).

Foreign Protein Genes and Agronomic Genes

With transgenic plants, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.*, 114:92-6 (1981).

According to an embodiment, the transgenic plant provided for commercial production of foreign protein is a *Stevia* plant. In another embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton, 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, agronomic genes can be expressed in transformed plants. More particularly, plants can be genetically engineered to express various phenotypes of agronomic interest. Exemplary genes implicated in this regard include, but are not limited to, those categorized below:

A. Genes that Confer Resistance to Pests or Disease and that Encode:
1. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., *Science*, 266:789 (1994) (cloning of the tomato Cf-9 gene for resistance to *Cladosporium fulvum*); Martin, et al., *Science*, 262:1432 (1993) (tomato Pto gene for resistance to *Pseudomonas syringae* pv. tomato encodes a protein kinase); Mindrinos, et al., *Cell*, 78:1089 (1994) (*Arabidopsis* RSP2 gene for resistance to *Pseudomonas syringae*).
2. A gene conferring resistance to a pest, such as nematodes. See, e.g., PCT Application No. WO 96/30517; PCT Application No. WO 93/19181.
3. A *Bacillus thuringiensis* protein, a derivative thereof or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.
4. A lectin. See, for example, the disclosure by Van Damme, et al., *Plant Molec. Biol.*, 24:25 (1994), who disclose the nucleotide sequences of several *Clivia miniata* mannose-binding lectin genes.
5. A vitamin-binding protein such as avidin. See PCT Application No. US 93/06487. The application teaches the use of avidin and avidin homologues as larvicides against insect pests.
6. An enzyme inhibitor, for example, a protease or proteinase inhibitor or an amylase inhibitor. See, for example, Abe, et al., *J. Biol. Chem.*, 262:16793 (1987) (nucleotide sequence of rice cysteine proteinase inhibitor); Huub, et al., *Plant Molec. Biol.*, 21:985 (1993) (nucleotide sequence of cDNA encoding tobacco proteinase inhibitor I); Sumitani, et al., *Biosci. Biotech. Biochem.*, 57:1243 (1993) (nucleotide sequence of *Streptomyces nitrosporeus* α-amylase inhibitor); and U.S. Pat. No. 5,494,813 (Hepher and Atkinson, issued Feb. 27, 1996).
7. An insect-specific hormone or pheromone, such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.
8. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor) and Pratt, et al., *Biochem. Biophys. Res. Comm.*, 163:1243 (1989) (an allostatin is identified in *Diploptera puntata*). See also, U.S. Pat. No. 5,266,317 to Tomalski, et al., who disclose genes encoding insect-specific, paralytic neurotoxins.
9. An insect-specific venom produced in nature by a snake, a wasp, etc. For example, see Pang, et al., *Gene*, 116:165 (1992), for disclosure of heterologous expression in plants of a gene coding for a scorpion insectotoxic peptide.
10. An enzyme responsible for a hyper-accumulation of a monoterpene, a sesquiterpene, a steroid, a hydroxamic acid, a phenylpropanoid derivative, or another non-protein molecule with insecticidal activity.
11. An enzyme involved in the modification, including the post-translational modification, of a biologically active molecule. For example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Molec. Biol.*, 23:691 (1993), who teach the nucleotide sequence of a cDNA encoding tobacco hornworm chitinase, and Kawalleck, et al., *Plant Molec. Biol.*, 21:673 (1993), who provide the nucleotide sequence of the parsley ubi4-2 polyubiquitin gene.
12. A molecule that stimulates signal transduction. For example, see the disclosure by Botella, et al., *Plant Molec. Biol.*, 24:757 (1994), of nucleotide sequences for mung bean calmodulin cDNA clones and Griess, et al., *Plant Physiol.,* 104:1467 (1994), who provide the nucleotide sequence of a maize calmodulin cDNA clone.
13. A hydrophobic moment peptide. See PCT Application No. WO 95/16776 (disclosure of peptide derivatives of Tachyplesin which inhibit fungal plant pathogens) and PCT Application No. WO 95/18855 (teaches synthetic antimicrobial peptides that confer disease resistance).
14. A membrane permease, a channel former or a channel blocker. For example, see the disclosure of Jaynes, et al., Plant Sci., 89:43 (1993), of heterologous expression of a cecropin-β-lytic peptide analog to render transgenic tobacco plants resistant to *Pseudomonas solanacearum.*
15. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.,* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.
16. An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Intl Symposium on Molecular Plant-Microbe Interactions (Edinburgh, Scotland) (1994) (enzymatic inactivation in transgenic tobacco via production of single-chain antibody fragments).
17. A virus-specific antibody. See, for example, Tavladoraki, et al., *Nature,* 366:469 (1993), who show that transgenic plants expressing recombinant antibody genes are protected from virus attack.
18. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., *Bio/technology,* 10:1436 (1992). The cloning and characterization of a gene which encodes a bean endopolygalacturonase-inhibiting protein is described by Toubart, et al., *Plant J.* 2:367 (1992).
19. A developmental-arrestive protein produced in nature by a plant. For example, Logemann, et al., *Bio/technology,* 10:305 (1992), have shown that transgenic plants expressing the barley ribosome-inactivating gene have an increased resistance to fungal disease.

B. Genes that Confer Resistance to an Herbicide:
1. An herbicide that inhibits the growing point or meristem, such as an imidazolinone or a sulfonylurea. Exemplary genes in this category code for mutant ALS and AHAS enzyme as described, for example, by Lee, et al., *EMBO J.,* 7:1241 (1988), and Miki, et al., *Theor. Appl. Genet.,* 80:449 (1990), respectively. Other herbicides such as dicamba increase plant growth.
2. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada, et al., and U.S. Pat. No. 4,975,374 to Goodman, et al., disclose nucleotide sequences of glutamine synthetase genes which confer resistance to herbicides such as L-phosphinothricin or cyclohexanedione. The nucleotide sequence of a PAT gene is provided in European Application No. 0 242 246 to Leemans, et al. DeGreef, et al., *Bio/technology,* 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2, and Acc1-S3 genes described by Marshall, et al., *Theor. Appl. Genet.,* 83:435 (1992).
3. An herbicide that inhibits photosynthesis, such as a triazine (psbA and gs+ genes) bromoxynil or a benzonitrile (nitrilase gene). Przibila, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.,* 285:173 (1992).
4. Herbicides that inhibit protox, including many different structural classes of molecules (Duke et al., Weed Sci. 39: 465 (1991); Nandihalli et al., Pesticide Biochem. Physiol. 43: 193 (1992); Matringe et al., *FEBS Lett.* 245: 35 (1989) Yanase and Andoh, Pesticide Biochem. Physiol. 35: 70 (1989)), including the diphenylethers {e.g. acifluorifen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82-556), and phenopylate and its O-phenylpyrrolidino—and piperidinocarbamate analogs.

C. Genes that Confer or Contribute to a Value-Added Trait, Such as:
1. Modified fatty acid metabolism, for example, by transforming a plant with an antisense gene of stearyl-ACP desaturase to increase stearic acid content of the plant. See Knultzon, et al., *PNAS,* 89:2624 (1992).
2. Decreased phytate content: (a) Introduction of a phytase-encoding gene would enhance breakdown of phytate, adding more free phosphate to the transformed plant. See, for example, Van Hartingsveldt, et al., *Gene,* 127:87 (1993), for a disclosure of the nucleotide sequence of an *Aspergillus niger* phytase gene; and (b) A gene could be introduced that reduced phytate content. For example, in maize, this could be accomplished by cloning and then reintroducing DNA associated with the single allele, which is responsible for maize mutants characterized by low levels of phytic acid. See, Raboy, et al., *Maydica,* 35:383 (1990).

3. Modified carbohydrate composition effected, for example, by transforming plants with a gene coding for an enzyme that alters the branching pattern of starch. See, Shiroza, et al., *J. Bacteol.,* 170:810 (1988) (nucleotide sequence of *Streptococcus* mutants fructosyltransferase gene); Steinmetz, et al., *Mol. Gen. Genet.,* 20:220 (1985) (nucleotide sequence of *Bacillus subtilis* levansucrase gene); Pen, et al., *Bio/technology,* 10:292 (1992) (production of transgenic plants that express *Bacillus licheniformis* α-amylase); Elliot, et al., *Plant Molec. Biol.,* 21:515 (1993) (nucleotide sequences of tomato invertase genes); Sorgaard, et al., *J. Biol. Chem.,* 268:22480 (1993) (site-directed mutagenesis of barley α-amylase gene); and Fisher, et al., *Plant Physiol.,* 102:1045 (1993) (maize endosperm starch branching enzyme II).

4. Modified fiber characteristics, such as fiber quality represent another example of a trait that may be modified in *Stevia* varieties. For example, U.S. Pat. No. 6,472,588 describes transgenic *Stevia* plants transformed with a sucrose phosphate synthase nucleic acid to alter fiber characteristics such as strength, length, fiber fineness, fiber maturity ratio, immature fiber content, fiber uniformity, and micronaire. *Stevia* plants comprising one or more genes coding for an enzyme selected from the group consisting of endoxyloglucan transferase, catalase and peroxidase for the improvement of *Stevia* fiber characteristics are also described in U.S. Pat. No. 6,563,022. *Stevia* fiber modification using ovary-tissue transcriptional factors preferentially directing gene expression in ovary tissue, particularly in very early fruit development, utilized to express genes encoding isopentenyl transferase in *Stevia* ovule tissue and modify the characteristics of boll set in *Stevia* plants and alter fiber quality characteristics including fiber dimension and strength is discussed in U.S. Pat. No. 6,329,570. A gene controlling the fiber formation mechanism in *Stevia* plants is described in U.S. Pat. No. 6,169,174. Genes involved in lignin biosynthesis are described in U.S. Pat. No. 5,451,514.

Methods for *Stevia* Transformation

Numerous methods for plant transformation have been developed, including biological and physical, plant transformation protocols. See, for example, Mild, et al., "Procedures for Introducing Foreign DNA into Plants" in *Methods in Plant Molecular Biology and Biotechnology,* Glick and Thompson (Eds.), CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology,* Glick and Thompson (Eds.), CRC Press, Inc., Boca Raton, pp. 89-119 (1993).

A. *Agrobacterium*-Mediated Transformation:

One method for introducing an expression vector into plants is based on the natural transformation system of *Agrobacterium.* See, for example, Horsch, et al., *Science,* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.,* 8:238 (1989). See also, U.S. Pat. No. 5,563,055 (Townsend and Thomas), issued Oct. 8, 1996.

B. Direct Gene Transfer:

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 µm to 4 µm. The expression vector is introduced into plant tissues with a biolistic device that accelerates the microprojectiles to speeds of 300 m/s to 600 m/s which is sufficient to penetrate plant cell walls and membranes. Sanford, et al., *Part. Sci. Technol.,* 5:27 (1987); Sanford, J. C., *Trends Biotech.,* 6:299 (1988); Klein, et al., *Bio/technology,* 6:559-563 (1988); Sanford, J. C., *Physiol Plant,* 7:206 (1990); Klein, et al., *Bio/technology,* 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., *Bio/technology,* 9:996 (1991). Alternatively, liposome and spheroplast fusion have been used to introduce expression vectors into plants. Deshayes, et al., *EMBO J.,* 4:2731 (1985); Christou, et al., *PNAS,* 84:3962 (1987). Direct uptake of DNA into protoplasts using $CaCl_2$ precipitation, polyvinyl alcohol, or poly-L-ornithine has also been reported. Hain, et al., *Mol. Gen. Genet.,* 199:161 (1985) and Draper, et al., *Plant Cell Physiol.* 23:451 (1982). Electroporation of protoplasts and whole cells and tissues has also been described. Donn, et al., In Abstracts of VIIth International Congress on Plant Cell and Tissue Culture IAPTC, A2-38, p. 53 (1990); D'Halluin, et al., *Plant Cell,* 4:1495-1505 (1992); and Spencer, et al., *Plant Mol. Biol.,* 24:51-61 (1994).

Following transformation of *Stevia* target tissues, expression of the above-described selectable marker genes allows for preferential selection of transformed cells, tissues, and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular *Stevia* cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

C. Single-Gene Conversion

When the term "*Stevia* plant" is used herein, this also includes any single gene conversions of that variety. The term "single gene converted plant" as used herein refers to those *Stevia* plants which are developed by a plant breeding technique called backcrossing wherein essentially all of the desired morphological and physiological characteristics of a variety are recovered in addition to the single gene transferred into the variety via the backcrossing technique. Backcrossing methods can be used herein to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental *Stevia* plant which contributes the gene for the desired characteristic is termed the "nonrecurrent" or "donor parent". This terminology refers to the fact that the nonrecurrent parent is used one time in the backcross protocol and therefore does not recur. The parental *Stevia* plant to which the gene or genes from the nonrecurrent parent are transferred is known as the recurrent parent as it is used for several rounds in the backcrossing protocol (Poehlman & Sleper (1994); Fehr (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *Stevia* plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185; 5,973,234; and 5,977,445, the disclosures of which are specifically hereby incorporated by reference.

Further reproduction of the variety can occur by tissue culture and regeneration. Tissue culture of various tissues of *Stevia* and regeneration of plants therefrom is well known and widely published. For example, reference may be had to Komatsuda, T., et al., Crop Sci., 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al. *Plant Cell Rep.,* 11:285-289 (1992); Pandey, P., et al., *Japan J. Breed.*, 42:1-5 (1992); and Shetty, K., et al., *Plant Science,* 81:245-251 (1992); as well as U.S. Pat. No. 5,024,944 issued Jun. 18, 1991 to Collins, et al., and U.S. Pat. No. 5,008,200 issued Apr. 16, 1991 to Ranch, et al. Thus, another aspect of this invention is to provide cells which upon growth and differentiation produce *Stevia* plants having high RebD and RebM as well as the markers SNPs disclosed herein.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185; 5,973,234; and U.S. Pat. No. 5,977,445, described certain techniques.

Methods for Extraction and Purification of Glycosides

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845. Processes for the extraction of RebD are described in U.S. Pat. No. 9,029,426, and the extraction of RebM are provided in U.S. application Ser. No. 14/254,653.

The compositions can be used as sweetness enhancers, flavor enhancers and sweeteners in various food and beverage products. Examples of food and beverage products include, but are not limited to, carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables. Additionally the compositions can be used in drug or pharmaceutical preparations and cosmetics, including but not limited to toothpaste, mouthwash, cough syrup, chewable tablets, lozenges, vitamin preparations, and the like. The compositions can be used "as-is" or in combination with other sweeteners, flavors and food ingredients.

DEPOSIT INFORMATION

A deposit of plant tissue of the *Stevia* variety named '807086' disclosed above and recited in the appended claims has been made with the China General Microbiological Culture Collection Center (CGMCC), Institute of Microbiology, Chinese Academy of Sciences, Datun Road, Chaoyang District 100101 China. The date of deposit was Sep. 24, 2014. The CGMCC accession number is CGMCC No. 9702. All restrictions upon the deposit have been removed, and the deposit is intended to meet all of the requirements of 37 C.F.R. § 1.801-1.809.

A deposit of plant tissue of the *Stevia* variety named '817096' disclosed above and recited in the appended claims has been made with the China General Microbiological Culture Collection Center (CGMCC), Institute of Microbiology, Chinese Academy of Sciences, Datun Road, Chaoyang District 100101 China. The date of deposit was Sep. 24, 2014. The CGMCC accession number is CGMCC No. 9703. All restrictions upon the deposit have been removed, and the deposit is intended to meet all of the requirements of 37 C.F.R. § 1.801-1.809.

A deposit of plant tissue of the *Stevia* variety named '814011' disclosed above and recited in the appended claims has been made with the China General Microbiological Culture Collection Center (CGMCC), Institute of Microbiology, Chinese Academy of Sciences, Datun Road, Chaoyang District 100101 China. The date of deposit was Sep. 24, 2014. The CGMCC accession number is CGMCC No. 9701. All restrictions upon the deposit have been removed, and the deposit is intended to meet all of the requirements of 37 C.F.R. § 1.801-1.809.

While a number of exemplary aspects and embodiments have been discussed above, those of skill in the art will recognize certain modifications, permutations, additions, and sub-combinations thereof. It is therefore intended that the following appended claims and claims hereafter are interpreted to include all such modifications, permutations, additions, and sub-combinations as are within their true spirit and scope.

What is claimed is:

1. A method for producing a *Stevia* plant comprising:
   (a) screening a population of *Stevia* plants for at least one SNP comprising: SNP2 in SEQ ID NO:1, SNP10 in SEQ ID NO:2, SNP12 in SEQ ID NO:3, SNP17 in SEQ ID NO:4, SNP19 in SEQ ID NO:5, SNP20 in SEQ ID NO:6, SNP22 in SEQ ID NO:7, and SNP24 in SEQ ID NO:8;
   (b) selecting a first *Stevia* plant having at least one said SNP;
   (c) selecting a second *Stevia* plant having at least one said SNP, wherein the SNP of the second *Stevia* plant is different from the SNP of the first *Stevia* plant of step (b);
   (d) crossing said first selected *Stevia* plant with said second selected *Stevia* plant, wherein said second *Stevia* plant is genetically distinct from said first selected *Stevia* plant;
   (e) repeating steps (b), (c) and (d) on plants resulting from said crossing to obtain *Stevia* plants homozygous for all said SNPs; and
   (f) screening said *Stevia* plants homozygous for all said SNPs to confirm the presence of all said SNPs in homozygous form to produce a *Stevia* plant, wherein the leaves of said *Stevia* plant have a high rebaudioside D content, a high rebaudioside M content, or a high rebaudioside D and high rebaudioside M content.

2. The method of claim 1, wherein said screening comprises a PCR reaction followed by DNA sequencing, wherein said PCR reaction uses at least one of the following primers: SEQ ID NO: 117, SEQ, SEQ ID NO: 118, SEQ ID NO: 119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, or SEQ ID NO:138.

* * * * *

SEQUENCE LISTING

```
<160> NUMBER OF SEQ ID NOS: 138

<210> SEQ ID NO 1
<211> LENGTH: 481
<212> TYPE: DNA
<213> ORGANISM: Stevia rebaudiana

<400> SEQUENCE: 1
tcagccacct ttctatcttg caaaagaacc aaaaaaagat gaaaaatatt gtgcttttta      60
aactcatgta agttaaaaag caaaagaaac aaaaatcaag aaaatctttg atcttgatga     120
agagtgtact tgccttttct tggaaacttg aatatcttcc attttgatgt tgtttatatg     180
atgaagaaac tgaaaaaagt gttgttgaat gagtaagtat ggaactagga agaggatgaa     240
agtattaaag aaggacaatt gattaagagg gaaagaaagg gaaataaagc aataggtgac     300
aagatcccca tcatgcactt caccacttcc atccatgtgc taattacttc aatacccttg     360
ttcccatgga tatagttttt tatccaaaaa ttaattaaat atacaagtgg ccgattttta     420
ttattatttc tattatgtag tagttgggtg aggttaaatc ctctaactaa cacattgcag     480
t                                                                    481

<210> SEQ ID NO 2
<211> LENGTH: 359
<212> TYPE: DNA
<213> ORGANISM: Stevia rebaudiana

<400> SEQUENCE: 2
tcgtatactg ctttgggttg ccggaagttg ccgtgttaag ggaagaagcc acgtctggtt      60
gtctctctta ggtactcagc ggctccgaaa aaggttcggt cgatttaggt ttaatcgtga     120
ccgaagacaa ggttttgggt cgccattgat gtttcacgaa ggaatttagt ttctgcctac     180
tggtttattt tttattgaac agggaaaaag gatttttcaa ttcctgactt ggaataggta     240
gatcttctaa tctaactttg acttcatgac cttgattctc caagaactcc tttcgatctc     300
tagtagtgtt gtttcggctc ctcatagctc gaacaatctt gtgaccctgt tcttgacca     359

<210> SEQ ID NO 3
<211> LENGTH: 681
<212> TYPE: DNA
<213> ORGANISM: Stevia rebaudiana

<400> SEQUENCE: 3
ttacatttca ttttgataca caaacatatg tttatgtgtg tcaatcaaag tagaagaact      60
tacttaccaa gtggattga ttgattttag catcattaat cttgattaca ccaacataca     120
cctaaatata gatgagatgt gtgtgtggag aatgatagag agagagaact ataagctaga     180
```

| aggaaaaggc ttgatcttta tgaatgatat acacatgtgt atatgtgtat atatatatag | 240 |
| agagagagag agacttcaag aaatatatgg tttaatcttt ctgggttata tggtttaatc | 300 |
| tttatgggtg cacatgggat gacctcatgt atcttggatt tacatattag tgggagttgg | 360 |
| tttcttcatt taattcaata attaatttac tcaatttgaa atcacatact aaaatattgc | 420 |
| catcttgatt tatttataaa caaagctttt acacctattt tttattgcgc ggagcttgaa | 480 |
| tccatgattt taagaagagt aatacattta ctctttgtaa aatcaacaaa tattgaatgc | 540 |
| ctcgtatacc atttaaataa aaatcaacat ttttaatccc aaacgttgaa tataattatt | 600 |
| ataaataata tcttaaggca caaagataca aacgacgaca aagtttataa tatgatacac | 660 |
| gttccaaata actaggaatc t | 681 |

<210> SEQ ID NO 4
<211> LENGTH: 285
<212> TYPE: DNA
<213> ORGANISM: Stevia rebaudiana

<400> SEQUENCE: 4

| ctttctttga gtcggcggag atcagattgt aacttcgttt ttctgtttgg tgaacaagca | 60 |
| aacttatttt ttttcttggt attttaatct tttatgattc ttgtagtgtt ttgttttttg | 120 |
| tcttgatacg atggctagct taagttccca ttcgtgtttt tgatgctcg attttacgaa | 180 |
| tgagcgttta ttttgcattc gtgttctttt atgctcgttt ttatagattc gcccagtcat | 240 |
| aaaacaaaag ggataaaact tgttgcaacg tacgtagtaa acccc | 285 |

<210> SEQ ID NO 5
<211> LENGTH: 396
<212> TYPE: DNA
<213> ORGANISM: Stevia rebaudiana

<400> SEQUENCE: 5

| tcgcacctta caaaaacaaa gagtgtacaa ttgtacataa tcatttcatc tccaaaagcc | 60 |
| ccaaataatt tccatagttt cctggcggga accatcattt tcacacacta cacacagtga | 120 |
| cgcgatggaa gatgaacctg atgttcctga acaactcgtt cgccgatcgg tttgtctcga | 180 |
| aatccattca caagttcttt tatattgcac tgatttgata cttagggttt taattttgtt | 240 |
| atactgtata attgtgtata tttgagtgag tgtatgtgta attgctgtgt ttatgatcga | 300 |
| tagaaaaggc ctagggttcc gacgaagaac tttgacgggg aacctagtag gaatcgagat | 360 |
| gtttttgagt ccgaggagga gtccggtgat gaattg | 396 |

<210> SEQ ID NO 6
<211> LENGTH: 500
<212> TYPE: DNA
<213> ORGANISM: Stevia rebaudiana

<400> SEQUENCE: 6

| tttggatgga cttggtttga acttgtgtta tgttaaactt acttttcata tgttttatc | 60 |
| atattataat ttacgctgtt taatatattg tgtatttaa tttattcatt gaattgagtc | 120 |
| aaaaacaaat tgagccgaac tcgagctcag attgtaagct cagtttaaaa tcaagtcgag | 180 |
| tccgagcttt gcctggctta attagctcgg ctcatgaaca accctaaccg tgagtcgttt | 240 |
| gaccggattt atctgtttcc ttcttagtta tttcttttgc tcttcttgtt tgacttggcg | 300 |
| gttgtttgat accaaattaa ttaattacct cgttaaaatg ctacctcgaa tcggccagag | 360 |
| gtatagtctg tttggttcac tataataatg actatgaatc gatcaacaag tttcttaccc | 420 |

```
attcaacttt aaacacataa tgaatcattt agacctttac ccatcaagcc ttttacacgt    480
caagctccac caaacaacct                                                500

<210> SEQ ID NO 7
<211> LENGTH: 486
<212> TYPE: DNA
<213> ORGANISM: Stevia rebaudiana

<400> SEQUENCE: 7
aacctgtctc aatgggacct aaaagttatt atgtataact attattatat acttgaaata     60
ttgacaatca ctaagtgtct atttcattat ctgcaagcat atattttaat gttgcatggc    120
tttagctgat gcttcttgaa ttatttactg atctaacttg tttcttattt ttcgtcagtt    180
gatggcagtt aaatcctgtc atgaccgtaa catcacccac agggatatta accaggtga    240 gaatattatt gtcttctaac caaaagtgca actgtttctt gttttcatct ataaaagcat    300
tcgttctttt ttaaatggaa aattggattt taagaatccc aactttgacc tattggcctg    360
taataatccc aattctggaa attgttacca ccaatccgaa cttttatatc atttacctat    420
gacagtctcc agccaacaga acctaactcc gttagcattt tgttaacgtg gcatggctag    480
caatat                                                              486

<210> SEQ ID NO 8
<211> LENGTH: 500
<212> TYPE: DNA
<213> ORGANISM: Stevia rebaudiana

<400> SEQUENCE: 8
tggggaattg tgttgactgt tgacacaaac acttttttg accattttcc gaatctttaa      60
tataaataat taatgtgcca attatgatta gatgacaaat gatttaaatc ttgactataa    120
tgattttgga ggttggatga aatatagaca ttgttgactt tcaacctgtt tgactttctt    180
ttttatctaa ctttttttctt atttgaccag tttcagataa aacacaaccc aaattgacat    240
gtaactaaat gcgtcaaaat tacaacctct actatttta tagttaaaga agtcaaaca     300 tgtcaaagac tgtttctttt gattatgaat ctgattttag ggttttttgtt gtattttagg    360 ggttgttact ttcaagaagc agatgatgtg aaaatgaata tgagtattgc aactgcatac    420
cagaaatcag ttgatacact tttgaattgg ataaataaag aagtaaatat aaataaaaca    480
caagttattt tccgaagctt                                                500

<210> SEQ ID NO 9
<211> LENGTH: 2127
<212> TYPE: DNA
<213> ORGANISM: Stevia rebaudiana

<400> SEQUENCE: 9
cgtgggttgg cgagtgaaga taataacaat aataataata ttaagggaga gtgaacgtgg     60
tgctctaatt cacctaagaa atttgcagga attgaggaca attatgaaaa atgatgaatt    120
aaacaacact aagttacaac tcaactgtcg gtgatcaaat gctattatta ttcaaagaga    180
atgaagatcg atcagaaagc tttcgtttta ttggttgcat aaacagaaac aataagaaac    240
atatgaaggc ttttatagcc tacaaaacat aacataaact agctcacata accaacaacc    300
atcctttatt taatttaaac caagtagtct ttgcttctaa taactcaaat taccagctac    360
tcagctagca tgcaatccaa gtgcttgatt aatcatcgtg ttatttacaa cgatgaaatg    420
```

```
taagaaacta gagactctaa tgattcgtaa gatgaaccac ccttcatcaa agaaacatct    480 gcctttgtt tcaaaactct tgcattctgt ctaatgtatt ctccttcttc atccaccata    540
actcttctta ttgcatttgc tatctctcct ctttcccacc cattttccaa atacacccct    600
accttcaaaa catcactcat gtatctagca ttcaacggtt gatcgagccc aaaatccgag    660
aaaatcatag gaacaccttc acaaacgctt tccaacgtag agttccatcc gctatgagtc    720
cagaatgcgc ctattgctcc atgagctagc acttcttgct gcggaaccca tttcacaata    780
cgtcctcttt cacccaagaa cccatctggc aacggttcga cccacgtcga acccttgaca    840
aacccaggtc gaaccaccca taaaaacgac tgcttgctat caaccaaccc acgagctatt    900
tccaagaaat ctttctcatc cagtacttca gtaccactac caaaactaac atacagtacc    960
gaacgtgacg gttgttggtc taaccatgga aaaacggttc gatcgtggtc tagtaagctg   1020
ctggaagagg ctgtcaaatg cttggggagt ggtatcaaga aacttggagc cgggatctca   1080
cggataacag tttcgagctc agactcttcg agttccttaa atgagttcca gatgactcct   1140
gaagatgctt tgtttgttt cgtaatgttc tcgaaatact ctttgtattt tttccacatc   1200
gaaaaactac acttgatatc tttcacttttc agcataggaa acccactcgc ttgttcttcc   1260
aaacgggttt tgtcatcagg atcgaggtaa ccaagctcat caaactgagg aagtgaaaca   1320
tgtgcatgaa aattaaacaa gctgcttgtc accaaaacaa gccgtcggag gttaagactg   1380
tcagcaacag attgcgtgaa gtaccaaatc tgatcggcga ttaaacacga tacctctcca   1440
tcttcttcag aagctaacat caacagttcc agttcgcgtc gtaattcgtc agctccgtgt   1500
tcgttgataa tcagaatccg cataacagcg agcggaccat gagtcggtag attggaaatg   1560
cgtacgtctt gtgggtcgtt gtcgaggatg aatctgaaag tgaagtgagg gtaattagat   1620
gttttgggtt tgttgaagtt ggtgtgaaag atggtgatac tgaatccttt ggagtacaac   1680
acattggcta gctgaagcat tgggtttatg tgaccttgaa atggtaccgg gaataatatt   1740
attctccggc gccggcgaac ggtggtctcc gttttatttt ccattgggtt tgactgatgt   1800
ttacacacaa gaattattaa atatataac aataaaatag tgtcggcaag caattcattt   1860
aatttacaga ggttaggtag ctgagatctg catgtggaaa atgcacatct tgtgtggtcc   1920
aggttgttat tgccgatcct tatccttatt atacagatga ttggtcctga agatcttgtg   1980
ttgtatctat gtatttgtca aattaataat aaaagacaaa gattccaata attctgcaac   2040
catgcaaaaa agttccccat aattttttaaa ttttttttata tataatttgt atgcaaaaat   2100
attttatata aaggtttatt ttatttta                                      2127
```

<210> SEQ ID NO 10
<211> LENGTH: 2195
<212> TYPE: DNA
<213> ORGANISM: Stevia rebaudiana

<400> SEQUENCE: 10

```
cgtgggttgg cgagtgaaga taataacaat aataataata ttaagggaga gtgaacgtgg     60
tgctctaatt cacctaagaa atttgcagga attgaggaca attatgaaaa atgatgaatt    120
aaacaacact aagttacaac tcaactgtcg gtgatcaaat gctattatta ttcaaagaga    180
atgaagatcg atcagaaagc tttcgtttta ttggttgcat aaacagaaac aataagaaac    240
atatgaaggc tttatagcc tacaaaacat aacataaact agctcacata accaacaacc    300
atcctttatt taatttaaac caagtagtct ttgcttctaa taactcaaat taccagctac    360
tcagctagca tgcaatccaa gtgcttgatt aatcatcgtg ttatttacaa cgatgaaatg    420
```

```
taagaaacta gagactctaa tgattcgtaa gatgaaccac ccttcatcaa agaaacatct    480
gccttttgtt tcaaaactct tgcattctgt ctaatgtatt ctccttcttc atccaccata    540
actcttctta ttgcatttgc tatctctcct ctttcccacc catttttccaa atacacccct   600 accttcaaaa catcactcat gtatctagca ttcaacggtt gatcgagccc aaaatccgag    660
aaaatcatag gaacaccttc acaaacgctt ccaacgtag agttccatcc gctatgagtc     720
cagaatgcgc ctattgctcc atgagctagc acttcttgct gcggaaccca tttcacaata    780
cgtcctcttt cacccaagaa cccatctggc aacggttcga cccacgtcga acccttgaca    840
aacccaggtc gaaccaccca taaaaacgac tgcttgctat caaccaaccc acgagctatt    900
tccaagaaat ctttctcatc cagtacttca gtaccactac caaaactaac atacagtacc    960
gaacgtgacg gttgttggtc taaccatgga aaaacggttc gatcgtggtc tagtaagctg   1020
ctggaagagg ctgtcaaatg cttggggagt ggtatcaaga aacttggagc cgggatctca   1080
cggataacag tttcgagctc agactcttcg agttccttaa atgagttcca gatgactcct   1140
gaagatgctt ttgtttgttt cgtaatgttc tcgaaatact ctttgtattt tttccacatc   1200
gaaaaactac acttgatatc tttcactttc agcataggaa acccactcgc ttgttcttcc   1260
aaaccttaaa tcaaataatt cacaacgtaa ctgaaacata aaaacgagaa actaaattaa   1320
ttaatgactc acgggttttg tcatcaggat cgaggtaacc aagctcatca aactgaggaa   1380
gtgaaacatg tgcatgaaaa ttaaacaagc tgcttgtcac caaaacaagc cgtcggaggt   1440
taagactgtc agcaacagat tgcgtgaagt accaaatctg atcggcgatt aaacacgata   1500
cctctccatc ttcttcagaa gctaacatca acagttccag ttcgcgtcgt aattcgtcag   1560
ctccgtgttc gttgataatc agaatccgca taacagcgag cggaccatga gtcggtagat   1620
tggaaatgcg tacgtcttgt gggtcgttgt cgaggatgaa tctgaaagtg aagtgagggt   1680
aattagatgt tttgggtttg ttgaagttgg tgtgaaagat ggtgtactg  aatcctttgg   1740 agtacaacac attggctagc tgaagcattg ggtttatgtg accttgaaat ggtaccggga   1800
ataatattat tctccggcgc cggcgaacgg tggtctccgt tttatttttcc attgggtttg   1860 actgatgttt acacacaaga attattaaaa tatataacaa taaaatagtg tcggcaagca   1920
attcatttaa tttacagagg ttaggtagct gagatctgca tgtggaaaat gcacatcttg   1980
tgtggtccag gttgttattg ccgatcctta tccttattat acagatgatt ggtcctgaag   2040
atcttgtgtt gtatctatgt atttgtcaaa ttaataataa aagacaaaga ttccaataat   2100
tctgcaacca tgcaaaaaag ttccccataa tttttaaatt tttttatata taatttgtat   2160
gcaaaaatat tttatataaa ggtttatttt attta                             2195
```

<210> SEQ ID NO 11
<211> LENGTH: 807
<212> TYPE: DNA
<213> ORGANISM: Stevia rebaudiana

<400> SEQUENCE: 11

```
catccgctat gagtccagaa tgcgcctatt gctccatgag ctagcacttc ttgctgcgga    60
acccatttca caatacgtcc tctttcaccc aagaacccat ctggcaacgg ttcgacccac   120
gtcgaaccct tgacaaaccc aggtcgaacc acccataaaa acgactgctt gctatcaacc   180
aacccacgag ctatttccaa gaaatctttc tcatccactt cactagtact accaaaacta   240
acatacagta ccgaacttgg cggttgttgg tctaaccatg gaaaaacggt tcgatcgtgg   300
```

-continued

```
tctagtaagc tgctggaaga ggctgtcaaa tgcttgggga gtggtatcaa gaaacttgga      360
gccgggagga agtcacgggt aatcgtttcg acctcgggct cttcgagttc cttaaatgag      420
ttccagatga ctcctgaaga tgcttttgtt tgtttcgtaa tgttctcgaa atactctttg      480 tatttttttcc acatcgaaaa actacacttg atatctttca ctttcagcat aggaaaccca     540
ctcgcttgtt cttccaaacg ggttttgtca tcaggatcga ggtaaccaag ctcatcaaac      600
tgaggaagtg aaacatgtgc atgaaaatta acaagctgc ttgtcaccaa acaagccgt        660 cggaggttaa gactgtcagc aacagattgc gtgaagtacc aaatctgatc ggcgattaaa      720
cacgatacct ctccatcttc ttcagaagct aacatcaaca gttccagttc gcgtcgtaat      780
tcgtcagctc cgtgttcgtt gataatc                                         807
```

<210> SEQ ID NO 12
<211> LENGTH: 799
<212> TYPE: DNA
<213> ORGANISM: Stevia rebaudiana

<400> SEQUENCE: 12

```
actctgagtg cagaatgcac cgattgctcc atgagctagc acttcttgct gcggaaccca      60
tttcacaata cgtcctcttt cacccaagaa cccatctggc aacggttcga cccacgtcga     120
acccttgaca aacccaggtc gaaccaccca taaaaacgac tgcttgctat caaccaaccc     180
acgagctatt tccaagaaat ctttctcatc cacttcagta ccactaccaa actaacata     240 cagtaccgaa cgtgacggtt gttggtctaa ccatggaaaa acggttcgat cgtggtctag     300
taagctgctg gaagaggctg tcaaatgctt ggggagtggt atcaagaaac ttggagccgg     360
gatctcacgg ataacagttt cgagctcaga ctcttcgagt tccttaaatg agttccagat     420
gactcctgaa gatgcttttg tttgtttcgt aatgttctcg aaatactctt tgtatttttt     480
ccacatcgaa aaactacact tgatatcttt cactttcagc ataggaaacc cactcgcttg     540
ttcttccaaa cgggttttgt catcaggatc gaggtaacca agctcatcaa actgaggaag     600
tgaaacatgt gcatgaaaat taaacaagct gcttgtcacc aaaacaagcc gtcggaggtt     660
aagactgtca gcaacagatt gcgtgaagta ccaaatctga tcggcgatta aacacgatac     720
ctctccatct tcttcagaag ctaacatcaa cagttccagt tcgcgtcgta attcgtcagc     780
tccgtgttcg ttgataatc                                                  799
```

<210> SEQ ID NO 13
<211> LENGTH: 875
<212> TYPE: DNA
<213> ORGANISM: Stevia rebaudiana

<400> SEQUENCE: 13

```
catccgctat gagtccagaa tgcgcctatt gctccatgag ctagcacttc ttgctgcgga      60
acccatttca caatacgtcc tctttcaccc aagaacccat ctggcaacgg ttcgacccac     120
gtcgaaccct tgacaaaccc aggtcgaacc acccataaaa acgactgctt gctatcaacc     180
aacccacgag ctatttccaa gaaatctttc tcatccactt cactagtact accaaaacta     240
acatacagta ccgaacgtgg cggttgttgg tctaaccatg gaaaacggt tcgatcgtgg     300 tctagtaagc tgctggaaga ggctgtcaaa tgcttgggga gtggtatcaa gaaacttgga     360
gccgggagga agtcacgggt aatcgtttcg acctcgggct cttcgagttc cttaaatgag     420
ttccagatga ctcctgaaga tgcttttgtt tgtttcgtaa tgttctcgaa atactctttg     480 tatttttttcc acatcgaaaa actacacttg atatctttca ctttcagcat aggaaaccca     540
```

```
ctcgcttgtt cttccaaacc ttaaatcaaa taattcacaa cgtaactgaa acataaaaac      600
gagaaactaa attaattaat gactcacggg ttttgtcatc aggatcgagg taaccaagct      660
catcaaactg aggaagtgaa acatgtgcat gaaaattaaa caagctgctt gtcaccaaaa      720
caagccgtcg gaggttaaga ctgtcagcaa cagattgcgt gaagtaccaa atctgatcgg      780
cgattaaaca cgatacctct ccatcttctt cagaagctaa catcaacagt tccagttcgc      840
gtcgtaattc gtcagctccg tgttcgttga taatc                                 875

<210> SEQ ID NO 14
<211> LENGTH: 2127
<212> TYPE: DNA
<213> ORGANISM: Stevia rebaudiana

<400> SEQUENCE: 14
cgtgggttgg cgagtgaaga taataacaat aataataata ttaagggaga gtgaacgtgg       60
tgctctaatt cacctaagaa atttgcagga attgaggaca attatgaaaa atgatgaatt      120
aaacaacact aagttacaac tcaactgtcg gtgatcaaat gctattatta ttcaaagaga      180
atgaagatcg atcagaaagc tttcgtttta ttggttgcat aaacagaaac aataagaaac      240
atatgaaggc ttttatagcc tacaaaacat aacataaact agctcacata accaacaacc      300
atcctttatt taatttaaac caagtagtct ttgcttctaa taactcaaat taccagctac      360
tcagctagca tgcaatccaa gtgcttgatt aatcatcgtg ttatttacaa cgatgaaatg      420
taagaaacta gagactctaa tgattcgtaa atgaaccac ccttcatcaa agaaacatct      480
gccttttgtt tcaaaactct tgcattctgt ctaatgtatt ctccttcttc atccaccata      540
actcttctta ttgcatttgc tatctctcct ctttcccacc cattttccaa atacacccct      600
accttcaaaa catcactcat gtatctagca ttcaacggtt gatcgagccc aaaatccgag      660
aaaatcatag gaacaccttc acaaacgctt tccaacgtag agttccatcc gctatgagtc      720
cagaatgcgc ctattgctcc atgagctagc acttcttgct gcggaaccca tttcacaata      780
cgtcctcttt cacccaagaa cccatctggc aacggttcga cccacgtcga acccttgaca      840
aacccaggtc gaaccaccca taaaaacgac tgcttgctat caaccaaccc acgagctatt      900
tccaagaaat cttctctcatc cagtacttca gtaccactac caaaactaac atacagtacc      960
gaacgtgacg gttgttggtc taaccatgga aaaacggttc gatcgtggtc tagtaagctg     1020
ctggaagagg ctgtcaaatg cttggggagt ggtatcaaga aacttggagc cgggatctca     1080
cggataacag tttcgagctc agactcttcg agttccttaa atgagttcca gatgactcct     1140
gaagatgctt ttgtttgttt cgtaatgttc tcgaattact ctttgtattt tttccacatc     1200
gaaaaactac acttgatatc tttcactttc agcataggaa acccactcgc ttgttcttcc     1260
aaacgggttt tgtcatcagg atcgaggtaa ccaagctcat caaactgagg aagtgaaaca     1320
tgtgcatgaa aattaaacaa gctgcttgtc accaaaacaa gccgtcggag gttaagactg     1380
tcagcaacag attgcgtgaa gtaccaaatc tgatcggcga ttaaacacga tacctctcca     1440
tcttcttcag aagctaacat caacagttcc agttcgcgtc gtaattcgtc agctccgtgt     1500
tcgttgataa tcagaatccg cataacagcg agcggaccat gagtcggtag attggaaatg     1560
cgtacgtctt gtgggtcgtt gtcgaggatg aatctgaaag tgaagtgagg gtaattagat     1620
gttttgggtt tgttgaagtt ggtgtgaaag atggtgatac tgaatccttt ggagtacaac     1680
acattggcta gctgaagcat tgggtttatg tgaccttgaa atggtaccgg gaataatatt     1740
```

```
attctccggc gccggcgaac ggtggtctcc gttttatttt ccattgggtt tgactgatgt   1800
ttacacacaa gaattattaa aatatataac aataaaatag tgtcggcaag caattcattt   1860
aatttacaga ggttaggtag ctgagatctg catgtggaaa atgcacatct tgtgtggtcc   1920
aggttgttat tgccgatcct tatccttatt atacagatga ttggtcctga agatcttgtg   1980
ttgtatctat gtatttgtca aattaataat aaaagacaaa gattccaata attctgcaac   2040
catgcaaaaa agttccccat aattttttaaa ttttttttata tataatttgt atgcaaaaat   2100
attttatata aaggtttatt ttattta                                       2127
```

<210> SEQ ID NO 15
<211> LENGTH: 2195
<212> TYPE: DNA
<213> ORGANISM: Stevia rebaudiana

<400> SEQUENCE: 15

```
cgtgggttgg cgagtgaaga taataacaat aataataata ttaagggaga gtgaacgtgg     60
tgctctaatt cacctaagaa atttgcagga attgaggaca attatgaaaa atgatgaatt    120
aaacaacact aagttacaac tcaactgtcg gtgatcaaat gctattatta ttcaaagaga    180
atgaagatcg atcagaaagc tttcgtttta ttggttgcat aaacagaaac aataagaaac    240
atatgaaggc ttttatagcc tacaaaacat aacataaact agctcacata accaacaacc    300
atcctttatt taatttaaac caagtagtct ttgcttctaa taactcaaat taccagctac    360
tcagctagca tgcaatccaa gtgcttgatt aatcatcgtg ttatttacaa cgatgaaatg    420
taagaaacta gagactctaa tgattcgtaa gatgaaccac ccttcatcaa agaaacatct    480
gccttttgtt tcaaaactct tgcattctgt ctaatgtatt ctccttcttc atccaccata    540
actcttctta ttgcatttgc tatctctcct ctttcccacc cattttccaa atacacccct    600
accttcaaaa catcactcat gtatctagca ttcaacggtt gatcgagccc aaaatccgag    660
aaaatcatag gaacaccttc acaaacgctt ccaacgtag agttccatcc gctatgagtc    720
cagaatgcgc ctattgctcc atgagctagc acttcttgct gcggaaccca tttcacaata    780
cgtcctcttt cacccaagaa cccatctggc aacggttcga cccacgtcga acccttgaca    840
aacccaggtc gaaccacccca taaaaacgac tgcttgctat caaccaaccc acgagctatt    900
tccaagaaat ctttctcatc cagtacttca gtaccactac caaaactaac atacagtacc    960
gaacgtgacg gttgttggtc taaccatgga aaaacggttc gatcgtggtc tagtaagctg   1020
ctggaagagg ctgtcaaatg cttggggagt ggtatcaaga acttggagc cgggatctca   1080 cggataacag tttcgagctc agactcttcg agttccttaa atgagttcca gatgactcct   1140
gaagatgctt tgtttgtttt cgtaatgttc tcgaattact ctttgtattt tttccacatc   1200
gaaaaactac acttgatatc tttcactttc agcataggaa acccactcgc ttgttcttcc   1260
aaaccttaaa tcaaataatt cacaacgtaa ctgaaacata aaaacgagaa actaaattaa   1320
ttaatgactc acgggttttg tcatcaggat cgaggtaacc aagctcatca aactgaggaa   1380
gtgaaacatg tgcatgaaaa ttaaacaagc tgcttgtcac caaaacaagc cgtcggaggt   1440
taagactgtc agcaacagat tgcgtgaagt accaaatctg atcggcgatt aaacacgata   1500
cctctccatc ttcttcagaa gctaacatca acagttccag ttcgcgtcgt aattcgtcag   1560
ctccgtgttc gttgataatc agaatccgca taacagcgag cggaccatga gtcggtagat   1620
tggaaatgcg tacgtcttgt gggtcgttgt cgaggatgaa tctgaaagtg aagtgagggt   1680
aattagatgt tttgggtttg ttgaagttgg tgtgaaagat ggtgatactg aatcctttgg   1740
```

```
agtacaacac attggctagc tgaagcattg ggtttatgtg accttgaaat ggtaccggga    1800
ataatattat tctccggcgc cggcgaacgg tggtctccgt tttatttcc attgggtttg     1860 actgatgttt acacacaaga attattaaaa tatataacaa taaaatagtg tcggcaagca    1920
attcatttaa tttacagagg ttaggtagct gagatctgca tgtggaaaat gcacatcttg    1980
tgtggtccag ttgttattg ccgatcctta tccttattat acagatgatt ggtcctgaag     2040
atcttgtgtt gtatctatgt atttgtcaaa ttaataataa aagacaaaga ttccaataat    2100
tctgcaacca tgcaaaaaag ttccccataa ttttaaatt tttttatata taatttgtat     2160
gcaaaaatat tttatataaa ggtttatttt attta                               2195
```

<210> SEQ ID NO 16
<211> LENGTH: 807
<212> TYPE: DNA
<213> ORGANISM: Stevia rebaudiana

<400> SEQUENCE: 16

```
catccgctat gagtccagaa tgcgcctatt gctccatgag ctagcacttc ttgctgcgga    60
acccatttca caatacgtcc tctttcaccc aagaacccat ctggcaacgg ttcgacccac    120
gtcgaaccct tgacaaaccc aggtcgaacc acccataaaa acgactgctt gctatcaacc    180
aacccacgag ctatttccaa gaaatctttc tcatccactt cactagtact accaaaacta    240
acatacagta ccgaacttgg cggttgttgg tctaaccatg gaaaaacggt tcgatcgtgg    300
tctagtaagc tgctggaaga ggctgtcaaa tgtttgggta atggtatcag gaaacttggt    360
gtcgggagga agtcacgggt aatcgtttcg acctcgggct cttggagttc cttaaacgag    420
ttccagatga ctcctgaaga tgcttttgtt tgtttcgtaa tgttctcgaa atactctttg    480
tattttttcc acatcgaaaa actacacttg atatctttca ctttcagcat aggaaaccca    540
ctcgcttgtt cttccaaacg gttttgtca tcaggatcga ggtaaccaag ctcatcaaac     600
tgaggaagtg aaacatgtgc atgaaaatta acaagctgc ttgtcaccaa acaagccgt      660 cggaggttaa gactgtcagc aacagattgc gtgaagtacc aaatctgatc ggcgattaaa    720
cacgatacct ctccatcttc ttcagaagct aacatcaaca gttccagttc gcgtcgtaat    780
tcgtcagctc cgtgttcgtt gataatc                                       807
```

<210> SEQ ID NO 17
<211> LENGTH: 799
<212> TYPE: DNA
<213> ORGANISM: Stevia rebaudiana

<400> SEQUENCE: 17

```
actctgagtg caaatgcac cgattgctcc atgagctatc acttcttgct gcggaaccca     60
tttcacaata cgtcctcttt cacccaagaa cccatctggc aacggttcga cccacgtcga    120
acccttgaca aacccaggtc gaaccaccca taaaaacgac tgcttgctat caaccaaccc    180
acgagctatt tccaagaaat ctttctcatc cacttcacta ctactaccaa aactaacata    240
cagtaccgaa cttggcggtt gttggtctaa ccatggaaaa acggttcgat cgtggtctag    300
taagctgctg gaagaggctg tcaaatgctt ggggagtggt atcaagaaac ttggagccgg    360
gatctcacgg ataacagttt cgagctcaga ctcttcgagt tccttaaatg agttccagat    420
gactcctgaa gatgcttttg tttgtttcgt aatgttctcg aaatactctt tgtatttttt    480
ccacatcgaa aaactacact tgatatcttt cactttcagc ataggaaacc cactcgcttg    540
```

| | |
|---|---|
| ttcttccaaa cgggttttgt catcaggatc gaggtaacca agctcatcaa actgaggaag | 600 |
| tgaaacatgt gcatgaaaat taaacaagct gcttgtcacc aaaacaagcc gtcggaggtt | 660 |
| aagactgtca gcaacagatt gcgtgaagta ccaaatctga tcggcgatta aacacgatac | 720 |
| ctctccatct tcttcagaag ctaacatcaa cagttccagt tcgcgtcgta attcgtcagc | 780 |
| tccgtgttcg ttgataatc | 799 |

<210> SEQ ID NO 18
<211> LENGTH: 875
<212> TYPE: DNA
<213> ORGANISM: Stevia rebaudiana

<400> SEQUENCE: 18

| | |
|---|---|
| catccgctat gagtccagaa tgcgcctatt gctccatgag ctagcacttc ttgctgcgga | 60 |
| acccatttca caatacgtcc tctttcaccc aagaacccat ctggcaacgg ttcgacccac | 120 |
| gtcgaaccct tgacaaaccc aggtcgaacc acccataaaa acgactgctt gctatcaacc | 180 |
| aacccacgag ctatttccaa gaaatctttc tcatccactt cactagtact accaaaacta | 240 |
| acatacagta ccgaacttgg cggttgttgg tctaaccatg gaaaaacggt tcgatcgtgg | 300 |
| tctagtaagc tgctggaaga ggctgtcaaa tgtttgggta atggtatcag gaaacttggt | 360 |
| gtcgggagga agtcacgggt aatcgtttcg acctcgggct cttggagttc cttaaacgag | 420 |
| ttccagatga ctcctgaaga tgcttttgtt tgtttcgtaa tgttctcgaa atactctttg | 480 |
| tatttttcc acatcgaaaa actacacttg atatctttca ctttcagcat aggaaaccca | 540 |
| ctcgcttgtt cttccaaacc ttaaatcaaa taattcacaa cgtaactgaa acataaaaac | 600 |
| gagaaactaa attaattaat gactcacggg ttttgtcatc aggatcgagg taaccaagct | 660 |
| catcaaactg aggaagtgaa acatgtgcat gaaaattaaa caagctgctt gtcaccaaaa | 720 |
| caagccgtcg gaggttaaga ctgtcagcaa cagattgcgt gaagtaccaa atctgatcgg | 780 |
| cgattaaaca cgataccctt ccatcttctt cagaagctaa catcaacagt tccagttcgc | 840 |
| gtcgtaattc gtcagctccg tgttcgttga taatc | 875 |

<210> SEQ ID NO 19
<211> LENGTH: 2127
<212> TYPE: DNA
<213> ORGANISM: Stevia rebaudiana

<400> SEQUENCE: 19

| | |
|---|---|
| cgtgggttgg cgagtgaaga taataacaat aataataata ttaagggaga gtgaacgtgg | 60 |
| tgctctaatt cacctaagaa atttgcagga attgaggaca attatgaaaa atgatgaatt | 120 |
| aaacaacact aagttacaac tcaactgtcg gtgatcaaat gctattatta ttcaaagaga | 180 |
| atgaagatcg atcagaaagc tttcgtttta ttggttgcat aaacagaaac aataagaaac | 240 |
| atatgaaggc ttttatagcc tacaaaacat aacataaact agctcacata accaacaacc | 300 |
| atcctttatt taatttaaac caagtagtct ttgcttctaa taactcaaat taccagctac | 360 |
| tcagctagca tgcaatccaa gtgcttgatt aatcatcgtg ttatttacaa cgatgaaatg | 420 |
| taagaaacta gagactctaa tgattcgtaa gacgaaccac ccttcatcaa agaaacatct | 480 |
| gccttttgtt tcaaaactct tgcattctgt ctaatgtatt ctccttcttc atccaccata | 540 |
| actcttctta ttgcatttgc tatctctcct ctttcccacc catttttcaa atacacccct | 600 |
| accttcaaaa catcactcat gtatctagca ttcaacggtt gatcgagccc aaaatccgag | 660 |
| aaaatcatag gaacaccttc acaaacgctt tccaacgtag agttccatcc gctatgagtc | 720 |

```
cagaatgcgc ctattgctcc atgagctagc acttcttgct gcggaaccca tttcacaata      780
cgtcctcttt cacccaagaa cccatctggc aacggttcga cccacgtcga acccttgaca      840
aacccaggtc gaaccaccca taaaaacgac tgcttgctat caaccaaccc acgagctatt      900
tccaagaaat ctttctcatc cagtacttca gtaccactac caaaactaac atacagtacc      960
gaacgtgacg gttgttggtc taaccatgga aaacggttc gatcgtggtc tagtaagctg      1020
ctggaagagg ctgtcaaatg cttggggagt ggtatcaaga acttggagc cgggatctca      1080
cggataacag tttcgagctc agactcttcg agttccttaa atgagttcca gatgactcct      1140
gaagatgctt ttgtttgttt cgtaatgttc tcgaatatct ctttgccttg tttccacatc      1200
gaaaaaccac acttgatatc tttcactttc agcataggaa acccactcgc ttgttcttcc      1260
aaacgggttt tgtcatcagg atcgaggtaa ccaagctcat caaactgagg aagtgaaaca      1320
tgtgcatgaa aattaaacaa gctgcttgtc atcaaaacaa gccgtcggag gttaagactg      1380
tcagcaacag attgcgtgaa gtaccaaatc tgatcggcga ttaaacacga tacctctcca      1440
tcttcttcag aagctaacat caacagttcc agttcgcgtc gtaattcgtc agctccgtgt      1500
tcgttgataa tcagaatccg cataacagcg agcggaccat gagtcggtag attggaaatg      1560
cgttcgtctt gtgggtcgtt gtcgaggatg aatctgaaag tgaagtgagg gtaattagat      1620
gttttgggtt tgttgaagtt ggtgtgaaag atggtgatac tgaatccttt ggagtacaac      1680
acattggcta gctgaagcat tgggtttatg tgaccttgaa atggtaccgg gaataatatt      1740
attctccggc gccggcgaac ggtggtctcc gttttatttt ccattgggtt tgactgatgt      1800
ttacacacaa gaattattaa atatataac aataaaatag tgtcggcaag caattcattt      1860
aatttacaga ggttaggtag ctgagatctg catgtggaaa atgcacatct tgtgtggtcc      1920
aggttgttat tgccgatcct tatccttatt atacagatga ttggtcctga agatcttgtg      1980
ttgtatctat gtatttgtca aattaataat aaaagacaaa gattccaata attctgcaac      2040
catgcaaaaa agttccccat aatttttaaa ttttttttata tataatttgt atgcaaaaat      2100
attttatata aaggtttatt ttatttta                                         2127
```

<210> SEQ ID NO 20
<211> LENGTH: 2195
<212> TYPE: DNA
<213> ORGANISM: Stevia rebaudiana

<400> SEQUENCE: 20

```
cgtgggttgg cgagtgaaga taataacaat aataataata ttaagggaga gtgaacgtgg       60
tgctctaatt cacctaagaa atttgcagga attgaggaca attatgaaaa atgatgaatt      120
aaacaacact aagttacaac tcaactgtcg gtgatcaaat gctattatta ttcaaagaga      180
atgaagatcg atcagaaagc tttcgtttta ttggttgcat aaacagaaac aataagaaac      240
atatgaaggc tttatagcc tacaaaacat aacataaact agctcacata accaacaacc      300
atcctttatt taatttaaac caagtagtct ttgcttctaa taactcaaat taccagctac      360
tcagctagca tgcaatccaa gtgcttgatt aatcatcgtg ttatttacaa cgatgaaatg      420
taagaaacta gagactctaa tgattcgtaa gacgaaccac ccttcatcaa agaaacatct      480
gcctttgtt tcaaaactct tgcattctgt ctaatgtatt ctccttcttc atccaccata      540
actcttctta ttgcatttgc tatctctcct ctttcccacc catttccaa atacaccccc      600
accttcaaaa catcactcat gtatctagca ttcaacggtt gatcgagccc aaaatccgag      660
```

-continued

| | |
|---|---|
| aaaatcatag gaacaccttc acaaacgctt tccaacgtag agttccatcc gctatgagtc | 720 |
| cagaatgcgc ctattgctcc atgagctagc acttcttgct gcggaaccca tttcacaata | 780 |
| cgtcctcttt cacccaagaa cccatctggc aacggttcga cccacgtcga acccttgaca | 840 |
| aacccaggtc gaaccaccca taaaaacgac tgcttgctat caaccaaccc acgagctatt | 900 |
| tccaagaaat ctttctcatc cagtacttca gtaccactac caaaactaac atacagtacc | 960 |
| gaacgtgacg gttgttggtc taaccatgga aaaacggttc gatcgtggtc tagtaagctg | 1020 |
| ctggaagagg ctgtcaaatg cttggggagt ggtatcaaga aacttggagc cgggatctca | 1080 |
| cggataacag tttcgagctc agactcttcg agttccttaa atgagttcca gatgactcct | 1140 |
| gaagatgctt ttgtttgttt cgtaatgttc tcgaatatct ctttgccttg tttccacatc | 1200 |
| gaaaaaccac acttgatatc tttcactttc agcataggaa acccactcgc ttgttcttcc | 1260 |
| aaaccttaaa tcaaataatt cacaacgtaa ctgaaacata aaaacgagaa actaaattaa | 1320 |
| ttaatgactc acgggttttg tcatcaggat cgaggtaacc aagctcatca aactgaggaa | 1380 |
| gtgaaacatg tgcatgaaaa ttaaacaagc tgcttgtcat caaaacaagc cgtcggaggt | 1440 |
| taagactgtc agcaacagat tgcgtgaagt accaaatctg atcggtgatt aaacacgata | 1500 |
| cctcttcatc ttcttcagaa gctaacatca acagttccag ttcgcgtcgt aattcgtcag | 1560 |
| ctccgtgttc gttgataatc agaatccgca taacagcgag cggaccatga gtcggtagat | 1620 |
| tggaaatgcg ttcgtcttgt gggtcgttgt cgaggatgaa tctgaaagtg aagtgagggt | 1680 |
| aattagatgt tttgggtttg ttgaagttgg tgtgaaagat ggtgatactg aatcctttgg | 1740 |
| agtacaacac attggctagc tgaagcattg ggttaatgtg gccttgaaat ggtaccggga | 1800 |
| ataatattat tctccggcgc cggcgaacgg tggtctccgt tttatttttcc attgggtttg | 1860 |
| actgatgttt acacacaaga attattaaaa tatataacaa taaatagtg tcggcaagca | 1920 |
| attcatttaa tttacagagg ttaggtagct gagatctgca tgtggaaaat gcacatcttg | 1980 |
| tgtggtccag gttgttattg ccgatcctta tccttattat acagatgatt ggtcctgaag | 2040 |
| atcttgtgtt gtatctatgt atttgtcaaa ttaataataa aagacaaaga ttccaataat | 2100 |
| tctgcaacca tgcaaaaaag ttccccataa tttttaaatt tttttatata taatttgtat | 2160 |
| gcaaaaatat tttatataaa ggtttatttt attta | 2195 |

<210> SEQ ID NO 21
<211> LENGTH: 807
<212> TYPE: DNA
<213> ORGANISM: Stevia rebaudiana

<400> SEQUENCE: 21

| | |
|---|---|
| catccgctat gagtccagaa tgcgcctatt gctccatgag ctagcacttc ttgctgcgga | 60 |
| acccatttca caatacgtcc tctttcaccc aagaacccat ctggcaacgg ttcgacccac | 120 |
| gtcgaaccct tgacaaaccc aggtcgaacc acccataaaa acgactgctt gctatcaacc | 180 |
| aacccacgag ctatttccaa gaaatctttc tcatccactt cactagtact accaaaacta | 240 |
| acatacagta ccgaacttgg cggttgttgg tctaaccatg gaaaaacggt tcgatcttcg | 300 |
| tctagtaagc tgcttgatga ggctgtcaaa tgtttgggta atggtatcag gaaacttggt | 360 |
| gtcgggagga agtcacgggt aatcgtttcg acctcgggct cttggagttc cttaaacgag | 420 |
| ttccatatga ttcctgaaga tgcttttgtt tgttttatca tcttcccgaa tatctctttg | 480 |
| actacttgcc agttcgaata cgcagacttg atgtctttca ctttcagcat aggaaaccca | 540 |
| ctcgcttgtt cttccaaacg ggttttgtca tcaggatcga ggtaaccaag ctcatcaaac | 600 |

```
tgaggaagtg aaacatgtgc atgaaaatta acaagctgc ttgtcatcaa acaagccgt    660 cggaggttaa gactgtcagc aacagattgc gtgaagtacc aaatctgatc ggtgattaaa   720
cacgatacct cttcatcttc ttcagaagct aacatcaaca gttccagttc gcgtcgtaat   780
tcgtcagctc cgtgttcgtt gataatc                                      807

<210> SEQ ID NO 22
<211> LENGTH: 799
<212> TYPE: DNA
<213> ORGANISM: Stevia rebaudiana

<400> SEQUENCE: 22
actctgagtg cagaatgcac cgattgctcc atgagctatc acttcttgct gcggaaccca    60
tttcacaata cgtcctcttt cacccaagaa cccatctggc aacggttcga cccacgtcga   120
acccttgaca acccaggtc gaaccaccca taaaaacgac tgcttgctat caaccaaccc   180
acgagctatt ccaagaaat ctttctcatc cacttcacta gcactaccaa aactaacata   240
cagtaccgaa cgtgacggtt gttggtctaa ccatggaaaa acggttcgat cgtggtctag   300
taagctgctg gaagaggctg tcaaatgctt ggggagtggg atcaagaaac ttggagccgg   360
gatctcacgg ataacagttt cgagctcaga ctcttcgagt tccttaaatg agttccagat   420
gactcctgaa gatgcttttg tttgttttgt aatgttctcg aatatctctt tggcttcttt   480
ccagttcgaa aaaccagact tgatgtcttt cactttcagc ataggaaacc cactcgcttg   540
ttcttccaaa cgggttttgt catcaggatc gaggtaacca agctcatcaa actgaggaag   600
tgaaacatgt gcatgaaaat taaacaagct gcttgtcatc aaaacaagcc gtcggaggtt   660
aagactgtca gcaacagatt gcgtgaagta ccaaatctga tcggtgatta aacacgatac   720
ctcttcatct tcttcagaag ctaacatcaa cagttccagt tcgcgtcgta attcgtcagc   780
tccgtgttcg ttgataatc                                                799

<210> SEQ ID NO 23
<211> LENGTH: 875
<212> TYPE: DNA
<213> ORGANISM: Stevia rebaudiana

<400> SEQUENCE: 23
catccgctat gagtccagaa tgcgcctatt gctccatgag ctagcacttc ttgctgcgga    60
acccatttca caatacgtcc tctttcaccc aagaacccat ctggcaacgg ttcgacccac   120 gtcgaacccct tgacaaaccc aggtcgaacc acccataaaa acgactgctt gctatcaacc   180
aacccacgag ctatttccaa gaaatctttc tcatccactt cactagtact accaaaacta   240
acatacagta ccgaacttgg cggttgttgg tctaaccatg aaaaacggt tcgatcttcg   300 tctagtaagc tgcttgatga ggctgtcaaa tgtttgggta atggtatcag gaaacttggt   360
gtcgggagga agtcacgggt aatcgtttcg acctcgggct cttggagttc cttaaacgag   420
ttccatatga ttcctgaaga tgcttttgtt tgttttatca tcttcccgaa tatctctttg   480
actacttgcc agttcgaata cgcagacttg atgtctttca cttttagcat aggaaaccca   540
ctcgcttgtt cttccaaacc ttaaatcaaa taattcacaa cgtaactgaa acataaaaac   600
gagaaactaa attaattaat gactcacggg ttttgtcatc aggatcgagg taaccaagct   660
catcaaactg aggaagtgaa acatgtcat gaaaattaaa caagctgctt gtcatcaaaa   720
caagccgtcg gaggttaaga ctgtcagcaa cagattgcgt gaagtaccaa atctgatcgg   780
```

| | |
|---|---|
| tgattaaaca cgatacctct tcatcttctt cagaagctaa catcaacagt tccagttcgc | 840 |
| gtcgtaattc gtcagctccg tgttcgttga taatc | 875 |

<210> SEQ ID NO 24
<211> LENGTH: 1370
<212> TYPE: DNA
<213> ORGANISM: Stevia rebaudiana

<400> SEQUENCE: 24

| | |
|---|---|
| ggctggagtc aattgttttt atacaataca taatatagcg ttaaatggct ttataataac | 60 |
| gacggaaaag ttaatgactc gattctacca acgacttagc aattccaaca tgtgattaaa | 120 |
| aaagaagtgt aacaaggaca atcataacat catatgaatc attccaaaga aacccaacaa | 180 |
| ctaacttact tatagtctgt gaaacgactt atatattctt tttggttaac tctcatggtt | 240 |
| gttggcaacc acacgtacgt tcttttccat atagtctgtg aaacgactta tatattcttt | 300 |
| ttggttaact ctcatggttg ttggcaacca cacgtacgtt cttttccata tagtctgtga | 360 |
| aacgacttat atattccttt tgcagcttag tgtcgctgaa tattttactc atctctctcg | 420 |
| cattcgcctt gtagatctct ccttcatcgt ctacaacaac cgacctcagt gacgtggcaa | 480 |
| ccgactcctt ggtgaagtag ccatcttcct catttcttgg tatctcgatc cccacctgtt | 540 |
| tgtccgctaa tagtcgagca ttcagacatt ggtccccgaa atcggtagc atgattaaag | 600 |
| ggtgaccgaa cattaaccct tccaccactg aactccaacc acagtgagtc aagaaaccac | 660 |
| acaccgactc atggctcagt attcgtaact gaggtgccca actcgtccaa accatcccac | 720 |
| ggttactagt tcgttccaag aacccgttag gcaactccac cgagtctgac tcggtggaac | 780 |
| ctgcgggttt tctgagaacc cacaaaaatg gcaacccaga gagctcgaga cctagcgcta | 840 |
| actcagccag ctcgcttttg gtcaccgtaa cttcacttcc taatgcgacg tacaccacat | 900 |
| gccctattgg ttgaccatcg agccacttct tgattgacac ccatgggtct ccggtgctgg | 960 |
| tgggtggttc gggtggcaat aatcccacgg gaaccaccgg tagctgatgc agcttttcta | 1020 |
| aaagggttag ccattggggt tcgaactcat ggcaatgtct tataaacata caatctgatc | 1080 |
| cctttataac cattcctaaa cgatataaat ctgatacacc agaagaatta acagaaatat | 1140 |
| tatcagcaaa tatcaaattg gcctcatgct tccggtagca tactttgctc ggaaacggaa | 1200 |
| tccacttcgg cggtgtcata aaattctcaa ccctcgttcg atgatcataa ccggaaccac | 1260 |
| ttatcaagtc gtcagccgac gctccgagaa aagcaatgaa ccatgcgtta aaattcgagt | 1320 |
| aaaaggctcg cgaggtccgt agtccagctg cgacggacgg caaccaatac | 1370 |

<210> SEQ ID NO 25
<211> LENGTH: 1205
<212> TYPE: DNA
<213> ORGANISM: Stevia rebaudiana

<400> SEQUENCE: 25

| | |
|---|---|
| tagtgaatgt atataacata atgatatgt ttcaacctaa caaacggtta tttcatacac | 60 |
| ggaaaacaaa aatttatgat tattcaaaga acatttgat catctagcta gacaaaccca | 120 |
| ataacacata tattcttcat acgatcaaag ctcatgctca atagcaacca cacgaccttt | 180 |
| ttgttccaaa tagtctataa aagggtttat atacttattt tccggcttac tatccccgaa | 240 |
| tcgttgactc aactccatcg ccttcgcctt gtagatcttc ccttcatcat cgactaaaac | 300 |
| caacctcaat gatctggcca ccgactcctt ggtgaatgaa ccatcttcct catttcttgg | 360 |
| tatctcgatt cccacctgtt tatccgccat tactcgagca tttagacctt ggtccccaa | 420 |

```
aatcggtagc atgattagag ggtgaccgaa catcatcgct tccacaattg aactccaacc    480
acaatgagtc aagaaaccac aaaccgactc atggctcagt attcgtaact gaggtgccca    540
actcgtccag accaacccac ggtcacgagt tcgttccacg aacccgtctg caactccac     600
cgagttacca gagccaaccg gttttctaag aacccaaaag aatggcaacc cggagagctc    660
gagacccaga gctaactcag ccagctcgct ttggctcatc gtaccttcac ttccaaatgc    720
cacgtacacc acatgcccta ttggttgacc atcgagccac ttcttgattg tcacccatgg    780
gtctccggtg ctggtgggtg gttcgggtgg caataatccc acgggaacca ccggtagctg    840
atgcagcttt tctaaaaggg ttagccattg gggttcgaac tcatggcaat gtcttataaa    900
catacaatct gatcccttta taaccattcc taaacgatat aaatctgata caccagaaga    960
attaacagaa atattatcag caaatatcaa attggcctca tgcttccggt agcatacttt   1020
acttgggaac ggaaaccact tcggcggtgt caggaaatcg tcggctgttt tccgatcgtc   1080
tgtaccgttt atgatgtcat cgggagaaga tccgaaaaaa gagacggtcc atgcgttaaa   1140
aattgagaaa aaacctcgtg aaattccaag gctagtggct accgccggca accaataggg   1200
agcaa                                                               1205

<210> SEQ ID NO 26
<211> LENGTH: 1266
<212> TYPE: DNA
<213> ORGANISM: Stevia rebaudiana

<400> SEQUENCE: 26
tttttttttt tttacggctg gaatcaattg ctttattcat cacataattt ggctttaaat     60
agccttacaa taacaactta ttaatatagt agcttaaaac aattaactag gacacctcct    120
aagactcgat cgattctacc aacatattta gcaattccaa catttcattt gaatctttcc    180
aaaagaaacc caacaactca cacatacttg atgatatagt taactctcat gatcgatggc    240
aaccgcacgc gcattctttt ccaaatagtc tacgaattgg cttacatatt cttttcaac     300
cttagtgtcg ttatagattt tactcagctc cctcgcgttc gccttgtaga tctcccttc     360
tttttccaca acaacggacc tcagtgatct agcaaccgac tccttggtca agcaaccatc    420
ttcctcattt cttggtatct cgattcccac ctgtttgtcc tccagtaatc gagcattcag    480
aggttggtcc ccaaaaatcg gtagcatgat tagagggtga ccaaacatta gcccttccac    540
aattgatcca gaaccacaat gagtcaagaa accacaaacc gactcatggc tcagtattcg    600
taactgaggt gcccaactcg tccagaccaa ccccacggtca cgagttcgtt ccacgaaccc    660
gtctggcaac tccaccgagt taccagagcc aaccggtttt ctaagaaccc acaagaatgg    720
caacccagag agctcgagac ctaacgctaa ctcagccagc tcgcttttgg tcaccgtaac    780
ttcacttcct aatgcgacgt acaccacatg gttaacttgc tgaccatcga gccacttctt    840
gattgtcacc catgggtctc cggtgctggt gggtggttcg ggtggcaata atcccacggg    900
aaccaccggt aggtgatgca gcttttccaa aagggttagc cattggggtt cgacctcata    960
acaacttctt ataaacagac aatcagattc cttcaaaacc gtcatcattc tgtgctttag   1020
acctgaaatc acaggattat tagcagcaga catcttgcgc acaaactcat gcttccggta   1080
gcatactttg ctcggaaacg gaatccactt gggcggtgtc atgaaatcct caactgtcgt   1140
tcgactctcg aaactatttt tcatgtcatc gggtaacggt cccacgtgcg ccatgaacca   1200
tggtgaggca gtgataaaaa aggctcgcga gatcccaagg tccgccgcga cggatggcaa   1260
``` ccagtg 1266

<210> SEQ ID NO 27
<211> LENGTH: 1292
<212> TYPE: DNA
<213> ORGANISM: Stevia rebaudiana

<400> SEQUENCE: 27

```
cacaatacta ctctttagtt accaatatac cataaccaaa attgtttgat agataagatt      60
atcctatatt aaaattgatg aaacccagtc gatttatcaa taaaagaaat agatcaatga     120
aattatctag tttgtgaatt ttatcacatt gatgtttcta ccttatttca aacaaaccag     180
atacttcaat taattcaagc aacatttgat catgaagaca aacccaacaa cgcacattct     240
tcatacggtt aacgtacgtc gtgtcttctc caaataatct atgaaatggt ttatatactt     300
cttcccatc ttagtgtctc cgaacaatct acttaactcc atcgcatttt ccttgtaaat      360
cttcccttca tcatcagcta caaccgaccg cactgatctt gccactgact ccttgttgaa     420
ggagccatct tcgtcatttc ttggtatctc aattcccacc tgattatccg ccattactcg     480
agcatttaga cctgatcca ccgaaagcgg tagcattatt aaagggtgac cgaacatcat      540
cgcttccaca attgaactcc aaccacaatg agtcaagaaa ccacaaaccg actcatggct     600
cagtattcgt aactgaggtg cccaactcgt ccagaccaac ccacggtcac gagttcgttc     660
cacgaacccg tctggcaact ccaccgagtt accagagcca accggttttc taagaaccca     720
aaagaatggc aacccggaga gctcgagacc cagagctaac tcagccagct cgctttggct     780
caccgtaact tcacttccta atgcgacgta caccacatgg ttaacttgct gaccatcgag     840
ccacttcttg actgacaccc atgtatcatc tttctcgtct ccgtatgttt caggtggcat     900
taatccaacc ggaactaccg gtatacggta gcttcccc aaaagggtta gccattgggg      960
ttcgaactca tggcaatgtc ttataaacat acaatctgat ccctttataa ccattcctaa    1020
acgatataaa tctgatacac cagaagaatt aacagaaata ttatcagcaa atatcaaatt    1080
ggcctcatgc ttccggtagc atactttgct tgggaacgga aaccacttcg gcggtgtcag    1140
gaaatcgtcg gctgttttcc gatcgtctgt accgtttatg atgtcatcgg agaagatcc     1200
gaaaaagag acggtccatg cgttaaaaat tgagaaaaa cctcgtgaaa ttccaaggct     1260
agtggctacc gccggcaacc aatagggagc aa                                 1292
```

<210> SEQ ID NO 28
<211> LENGTH: 1213
<212> TYPE: DNA
<213> ORGANISM: Stevia rebaudiana

<400> SEQUENCE: 28

```
tagtgaatgt atataacata atgatatgt ttcaacctaa caaacggtta tttcatacac       60
ggaaaacaaa aatttatgat tattcaaaga acatttgat catctagcta gacaaaccca      120
ataacacata tattcttcat acgatcaaag ctcatgctca atagcaacca cacgaccttt     180
ttgttccaaa tagtctataa aagggtttat atacttattt tccggcttac tatccccgaa     240
tcgttgactc aactccatcg ccttcgcctt gtagatcttc ccttcatcat cgactacaac     300
caacctcaat gatctggcca ccgactcctt ggtgaatgaa ccatcttcct catttcttgg     360
tatctcgatt cccacctgtt tatccgccat tactcgagca tttagacctt ggtccaccaa    420
aatcggtagc atgattagag ggtgaccgaa catcatcgct tccacaattg aactccaacc    480
acaatgagtc aagaaaccac aaaccgactc atggctcagt attcgtaact gaggtgccca    540
```

```
actcgtccag accaacccac ggtcacgagt tcgttccacg aacccgtctg gcaactccac     600
cgagttacca gagccaaccg gttttctaag aacccaaaag aatggcaacc cggagagctc     660
gagacccaga gctaactcag ccagctcgct ttggctcatc gtaccttcac ttccaaatgc     720
cacgtacacc acatgcccta ttggttgacc atcgagccac ttcttgactg tgacccatgt     780
ctcatctttc ccgtctccga tgttggtggg ttttctggt ggcaataatc cgacaggaac     840
caccggtagg tgatggagct tctctaaaag ggttaaccat tgaggttcga actcataact     900
atgtcttata aacatacagt cagatccttt caaaatcatt cccacacgat acacacttga     960
tattccagaa gcattagccg aagtattccc taccatccga accgcctcat acttccggta    1020
gcacacgttt gtcggaaacg gaacccactt cggcggtgtc ataaaattct caaccctcgt    1080
tcgatgatca taaccggaac cacttatcaa gtcgtcagcc gacgctccga gaaaagcaat    1140
gaaccatgcg ttaaaattcg agtaaaaggc tcgcgaggtc cgtagtccag ctgcgacgga    1200
cggcaaccaa tac                                                      1213
```

<210> SEQ ID NO 29
<211> LENGTH: 1280
<212> TYPE: DNA
<213> ORGANISM: Stevia rebaudiana

<400> SEQUENCE: 29

```
tttttttttt tttacggctg gaatcaattg ctttattcat cacataattt ggctttaaat      60
agccttacaa taacaactta ttaatatagt agcttaaaac aattaactag gacacctcct     120
aagactcgat cgattctacc aacatattta gcaattccaa catttcattt gaatctttcc     180
aaaagaaacc caacaactca cacatacttg atgatatagt taactctcat gatcgatggc     240
aaccgcacgc gcattctttt ccaaatagtc tacgaattgg cttacatatt cttttttcaac    300 cttagtgtcg ttatagattt tactcagctc cctcgcgttc gccttgtaga tctcccctt     360 ttttccaca acaacggacc tcagtgatct agcaaccgac tccttggtca agcaaccatc     420
ttcctcattt cttggtatct cgattccac ctgtttgtcc tccagtaatc gagcattcag     480
aggttggtcc ccaaaaatcg gtagcatgat tagagggtga ccaaacatta gcccttccac     540
aattgatcca gaaccacaat gagtcaagaa accacaaacc gactcatggc tcagtattcg     600
taactgaggt gcccaactcg tccagaccaa cccacggtca cgagttcgtt ccacgaaccc     660
gtctggcaac tccaccgagt taccagagcc aaccggtttt ctaagaaccc acaaaaatgg     720
caacccagag agctcgagac ctaacgctaa ctcagccagc tcgcttttgg tcaccgtaac     780
ttcacttcct aatgcgacgt acaccacatg gttaacttgc tgaccatcga gccacttctt     840
gattgtcacc catgggtctc cggtgctggt gggtggttcg ggtggcaata atcccacggg     900
aaccaccggt aggtgatgca gcttttctaa aagggttagc cattggggtt cgaactcatg     960
gcaatgtctt ataaacatac aatctgatcc ctttataacc attcctaaac gatataaatc    1020
tgatacacca gaagaattaa cagaaatatt atcagcaaat atcaaattgg cctcatgctt    1080
ccggtagcat actttacttg ggaacggaaa ccacttcggc ggtgtcagga aatcgtcggc    1140 tgtttttccga tcgtctgtac cgtttatgat gtcatcggga gaagatccga aaaagagac    1200 ggtccatgcg ttaaaaattg agaaaaaacc tcgtgaaatt ccaaggctag tggctaccgc    1260
cggcaaccaa tagggagcaa                                               1280
```

<210> SEQ ID NO 30

<211> LENGTH: 1288
<212> TYPE: DNA
<213> ORGANISM: Stevia rebaudiana

<400> SEQUENCE: 30

```
tttttttttt tttacggctg gaatcaattg ctttattcat cacataattt ggctttaaat      60
agccttacaa taacaactta ttaatatagt agcttaaaac aattaactag gacacctcct     120
aagactcgat cgattctacc aacatattta gcaattccaa catttcattt gaatctttcc     180
aaaagaaacc caacaactca cacatacttg atgatatagt taactctcat gatcgatggc     240
aaccgcacgc gcattctttt ccaaatagtc tacgaattgg cttacatatt cttttcaac     300
cttagtgtcg ttatagattt tactcagctc cctcgcgttc gccttgtaga tctccccttc     360
tttttccaca acaacggacc tcagtgatct agcaaccgac tccttggtca agcaaccatc     420
ttcctcattt cttggtatct cgattcccac ctgtttgtcc tccagtaatc gagcattcag     480
aggttggtcc ccaaaaatcg gtagcatgat tagagggtga ccaaacatta gcccttccac     540
aattgatcca gaaccacaat gagtcaagaa accacacacc gactcatggc tcagtattcg     600
taactgaggt gcccaactcg tccagaccaa cccacggtca cgagttcgtt ccacgaaccc     660
gtctggcaac tccaccgagt taccagagcc aaccggtttt ctaagaaccc acaaaaatgg     720
caacccagag agctcgagac ctaacgctaa ctcagccagc tcgcttttgg tcaccgtaac     780
ttcacttcct aatgcgacgt acaccacatg gttaacttgc tgaccatcga gccacttctt     840
gactgtcacc cacgtctcat cattcccgtc tccgatgttg gtgggttttt ctggtggcaa     900
taatccgaca ggaaccaccg gtaggtgatg gagcttctct aaaagggtta accattgagg     960
ttcgaactca taactatgtc ttataaacat acagtcagat cctttcaaaa tcattcccac    1020
acgatacaca cttgatattc cagaagcatt agccgaagta ttccctacca tccgaaccgc    1080
ctcatacttc cggtagcaca cgtttgtcgg aaacggaacc cacttcggcg gtgtcataaa    1140
attctcaacc ctcgttcgat gatcataacc ggaaccactt atcaagtcgt cagccgacgc    1200
tccgagaaaa gcaatgaacc atgcgttaaa attcgagtaa aaggctcgcg aggtccgtag    1260
tccagctgcg acggacggca accaatac                                       1288
```

<210> SEQ ID NO 31
<211> LENGTH: 1283
<212> TYPE: DNA
<213> ORGANISM: Stevia rebaudiana

<400> SEQUENCE: 31

```
tttttttttt tttacggctg gaatcaattg ctttattcat cacataattt ggctttaaat      60
agccttacaa taacaactta ttaatatagt agcttaaaac aattaactag gacacctcct     120
aagactcgat cgattctacc aacatattta gcaattccaa catttcattt gaatctttcc     180
aaaagaaacc caacaactca cacatacttg atgatatagt taactctcat gatcgatggc     240
aaccgcacgc gcattctttt ccaaatagtc tacgaattgg cttacatatt cttttcaac     300
cttagtgtcg ttatagattt tactcagctc cctcgcgttc gccttgtaga tctccccttc     360
tttttccaca acaacggacc tcagtgatct agcaaccgac tccttggtca agcaaccatc     420
ttcctcattt cttggtatct cgattcccac ctgtttgtcc tccagtaatc gagcattcag     480
aggttggtcc ccaaaaatcg gtagcatgat tagagggtga ccaaacatta gcccttccac     540
aattgatcca gaaccacaat gagtcaagaa accacaaacc gactcatggc tcagtattcg     600
taactgaggt gcccaactcg tccagaccaa cccacggtca cgagttcgtt ccacgaaccc     660
```

```
gtctggcaac tccaccgagt taccagagcc aaccggtttt ctaagaaccc aaaagaatgg      720
caacccggag agctcgagac ccagagctaa ctcagccagc tcgcttttgc tcaccgtaac      780
ttcacttcct aatgcgacgt acaccacatg gttaacttgc tgaccatcga gccacttctt      840
gattgacacc catgtatcat ctttctcgtc tccgtatgtt tcaggtggca ttaatccaac      900
cggaactacc ggtatacggt atagcttccc caaaagggtt agccattggg gttcgaactc      960
atggcaatgt cttataaaca tacaatctga tccctttata accattccta aacgatataa     1020
atctgataca ccagaagaat taacagaaat tattcagca aatatcaaat tggcctcatg     1080
cttccggtag catactttgc ttgggaacgg aaaccacttc ggcggtgtca ggaaatcgtc     1140
ggctgttttc cgatcgtctg taccgtttat gatgtcatcg ggagaagatc cgaaaaaga     1200 gacggtccat gcgttaaaaa ttgagaaaaa acctcgtgaa attccaaggc tagtggctac     1260
cgccggcaac caatagggag caa                                             1283

<210> SEQ ID NO 32
<211> LENGTH: 1379
<212> TYPE: DNA
<213> ORGANISM: Stevia rebaudiana

<400> SEQUENCE: 32
ggctggagtc aattgttttt atacaataca taatatagcg ttaaatggct ttataataac       60
gacggaaaag ttaatgactc gattctacca acgacttagc aattccaaca tgtgattaaa      120
aaagaagtgt aacaaggaca atcataacat catatgaatc attccaaaga aacccaacaa      180
ctaacttact tatagtctgt gaaacgactt atatattctt tttggttaac tctcatggtt      240
gttggcaacc acacgtacgt tcttttccat atagtctgtg aaacgactta tatattcttt      300
ttggttaact ctcatggttg ttggcaacca cacgtacgtt cttttccata tagtctgtga      360
aacgacttat atattccttt tgcagcttag tgtcgctgaa tattttactc atctctctcg      420
cattcgcctt gtagatctct cctcatcgt ctacaacaac cgacctcagt gacgtggcaa      480
ccgactcctt ggtgaagtag ccatcttcct catttcttgg tatctcgatc cccacctgtt      540
tgtccgctaa tagtcgagca ttcagacatt ggtccccgaa atcggtagc atgattaaag      600 ggtggccgaa cattaaccct tccaccattg aactccaacc acagtgagtc aagaaaccac      660
acaccgactc atggctcagt attcgtaact gaggtgccca actcgtccaa accatcccac      720
ggttactagt tcgttccaag aacccgttag gcaactccac cgagtctgac tcggtggaac      780 ctgcggggttt tctgagaacc cacaaaaatg gcaacccaga gagctcgaga cctagagcta      840
actcagccag ctcgcttttg gtcaccgtaa cttcacttcc taatgccacg tacaccacat      900
gccctattgg ttgaccatcg agccacttct tgactgtgac ccatgtctca tctttcccgt      960
ctccgatgtt ggtgggtttt tctggtggca ataatccgac aggaaccacc ggtaggtgat     1020
ggagcttctc taaagggtt aaccattgag gttcgaactc ataactatgt cttataaaca     1080
tacagtcaga tcctttcaaa atcattccca cacgatacac acttgatatt ccagaagcat     1140
tagccgaagt attccctacc atccgaaccg cctcatactt ccggtagcac acgtttgtcg     1200
gaaacggaac ccacttcggc ggtgtcataa aattctcaac cctcgttcga tgatcataac     1260
cggaaccact tatcaagtcg tcagccgacg ctccgagaaa agcaatgaac catgcgttaa     1320
aattcgagta aaaggctcgc gaggtccgta gtccagctgc gacggacggc aaccaatac     1379

<210> SEQ ID NO 33
```

<211> LENGTH: 1197
<212> TYPE: DNA
<213> ORGANISM: Stevia rebaudiana

<400> SEQUENCE: 33

```
tagtgaatgt atataacata aatgatatgt tcaacctaa caaacggtta tttcatacac      60
ggaaaacaaa aatttatgat tattcaaaga aacatttgat catctagcta gacaaaccca     120
ataacacata tattcttcat acgatcaaag ctcatgctca atagcaacca cacgaccttt     180
ttgttccaaa tagtctataa aagggtttat atacttattt tccggcttac tatccccgaa     240
tcgttgactc aactccatcg ccttcgcctt gtagatcttc ccttcatcat cgactaaaac     300
caacctcaat gatctggcca ccgactcctt ggtgaatgaa ccatcttcct catttcttgg     360
tatctcgatt cccacctgat tatccgccat tactcgagca tttagacctt ggtccaccga     420
aatcggtagc atgattagag ggtgaccgaa catcatcgct tccacaattg aactccaacc     480
acaatgagtc aagaaaccac aaaccgactc atggctcagt attcgtaact gaggtgccca     540
actcgtccag accaacccac ggtcacgagt tcgttccacg aacccctctg caactccac     600
cgagttacca gagccaaccg gttttctaag aacccaaaag aatggcaacc cggagagctc     660
gagacccaga gctaactcag ccagctcgct ttggctcatc gtaccttcac ttccaaatgc     720
cacgtacacc acatgcccta ttggttgacc atcgagccac ttcttgattg tcacccatgg     780
gtctccggtg ctggtgggtg gttcgggtgg caataatccc acgggaacca ccggtagctg     840
atgcagcttt tctaaaaggg ttagccattg gggttcgaac tcatggcaat gtcttataaa     900
catacaatct gatcccttta taaccattcc taaacgatat aaatctgata caccagaaga     960
attaacagaa atattatcag caaatatcaa attggcctca tgcttccggt agcatacttt    1020
gctcggaaac ggaatccact tgggcggtgt catgaaatcc tcaactgtcg ttcgactctc    1080
gaaactattt ttcatgtcat cgggtaacgg tcccacgtgc gccatgaacc atggtgaggc    1140
agtgataaaa aaggctcgcg agatcccaag gtccgccgcg acggatggca accagtg      1197
```

<210> SEQ ID NO 34
<211> LENGTH: 573
<212> TYPE: DNA
<213> ORGANISM: Stevia rebaudiana

<400> SEQUENCE: 34

```
cacaatacta ctctttagtt accaatatac cataaccaaa attgtttgat agataagatt      60
atcctatatt aaaattgatg aaacccagtc gatttatcaa taaagaaat agatcaatga     120
aattatctag tttgtgaatt ttatcacatt gatgtttcta ccttatttca aacaaaccag     180
atacttcaat taattcaagc aacatttgat catgaagaca aacccaacaa cgcacattct     240
tcatacggtt aacgtacgtc gtgtcttctc caaataatct atgaaatggt ttatatactt     300
ctttcccatc ttagtgtctc cgaacaatct acttaactcc atcggtagga accaccggta     360
ggtgatggag cttctctaaa agggttaacc attgaggttc gaactcataa ctatgtctta     420
taaacataca gtcagatcct ttcaaaatca ttcccacacg atacacactt gatattccag     480
aagcattagc cgaagtattc cctaccatcc gaaccgcctc atacttccgg tagcacacgt     540
ttgtcggaaa cggaacccac ttcggcggtg tca                                  573
```

<210> SEQ ID NO 35
<211> LENGTH: 1281
<212> TYPE: DNA
<213> ORGANISM: Stevia rebaudiana

<400> SEQUENCE: 35

```
cacaatacta ctctttagtt accaatatac cataaccaaa attgtttgat agataagatt        60
atcctatatt aaaattgatg aaacccagtc gatttatcaa taaaagaaat agatcaatga       120
aattatctag tttgtgaatt ttatcacatt gatgtttcta ccttatttca aacaaaccag       180
atacttcaat taattcaagc aacatttgat catgaagaca aacccaacaa cgcacattct       240
tcatacggtt aacgtacgtc gtgtcttctc caaataatct atgaaatggt ttatatactt       300
ctttcccatc ttagtgtctc cgaacaatct acttaactcc atcgcatttt ccttgtaaat       360
cttcccttca tcatcagcta caaccgaccg cactgatctt gccactgact ccttgttgaa       420
ggagccatct tcgtcatttc ttggtatctc aattcccacc tgattatccg ccattactcg       480
agcatttaga ccttgatcca ccgaaagcgg tagcattatt aaagggtgac cgaacatcat       540
cgcttccaca attgaactcc aaccacaatg agtcaagaaa ccacaaaccg actcatggct       600
cagtattcgt aactgaggtg cccaactcgt ccagaccaac ccacggtcac gagttcgttc       660
cacgaacccc tctggcaact ccaccgagtt accagagcca accggttttc taagaaccca       720
aaagaatggc aacccggaga gctcgagacc cagagctaac tcagccagct cgctttggct       780
catcgtacct tcacttccaa atgccacgta caccacatgc cctattggtt gaccatcgag       840
ccacttcttg attgtcaccc atgggtctcc ggtgctggtg ggtggttcgg gtggcaataa       900
tcccacggga accaccggta ggtgatgcag cttttctaaa agggttagcc attggggttc       960
gaactcatgg caatgtctta taaacataca atctgatccc tttataacca ttcctaaacg      1020
atataaatct gatacaccag aagaattaac agaaatatta tcagcaaata tcaaattggc      1080
ctcatgcttc cggtagcata ctttgctcgg aaacggaatc cacttgggcg gtgtcatgaa      1140
atcctcaact gtcgttcgac tctcgaaact attttcatg tcatcgggta acggtcccac      1200
gtgcgccatg aaccatggtg aggcagtgat aaaaaaggct cgcgagatcc caaggtccgc      1260
cgcgacggat ggcaaccagt g                                                1281
```

<210> SEQ ID NO 36
<211> LENGTH: 1275
<212> TYPE: DNA
<213> ORGANISM: Stevia rebaudiana

<400> SEQUENCE: 36

```
tttttttttt tttacggctg gaatcaattg ctttattcat cacataattt ggctttaaat        60
agccttacaa taacaactta ttaatatagt agcttaaaac aattaactag gacacctcct       120
aagactcgat cgattctacc aacatattta gcaattccaa catttcattt gaatctttcc       180
aaaagaaacc caacaactca cacatacttg atgatatagt taactctcat gatcgatggc       240
aaccgcacgc gcattctttt ccaaatagtc tacgaattgg cttacatatt cttttcaac       300
cttagtgtcg ttatagattt tactcagctc cctcgcgttc gccttgtaga tctcccttc       360
ttttccaca acaacggacc tcagtgatct agcaaccgac tccttggtca agcaaccatc       420
ttcctcattt cttggtatct cgattccac ctgtttgtcc tccagtaatc gagcattcag       480
aggttggtcc ccaaaaatcg gtagcatgat tagagggtga ccaaacatta gcccttccac       540
aattgatcca gaaccacaat gagtcaagaa accacaaacc gactcatggc tcagtattcg       600
taactgaggt gcccaactcg tccagaccaa cccacggtca cgagttcgtt ccacgaaccc       660
gtctggcaac tccaccgagt taccagagcc aaccggtttt ctaagaaccc aaaagaatgg       720
```

| caacccggag | agctcgagac | ccagagctaa | ctcagccagc | tcgctttggc | tcaccgtaac | 780 |
| ttcacttcct | aatgcgacgt | acaccacatg | gttaacttgc | tgaccatcga | gccacttctt | 840 |
| gactgacacc | catgtatcat | ctttctcgtc | tccgtatgtt | tcaggtggca | ttaatccaac | 900 |
| cggaactacc | ggtatacggt | atagcttccc | caaaagggtt | agccattggg | gttcgaactc | 960 |
| atggcaatgt | cttataaaca | tacaatctga | tccctttata | accattccta | aacgatataa | 1020 |
| atctgataca | ccagaagaat | taacagaaat | attatcagca | aatatcaaat | tggcctcatg | 1080 |
| cttccggtag | catactttgc | tcggaaacgg | aatccacttg | ggcggtgtca | tgaaatcctc | 1140 |
| aactgtcgtt | cgactctcga | aactattttt | catgtcatcg | ggtaacggtc | ccacgtgcgc | 1200 |
| catgaaccat | ggtgaggcag | tgataaaaaa | ggctcgcgag | atcccaaggt | ccgccgcgac | 1260 |
| ggatggcaac | cagtg | | | | | 1275 |

<210> SEQ ID NO 37
<211> LENGTH: 1307
<212> TYPE: DNA
<213> ORGANISM: Stevia rebaudiana

<400> SEQUENCE: 37

| tttttttttt | tttacggctg | gaatcaattg | ctttattcat | cacataatttt | ggctttaaat | 60 |
| agccttacaa | taacaactta | ttaatatagt | agcttaaaac | aattaactag | gacacctcct | 120 |
| aagactcgat | cgattctacc | aacatatttta | gcaattccaa | catttcattt | gaatctttcc | 180 |
| aaaagaaacc | caacaactca | cacatacttg | atgatatagt | taactctcat | gatcgatggc | 240 |
| aaccgcacgc | gcattctttt | ccaaatagtc | tacgaattgg | cttacatatt | cttttttcaac | 300 |
| cttagtgtcg | ttatagattt | tactcagctc | cctcgcgttc | gccttgtaga | tctcccttc | 360 |
| tttttccaca | acaacggacc | tcagtgatct | agcaaccgac | tccttggtca | agcaaccatc | 420 |
| ttcctcattt | cttggtatct | cgattcccac | ctgtttgtcc | tccagtaatc | gagcattcag | 480 |
| aggttggtcc | ccaaaaatcg | gtagcatgat | tagagggtga | ccaaacatta | gcccttccac | 540 |
| aattgatcca | gaaccacaat | gagtcaagaa | accacaaacc | gactcatggc | tcagtattcg | 600 |
| taactgaggt | gcccaactcg | tccagaccaa | cccacggtca | cgagttcgtt | ccacgaaccc | 660 |
| gtctggcaac | tccaccgagt | ctgacttcgc | gggacctttt | ggttttctat | aagcccaaac | 720 |
| aaatggcaac | ccagaaagct | cgagacccaa | tgctaactca | acaacctcgg | tttggctcac | 780 |
| caaaacctcg | cttcctaatg | caacgtacac | cacactgcct | ttttgtttac | catcgagcca | 840 |
| tttcttgatt | gacacccatg | tttcatcttt | ctcgtctccg | ggtatttccg | gcggcagtaa | 900 |
| tcccaccgga | accaccggta | cttggtgtag | tgtctccaaa | agaggtagcc | attgagttcc | 960 |
| aaactcatgg | taacatttgg | aaagcaaaca | atcagatccc | ttaaaaacca | gccccatacg | 1020 |
| gtatccatca | gatatcccccg | gagctttgta | aggcaccagt | cgggcaagat | catgcttccg | 1080 |
| ccagcatact | ttggtcggaa | agggaaacca | cttgggcggt | gtcgtgagat | cctcaaccgt | 1140 |
| ggttcgacca | tctgaaccat | ttatcatggc | gtcagctgag | ggtcccatat | aagcaatggc | 1200 |
| ccatggagtg | gtgacggaga | agtgggctcg | tgagataccg | aggctagccg | cgatggatgg | 1260 |
| caaccagtag | tgagtataat | cataaataat | ccagtccgga | gactctt | | 1307 |

<210> SEQ ID NO 38
<211> LENGTH: 1208
<212> TYPE: DNA
<213> ORGANISM: Stevia rebaudiana

<400> SEQUENCE: 38

| | | | | |
|---|---|---|---|---|
| tagtgaatgt | atataacata | aatgatatgt | ttcaacctaa | caaacggtta | tttcatacac | 60 |
| ggaaaacaaa | aatttatgat | tattcaaaga | aacatttgat | catctagcta | gacaaaccca | 120 |
| ataacacata | tattcttcat | acgatcaaag | ctcatgctca | atagcaacca | cacgaccttt | 180 |
| ttgttccaaa | tagtctataa | aagggtttat | atacttattt | tccggcttac | tatccccgaa | 240 |
| tcgttgactc | aactccatcg | ccttcgcctt | gtagatcttc | ccttcatcat | cgactaaaac | 300 |
| caacctcaat | gatctggcca | ccgactcctt | ggtgaatgaa | ccatcttcct | catttcttgg | 360 |
| tatctcgatt | cccacctgat | tatccgccat | tactcgagca | tttagacctt | ggtccaccga | 420 |
| aatcggtagc | atgattagag | ggtgaccgaa | catcatcgct | tccacaattg | aactccaacc | 480 |
| acaatgagtc | aagaaaccac | aaaccgactc | atggctcagt | attcgtaact | gaggtgccca | 540 |
| actcgtccag | accaacccac | ggtcacgagt | tcgttccacg | aacccgtctg | gcaactccac | 600 |
| cgagttacca | gagccaaccg | gttttctaag | aacccaaaag | aatggcaacc | cggagagctc | 660 |
| gagacccaga | gctaactcag | ccagctcgct | ttggctcacc | gtaacttcac | ttcctaatgc | 720 |
| gacgtacacc | acatggtcaa | cttgctgacc | atcgagccac | ttcttgactg | acacccatgt | 780 |
| atcatctttc | tcgtctccgt | atgtttcagg | tggcattaat | ccaaccggaa | ctaccggtat | 840 |
| acggtatagc | ttccccaaaa | gggttagcca | ttggggttcg | aactcatggc | aatgtcttat | 900 |
| aaacatacaa | tctgatccct | ttataaccat | tcctaaacga | tataaatctg | atacaccaga | 960 |
| agaattaaca | gaaatattat | cagcaaatat | caaattggcc | tcatgcttcc | ggtagcatac | 1020 |
| tttgcttggg | aacggaaacc | acttcggcgg | tgtcaggaaa | tcgtcggctg | ttttccgatc | 1080 |
| gtctgtaccg | tttatgatgt | catcgggaga | agatccgaaa | aaagagacgg | tccatgcgtt | 1140 |
| aaaaattgag | aaaaaacctc | gtgaaattcc | aaggctagtg | gctaccgccg | gcaaccaata | 1200 |
| gggagcaa | | | | | 1208 |

<210> SEQ ID NO 39
<211> LENGTH: 1341
<212> TYPE: DNA
<213> ORGANISM: Stevia rebaudiana

<400> SEQUENCE: 39

| | | | | |
|---|---|---|---|---|
| tttataataa | cgacggaaaa | gtagcgcacc | acttaatgac | tcgattctac | caacgactta | 60 |
| gcaattccaa | catgtgatta | aaaaagaagt | gtaacaagga | caatcataac | atcatatgaa | 120 |
| tcattccaaa | gaaacccaac | aactaactta | cttatagtct | gtgaaacgac | ttatatattc | 180 |
| ttttttggtta | actctcatgg | ttgttggcaa | ccacacgtac | gttctttttcc | atatagtctg | 240 |
| tgaaacgact | tatatattct | ttttggttaa | ctctcatggt | tgttggcaac | cacacgtacg | 300 |
| ttcttttcca | tatagtctgt | gaaacgactt | atatattcct | tttgcagctt | agtgtcgctg | 360 |
| aatattttac | tcatctctct | cgcattcgcc | ttgtagatct | ctccttcatc | gtctacaaca | 420 |
| accgacctca | gtgacgtggc | aaccgactcc | ttggtgaagt | agccatcttc | ctcatttctt | 480 |
| ggtatctcga | tccccacctg | tttgtccgct | aatagtcgag | cattcagaca | ttggtccccg | 540 |
| aaaatcggta | gcatgattaa | agggtggccg | aacattaacc | cttccaccac | tgaactccaa | 600 |
| ccacagtgag | tcaagaaacc | acacaccgac | tcatgactca | gtattcgtaa | ctgaggtgcc | 660 |
| caactcgtcc | aaaccatccc | acggttacta | gttcgttcca | agaacccgtt | aggcaactcc | 720 |
| accgagtctg | actcggtgga | acctgcgggt | tttctgagaa | cccacaaaaa | tggcaaccca | 780 |
| gagagctcga | gacctagcgc | taactcagcc | agctcgcttt | tggtcaccgt | aacttcactt | 840 |

| cctaatgcca cgtacaccac atgccctatt ggttgaccat cgagccactt cttgactgtg | 900 |
| acccatgtct catctttccc gtctccgatg ttggtgggtt tttctggtgg caataatccg | 960 |
| acaggaacca ccggtaggtg atggagcttc tctaaaaggg ttaaccattg aggttcgaac | 1020 |
| tcataactat gtcttataaa catacagtca gatcctttca aaatcattcc cacacgatac | 1080 |
| acacttgata ttccagaagc attagccgaa gtattcccta ccatccgaac cgcctcatac | 1140 |
| ttccggtagc acacgtttgt cggaaacgga acccacttcg gcggtgtcat aaaattctca | 1200 |
| accctcgttc gatgatcata accggaacca cttatcaagt cgtcagccga cgctccgaga | 1260 |
| aaagcaatga accatgcgtt aaaattcgag taaaaggctc gcgaggtccg tagtccagct | 1320 |
| gcgacggacg gcaaccaata c | 1341 |

<210> SEQ ID NO 40
<211> LENGTH: 1289
<212> TYPE: DNA
<213> ORGANISM: Stevia rebaudiana

<400> SEQUENCE: 40

| cacaatacta ctctttagtt accaatatac cataaccaaa attgtttgat agataagatt | 60 |
| atcctatatt aaaattgatg aaacccagtc gatttatcaa taaaagaaat agatcaatga | 120 |
| aattatctag tttgtgaatt ttatcacatt gatgtttcta ccttatttca aacaaaccag | 180 |
| atacttcaat taattcaagc aacatttgat catgaagaca aacccaacaa cgcacattct | 240 |
| tcatacggtt aacgtacgtc gtgtcttctc caaataatct atgaaatggt ttatatactt | 300 |
| ctttcccatc ttagtgtctc cgaacaatct acttaactcc atcgcatttt ccttgtaaat | 360 |
| cttcccttca tcatcagcta caaccgaccg cactgatctt gccactgact ccttgttgaa | 420 |
| ggagccatct tcgtcatttc ttggtatctc aattcccacc tgattatccg ccattactcg | 480 |
| agcatttaga ccttgatcca ccgaaagcgg tagcattatt aaagggtgac cgaacatcat | 540 |
| cgcttccaca attgaactcc aaccacaatg agtcaagaaa ccacaaaccg actcatggct | 600 |
| cagtattcgt aactgaggtg cccaactcgt ccagaccaac ccacggtcac gagttcgttc | 660 |
| cacgaacccg tctggcaact ccaccgagtt accagagcca accggttttc taagaaccca | 720 |
| aaagaatggc aacccggaga gctcgagacc cagagctaac tcagccagct cgctttggct | 780 |
| catcgtacct tcacttccaa atgccacgta caccacatgc cctattggtt gaccatcgag | 840 |
| ccacttcttg attgacaccc atgggtctcc ggtgctggtg ggtggttcgg gtggcaataa | 900 |
| tcccacggga accaccggta ggtgatgcag ctttttctaaa agggttagcc attgggggttc | 960 |
| gaactcatgg caatgtctta taaacataca atctgatccc tttataacca ttcctaaacg | 1020 |
| atataaatct gatacaccag aagaattaac agaaatatta tcagcaaata tcaaattggc | 1080 |
| ctcatgcttc cggtagcata ctttacttgg gaacggaaac cacttcggcg gtgtcaggaa | 1140 |
| atcgtcggct gttttccgat cgtctgtacc gtttatgatg tcatcgggag aagatccgaa | 1200 |
| aaaagagacg gtccatgcgt taaaaattga gaaaaaacct cgtgaaattc caaggctagt | 1260 |
| ggctaccgcc ggcaaccaat agggagcaa | 1289 |

<210> SEQ ID NO 41
<211> LENGTH: 1279
<212> TYPE: DNA
<213> ORGANISM: Stevia rebaudiana

<400> SEQUENCE: 41

| tttttttttt tttacggctg gaatcaattg ctttattcat cacataattt ggctttaaat | 60 |

```
agccttacaa taacaactta ttaatatagt agcttaaaac aattaactag gacacctcct    120
aagactcgat cgattctacc aacatattta gcaattccaa catttcattt gaatctttcc    180
aaaagaaacc caacaactca cacatacttg atgatatagt taactctcat gatcgatggc    240
aaccgcacgc gcattctttt ccaaatagtc tacgaattgg cttacatatt cttttcaac    300 cttagtgtcg ttatagattt tactcagctc cctcgcgttc gccttgtaga tctcccttc    360 ttttccaca acaacggacc tcagtgatct agcaaccgac tccttggtca agcaaccatc    420
ttcctcattt cttggtatct cgattcccac ctgtttgtcc tccagtaatc gagcattcag    480
aggttggtcc ccaaaaatcg gtagcatgat tagagggtga ccaaacatta gcccttccac    540
aattgatcca gaaccacaat gagtcaagaa accacaaacc gactcatggc tcagtattcg    600
taactgaggt gcccaactcg tccagaccaa cccacggtca cgagttcgtt ccacgaaccc    660
gtctggcaac tccaccgagt taccagagcc aaccggtttt ctaagaaccc aaaagaatgg    720
caacccggag agctcgagac ccagagctaa ctcagccagc tcgctttggc tcatcgtacc    780
ttcacttcca aatgccacgt acaccacatg ccctattggt tgaccatcga gccacttctt    840
gattgacacc catgggtctc cggtgctggt gggtggttcg ggtggcaata atcccacggg    900
aaccaccggt aggtgatgca gcttttctaa aagggttagc cattggggtt cgaactcatg    960
gcaatgtctt ataaacatac aatctgatcc ctttataacc attcctaaac gatataaatc    1020
tgatacacca gaagaattaa cagaaatatt atcagcaaat atcaaattgg cctcatgctt    1080
ccggtagcat actttgctcg gaaacggaat ccacttcggc ggtgtcataa aattctcaac    1140
cctcgttcga tgatcataac cggaaccact tatcaagtcg tcagccgacg ctccgagaaa    1200
agcaatgaac catgcgttaa aattcgagta aaaggctcgc gaggtccgta gtccagctgc    1260
gacggacggc aaccaatac                                                1279
```

<210> SEQ ID NO 42
<211> LENGTH: 1322
<212> TYPE: DNA
<213> ORGANISM: Stevia rebaudiana

<400> SEQUENCE: 42

```
tttataataa cgacggaaaa gtagcgcacc acttaatgac tcgattctac caacgactta     60
gcaattccaa catgtgatta aaaagaagt gtaacaagga caatcataac atcatatgaa    120
tcattccaaa gaaacccaac aactaactta cttatagtct gtgaaacgac ttatatattc    180
tttttggtta actctcatgg ttgttggcaa ccacacgtac gttcttttcc atatagtctg    240
tgaaacgact tatatattct ttttggttaa ctctcatggt tgttggcaac cacacgtacg    300
ttcttttcca tatagtctgt gaaacgactt atatattcct tttgcagctt agtgtcgctg    360
aatattttac tcatctctct cgcattcgcc ttgtagatct ctccttcatc gtctacaaca    420
accgacctca gtgacgtggc aaccgactcc ttggtgaagt agccatcttc ctcatttctt    480
ggtatctcga tccccacctg tttgtccgct aatagtcgag cattcagaca ttggtccccg    540
aaaatcggta gcatgattaa agggtggccg aacattaacc cttccaccac tgaactccaa    600
ccacagtgag tcaagaaacc acacaccgac tcatggctca gtattcgtaa ctgaggtgcc    660
caactcgtcc aaaccatccc acggttacta gttcgttcca agaacccgtt aggcaactcc    720
accgagtctg actcggtgga acctgcgggt tttctgagaa cccacaaaaa tggcaaccca    780
gagagctcga gacctaacgc taactcagcc agctcgcttt tggtcaccgt aacttcactt    840
```

```
cctaatgcga cgtacaccac atggttaact tgctgaccat cgagccactt cttgactgac    900
acccatgtat catctttctc gtctccgtat gtttcaggtg gcattaatcc aaccggaact    960
accggtatac ggtatagctt ccccaaaagg gttagccatt ggggttcgac ctcataacaa   1020
cttcttataa acagacaatc agattccttc aaaaccgtca tcattctgtg ctttagacct   1080
gaaatcacag gattattagc agcagacatc ttgcgcacaa actcatgctt ccggtagcat   1140
actttgctcg gaaacggaat ccacttgggc ggtgtcatga atcctcaac  tgtcgttcga   1200 ctctcgaaac tattttcat  gtcatcgggt aacggtccca cgtgcgccat gaaccatggt   1260
gaggcagtga taaaaaggc  tcgcgagatc ccaaggtccg ccgcgacgga tggcaaccag   1320
tg                                                                  1322
```

<210> SEQ ID NO 43
<211> LENGTH: 674
<212> TYPE: DNA
<213> ORGANISM: Stevia rebaudiana

<400> SEQUENCE: 43

```
tcctcatttc ttggtatctc gatccccacc tgtttgtccg ctaatagtcg agcattcaga     60
cattggtccc cgaaaatcgg tagcatgatt aaagggtggc cgaacattaa cccttccacc    120
actgaactcc aaccacagtg agttaagaaa ccacacaccg actcatgact cagtattcgt    180
aactgaggtg cccaactcgt ccaaaccatc ccacggttac tagttcgttc caagaacccg    240
ttaggcaact ccaccgagtc tgactcggtg gaacctgcgg gttttctgag aacccacaaa    300
aatggcaacc cagagagctc gagacctaga gctaactcag ccagctcgct tttggtcacc    360
gtaacttcac ttcctaatgc gacgtacacc acatgcccta ttggttgacc atcgagccac    420
ttcttgattg acacccatgg gtctccggtg ctggtgggtg gttcgggtgg caataatccc    480
accggaacca ccggtagctg gtgtagcttc tccaaaaggg ttagccattg gggttcgacc    540
tcataacaac ttcttataaa cagacaatca gattccttca aaaccgtcat cattctgtgc    600
tttagacctg aaatcacagg attattagca gcagacatct tgcgcacaaa ctcatgcttc    660
cggtagcata cttt                                                     674
```

<210> SEQ ID NO 44
<211> LENGTH: 1360
<212> TYPE: DNA
<213> ORGANISM: Stevia rebaudiana

<400> SEQUENCE: 44

```
ggctggagtc aattgttttt atacaataca taatatagcg ttaaatggct ttataataac     60
gacggaaaag ttaatgactc gattctacca acgacttagc aattccaaca tgtgattaaa    120
aaagaagtgt aacaaggaca atcataacat catatgaatc attccaaaga aacccaacaa    180
ctaacttact tatagtctgt gaaacgactt atatattctt tttggttaac tctcatggtt    240
gttggcaacc acacgtacgt tcttttccat atagtctgtg aaacgactta tatattcttt    300
ttggttaact ctcatggttg ttggcaacca cacgtacgtt cttttccata gtctgtga     360 aacgacttat atattccttt tgcagcttag tgtcgctgaa tattttactc atctctctcg    420
cattcgcctt gtagatctct ccttcatcgt ctacaacaac cgacctcagt gacgtggcaa    480
ccgactcctt ggtgaagtag ccatcttcct catttcttgg tatctcgatc cccacctgtt    540
tgtccgctaa tagtcgagca ttcagacatt ggtcccgaa  atcggtagc  atgattaaag    600 ggtgaccgaa cattaaccct tccaccactg aactccaacc acagtgagtc aagaaaccac    660
```

```
acaccgactc atggctcagt attcgtaact gaggtgccca actcgtccaa accatcccac    720
ggttactagt tcgttccaag aacccgttag gcaactccac cgagtctgac tcggtggaac    780
ctgcgggttt tctgagaacc cacaaaaatg gcaacccaga gagctcgaga cctaacgcta    840
actcagccag ctcgcttttg gtcaccgtaa cttcacttcc taatgcgacg tacaccacat    900
ggttaacttg ctgaccatcg agccacttct tgactgacac ccatgtatca tctttctcgt    960
ctccgtatgt ttcaggtggc attaatccaa ccggaactac cggtatacgg tatagcttcc   1020
ccaaaagggt tagccattgg ggttcgacct cataacaact tcttataaac agacaatcag   1080
attccttcaa aaccgtcatc attctgtgct ttagacctga aatcacagga ttattagcag   1140
cagacatctt gcgcacaaac tcatgcttcc ggtagcatac tttgctcgga acggaatcc    1200
acttgggcgg tgtcatgaaa tcctcaactg tcgttcgact ctcgaaacta tttttcatgt   1260
catcgggtaa cggtcccacg tgcgccatga accatggtga ggcagtgata aaaaaggctc   1320
gcgagatccc aaggtccgcc gcgacggatg gcaaccagtg                         1360

<210> SEQ ID NO 45
<211> LENGTH: 539
<212> TYPE: DNA
<213> ORGANISM: Stevia rebaudiana

<400> SEQUENCE: 45
actgaactcc aaccacagtg agttaagaaa ccacacaccg actcatgact cagtattcgt     60
aactgaggtg cccaactcgt ccaaaccatc ccacggttac tagttcgttc caagaacccg    120
ttaggcaact ccaccgagtc tgactcggtg gaacctgcgg gttttctgag aacccacaaa    180
aatggcaacc cagagagctc gagacctaga gctaactcag ccagctcgct tttggtcacc    240
gtaacttcac ttcctaatgc gacgtacacc acatggttaa cttgctgacc atcgagccac    300
ttcttgactg acacccatgt atcatctttc tcgtctccgt atgtttcagg tggcattaat    360
ccaaccggaa ctaccggtat acggtatagc ttccccaaaa gggttagcca ttggggttcg    420
aactcatggc aatgtcttat aaacatacaa tctgatccct ttataaccat tcctaaacga    480
tataaatctg atacaccaga agaattaaca gaaatattat cagcaaatat caaattggc     539

<210> SEQ ID NO 46
<211> LENGTH: 1332
<212> TYPE: DNA
<213> ORGANISM: Stevia rebaudiana

<400> SEQUENCE: 46
tttataataa cgacggaaaa gtagcgcacc acttaatgac tcgattctac caacgactta     60
gcaattccaa catgtgatta aaaagaagt gtaacaagga caatcataac atcatatgaa    120
tcattccaaa gaaacccaac aactaactta cttatagtct gtgaaacgac ttatatattc    180
ttttttggtta actctcatgg ttgttggcaa ccacacgtac gttctttttcc atatagtctg    240
tgaaacgact tatatattct ttttggttaa ctctcatggt tgttggcaac cacacgtacg    300
ttcttttcca tatagtctgt gaaacgactt atatattcct tttgcagctt agtgtcgctg    360
aatattttac tcatctctct cgcattcgcc ttgtagatct ctccttcatc gtctacaaca    420
accgacctca gtgacgtggc aaccgactcc ttggtgaagt agccatcttc ctcatttctt    480
ggtatctcga tccccacctg tttgtccgct aatagtcgag cattcagaca ttggtccccg    540
aaaatcggta gcatgattaa agggtggccg aacattaacc cttccaccac tgaactccaa    600
```

```
ccacagtgag tcaagaaacc acacaccgac tcatggctca gtattcgtaa ctgaggtgcc      660
caactcgtcc aaaccatccc acggttacta gttcgttcca agaacccgtt aggcaactcc      720
accgagtctg actcggtgga acctgcgggt tttctgagaa cccacaaaaa tggcaaccca      780
gagagctcga gacctagcgc taactcagcc agctcgcttt tggtcaccgt aacttcactt      840
cctaatgcga cgtacaccac atgccctatt ggttgaccat cgagccactt cttgattgtc      900
acccatgggt ctccggtgct ggtgggtggt tcggtggca ataatcccac gggaaccacc       960
ggtagctgat gcagctttc taaaagggtt agccattggg gttcgaactc atggcaatgt      1020
cttataaaca tacaatctga tccctttata accattccta acgatataaa atctgataca     1080
ccagaagaat taacagaaat attatcagca aatatcaaat tggcctcatg cttccggtag     1140
catactttgc tcggaaacgg aatccacttc ggcggtgtca taaaattctc aaccctcgtt     1200
cgatgatcat aaccggaacc acttatcaag tcgtcagccg acgctccgag aaaagcaatg     1260
aaccatgcgt taaattcga gtaaaaggct cgcgaggtcc gtagtccagc tgcgacggac      1320
ggcaaccaat ac                                                        1332

<210> SEQ ID NO 47
<211> LENGTH: 1284
<212> TYPE: DNA
<213> ORGANISM: Stevia rebaudiana

<400> SEQUENCE: 47
cacaatacta ctctttagtt accaatatac cataaccaaa attgtttgat agataagatt       60
atcctatatt aaaattgatg aaacccagtc gatttatcaa taaagaaat agatcaatga      120 aattatctag tttgtgaatt ttatcacatt gatgtttcta ccttatttca aacaaaccag     180
atacttcaat taattcaagc aacatttgat catgaagaca aacccaacaa cgcacattct     240
tcatacggtt aacgtacgtc gtgtcttctc caaataatct atgaaatggt ttatatactt     300
cttccccatc ttagtgtctc cgaacaatct acttaactcc atcgcatttt ccttgtaaat     360
cttcccttca tcatcagcta caaccgaccg cactgatctt gccactgact ccttgttgaa     420
ggagccatct tcgtcattc ttggtatctc aattcccacc tgattatccg ccattactcg      480
agcatttaga ccttgatcca ccgaaagcgg tagcattatt aaagggtgac cgaacatcat     540
cgcttccaca attgaactcc aaccacaatg agtcaagaaa ccacaaaccg actcatggct     600
cagtattcgt aactgaggtg cccaactcgt ccagaccaac ccacggtcac gagttcgttc     660
cacgaacccg tctggcaact ccaccgagtt accagagcca accggttttc taagaaccca     720
aaagaatggc aacccggaga gctcgagacc cagagctaac tcagccagct cgctttggct     780
caccgtacct tcacttccta atgcgacgta caccacatgg ttaacttgct gaccatcgag     840
ccacttcttg actgacaccc atgtatcatc tttctcgtct ccgtatgttt caggtggcat     900
taatccaacc ggaactaccg gtatacggta tagcttcccc aaaagggtta gccattgggg     960
ttcgaactca tggcaatgtc ttataaacat acaatctgat cccttttataa ccattcctaa    1020 acgatataaa tctgatacac cagaagaatt aacagaaata ttatcagcaa atatcaaatt     1080
ggcctcatgc ttccggtagc atactttgct cggaacgga atccacttgg gcggtgtcat     1140
gaaatcctca actgtcgttc gactctcgaa actattttc atgtcatcgg gtaacggtcc     1200
cacgtgcgcc atgaaccatg gtgaggcagt gataaaaaag gctcgcgaga tcccaaggtc     1260
cgccgcgacg gatggcaacc agtg                                           1284
```

-continued

```
<210> SEQ ID NO 48
<211> LENGTH: 1297
<212> TYPE: DNA
<213> ORGANISM: Stevia rebaudiana

<400> SEQUENCE: 48
cacaatacta ctctttagtt accaatatac cataaccaaa attgtttgat agataagatt      60
atcctatatt aaaattgatg aaacccagtc gatttatcaa taaaagaaat agatcaatga     120
aattatctag tttgtgaatt ttatcacatt gatgttccta ccttatttca aacaaaccag     180
atacttcaat taattcaagc aacatttgat catgaagaca aacccaacaa cgcacattct     240
tcatacggtt aacgtacgtc gtgtcttctc caaataatct atgaaatggt ttatatactt     300
ctttcccatc ttagtgtctc cgaacaatct acttaactcc atcgcatttt ccttgtaaat     360
cttcccttca tcatcagcta caaccgaccg cactgatctt gccactgact ccttgttgaa     420
ggagccatct tcgtcatttc ttggtatctc aattcccacc tgattatccg ccattactcg     480
agcatttaga ccttgatcca ccgaaagcgg tagcattatt aaagggtgac cgaacatcat     540
cgcttccaca attgaactcc aaccacaatg agtcaagaaa ccacaaaccg actcatggct     600
cagtattcgt aactgaggtg cccaactcgt ccagaccaac ccacggtcac gagttcgttc     660
cacgaacccc tctggcaact ccaccgagtt accagagcca accggttttc taagaaccca     720
aaagaatggc aacccggaga gctcgagacc cagagctaac tcagccagct cgctttggct     780
catcgtacct tcacttccaa atgccacgta caccacatgc cctattggtt gaccatcgag     840
ccacttcttg actgtgaccc atgtctcatc tttcccgtct ccgatgttgg tgggttttc      900 tggtggcaat aatccgacag gaaccaccgg taggtgatgg agcttctcta aaagggttaa     960
ccattgaggt tcgaactcat aactatgtct tataaacata cagtcagatc ctttcaaaat    1020
cattcccaca cgatacacac ttgatattcc agaagcatta gccgaagtat tccctaccat    1080
ccgaaccgcc tcatacttcc ggtagcacac gtttgtcgga aacggaaccc acttcggcgg    1140
tgtcataaaa ttctcaaccc tcgttcgatg atcataaccg gaaccactta tcaagtcgtc    1200
agccgacgct ccgagaaaag caatgaacca tgcgttaaaa ttcgagtaaa aggctcgcga    1260
ggtccgtagt ccagctgcga cggacggcaa ccaatac                             1297

<210> SEQ ID NO 49
<211> LENGTH: 1194
<212> TYPE: DNA
<213> ORGANISM: Stevia rebaudiana

<400> SEQUENCE: 49
tagtgaatgt atataacata aatgatatgt ttcaacctaa caaacggtta tttcatacac      60
ggaaaacaaa aatttatgat tattcaaaga aacatttgat catctagcta gacaaaccca     120
ataacacata tattcttcat acgatcaaag ctcatgctca atagcaacca cacgaccttt     180
ttgttccaaa tagtctataa aagggttat ataccttattt tccggcttac tatccccgaa     240
tcgttgactc aactccatcg ccttcgcctt gtagatcttc ccttcatcat cgactaaaac     300
caacctcaat gatctggcca ccgactcctt ggtgaatgaa ccatcttcct catttcttgg     360
tatctcgatt cccacctgat tatccgccat tactcgagca tttagacctt ggtcccccaa     420
aatcggtagc atgattagag ggtgaccgaa catcatcgct tccacaattg aactccaacc     480
acaatgagtc aagaaaccac aaaccgactc atggctcagt attcgtaact gaggtgccca     540
actcgtccag accaacccac ggtcacgagt tcgttccacg aacccgtctg gcaactccac     600
```

| | |
|---|---|
| cgagttacca gagccaaccg gttttctaag aacccaaaag aatggcaacc cggagagctc | 660 |
| gagacccaga gctaactcag ccagctcgct ttggctcacc gtaacttcac ttcctaatgc | 720 |
| gacgtacacc acatggttaa cttgctgacc atcgagccac ttcttgactg acacccatgt | 780 |
| atcatctttc tcgtctccgt atgtttcagg tggcattaat ccaaccggaa ctaccggtat | 840 |
| acggtatagc ttccccaaaa gggttagcca ttggggttcg acctcataac aacttcttat | 900 |
| aaacagacaa tcagattcct tcaaaaccgt catcattctg tgctttagac ctgaaatcac | 960 |
| aggattatta gcagcagaca tcttgcgcac aaactcatgc ttccggtagc atactttgct | 1020 |
| cggaaacgga atccacttgg gcggtgtcat gaaatcctca actgtcgttc gactctcgaa | 1080 |
| actattttc atgtcatcgg gtaacggtcc cacgtgcgcc atgaaccatg gtgaggcagt | 1140 |
| gataaaaaag gctcgcgaga tcccaaggtc cgccgcgacg gatggcaacc agtg | 1194 |

<210> SEQ ID NO 50
<211> LENGTH: 575
<212> TYPE: DNA
<213> ORGANISM: Stevia rebaudiana

<400> SEQUENCE: 50

| | |
|---|---|
| ggtagcatga ttagagggtg accaaacatt agcccttcca caattgatcc agaaccacaa | 60 |
| tgagtcaaga aaccacaaac cgactcatgg ctcagtattc gtaactgagg tgcccaactc | 120 |
| gtccagacca acccacggtc acgagttcgt tccacgaacc cgtctggcaa ctccaccgag | 180 |
| ttaccagagc caaccggttt tctaagaacc cacaaaaatg gcaacccaga gagctcgaga | 240 |
| cctaacgcta actcagccag ctcgcttttg gtcaccgtaa cttcacttcc taatgcgacg | 300 |
| tacaccacat ggttaacttg ctgaccatcg agccacttct tgactgacac ccatgtatca | 360 |
| tctttctcgt ctccgtatgt ttcaggtggc attaatccaa ccggaactac cggtatacgg | 420 |
| tatagcttcc ccaaaagggt tagccattgg ggttcgaact catggcaatg tcttataaac | 480 |
| atacaatctg atccctttat aaccattcct aaacgatata atctgatac accagaagaa | 540 |
| ttaacagaaa tattatcagc aaatatcaaa ttggc | 575 |

<210> SEQ ID NO 51
<211> LENGTH: 1232
<212> TYPE: DNA
<213> ORGANISM: Stevia rebaudiana

<400> SEQUENCE: 51

| | |
|---|---|
| tagtgaatgt atataacata atgatatgt ttcaacctaa caaacggtta tttcatacac | 60 |
| ggaaaacaaa aatttatgat tattcaaaga aacatttgat catctagcta gacaaaccca | 120 |
| ataacacata tattcttcat acgatcaaag ctcatgctca atagcaacca cacgaccttt | 180 |
| ttgttccaaa tagtctataa aagggtttat atacttattt tccggcttac tatccccgaa | 240 |
| tcgttgactc aactccatcg ccttcgcctt gtagatcttc ccttcatcat cgactaaaac | 300 |
| caacctcaat gatctggcca ccgactcctt ggtgaaggaa ccatcttcct catttcttgg | 360 |
| tatctcgatt cccacctgtt tatccgccat tactcgagca tttagacctt gatccaccaa | 420 |
| aatcggtagc atgattagag ggtgaccgaa catcatcgct tccacaattg aactccaacc | 480 |
| acaatgagtc aagaaaccac aaaccgactc atggctcagt attcgtaact gaggtgccca | 540 |
| actcgtccag accaacccac ggtcacgagt tcgttccacg aacccgtctg caactccac | 600 |
| cgagtctgac ttcgcgggac cttttggttt tctataagcc caaacaaatg caacccaga | 660 |
| aagctcgaga cccaatgcta actcaacaac ctcggtttgg ctcaccaaag cctcgcttcc | 720 |

```
taatgcaacg tacaccacac tgccttttg tttaccatcg agccatttct tgattgacac    780
ccatgtttca tctttctcgt ctccgggtat ttccggtggc agtaatccca ccggaaccac    840
cggtacttgg tgtagtgtct ccaaaagagg tagccattga gttccaaact catggtaaca    900
tttgaaaagc aaacaatcag atcccttaaa aaccagcccc atacggtatc catcagatat    960
ccccggagct ttgtaaggca ccagtcgggc aagatcatgc ttccgccagc atactttggt   1020
cggaaaggga aaccacttgg gcggtgtcgt gagatcctca accgtggttc gaccatctga   1080
accatttatc atggcgtcag ctgagggtcc catataagca atggcccatg gagtggtgac   1140
ggagaagtag gctcgtgaga taccgaggct agccgcgatg gatggcaacc agtagtgagt   1200
ataatcataa ataatccagt ccggagactc tt                                  1232
```

```
<210> SEQ ID NO 52
<211> LENGTH: 1310
<212> TYPE: DNA
<213> ORGANISM: Stevia rebaudiana

<400> SEQUENCE: 52
```

```
ggctggagtc aattgttttt atacaataca taatatagcg ttaaatggct ttataataac     60
gacggaaaag ttaatgactc gattctacca acgacttagc aattccaaca tgtgattaaa    120
aaagaagtgt aacaaggaca atcataacat catatgaatc attccaaaga aacccaacaa    180
ctaacttact tatagtctgt gaaacgactt atatattctt tttggttaac tctcatggtt    240
gttggcaacc acacgtacgt tcttttccat atagtctgtg aaacgactta tatattcttt    300
ttggttaact ctcatggttg ttggcaacca cacgtacgtt cttttccata tagtctgtga    360
aacgacttat atattccttt tgcagcttag tgtcgctgaa tattttactc atctctctcg    420
cattcgcctt gtagatctct ccttcatcgt ctacaacaac cgacctcagt gacgtggcaa    480
ccgactcctt ggtgaagtag ccatcttcct catttcttgg tatctcgatc cccacctgtt    540
tgtccgctaa tagtcgagca ttcagacatt ggtccccgaa atcggtagc atgattaaag     600
ggtggccgaa cattaaccct tccaccactg aactccaacc acagtgagtc aagaaaccac    660
acaccgactc atggctcagt attcgtaact gaggtgccca actcgtccaa accatcccac    720
ggttactagt tcgttccaag aacccgttag gcaactccac cgagtctgac tcggtggaac    780
ctgcgggttt tctgagaacc cacaaaaatg gcaacccaga gagctcgaga cctaacgcta    840
actcagccag ctcgcttttg gtcaccgtaa cttcacttcc taatgcgacg tacaccacat    900
ggttaacttg ctgaccatcg agccacttct tgactgacac ccatgtatca tctttctcgt    960
ctccgtatgt ttcaggtggc attaatccaa ccggaactac cggtatacgg tatagcttcc   1020
ccaaagggt tagccattgg ggttcgaact catggcaatg tcttataaac atacaatctg    1080
atcccttat aaccattcct aaacgatata aatctgatac accagaagaa ttaacagaaa    1140
tattatcagc aaatatcaaa ttggcctcat gcttccggta gcatactttg ctcggaaacg   1200
gaaaccactt cggcggtgtc aggaaatcgt cgggtgtttt ccgattgtct gtaccgttta   1260
tcatgttatc gggagacgat ccgaaaaaag agacggtcca tgcgttatag                1310
```

```
<210> SEQ ID NO 53
<211> LENGTH: 1316
<212> TYPE: DNA
<213> ORGANISM: Stevia rebaudiana

<400> SEQUENCE: 53
```

-continued

| | | | | | |
|---|---|---|---|---|---|
| cacaatacta | ctctttagtt | accaatatac | cataaccaaa | attgtttgat | agataagatt | 60
| atcctatatt | aaaattgatg | aaacccagtc | gatttatcaa | taaagaaaat | agatcaatga | 120
| aattatctag | tttgtgaatt | ttatcacatt | gatgtttcta | ccttatttca | aacaaaccag | 180
| atacttcaat | taattcaagc | aacatttgat | catgaagaca | aacccaacaa | cgcacattct | 240
| tcatacggtt | aacgtacgtc | gtgtcttctc | caaataatct | atgaaatggt | ttatatactt | 300
| cttcccatc | ttagtgtctc | cgaacaatct | acttaactcc | atcgcatttt | ccttgtaaat | 360
| cttcccttca | tcatcagcta | caaccgaccg | cactgatctt | gccactgact | ccttgttgaa | 420
| ggagccatct | tcgtcatttc | ttggtatctc | aattcccacc | tgattatccg | ccattactcg | 480
| agcatttaga | ccttgatcca | ccgaaagcgg | tagcattatt | aaagggtgac | cgaacatcat | 540
| cgcttccaca | attgaactcc | aaccacaatg | agtcaagaaa | ccacaaaccg | actcatggct | 600
| cagtattcgt | aactgaggtg | cccaactcgt | ccagaccaac | ccacggtcac | gagttcgttc | 660
| cacgaacccg | tctggcaact | ccaccgagtc | tgacttcgcg | ggaccttttg | gttttctata | 720
| agcccaaaca | aatggcaacc | cagaaagctc | gagacccaat | gctaactcaa | caacctcggt | 780
| ttggctcacc | aaaacctcgc | ttcctaatgc | aacgtacacc | acactgcctt | tttgtttacc | 840
| atcgagccat | ttcttgattg | acaccatgt | ttcatctttc | tcgtctccgg | gtatttccgg | 900
| tggcagtaat | cccaccggaa | ccaccggtac | ttggtgtagt | gtctccaaaa | gaggtagcca | 960
| ttgagttcca | aactcatggt | aacatttgaa | aagcaaacaa | tcagatccct | taagaaccag | 1020
| ccccatacgg | tatccatcag | atatccccgg | agctttgtaa | ggcaccagtc | gggcaagatc | 1080
| atgcttccgc | cagcatactt | tggtcggaaa | gggaaaccac | ttgggcggtg | tcgtgagatc | 1140
| ctcaaccgtg | gttcgaccat | ctgaaccatt | tatcatggcg | tcagctgagg | gtcccatata | 1200
| agcaatggcc | catggagtgg | tgacggagaa | gtgggctcgt | gagataccga | ggctagccgc | 1260
| gatggatggc | aaccagtagt | gagtataatc | ataaataatc | cagtccggag | actctt | 1316

<210> SEQ ID NO 54
<211> LENGTH: 1272
<212> TYPE: DNA
<213> ORGANISM: Stevia rebaudiana

<400> SEQUENCE: 54

| | | | | | |
|---|---|---|---|---|---|
| tttataataa | cgacggaaaa | gtagcgcacc | acttaatgac | tcgattctac | caacgactta | 60
| gcaattccaa | catgtgatta | aaaaagaagt | gtaacaagga | caatcataac | atcatatgaa | 120
| tcattccaaa | gaaacccaac | aactaactta | cttatagtct | gtgaaacgac | ttatatattc | 180
| tttttggtta | actctcatgg | ttgttggcaa | ccacacgtac | gttcttttcc | atatagtctg | 240
| tgaaacgact | tatatattct | ttttggttaa | ctctcatggt | tgttggcaac | cacacgtacg | 300
| ttcttttcca | tatagtctgt | gaaacgactt | atatattcct | tttgcagctt | agtgtcgctg | 360
| aatatttttac | tcatctctct | cgcattcgcc | ttgtagatct | ctccttcatc | gtctacaaca | 420
| accgacctca | gtgacgtggc | aaccgactcc | ttggtgaagt | agccatcttc | ctcatttctt | 480
| ggtatctcga | tccccaccctg | tttgtccgct | aatagtcgag | cattcagaca | ttggtccccg | 540
| aaaatcggta | gcatgattaa | agggtggccg | aacattaacc | cttccaccac | tgaactccaa | 600
| ccacagtgag | tcaagaaacc | acacaccgac | tcatggctca | gtattcgtaa | ctgaggtgcc | 660
| caactcgtcc | aaaccatccc | acggttacta | gttcgttcca | agaacccgtt | aggcaactcc | 720
| accgagtctg | actcggtgga | acctgcgggt | tttctgagaa | cccacaaaaa | tggcaaccca | 780
| gagagctcga | gacctaacgc | taactcagcc | agctcgcttt | tggtcaccgt | aacttcactt | 840

```
cctaatgcga cgtacaccac atggttaact tgctgaccat cgagccactt cttgactgac    900
acccatgtat catctttctc gtctccgtat gtttcaggtg gcattaatcc aaccggaact    960
accggtatac ggtatagctt ccccaaaagg gttagccatt ggggttcgaa ctcatggcaa   1020
tgtcttataa acatacaatc tgatcccttt ataaccattc ctaaacgata taaatctgat   1080
acaccagaag aattaacaga aatattatca gcaaatatca aattggcctc atgcttccgg   1140
tagcatactt tgctcggaaa cggaaaccac ttcggcggtg tcaggaaatc gtcgggtgtt   1200
ttccgattgt ctgtaccgtt tatcatgtta tcgggagacg atccgaaaaa agagacggtc   1260
catgcgttat ag                                                       1272
```

<210> SEQ ID NO 55
<211> LENGTH: 1370
<212> TYPE: DNA
<213> ORGANISM: Stevia rebaudiana

<400> SEQUENCE: 55

```
ggctggagtc aattgttttt atacaataca taatatagcg ttaaatggct ttataataac     60
gacggaaaag ttaatgactc gattctacca acgacttagc aattccaaca tgtgattaaa    120
aaagaagtgt aacaaggaca atcataacat catatgaatc attccaaaga aacccaacaa    180
ctaacttact tatagtctgt gaaacgactt atatattctt tttggttaac tctcatggtt    240
gttggcaacc acacgtacgt tcttttccat atagtctgtg aaacgactta tatattcttt    300
ttggttaact ctcatggttg ttggcaacca cacgtacgtt cttttccata tagtctgtga    360
aacgacttat atattccttt tgcagcttag tgtcgctgaa tattttactc atctctctcg    420
cattcgcctt gtagatctcc ccttcatttt ccgcaacaac ggacctcagt gatctagcaa    480
ccgactcctt ggtcaagcaa ccatcttcct catttcttgg tatctcgatt cccacctgtt    540
tgtcctccag taatcgagca ttcagacgtt ggtcccaaaa atcggtagc atgattagag     600 ggtgaccgaa cattaaccct tccacaattg aactccaacc acaatgagtc aagaaaccac    660
acaccgactc atggctcagt attcgtaact gaggtgccca actcgtccag accaacccac    720
ggtcacgagt tcgttccaag aacccgtctg gcaaatccac cgagtctgac tcggtggagc    780
ctgcgggttt tctaagaacc caaaagaatg gcaacccgga gagctcgaga cccagagcta    840
actcagccag ctcgctttgg ctcatcgtac cttcacttcc aaatgccacg tacaccacat    900
gccctattgg ttgaccatcg agccacttct tgattgtcac ccatgggtct ccggtgctgg    960
tgggtggttc gggtggcaat aatcccacgg gaaccactgg taggtgatgc agcttttcta   1020
aaagggttag ccattggggt tcgaactcat ggcaatgtct tataaacata caatctgatc   1080
cctttataac cattccagca cgatatatat ctgaaacccc agaagaatta atagaaaaat   1140
tatcagcaaa tatcgaattg gcctcatgct tccggtagca tactttgctt ggaaacggaa   1200
cccacttcgg cggtgtcata aaatcctcaa ccctcgttcg atgatcataa ccggaaccac   1260
ttatcaagtc gtcagccgac gctccgagaa aagcaatgaa ccatgcgtta aaattcgagt   1320
aaaaggctcg cgagatccgt agtccagctg cgacggacgg caaccaatac                1370
```

<210> SEQ ID NO 56
<211> LENGTH: 1205
<212> TYPE: DNA
<213> ORGANISM: Stevia rebaudiana

<400> SEQUENCE: 56

-continued

| | | |
|---|---|---|
| tagtgaatgt atataacata aatgatatgt ttcaacctaa caaacggtta tttcatacac | 60 | |
| ggaaaacaaa aatttatgat tattcaaaga aacatttgat catctagcta gacaaaccca | 120 | |
| ataacacata tattcttcat acgatcaaag ctcatgctca atagcaacca cacgaccttt | 180 | |
| ttgttccaaa tagtctataa aagggtttat atacttattt tccggcttac tatccccgaa | 240 | |
| tcgttgactc aactccatcg ccttcgcctt gtagatcttc ccttcatcat cgactaaaac | 300 | |
| caacctcaat gatctggcca ccgactcctt ggtgaatgaa ccatcttcgt catttcttgg | 360 | |
| tatctcaatt cccacctgat tatccgccat tactcgagca tttagacctt gatccaccga | 420 | |
| aagcggtagc attatcaaag ggtgaccgaa catcatcgct tccacaaatg aactccaacc | 480 | |
| agaatgagtc aagaaaccac acaccgactc atggctcagt atttgtaact gaggtgccca | 540 | |
| actcgtccag accaacccac ggtcacgagt tcgttccaag aacccgtctg gcaactccac | 600 | |
| cgagttacca gagccaaccg gttttctaag aacccaaaag aatggcaacc cggagagctc | 660 | |
| gaggcccaga gctaactcag ccagctcgct ttggctcatc gtaccttcac ttccaaatgc | 720 | |
| cacgtacacc acatgcccta ttggttgacc atcgagccac ttcttgattg tcacccatgg | 780 | |
| gtctccggtg ctggtgggtg gttcgggtgg caataatccc acgggaacca ctggtaggtg | 840 | |
| atgcagcttt tctaaaaggg ttagccattg gggttcgaac tcatggcaat gtcttataaa | 900 | |
| catacaatct gatcccttta taaccattcc agcacgatat atatctgaaa ccccagaaga | 960 | |
| attaatagaa aaattatcag caaatatcga attggcctca tgcttccggt agcatacttt | 1020 | |
| gcttggaaac ggaacccact tcggcggtgt caggaaatcg tcgggtgttt tccgattgtc | 1080 | |
| tgtaccgttt atcatgttat cggaagacga tccgataaaa gagacggtcc atgcgttata | 1140 | |
| gattgagaaa aaacctcgtg aaattccaag gctagtggct accgccggca accaataggg | 1200 | |
| agcaa | 1205 | |

<210> SEQ ID NO 57
<211> LENGTH: 1266
<212> TYPE: DNA
<213> ORGANISM: Stevia rebaudiana

<400> SEQUENCE: 57

| | | |
|---|---|---|
| tttttttttt tttacggctg gaatcaattg ctttattcat cacataattt ggctttaaat | 60 | |
| agccttacaa taacaactta ttaatatagt agcttaaaac aattaactag gacacctcct | 120 | |
| aagactcgat cgattctacc aacatattta gcaattccaa catttcattt gaatctttcc | 180 | |
| aaaagaaacc caacaactca cacatacttg atgatatagt taactctcat gatcgatggc | 240 | |
| aaccgcacgc gcattctttt ccaaatagtc tacgaattgg cttacatatt cttttttccac | 300 | |
| cttagtgtcg ttatagattt tactcagcgc cctcgcgttc gccttgtaga tctccccttc | 360 | |
| gttttccaca acaacggacc tcagtgatct agcaaccgac tccttggtca agcaaccatc | 420 | |
| ttcctcattt cttggtatct cgattccac ctgtttgtcc tccagtaatc gagcattcag | 480 | |
| aggttggtcc ccaaaaatcg gtagcatgat tagagggtga ccaaacatta gcccttccac | 540 | |
| aattgatcca gaaccacaat gagtcaagaa accacacacc gactcatggc tcagtatttg | 600 | |
| taactgaggt acccaactcg tccacaccaa cccacggtca cgagttcgtt ccaagaaccc | 660 | |
| gtctggcaac tccaccgagt taccagagcc aaccggtttt ctaagaaccc aaaagaatgg | 720 | |
| caacccggag agctcgagac ccagagctaa ctcagccagc tcgctttggc tcatcgtacc | 780 | |
| ttcacttcca aatgccacgt acaccacatg gcctatttgt tgaccatcga gccacttctt | 840 | |
| gattgtcacc catgggtctc cggtgctggt gggtggttcg ggtggcaata atcccacggg | 900 | |

```
aaccactggt aggtgatgca gcttttctaa aagggttagc cattggggtt cgacctcata    960
acaacttctt ataaacagac aatcagattc cttcaaaacc gtcatcattc tgtgctttag   1020
acctgaaatc acaggattat tagcagcaga catcttgcgc acaaactcat gcttccggta   1080
gcatactttg ctcggaaacg gaatccactt gggcggtgtc atgaaatcct caactgtcgt   1140
tcgactctcg aaactatttt tcatgtcatc gggtaacggt cccacgtgcg ccatgaacca   1200
tggtgaggca gtgataaaaa aggctcgcga gatcccaagg tccgccgcga cggatggcaa   1260
ccagtg                                                              1266
```

<210> SEQ ID NO 58
<211> LENGTH: 1292
<212> TYPE: DNA
<213> ORGANISM: Stevia rebaudiana

<400> SEQUENCE: 58

```
cacaatacta ctctttagtt accaatatac cataaccaaa attgtttgat agataagatt     60
atcctatatt aaaattgatg aaacccagtc gatttatcaa taaagaaat agatcaatga    120 aattatctag tttgtgaatt ttatcacatt gatgtttcta ccttatttca acaaaccag    180 atacttcaat taattcaagc aacatttgat catgaagaca aacccaacaa cgcacattct   240
tcatacggtt aacgtacgtc gtgtcttctc caaataatct atgaaatggt ttatatactt   300
ctttcccatc ttagtgtctc cgaacaatct acttaactcc atcgcatttt ccttgtaaat   360
cttcccttca tcatcagcta caaccgcccg cactgatctt gcgactgact ccttgttgaa   420
ggagccatct tcgtcatttc ttggtatctc aattcccacc tgattatccg ccattactcg   480
agcatttaga ccttgatcca ccgaaagcgg tagcattatc aaagggtgac cgaacatcat   540
cgcttccaca aatgaactcc aaccagaatg agtcaagaaa ccacacaccg actcatggct   600
cagtatttgt aactgaggtg cccaactcgt ccacaccaac ccacggtcac gagttcgttc   660 caagaaccc tctggcaact ccaccgagtt accagagcca accggttttc taagaaccca   720
aaagaatggc aacccggaga gctcgaggcc cagagctaac tcagccagct cgctttggct   780
catcgtacct tcacttccaa atgccacgta caccacatgc cctattggtt gaccatcgag   840
ccacttcttg attgacaccc atgtttcatc tttctcgtct ccgtatgttt caggtggcat   900
taatcccacc ggaaccaccg gtatatggtg tagcttctcc aaaagggtta gccattgggg   960
ttcgaactca tggcaatgtc ttataaacat acaatctgat ccctttataa ccattccagc   1020
acgatatata tctgaaaccc cagaagaatt aatagaaaaa ttatcagcaa atatcgaatt   1080
ggcctcatgc ttccggtagc atactttgct tggaaacgga acccacttcg gcggtgtcag   1140
gaaatcgtcg ggtgttttcc gattgtctgt accgtttatc atgttatcgg aagacgatcc   1200
gataaaagag acggtccatg cgttatagat tgagaaaaaa cctcgtgaaa ttccaaggct   1260
agtggctacc gccggcaacc aatagggagc aa                                 1292
```

<210> SEQ ID NO 59
<211> LENGTH: 1213
<212> TYPE: DNA
<213> ORGANISM: Stevia rebaudiana

<400> SEQUENCE: 59

```
tagtgaatgt atataacata aatgatatgt ttcaacctaa caaacggtta tttcatacac     60
ggaaaacaaa aatttatgat tattcaaaga aacatttgat catctagcta gacaaaccca    120
```

-continued

| | | | |
|---|---|---|---|
| ataacacata | tattcttcat | acgatcaaag ctcatgctca | atagcaacca cacgaccttt | 180 |
| ttgttccaaa | tagtctataa | aagggtttat atacttattt | tccggcttac tatccccgaa | 240 |
| tcgttgactc | aactccatcg | ccttcgcctt gtagatcttc | ccttcatcat cgactaaaac | 300 |
| caacctcaat | gatctggcca | ccgactcctt ggtgaatgaa | ccatcttcgt catttcttgg | 360 |
| tatctcaatt | cccacctgat | tatccgccat tactcgagca | tttagacctt gatccaccga | 420 |
| aagcggtagc | attatcaaag | ggtgaccgaa catcatcgct | tccacaaatg aactccaacc | 480 |
| agaatgagtc | aagaaaccac | acaccgactc atggctcagt | atttgtaact gaggtgccca | 540 |
| actcgtccac | accaacccac | ggtcacgagt tcgttccaag | aacccctctg caactccac | 600 |
| cgagttacca | gagccaaccg | gttttctaag aacccaaaag | aatggcaacc cggagagctc | 660 |
| gaggcccaga | gctaactcag | ccagctcgct ttggctcatc | gtaccttcac ttccaaatgc | 720 |
| cacgtacacc | acatgcccta | ttggttgacc atcgagccac | ttcttgactg tgtcacacgt | 780 |
| cttatcattc | ccgtcttcga | tgttggtggg ttttctggt | ggcaataatc cgacaggaac | 840 |
| caccggtagg | tgatggagct | tctctaaaag ggttaaccat | tgaggttcga actcataact | 900 |
| atgtctttata | aacatacagt | cagatccttt caaaatcatt | cccacacgat acacacttga | 960 |
| tattccagaa | gcattagccg | aagtattccc taccatccga | accgcctcat acttccggta | 1020 |
| gcacacgttt | gtcggaaacg | gaacccactt cggcggtgtc | ataaaattct caaccctcgt | 1080 |
| tcgatgatca | taaccggaac | cacttatcaa gtcgtcagcc | gacgctccga gaaaagcaat | 1140 |
| gaaccatgcg | ttaaaattcg | agtaaaaggc tcgcgagatc | cgtagtccag ctgcgacgga | 1200 |
| cggcaaccaa tac | | | 1213 |

<210> SEQ ID NO 60
<211> LENGTH: 1280
<212> TYPE: DNA
<213> ORGANISM: Stevia rebaudiana

<400> SEQUENCE: 60

| | | | |
|---|---|---|---|
| tttttttttt | tttacggctg | gaatcaattg ctttattcat | cacataattt ggctttaaat | 60 |
| agccttacaa | taacaactta | ttaatatagt agcttaaaac | aattaactag gacacctcct | 120 |
| aagactcgat | cgattctacc | aacatatttta gcaattccaa | catttcattt gaatctttcc | 180 |
| aaaagaaacc | caacaactca | cacatacttg atgatatagt | taactctcat gatcgatggc | 240 |
| aaccgcacgc | gcattctttt | ccaaatagtc tacgaattgg | cttacatatt ctttttccac | 300 |
| cttagtgtcg | ttatagattt | tactcagcgc cctcgcgttc | gccttgtaga tctcccttc | 360 |
| gttttccaca | acaacggacc | tcagtgatct agcaaccgac | tccttggtca agcaaccatc | 420 |
| ttcctcattt | cttggtatct | cgattccac ctgtttgtcc | tccagtaatc gagcattcag | 480 |
| aggttggtcc | ccaaaaatcg | gtagcatgat tagagggtga | ccaaacatta gcccttccac | 540 |
| aattgatcca | gaaccacaat | gagtcaagaa accacacacc | gactcatggc tcagtatttg | 600 |
| taactgaggt | acccaactcg | tccacaccaa cccacggtca | cgagttcgtt ccaagaaccc | 660 |
| gtctggcaac | tccaccgagt | taccagagcc aaccggtttt | ctaagaaccc aaaagaatgg | 720 |
| caacccggag | agctcgagac | ccagagctaa ctcagccagc | tcgctttggc tcatcgtacc | 780 |
| ttcacttcca | aatgccacgt | acaccacatg gcctatttgt | tgaccatcga gccacttctt | 840 |
| gattgtcacc | catgggtctc | cggtgctggt gggtggttcg | ggtggcaata atcccacggg | 900 |
| aaccactggt | aggtgatgca | gctttttctaa aagggttagc | cattgggggtt cgaactcatg | 960 |
| gcaatgtctt | ataaacatac | aatctgatcc ctttataacc | attccagcac gatatatatc | 1020 |

```
tgaaacccca gaagaattaa tagaaaaatt atcagcaaat atcgaattgg cctcatgctt      1080
ccggtagcat actttgcttg gaaacggaac ccacttcggc ggtgtcagga aatcgtcggg      1140
tgttttccga ttgtctgtac cgtttatcat gttatcggaa gacgatccga taaaagagac      1200
ggtccatgcg ttatagattg agaaaaaacc tcgtgaaatt ccaaggctag tggctaccgc      1260
cggcaaccaa tagggagcaa                                                  1280

<210> SEQ ID NO 61
<211> LENGTH: 1288
<212> TYPE: DNA
<213> ORGANISM: Stevia rebaudiana

<400> SEQUENCE: 61
tttttttttt tttacggctg gaatcaattg ctttattcat cacataattt ggctttaaat        60
agccttacaa taacaactta ttaatatagt agcttaaaac aattaactag gacacctcct       120
aagactcgat cgattctacc aacatattta gcaattccaa catttcattt gaatctttcc       180
aaaagaaacc caacaactca cacatacttg atgatatagt taactctcat gatcgatggc       240
aaccgcacgc gcattctttt ccaaatagtc tacgaattgg cttacatatt ctttttccac       300
cttagtgtcg ttatagattt tactcagctc cctcgcgttc gccttgtaga tctccccttc       360
tttttccaca acaacggacc tcagtgatct agcaaccgac tccttggtca agcaaccatc       420
ttcctcattt cttggtatct cgattcccac ctgtttgtcc tccagtaatc gagcattcag       480
aggttggtcc ccaaaaatcg gtagcatgat tagagggtga ccaaacatta gcccttccac       540
aattgatcca gaaccacaat gagtcaagaa accacacacc gactcatggc tcagtatttg       600
taactgaggt gcccaactcg tccacaccaa cccacggtca cgagttcgtt ccacgaaccc       660
gtctggcaac tccaccgagt taccagagcc aaccggtttt ctaagaaccc aaaagaatgg       720
caacccggag agctcgagac ccaaagctaa ctcagccagc tcgcttttgc tcaccgtaac       780
ttcacttcca aatgcgacgt acaccacatg gttaacttgt tgaccatcga gccacttctt       840
gactgtgtcc cacgtctcat cattcccgtc ttcgatgttg gtgggttttt ctggtggcaa       900
taatccgaca ggaaccaccg gtaggtgatg gagcttctct aaaagggtta accattgagg       960
ttcgaactca taactatgtc ttataaacat acagtcagat cctttcaaaa tcattcccac      1020
acgatacaca cttgatattc cagaagcatt agccgaagta ttccctacca tccgaaccgc      1080
ctcatacttc cggtagcaca cgtttgtcgg aaacggaacc cacttcggcg gtgtcataaa      1140
attctcaacc ctcgttcgat gatcataacc ggaaccactt atcaagtcgt cagccgacgc      1200
tccgagaaaa gcaatgaacc atgcgttaaa attcgagtaa aaggctcgcg agatccgtag      1260
tccagctgcg acggacggca accaatac                                         1288

<210> SEQ ID NO 62
<211> LENGTH: 1283
<212> TYPE: DNA
<213> ORGANISM: Stevia rebaudiana

<400> SEQUENCE: 62
tttttttttt tttacggctg gaatcaattg ctttattcat cacataattt ggctttaaat        60
agccttacaa taacaactta ttaatatagt agcttaaaac aattaactag gacacctcct       120
aagactcgat cgattctacc aacatattta gcaattccaa catttcattt gaatctttcc       180
aaaagaaacc caacaactca cacatacttg atgatatagt taactctcat gatcgatggc       240
```

```
aaccgcacgc gcattcttttt ccaaatagtc tacgaattgg cttacatatt ctttttccac    300
cttagtgtcg ttatagattt tactcagcgc cctcgcgttc gccttgtaga tctcccttc     360 tttttccaca acaacggacc tcagtgatct agcaaccgac tccttggtca agcaaccatc    420
ttcctcattt cttggtatct cgattccac ctgtttgtcc tccagtaatc gagcattcag     480
aggttggtcc ccaaaaatcg gtagcatgat tagagggtga ccaaacatta gcccttccac    540
aattgatcca gaaccacaat gagtcaagaa accacacacc gactcatggc tcagtatttg    600
taactgaggt acccaactcg tccacaccaa cccacggtca cgagttcgtt ccacgaaccc    660
ctctggcaac tccaccgagt taccagagcc aaccggtttt ctaagaaccc aaaagaatgg    720
caacccggag agctcgaggc ccagagctaa ctcagccagc tcgctttggc tcatcgtacc    780
ttcacttcca aatgccacgt acaccacatg ccctattggt tgaccatcga gccacttctt    840
gattgacacc catgtttcat cttttctcgtc tccgtatgtt tcaggtggca ttaatcccac    900
cggaaccacc ggtatatggt gtagcttctc caaaagggtt agccattggg gttcgaactc    960
atggcaatgt cttataaaca tacaatctga tccctttata accattccag cacgatatat   1020
atctgaaacc ccagaagaat taatagaaaa attatcagca aatatcgaat tggcctcatg   1080
cttccggtag catactttgc ttggaaacgg aacccacttc ggcggtgtca ggaaatcgtc   1140
gggtgttttc cgattgtctg taccgtttat catgttatcg gaagacgatc cgataaaaga   1200
gacggtccat gcgttataga ttgagaaaaa acctcgtgaa attccaaggc tagtggctac   1260
cgccggcaac caatagggag caa                                           1283

<210> SEQ ID NO 63
<211> LENGTH: 1379
<212> TYPE: DNA
<213> ORGANISM: Stevia rebaudiana

<400> SEQUENCE: 63
ggctggagtc aattgttttt atacaataca taatatagcg ttaaatggct ttataataac     60
gacggaaaag ttaatgactc gattctacca acgacttagc aattccaaca tgtgattaaa    120
aaagaagtgt aacaaggaca atcataacat catatgaatc attccaaaga aacccaacaa    180
ctaacttact tatagtctgt gaaacgactt atatattctt tttggttaac tctcatggtt    240
gttggcaacc acacgtacgt tcttttccat atagtctgtg aaacgactta tatattcttt    300
ttggttaact ctcatggttg ttggcaacca cacgtacgtt cttttccata tagtctgtga    360
aacgacttat atattccttt tgcagcttag tgtcgctgaa tattttactc atctctctcg    420
cattcgcctt gtagatctcc ccttcatttt ccgcaacaac ggacctcagt gatctagcaa    480
ccgactcctt ggtcaagcaa ccatcttcct catttcttgg tatctcgatt cccacctgtt    540
tgtcctccag taatcgagca ttcagacatt ggtccccaaa aatcggtagc atgattagag    600
ggtgaccgaa cattaaccct tccacaattg aactccaacc agaatgagtc aagaaaccac    660
acaccgactc atggctcagt attcgtaact gaggtgccca actcgtccag accaacccac    720
ggtcacgagt tcgttccaag aacccgtctg gcaaatccac cgagtctgac tcggtggagc    780
ctgcgggttt tctaagaacc caaaaaaatg gcaacccgga gagctcgagg cccagagcta    840
actcagccag ctcgctttgg ctcatcgtac cttcacttcc aaatgccacg tacaccacat    900 gcccctattgg ttgaccatcg agccacttct tgactgtgtc acgtctctta tcattcccgt   960
cttcgatgtt ggtgggtttt tctggtggca ataatccgac aggaaccacc ggtaggtgat    1020
ggagcttctc taaaagggtt aaccattgag gttcgaactc ataactatgt cttataaaca   1080
```

```
tacagtcaga tcctttcaaa atcattccca cacgatacac acttgatatt ccagaagcat    1140
tagccgaagt attccctacc atccgaaccg cctcatactt ccggtagcac acgtttgtcg    1200
gaaacggaac ccacttcggc ggtgtcataa aattctcaac cctcgttcga tgatcataac    1260
cggaaccact tatcaagtcg tcagccgacg ctccgagaaa agcaatgaac catgcgttaa    1320
aattcgagta aaaggctcgc gagatccgta gtccagctgc gacggacggc aaccaatac    1379
```

<210> SEQ ID NO 64
<211> LENGTH: 1197
<212> TYPE: DNA
<213> ORGANISM: Stevia rebaudiana

<400> SEQUENCE: 64

```
tagtgaatgt atataacata aatgatatgt ttcaacctaa caaacggtta tttcatacac      60
ggaaaacaaa aatttatgat tattcaaaga aacatttgat catctagcta gacaaaccca     120
ataacacata tattcttcat acgatcaaag ctcatgctca atagcaacca cacgaccttt     180
ttgttccaaa tagtctataa aagggtttat atacttattt tccggcttac tatccccgaa     240
tcgttgactc aactccatcg ccttcgcctt gtagatcttc ccttcatcat cgactaaaac     300
caacctcaat gatctggcca ccgactcctt ggtgaatgaa ccatcttcgt catttcttgg     360
tatctcaatt cccacctgat tatccgccat tactcgagca tttagacctt gatccaccga     420
aagcggtagc attatcaaag ggtgaccgaa catcatcgct tccacaaatg aactccaacc     480
agaatgagtc aagaaaccac acaccgactc atggctcagt atttgtaact gaggtgccca     540
actcgtccac accaacccac ggtcacgagt tcgttccaag aaccctctg gcaactccac       600 cgagttacca gagccaaccg gttttctaag aacccaaaag aatggcaacc cggagagctc     660
gaggcccaga gctaactcag ccagctcgct ttggctcatc gtaccttcac ttccaaatgc     720
cacgtacacc acatgcccta ttggttgacc atcgagccac ttcttgattg tcacccatgg     780
gtctccggtg ctggtgggtg gttcgggtgg caataatccc acgggaacca ctggtaggtg     840
atgcagcttt tctaaaaggg ttagccattg gggttcgaac tcatggcaat gtcttataaa     900
catacaatct gatcccttta taaccattcc agcacgatat atatctgaaa ccccagaaga     960
attaatagaa aaattatcag caaatatcga attggcctca tgcttccggt agcatacttt    1020
gctcggaaac ggaatccact tgggcggtgt catgaaatcc tcaactgtcg ttcgactctc    1080 gaaactatt tcatgtcat cgggtaacgg tcccacgtgc gccatgaacc atggtgaggc      1140
agtgataaaa aaggctcgcg agatcccaag gtccgccgcg acggatggca accagtg       1197
```

<210> SEQ ID NO 65
<211> LENGTH: 573
<212> TYPE: DNA
<213> ORGANISM: Stevia rebaudiana

<400> SEQUENCE: 65

```
cacaatacta ctctttagtt accaatatac cataaccaaa attgtttgat agataagatt      60
atcctatatt aaaattgatg aaacccagtc gatttatcaa taaaagaaat agatcaatga     120
aattatctag tttgtgaatt ttatcacatt gatgttccta ccttatttca aacaaaccag     180
atacttcaat taattcaagc aacatttgat catgaagaca aacccaacaa cgcacattct     240
tcatacggtt aacgtacgtc gtgtcttctc caaataatct atgaaatggt ttatatactt     300
ctttcccatc ttagtgtctc cgaacaatct acttaactcc atcggtagga accaccggta     360
```

| | |
|---|---|
| ggtgatggag cttctctaaa agggttaacc attgaggttc gaactcataa ctatgtctta | 420 |
| taaacataca gtcagatcct ttcaaaatca ttcccacacg atacacactt gatattccag | 480 |
| aagcattagc cgaagtattc cctaccatcc gaaccgcctc atacttccgg tagcacacgt | 540 |
| ttgtcggaaa cggaacccac ttcggcggtg tca | 573 |

<210> SEQ ID NO 66
<211> LENGTH: 1281
<212> TYPE: DNA
<213> ORGANISM: Stevia rebaudiana

<400> SEQUENCE: 66

| | |
|---|---|
| cacaatacta ctctttagtt accaatatac cataaccaaa attgtttgat agataagatt | 60 |
| atcctatatt aaaattgatg aaacccagtc gatttatcaa taaaagaaat agatcaatga | 120 |
| aattatctag tttgtgaatt ttatcacatt gatgtttcta ccttatttca aacaaaccag | 180 |
| atacttcaat taattcaagc aacatttgat catgaagaca aacccaacaa cgcacattct | 240 |
| tcatacggtt aacgtacgtc gtgtcttctc caaataatct atgaaatggt ttatatactt | 300 |
| ctttcccatc ttagtgtctc cgaacaatct acttaactcc atcgcatttt ccttgtaaat | 360 |
| cttcccttca tcatcagcta caaccgcccg cactgatctt gcgactgact ccttgttgaa | 420 |
| ggagccatct tcgtcatttc ttggtatctc aattcccacc tgattatccg ccattactcg | 480 |
| agcatttaga ccttgatcca ccgaaagcgg tagcattatc aaagggtgac cgaacatcat | 540 |
| cgcttccaca aatgaactcc aaccagaatg agtcaagaaa ccacacaccg actcatggct | 600 |
| cagtatttgt aactgaggtg cccaactcgt ccagaccaac ccacggtcac gagttcgttc | 660 |
| caagaacccg tctggcaact ccaccgagtt accagagcca accggttttc taagaaccca | 720 |
| aaagaatggc aacccggaga gctcgaggcc cagagctaac tcagccagct cgctttggct | 780 |
| catcgtacct tcacttccaa atgccacgta caccacatgc cctattggtt gaccatcgag | 840 |
| ccacttcttg attgtcaccc atgggtctcc ggtgctggtg ggtggttcgg gtggcaataa | 900 |
| tcccacggga accactggta ggtgatgcag cttttctaaa agggttagcc attggggttc | 960 |
| gaactcatgg caatgtctta taaacataca atctgatccc tttataacca ttccagcacg | 1020 |
| atatatatct gaaaccccag aagaattaat agaaaaatta tcagcaaata tcgaattggc | 1080 |
| ctcatgcttc cggtagcata ctttgcttgg aaacggaatc cacttgggcg gtgtcatgaa | 1140 |
| atcctcaact gtcgttcgac tctcgaaact attttttcatg tcatcgggta acggtccac | 1200 |
| gtgcgccatg aaccatggtg aggcagtgat aaaaaaggct cgcgagatcc caaggtccgc | 1260 |
| cgcgacggat ggcaaccagt g | 1281 |

<210> SEQ ID NO 67
<211> LENGTH: 1275
<212> TYPE: DNA
<213> ORGANISM: Stevia rebaudiana

<400> SEQUENCE: 67

| | |
|---|---|
| tttttttttt tttacggctg gaatcaattg ctttattcat cacataattt ggctttaaat | 60 |
| agccttacaa taacaactta ttaatatagt agcttaaaac aattaactag gacacctcct | 120 |
| aagactcgat cgattctacc aacatattta gcaattccaa catttcattt gaatctttcc | 180 |
| aaaagaaacc caacaactca cacatacttg atgatatagt taactctcat gatcgatggc | 240 |
| aaccgcacgc gcattctttt ccaaatagtc tacgaattgg cttacatatt cttttccac | 300 |
| cttagtgtcg ttatagattt tactcagcgc cctcgcgttc gccttgtaga tctcccctc | 360 |

```
ttttccaca acaacggacc tcagtgatct agcaaccgac tccttggtca agcaaccatc      420
ttcctcattt cttggtatct cgattcccac ctgtttgtcc tccagtaatc gagcattcag      480
aggttggtcc ccaaaaatcg gtagcatgat tagagggtga ccaaacatta gcccttccac      540
aattgatcca gaaccacaat gagtcaagaa accacacacc gactcatggc tcagtatttg      600
taactgaggt acccaactcg tccacaccaa cccacggtca cgagttcgtt ccaagaaccc      660
gtctggcaac tccaccgagt taccagagcc aaccggtttt ctaagaaccc aaaagaatgg      720
caacccggag agctcgaggc ccagagctaa ctcagccagc tcgctttggc tcatcgtacc      780
ttcacttcca aatgccacgt acaccacatg ccctattggt tgaccatcga gccacttctt      840
gactgacacc catgtttcat cttttctcgtc tccgtatgtt tcaggtggca ttaatcccac      900
cggaaccacc ggtatatggt gtagcttctc caaaagggtt agccattggg gttcgaactc      960
atggcaatgt cttataaaca tacaatctga tcccttata accattccag cacgatatat      1020
atctgaaacc ccagaagaat taatagaaaa attatcagca aatatcgaat tggcctcatg      1080
cttccggtag catactttgc ttggaaacgg aatccacttg ggcggtgtca tgaaatcctc      1140
aactgtcgtt cgactctcga aactattttt catgtcatcg ggtaacggtc ccacgtgcgc      1200
catgaaccat ggtgaggcag tgataaaaaa ggctcgcgag atcccaaggt ccgccgcgac      1260
ggatggcaac cagtg                                                     1275

<210> SEQ ID NO 68
<211> LENGTH: 1307
<212> TYPE: DNA
<213> ORGANISM: Stevia rebaudiana

<400> SEQUENCE: 68 ttttttttt ttacggctg gaatcaattg ctttattcat cacataattt ggctttaaat       60
agccttacaa taacaactta ttaatatagt agcttaaaac aattaactag gacacctcct     120
aagactcgat cgattctacc aacatattta gcaattccaa catttcattt gaatctttcc     180
aaaagaaacc caacaactca cacatacttg atgatatagt taactctcat gatcgatggc     240
aaccgcacgc gcattctttt ccaaatagtc tacgaattgg cttacatatt cttttccac     300 cttagtgtcg ttatagattt tactcagctc cctcgcgttc gccttgtaga tctcccttc     360 ttttccaca acaacggacc tcagtgatct agcaaccgac tccttggtca agcaaccatc     420
ttcctcattt cttggtatct cgattcccac ctgtttgtcc tccagtaatc gagcattcag     480
aggttggtcc ccaaaaatcg gtagcatgat tagagggtga ccaaacatta gcccttccac     540
aattgatcca gaaccacaat gagtcaagaa accacacacc gactcatggc tcagtattcg     600
taactgaggt gcccaactcg tccacaccaa cccacggtca cgagttcgtt ccacgaaccc     660
gtctggcaac tccaccgagt ctgacttcgc gggacctttt ggttttctat aagcccaaac     720
aaatggcaac ccagaaagct cgagacccaa tgctaactca acaacctcgg tttggctcac     780
caaagcctcg cttcctaatg caacgtacac cacactgcct ttttgtttac catcgagcca     840
tttcttgatt gacacccatg tttcatcttt ctcgtctccg ggtatttccg gtggcagtaa     900
tcccaccgga accaccggta cttggtgtag tgtctccaaa agaggtagcc attgagttcc     960
aaactcatgg taacatttga aaagcaaaca atcagatccc ttaaaaacca gccccatacg    1020
gtatccatca gatatccccg gagctttgta aggcaccagt cgggcaagat catgcttccg    1080
ccagcatact ttggtcggaa agggaaacca cttgggcggt gtcgtgagat cctcaaccgt    1140
```

```
ggttcgacca tctgaaccat ttatcatggc gtcagctgag ggtcccatat aagcaatggc    1200
ccatggagtg atgacggaga agtaggctcg tgagataccg aggctagccg cgatggatgg    1260
caaccagtag tgagtataat cataaataat ccagtccgga gactctt                  1307

<210> SEQ ID NO 69
<211> LENGTH: 1208
<212> TYPE: DNA
<213> ORGANISM: Stevia rebaudiana

<400> SEQUENCE: 69
tagtgaatgt atataacata aatgatatgt tcaacctaa caaacggtta tttcatacac       60
ggaaaacaaa aatttatgat tattcaaaga aacatttgat catctagcta gacaaaccca      120
ataacacata tattcttcat acgatcaaag ctcatgctca atagcaacca cacgaccttt      180
ttgttccaaa tagtctataa aagggtttat atacttattt tccggcttac tatccccgaa      240
tcgttgactc aactccatcg ccttcgcctt gtagatcttc ccttcatcat cgactaaaac      300
caacctcaat gatctggcca ccgactcctt ggtgaatgaa ccatcttcgt catttcttgg      360
tatctcaatt cccacctgat tatccgccat tactcgagca tttagacctt gatccaccga      420
aagcggtagc attatcaaag ggtgaccgaa catcatcgct tccacaaatg aactccaacc      480
agaatgagtc aagaaaccac acaccgactc atggctcagt atttgtaact gaggtgccca      540
actcgtccac accaacccac ggtcacgagt tcgttccaag aaccctctg  gcaactccac      600 cgagttacca gagccaaccg gttttctaag aacccaaaag aatggcaacc cggagagctc      660
gaggcccaga gctaactcag ccagctcgct ttggctcatc gtaccttcac ttccaaatgc      720
cacgtacacc acatgcccta ttggttgacc atcgagccac ttcttgattg acacccatgt      780
ttcatctttc tcgtctccgt atgtttcagg tggcattaat cccaccggaa ccaccggtat      840
atggtgtagc ttctccaaaa gggttagcca ttggggttcg aactcatggc aatgtcttat      900
aaacatacaa tctgatccct ttataaccat tccagcacga tatatatctg aaaccccaga      960
agaattaata gaaaaattat cagcaaatat cgaattggcc tcatgcttcc ggtagcatac     1020
tttgcttgga aacggaaccc acttcggcgg tgtcaggaaa tcgtcgggtg ttttccgatt     1080
gtctgtaccg tttatcatgt tatcggaaga cgatccgata aaagagacgg tccatgcgtt     1140
atagattgag aaaaaacctc gtgaaattcc aaggctagtg gctaccgccg gcaaccaata     1200
gggagcaa                                                              1208

<210> SEQ ID NO 70
<211> LENGTH: 1341
<212> TYPE: DNA
<213> ORGANISM: Stevia rebaudiana

<400> SEQUENCE: 70
tttataataa cgacggaaaa gtagcgcacc acttaatgac tcgattctac caacgactta       60
gcaattccaa catgtgatta aaaagaagt gtaacaagga caatcataac atcatatgaa       120
tcattccaaa gaaacccaac aactaactta cttatagtct gtgaaacgac ttatatattc       180
tttttggtta actctcatgg ttgttggcaa ccacacgtac gttcttttcc atatagtctg       240
tgaaacgact tatatattct ttttggttaa ctctcatggt tgttggcaac cacacgtacg       300
ttcttttcca tatagtctgt gaaacgactt atatattcct tttgcagctt agtgtcgctg       360
aatattttac tcatctctct cgcattcgcc ttgtagatct ccccttcatt ttccgcaaca       420
acggacctca gtgatctagc aaccgactcc ttggtcaagc aaccatcttc ctcatttctt       480
```

-continued

```
ggtatctcga ttcccacctg tttgtcctcc agtaatcgag cattcagacg ttggtcccca    540
aaaatcggta gcatgattag agggtgaccg aacattaacc cttccacaat tgaactccaa    600
ccacaatgag tcaagaaacc acacaccgac tcatggctca gtattcgtaa ctgaggtgcc    660
caactcgtcc agaccaaccc acggtcacga gttcgttcca agaacccgtc tggcaactcc    720
accgagtctg actcggtgga gcctgcgggt tttctaagaa cccaaaagaa tggcaacccg    780
gagagctcga gacccagagc taactcagcc agctcgcttt ggctcatcgt accttcactt    840
ccaaatgcca cgtacaccac atgccctatt ggttgaccat cgagccactt cttgactgtg    900
tcacacgtct tatcattccc gtcttcgatg ttggtgggtt tttctggtgg caataatccg    960
acaggaacca ccggtaggtg atggagcttc tctaaaaggg ttaaccattg aggttcgaac   1020
tcataactat gtcttataaa catacagtca gatcctttca aaatcattcc cacacgatac   1080
acacttgata ttccagaagc attagccgaa gtattcccta ccatccgaac cgcctcatac   1140
ttccggtagc acacgtttgt cggaaacgga acccacttcg gcggtgtcat aaaattctca   1200
accctcgttc gatgatcata accggaacca cttatcaagt cgtcagccga cgctccgaga   1260
aaagcaatga accatgcgtt aaaattcgag taaaaggctc gcgagatccg tagtccagct   1320
gcgacggacg gcaaccaata c                                              1341
```

<210> SEQ ID NO 71
<211> LENGTH: 1289
<212> TYPE: DNA
<213> ORGANISM: Stevia rebaudiana

<400> SEQUENCE: 71

```
cacaatacta ctctttagtt accaatatac cataaccaaa attgtttgat agataagatt     60
atcctatatt aaaattgatg aaacccagtc gatttatcaa taaaagaaat agatcaatga    120
aattatctag tttgtgaatt ttatcacatt gatgtttcta ccttatttca acaaaccag    180 atacttcaat taattcaagc aacatttgat catgaagaca aacccaacaa cgcacattct    240
tcatacggtt aacgtacgtc gtgtcttctc caaataatct atgaaatggt ttatatactt    300
ctttcccatc ttagtgtctc cgaacaatct acttaactcc atcgcatttt ccttgtaaat    360
cttcccttca tcatcagcta caaccgcccg cactgatctt gcgactgact ccttgttgaa    420
ggagccatct tcgtcatttc ttggtatctc aattcccacc tgattatccg ccattactcg    480
agcatttaga ccttgatcca ccgaaagcgg tagcattatc aaagggtgac cgaacatcat    540
cgcttccaca aatgaactcc aaccagaatg agtcaagaaa ccacacaccg actcatggct    600
cagtatttgt aactgaggtg cccaactcgt ccacaccaac ccacggtcac gagttcgttc    660
caagaacccg tctggcaact ccaccgagtt accagagcca accggttttc taagaaccca    720
aaagaatggc aacccggaga gctcgaggcc cagagctaac tcagccagct cgctttggct    780
catcgtacct tcacttccaa atgccacgta caccacatgc cctattggtt gaccatcgag    840
ccacttcttg attgtcaccc atgggtctcc ggtgctggtg ggtggttcgg gtggcaataa    900
tcccacggga accactggta ggtgatgcag cttttctaaa agggttagcc attggggttc    960
gaactcatgg caatgtctta taaacataca atctgatccc tttataacca ttccagcacg   1020
atatatatct gaaaccccag aagaattaat agaaaaatta tcagcaaata tcgaattggc   1080
ctcatgcttc cggtagcata cttttgcttgg aaacggaacc cacttcggcg gtgtcaggaa   1140
atcgtcgggt gttttccgat tgtctgtacc gtttatcatg ttatcggaag acgatccgat   1200
```

| | |
|---|---|
| aaaagagacg gtccatgcgt tatagattga gaaaaaacct cgtgaaattc caaggctagt | 1260 |
| ggctaccgcc ggcaaccaat agggagcaa | 1289 |

<210> SEQ ID NO 72
<211> LENGTH: 1279
<212> TYPE: DNA
<213> ORGANISM: Stevia rebaudiana

<400> SEQUENCE: 72

| | |
|---|---|
| tttttttttt tttacggctg gaatcaattg ctttattcat cacataattt ggctttaaat | 60 |
| agccttacaa taacaactta ttaatatagt agcttaaaac aattaactag gacacctcct | 120 |
| aagactcgat cgattctacc aacatattta gcaattccaa catttcattt gaatctttcc | 180 |
| aaaagaaacc caacaactca cacatacttg atgatatagt taactctcat gatcgatggc | 240 |
| aaccgcacgc gcattctttt ccaaatagtc tacgaattgg cttacatatt cttttccac | 300 |
| cttagtgtcg ttatagattt tactcagcgc cctcgcgttc gccttgtaga tctcccctc | 360 |
| tttttccaca acaacggacc tcagtgatct agcaaccgac tccttggtca agcaaccatc | 420 |
| ttcctcattt cttggtatct cgattccac ctgtttgtcc tccagtaatc gagcattcag | 480 |
| aggttggtcc ccaaaaatcg gtagcatgat tagagggtga ccaaacatta gcccttccac | 540 |
| aattgatcca gaaccacaat gagtcaagaa accacacacc gactcatggc tcagtatttg | 600 |
| taactgaggt acccaactcg tccacaccaa cccacgtca cgagttcgtt ccaagaaccc | 660 |
| gtctggcaac tccaccgagt taccagagcc aacggtttt ctaagaaccc aaaagaatgg | 720 |
| caacccggag agctcgaggc ccagagctaa ctcagccagc tcgctttggc tcatcgtacc | 780 |
| ttcacttcca aatgccacgt acaccacatg ccctattggt tgaccatcga gccacttctt | 840 |
| gattgtcacc catgggtctc cggtgctggt gggtggttcg ggtggcaata atcccacggg | 900 |
| aaccactggt aggtgatgca gcttttctaa aagggttagc cattggggtt cgaactcatg | 960 |
| gcaatgtctt ataaacatac aatctgatcc ctttataacc attccagcac gatatatatc | 1020 |
| tgaaacccca gaagaattaa tagaaaaatt atcagcaaat atcgaattgg cctcatgctt | 1080 |
| ccggtagcat actttgcttg gaaacggaac ccacttcggc ggtgtcataa aatcctcaac | 1140 |
| cctcgttcga tgatcataac cggaaccact tatcaagtcg tcagccgacg ctccgagaaa | 1200 |
| agcaatgaac catgcgttaa aattcgagta aaaggctcgc gagatccgta gtccagctgc | 1260 |
| gacggacggc aaccaatac | 1279 |

<210> SEQ ID NO 73
<211> LENGTH: 1322
<212> TYPE: DNA
<213> ORGANISM: Stevia rebaudiana

<400> SEQUENCE: 73

| | |
|---|---|
| tttataataa cgacggaaaa gtagcgcacc acttaatgac tcgattctac caacgactta | 60 |
| gcaattccaa catgtgatta aaaagaagt gtaacaagga caatcataac atcatatgaa | 120 |
| tcattccaaa gaaacccaac aactaactta cttatagtct gtgaaacgac ttatatattc | 180 |
| tttttggtta actctcatgg ttgttggcaa ccacacgtac gttcttttcc atatagtctg | 240 |
| tgaaacgact tatatattct ttttggttaa ctctcatggt tgttggcaac cacacgtacg | 300 |
| ttcttttcca tatagtctgt gaaacgactt atatattcct tttgcagctt agtgtcgctg | 360 |
| aatattttac tcatctctct cgcattcgcc ttgtagatct ccccttcatt ttccgcaaca | 420 |
| acggacctca gtgatctagc aaccgactcc ttggtcaagc aaccatcttc ctcatttctt | 480 |

```
ggtatctcga ttcccacctg tttgtcctcc agtaatcgag cattcagaca ttggtcccca      540
aaaatcggta gcatgattag agggtgaccg aacattaacc cttccacaat tgaactccaa      600
ccagaatgag tcaagaaacc acacaccgac tcatggctca gtattcgtaa ctgaggtgcc      660
caactcgtcc agaccaaccc acggtcacga gttcgttcca agaacccgtc tggcaactcc      720
accgagtctg actcggtgga gcctgcgggc tttctgagaa cccacaaaaa tggcaaccca      780
gagagctcga gacctaacgc taactcagcc agctcgcttt tggtcaccgt aacttcactt      840
cctaatgcga cgtacaccac atggttaact tgttgaccat cgagccactt cttgattgac      900
acccatgtat catctttctc gtctccgtat gtttcaggtg cattaatcc aaccggaact       960 accggtatac ggtatagctt ccccaaaagg gttagccatt ggggttcgac ctcataacaa     1020
cttcttataa acagacaatc agattccttc aaaaccgtca tcattctgtg ctttagacct     1080
gaaatcacag gattattagc agcagacatc ttgcgcacaa actcatgctt ccggtagcat     1140
actttgctcg gaaacggaat ccacttgggc ggtgtcatga atcctcaac tgtcgttcga      1200 ctctcgaaac tattttttcat gtcatcgggt aacggtccca cgtgcgccat gaaccatggt    1260
gaggcagtga taaaaaaggc tcgcgagatc ccaaggtccg ccgcgacgga tggcaaccag     1320
tg                                                                    1322

<210> SEQ ID NO 74
<211> LENGTH: 674
<212> TYPE: DNA
<213> ORGANISM: Stevia rebaudiana

<400> SEQUENCE: 74
tcctcatttc ttggtatctc gatccccacc tgtttgtccg ctaatagtcg agcattcaga      60
cattggtccc caaaaatcgg tagcatgatt agagggtgac cgaacattaa cccttccaca     120
attgaactcc aaccacaatg agtcaagaaa ccacacaccg actcatggct cagtattcgt     180
aactgaggtg cccaactcgt ccagaccaac ccacggtcac gagttcgttc caagaacccg     240
tctggcaact ccaccgagtc tgactcggtg gagcctaccg gttttctaag aacccaaaaa     300
aatggcaacc cggagagctc gagacccaga gctaactcag ccagctcgct ttggctcatc     360
gtaccttcac ttccaaatgc cacgtacacc acatgcccta ttggttgacc atcgagccac     420
ttcttgattg tcacccatgg gtctccggtg ctggtgggtg gttcgggtgg caataatccc     480
acgggaacca ctggtaggtg atgcagcttt tctaaaaggg ttagccattg gggttcgacc     540
tcataacaac ttcttataaa cagacaatca gattccttca aaaccgtcat cattctgtgc     600
tttagacctg aaatcacagg attattagca gcagacatct tgcgcacaaa ctcatgcttc     660
cggtagcata cttt                                                       674

<210> SEQ ID NO 75
<211> LENGTH: 1360
<212> TYPE: DNA
<213> ORGANISM: Stevia rebaudiana

<400> SEQUENCE: 75
ggctggagtc aattgttttt atacaataca taatatagcg ttaaatggct ttataataac      60
gacggaaaag ttaatgactc gattctacca acgacttagc aattccaaca tgtgattaaa     120
aaagaagtgt aacaaggaca atcataacat catatgaatc attccaaaga aacccaacaa     180
ctaacttact tatagtctgt gaaacgactt atatattctt tttggttaac tctcatggtt     240
```

| | |
|---|---:|
| gttggcaacc acacgtacgt tcttttccat atagtctgtg aaacgactta tatattcttt | 300 |
| ttggttaact ctcatggttg ttggcaacca cacgtacgtt cttttccata tagtctgtga | 360 |
| aacgacttat atattccttt tgcagcttag tgtcgctgaa tattttactc atctctctcg | 420 |
| cattcgcctt gtagatctcc ccttcatttt ccgcaacaac ggacctcagt gatctagcaa | 480 |
| ccgactcctt ggtcaagcaa ccatcttcct catttcttgg tatctcgatt cccacctgtt | 540 |
| tgtcctccag taatcgagca ttcagacatt ggtccccaaa atcggtagc atgattagag | 600 |
| ggtgaccgaa cattaaccct tccacaattg aactccaacc agaatgagtc aagaaaccac | 660 |
| acaccgactc atggctcagt attcgtaact gaggtgccca actcgtccag accaaccccac | 720 |
| ggtcacgagt tcgttccaag aacccgtctg gcaactccac cgagtctgac tcggtggagc | 780 |
| ctgcgggctt tctgagaacc cacaaaaatg gcaacccaga gagctcgaga cctaacgcta | 840 |
| actcagccag ctcgcttttg gtcaccgtaa cttcacttcc taatgcgacg tacaccacat | 900 |
| ggttaacttg ttgaccatcg agccacttct tgattgacac ccatgtatca tctttctcgt | 960 |
| ctccgtatgt ttcaggtggc attaatccaa ccggaactac cggtatacgg tatagcttcc | 1020 |
| ccaaaagggt tagccattgg ggttcgacct cataacaact tcttataaac agacaatcag | 1080 |
| attccttcaa aaccgtcatc attctgtgct ttagacctga aatcacagga ttattagcag | 1140 |
| cagacatctt gcgcacaaac tcatgcttcc ggtagcatac tttgctcgga aacggaatcc | 1200 |
| acttgggcgg tgtcatgaaa tcctcaactg tcgttcgact ctcgaaacta tttttcatgt | 1260 |
| catcgggtaa cggtcccacg tgcgccatga accatggtga ggcagtgata aaaaaggctc | 1320 |
| gcgagatccc aaggtccgcc gcgacggatg gcaaccagtg | 1360 |

<210> SEQ ID NO 76
<211> LENGTH: 539
<212> TYPE: DNA
<213> ORGANISM: Stevia rebaudiana

<400> SEQUENCE: 76

| | |
|---|---:|
| actgaactcc aaccacagtg agttaagaaa ccacacaccg actcatggct cagtattcgt | 60 |
| aactgaggtg cccaactcgt ccaaaccaac ccacggtcac gagttcgttc caagaacccg | 120 |
| tctggcaact ccaccgagtc tgactcggtg gagcctaccg gttttctaag aacccaaaag | 180 |
| aatggcaacc cggagagctc gaggcccaga gctaactcag ccagctcgct ttggctcatc | 240 |
| gtaccttcac ttccaaatgc cacgtacacc acatgcccta ttggttgacc atcgagccac | 300 |
| ttcttgactg tcacccatgt ttcatctttc tcgtctccgt atgtttcagg tggcattaat | 360 |
| cccaccggaa ccaccggtat atggtgtagc ttctccaaaa gggttagcca ttgggggttcg | 420 |
| aactcatggc aatgtcttat aaacataaa tctgatccct ttataaccat tccagcacga | 480 |
| tatatatctg aaacaccaga agaattaata gaaaaattat cagcaaatat cgaattggc | 539 |

<210> SEQ ID NO 77
<211> LENGTH: 1332
<212> TYPE: DNA
<213> ORGANISM: Stevia rebaudiana

<400> SEQUENCE: 77

| | |
|---|---:|
| tttataataa cgacggaaaa gtagcgcacc acttaatgac tcgattctac caacgactta | 60 |
| gcaattccaa catgtgatta aaaagaagt gtaacaagga caatcataac atcatatgaa | 120 |
| tcattccaaa gaaacccaac aactaactta cttatagtct gtgaaacgac ttatatattc | 180 |
| tttttggtta actctcatgg ttgttggcaa ccacacgtac gttcttttcc atatagtctg | 240 |

-continued

| | | |
|---|---|---|
| tgaaacgact tatatattct ttttggttaa ctctcatggt tgttggcaac cacacgtacg | 300 |
| ttcttttcca tatagtctgt gaaacgactt atatattcct tttgcagctt agtgtcgctg | 360 |
| aatattttac tcatctctct cgcattcgcc ttgtagatct cccctttcatt ttccgcaaca | 420 |
| acggacctca gtgatctagc aaccgactcc ttggtcaagc aaccatcttc ctcatttctt | 480 |
| ggtatctcga ttcccacctg tttgtcctcc agtaatcgag cattcagacg ttggtcccca | 540 |
| aaaatcggta gcatgattag agggtgaccg aacattaacc cttccacaat tgaactccaa | 600 |
| ccacaatgag tcaagaaacc acacaccgac tcatggctca gtattcgtaa ctgaggtgcc | 660 |
| caactcgtcc agaccaaccc acggtcacga gttcgttcca agaacccgtc tggcaaatcc | 720 |
| accgagtctg actcggtgga gcctgcgggt tttctaagaa cccaaaagaa tggcaacccg | 780 |
| gagagctcga ggcccagagc taactcagcc agctcgcttt ggctcatcgt accttcactt | 840 |
| ccaaatgcca cgtacaccac atgccctatt ggttgaccat cgagccactt cttgattgtc | 900 |
| acccatgggt ctccggtgct ggtgggtggt tcggtggca ataatcccac gggaaccact | 960 |
| ggtaggtgat gcagcttttc taaaagggtt agccattggg gttcgaactc atggcaatgt | 1020 |
| cttataaaca tacaatctga tccctttata accattccag cacgatatat atctgaaacc | 1080 |
| ccagaagaat aatagaaaa attatcagca aatatcgaat tggcctcatg cttccggtag | 1140 |
| catactttgc ttggaaacgg aacccacttc ggcggtgtca taaaatcctc aaccctcgtt | 1200 |
| cgatgatcat aaccggaacc acttatcaag tcgtcagccg acgctccgag aaaagcaatg | 1260 |
| aaccatgcgt taaaattcga gtaaaaggct cgcgagatcc gtagtccagc tgcgacggac | 1320 |
| ggcaaccaat ac | 1332 |

<210> SEQ ID NO 78
<211> LENGTH: 1284
<212> TYPE: DNA
<213> ORGANISM: Stevia rebaudiana

<400> SEQUENCE: 78

| | | |
|---|---|---|
| cacaatacta ctctttagtt accaatatac cataaccaaa attgtttgat agataagatt | 60 |
| atcctatatt aaaattgatg aaacccagtc gatttatcaa taaaagaaat agatcaatga | 120 |
| aattatctag tttgtgaatt ttatcacatt gatgtttcta ccttatttca aacaaaccag | 180 |
| atacttcaat taattcaagc aacatttgat catgaagaca aacccaacaa cgcacattct | 240 |
| tcatacggtt aacgtacgtc gtgtcttctc caaataatct atgaaatggt ttatatactt | 300 |
| ctttcccatc ttagtgtctc cgaacaatct acttaactcc atcgcatttt ccttgtaaat | 360 |
| cttcccttca tcatcagcta caaccgcccg cactgatctt gcgactgact ccttgttgaa | 420 |
| ggagccatct tcgtcatttc ttggtatctc aattcccacc tgattatccg ccattactcg | 480 |
| agcatttaga ccttgatcca ccgaaagcgg tagcattatc aaagggtgac cgaacatcat | 540 |
| cgcttccaca aatgaactcc aaccagaatg agtcaagaaa ccacacaccg actcatggct | 600 |
| cagtatttgt aactgaggtg cccaactcgt ccacaccaac ccacggtcac gagttcgttc | 660 |
| caagaacccg tctggcaact ccaccgagtt accagagcca accggttttc taagaaccca | 720 |
| aaagaatggc aacccggaga gctcgaggcc cagagctaac tcagccagct cgctttggct | 780 |
| catcgtacct tcacttccaa atgccacgta caccacatgc cctattggtt gaccatcgag | 840 |
| ccacttcttg actgacaccc atgtttcatc tttctcgtct ccgtatgttt caggtggcat | 900 |
| taatcccacc ggaaccaccg gtatatggtg tagcttctcc aaaagggtta gccattgggg | 960 |

```
ttcgaactca tggcaatgtc ttataaacat acaatctgat cccctttataa ccattccagc    1020 acgatatata tctgaaaccc cagaagaatt aatagaaaaa ttatcagcaa atatcgaatt    1080
ggcctcatgc ttccggtagc atactttgct tggaaacgga atccacttgg gcggtgtcat    1140
gaaatcctca actgtcgttc gactctcgaa actattttc atgtcatcgg gtaacggtcc    1200
cacgtgcgcc atgaaccatg gtgaggcagt gataaaaaag gctcgcgaga tcccaaggtc    1260
cgccgcgacg gatggcaacc agtg                                           1284
```

<210> SEQ ID NO 79
<211> LENGTH: 1297
<212> TYPE: DNA
<213> ORGANISM: Stevia rebaudiana

<400> SEQUENCE: 79

```
cacaatacta ctctttagtt accaatatac cataaccaaa attgtttgat agataagatt     60
atcctatatt aaaattgatg aaacccagtc gatttatcaa taaaagaaat agatcaatga    120
aattatctag tttgtgaatt ttatcacatt gatgtttcta ccttatttca aacaaaccag    180
atacttcaat taattcaagc aacatttgat catgaagaca aacccaacaa cgcacattct    240
tcatacggtt aacgtacgtc gtgtcttctc caaataatct atgaaatggt ttatatactt    300
ctttcccatc ttagtgtctc cgaacaatct acttaactcc atcgcatttt ccttgtaaat    360
cttcccttca tcatcagcta caaccgcccg cactgatctt gcgactgact ccttgttgaa    420
ggagccatct tcgtcatttc ttggtatctc aattcccacc tgattatccg ccattactcg    480
agcatttaga ccttgatcca ccgaaagcgg tagcattatc aaagggtgac cgaacatcat    540
cgcttccaca aatgaactcc aaccagaatg agtcaagaaa ccacacaccg actcatggct    600
cagtatttgt aactgaggtg cccaactcgt ccacaccaac ccacggtcac gagttcgttc    660
caagaacccc tctggcaact ccaccgagtt accagagcca accggttttc taagaaccca    720
aaagaatggc aacccggaga gctcgaggcc cagagctaac tcagccagct cgctttggct    780
catcgtacct tcacttccaa atgccacgta caccacatgc cctattggtt gaccatcgag    840
ccacttcttg actgtgtcac acgtcttatc attcccgtct tcgatgttgg tgggttttc    900 tggtggcaat aatccgacag gaaccaccgg taggtgatgg agcttctcta aaagggttaa    960
ccattgaggt tcgaactcat aactatgtct tataaacata cagtcagatc ctttcaaaat   1020
cattcccaca cgatacacac ttgatattcc agaagcatta gccgaagtat tccctaccat   1080
ccgaaccgcc tcatacttcc ggtagcacac gtttgtcgga aacggaaccc acttcggcgg   1140
tgtcataaaa ttctcaaccc tcgttcgatg atcataaccg gaaccactta tcaagtcgtc   1200
agccgacgct ccgagaaaag caatgaacca tgcgttaaaa ttcgagtaaa aggctcgcga   1260
gatccgtagt ccagctgcga cggacggcaa ccaatac                             1297
```

<210> SEQ ID NO 80
<211> LENGTH: 1194
<212> TYPE: DNA
<213> ORGANISM: Stevia rebaudiana

<400> SEQUENCE: 80

```
tagtgaatgt atataacata aatgatatgt ttcaacctaa caaacggtta tttcatacac     60
ggaaaacaaa aatttatgat tattcaaaga acatttgat catctagcta gacaaaccca    120
ataacacata tattcttcat acgatcaaag ctcatgctca atagcaacca cacgaccttt    180
ttgttccaaa tagtctataa aagggttttat atacttattt tccggcttac tatccccgaa    240
```

```
tcgttgactc aactccatcg ccttcgcctt gtagatcttc ccttcatcat cgactaaaac    300
caacctcaat gatctggcca ccgactcctt ggtgaatgaa ccatcttcgt catttcttgg    360
tatctcaatt cccacctgat tatccgccat tactcgagca tttagacctt gatccaccga    420
aagcggtagc attatcaaag ggtgaccgaa catcatcgct tccacaaatg aactccaacc    480
agaatgagtc aagaaaccac acaccgactc atggctcagt atttgtaact gaggtgccca    540
actcgtccac accaacccac ggtcacgagt tcgttccaag aacccctctg caactccac     600 cgagttacca gagccaaccg gttttctaag aacccaaaag aatggcaacc cggagagctc    660
gaggcccaga gctaactcag ccagctcgct ttggctcatc gtaccttcac ttccaaatgc    720
cacgtacacc acatgcccta ttggttgacc atcgagccac ttcttgactg acaccatgt     780 ttcatctttc tcgtctccgt atgtttcagg tggcattaat ccaaccggaa ctaccggtat    840
acggtatagc ttccccaaaa gggttagcca ttggggttcg acctcataac aacttcttat    900
aaacagacaa tcagattcct tcaaaaccgt catcattctg tgctttagac ctgaaatcac    960
aggattatta gcagcagaca tcttgcgcac aaactcatgc ttccggtagc atactttgct   1020
cggaaacgga atccacttgg gcggtgtcat gaaatcctca actgtcgttc gactctcgaa   1080
actatttttc atgtcatcgg gtaacggtcc cacgtgcgcc atgaaccatg gtgaggcagt   1140
gataaaaaag gctcgcgaga tcccaaggtc cgccgcgacg gatggcaacc agtg          1194
```

<210> SEQ ID NO 81
<211> LENGTH: 575
<212> TYPE: DNA
<213> ORGANISM: Stevia rebaudiana

<400> SEQUENCE: 81

```
ggtagcatga ttagagggtg accaaacatc atcgcttcca caattgatcc ccaaccacaa     60
tgagtcaaga aaccacaaac cgactcatgg ctcagtattc gtaactgagg tgcccaactc    120
gtccagacca acccacggtc acgagttcgt tccaagaacc cctctggcaa ctccaccgag    180
ttaccagagc caaccggttt tctaagaacc caaaagaatg gcaacccgga gagctcgaga    240
cccagagcta actcagccag ctcgctttgg ctcaccgtaa cttcacttcc taatgcgacg    300
tacaccacat ggttaacttg ttgaccatcg agccacttct tgattgacac ccatgtatca    360
tctttctcgt ctccgtatgt ttcaggtggc attaatccca ccggaaccac cggtatatgg    420
tgtagcttct ccaaaagggt tagccattgg ggttcgaact catggcaatg tcttataaac    480
atacaatctg atccctttat aaccattcca gcacgtatat atctgaaaac accagaagaa    540
ttaatagaaa aattatcagc aaatatcgaa ttggc                                575
```

<210> SEQ ID NO 82
<211> LENGTH: 1232
<212> TYPE: DNA
<213> ORGANISM: Stevia rebaudiana

<400> SEQUENCE: 82

```
tagtgaatgt atataacata aatgatatgt ttcaacctaa caaacggtta tttcatacac     60
ggaaaacaaa aatttatgat tattcaaaga aacatttgat catctagcta gacaaaccca    120
ataacacata tattcttcat acgatcaaag ctcatgctca atagcaacca cacgaccttt    180
ttgttccaaa tagtctataa aagggtttat atacttattt tccggcttac tatccccgaa    240
tcgttgactc aactccatcg ccttcgcctt gtagatcttc ccttcatcat cgactaaaac    300
```

| | |
|---|---:|
| caacctcaat gatctggcca ccgactcctt ggtgaatgaa ccatcttcgt catttcttgg | 360 |
| tatctcaatt cccacctgat tatccgccat tactcgagca tttagacctt gatccaccga | 420 |
| aagcggtagc attatcaaag ggtgaccgaa catcatcgct tccacaaatg aactccaacc | 480 |
| agaatgagtc aagaaaccac acaccgactc atggctcagt attcgtaact gaggtgccca | 540 |
| actcgtccag accaacccac ggtcacgagt tcgttccaag aacccgtctg gcaactccac | 600 |
| cgagtctgac ttcgcgggac cttttggttt tctataagcc caaacaaatg gcaacccaga | 660 |
| aagctcgaga cccaatgcta actcaacaac ctcggtttgg ctcaccaaag cctcgcttcc | 720 |
| taatgcaacg tacaccacac tgccttttgt ttaccatcg agccatttct tgattgacac | 780 |
| ccatgtttca tctttctcgt ctccgggtat ttccggcggc agtaatccca ccggaaccac | 840 |
| cggtacttgg tgtagtgtct ccaaaagagg tagccattga gttccaaact catggtaaca | 900 |
| tttgaaaagc aaacaatcag atcccttaaa aaccagcccc atacggtatc catcagatat | 960 |
| ccccggagct ttgtaaggca ccagtcgggc aagatcatgc ttccgccagc atactttggt | 1020 |
| cggaaaggga accacttggg gcggtgtcgt gagatcctca accgtggttc gaccatctga | 1080 |
| accatttatc atggcgtcag ctgagggtcc catataagca atggcccatg gagtggtgac | 1140 |
| ggagaagtag gctcgtgaga taccgaggct agccgcgatg gatggcaacc agtagtgagt | 1200 |
| ataatcataa ataatccagt ccggagactc tt | 1232 |

<210> SEQ ID NO 83
<211> LENGTH: 1310
<212> TYPE: DNA
<213> ORGANISM: Stevia rebaudiana

<400> SEQUENCE: 83

| | |
|---|---:|
| ggctggagtc aattgttttt atacaataca taatatagcg ttaaatggct ttataataac | 60 |
| gacggaaaag ttaatgactc gattctacca acgacttagc aattccaaca tgtgattaaa | 120 |
| aaagaagtgt aacaaggaca atcataacat catatgaatc attccaaaga aacccaacaa | 180 |
| ctaacttact tatagtctgt gaaacgactt atatattctt tttggttaac tctcatggtt | 240 |
| gttggcaacc acacgtacgt tcttttccat atagtctgtg aaacgactta tatattcttt | 300 |
| ttggttaact ctcatggttg ttggcaacca cacgtacgtt cttttccata tagtctgtga | 360 |
| aacgacttat atattccttt tgcagcttag tgtcgctgaa tattttactc atctctctcg | 420 |
| cattcgcctt gtagatctcc ccttcatttt ccgcaacaac ggacctcagt gatctagcaa | 480 |
| ccgactcctt ggtcaagcaa ccatcttcct catttcttgg tatctcgatt cccacctgtt | 540 |
| tgtcctccag taatcgagca ttcagacgtt ggtccccaaa atcggtagc atgattagag | 600 |
| ggtgaccgaa cattaaccct tccacaattg aactccaacc agaatgagtc aagaaaccac | 660 |
| acaccgactc atggctcagt attcgtaact gaggtgccca actcgtccag accaacccac | 720 |
| ggtcacgagt tcgttccaag aacccgtctg gcaaatccac cgagtctgac tcggtggagc | 780 |
| ctgcgggctt tctgagaacc cacaaaaatg gcaacccaga gagctcgaga cctaacgcta | 840 |
| actcagccag ctcgcttttg gtcaccgtaa cttcacttcc taatgcgacg tacaccacat | 900 |
| ggttaacttg ttgaccatcg agccacttct tgattgacac ccatgtatca tctttctcgt | 960 |
| ctccgtatgt ttcaggtggc attaatccca ccggaaccac cggtatatgg tgtagcttct | 1020 |
| ccaaagggt tagccattgg ggttcgaact catggcaatg tcttataaac atacaatctg | 1080 |
| atcccttttat aaccattcca gcacgatata tatctgaaac cccagaagaa ttaatagaaa | 1140 |
| aattatcagc aaatatcgaa ttggcctcat gcttccggta gcatactttg cttggaaacg | 1200 |

```
gaacccactt cggcggtgtc aagaaatcgt cgggtgtttt ccgattgtct gtaccgttta    1260
tcatgttatc ggaagacgat ctgataaaag agacggtcca tgcgttatag               1310

<210> SEQ ID NO 84
<211> LENGTH: 1316
<212> TYPE: DNA
<213> ORGANISM: Stevia rebaudiana

<400> SEQUENCE: 84
cacaatacta ctctttagtt accaatatac cataaccaaa attgtttgat agataagatt     60
atcctatatt aaaattgatg aaacccagtc gatttatcaa taaagaaat agatcaatga    120 aattatctag tttgtgaatt ttatcacatt gatgtttcta ccttatttca aacaaaccag   180
atacttcaat taattcaagc aacatttgat catgaagaca aacccaacaa cgcacattct   240
tcatacggtt aacgtacgtc gtgtcttctc caaataatct atgaaatggt ttatatactt   300
ctttcccatc ttagtgtctc cgaacaatct acttaactcc atcgcatttt ccttgtaaat   360
cttcccttca tcatcagcta caaccgcccg cactgatctt gcgactgact ccttgttgaa   420
ggagccatct tcgtcatttc ttggtatctc aattcccacc tgattatccg ccattactcg   480
agcatttaga ccttgatcca ccgaaagcgg tagcattatc aaagggtgac cgaacatcat   540
cgcttccaca aatgaactcc aaccagaatg agtcaagaaa ccacacaccg actcatggct   600
cagtatttgt aactgaggtg cccaactcgt ccagaccaac ccacggtcac gagttcgttc   660
caagaacccg tctggcaact ccaccgagtc tgacttcgcg ggacctttg gttttctata    720 agcccaaaca aatggcaacc cagaaagctc gagacccaat gctaactcaa caacctcggt   780
ttggctcacc aaagcctcgc ttcctaatgc aacgtacacc acactgcctt tttgtttacc   840
atcgagccat ttcttgattg acacccatgt ttcatctttc tcgtctccgg gtatttccgg   900
tggcagtaat cccaccggaa ccaccggtac ttggtgtagt gtctccaaaa gaggtagcca   960
ttgagttcca aactcatggt aacatttgaa aagcaaacaa tcagatccct taagaaccat   1020
ccccatacgg tatccatcag atatccccgg agcttcgtaa ggcaccagtc gggcaagatc   1080
atgcttccgc cagcatactt tggtcggaaa gggaaaccac ttgggcggtg tcgtgagatc   1140
ctcaaccgtg gttcgaccat ctgaaccatt tatcatggcg tcagctgagg gtcccatata   1200
agcaatggcc catggagtga tgacggagaa gtaggctcgt gagataccga ggctagccgc   1260
gatggatggc aaccagtagt gagtataatc ataaataatc cagtccggag actctt       1316

<210> SEQ ID NO 85
<211> LENGTH: 1272
<212> TYPE: DNA
<213> ORGANISM: Stevia rebaudiana

<400> SEQUENCE: 85
tttataataa cgacggaaaa gtagcgcacc acttaatgac tcgattctac caacgactta     60
gcaattccaa catgtgatta aaaagaagt gtaacaagga caatcataac atcatatgaa    120
tcattccaaa gaaacccaac aactaactta cttatagtct gtgaaacgac ttatatattc   180 ttttggtta actctcatgg ttgttggcaa ccacacgtac gttctttcc atatagtctg    240 tgaaacgact tatatattct ttttggttaa ctctcatggt tgttggcaac cacacgtacg   300 ttctttttcca tatagtctgt gaaacgactt atatattcct tttgcagctt agtgtcgctg   360 aatatttttac tcatctctct cgcattcgcc ttgtagatct cccccttcatt ttccgcaaca   420
```

| | |
|---|---|
| acggacctca gtgatctagc aaccgactcc ttggtcaagc aaccatcttc ctcatttctt | 480 |
| ggtatctcga ttcccacctg tttgtcctcc agtaatcgag cattcagacg ttggtcccca | 540 |
| aaaatcggta gcatgattag agggtgaccg aacattaacc cttccacaat tgaactccaa | 600 |
| ccagaatgag tcaagaaacc acacaccgac tcatggctca gtatttgtaa ctgaggtgcc | 660 |
| caactcgtcc agaccaaccc acggtcacga gttcgttcca agaacccgtc tggcaaatcc | 720 |
| accgagtctg actcggtgga gcctgcgggc tttctgagaa cccacaaaaa tggcaaccca | 780 |
| gagagctcga gacctaacgc taactcagcc agctcgcttt tggtcaccgt aacttcactt | 840 |
| cctaatgcga cgtacaccac atggttaact tgttgaccat cgagccactt cttgattgac | 900 |
| acccatgtat catcttctc gtctccgtat gtttcaggtg cattaatcc caccggaacc | 960 |
| accggtatat ggtgtagctt ctccaaaagg gttagccatt ggggttcgaa ctcatggcaa | 1020 |
| tgtcttataa acatacaatc tgatcccttt ataaccattc cagcacgata tatatctgaa | 1080 |
| accccagaag aattaataga aaattatca gcaaatatcg aattggcctc atgcttccgg | 1140 |
| tagcatactt tgcttggaaa cggaacccac ttcggcggtg tcaagaaatc gtcgggtgtt | 1200 |
| ttccgattgt ctgtaccgtt tatcatgtta tcggaagacg atctgataaa agagacggtc | 1260 |
| catgcgttat ag | 1272 |

<210> SEQ ID NO 86
<211> LENGTH: 1370
<212> TYPE: DNA
<213> ORGANISM: Stevia rebaudiana

<400> SEQUENCE: 86

| | |
|---|---|
| ggctggagtc aattgttttt atacaataca taatatagcg ttaaatggct ttataataac | 60 |
| gacggaaaag ttaatgactc gattctacca acgacttagc aattccaaca tgtgattaaa | 120 |
| aaagaagtgt aacaaggaca atcataacat catatgaatc attccaaaga aacccaacaa | 180 |
| ctaacttact tatagtctgt gaaacgactt atatattctt tttggttaac tctcatggtt | 240 |
| gttggcaacc acacgtacgt tcttttccat atagtctgtg aaacgactta tatattcttt | 300 |
| ttggttaact ctcatggttg ttggcaacca cacgtacgtt cttttccata tagtctgtga | 360 |
| aacgacttat atattccttt tgcagcttag tgtcgctgaa tattttactc atctctctcg | 420 |
| cattcgcctt gtagatctcc ccttctttt ccacaacaac ggacctcagt gatctagcaa | 480 |
| ccgactcctt ggtcaagcaa ccatcttcct catttcttgg tatctcgatt cccacctgtt | 540 |
| tgtcctccag taatcgagca ttcagaggtt ggtccccgaa atcggtagc atgattagag | 600 |
| ggtgaccaaa cattagccct tccacaattg atccagaacc acaatgagtc aagaaaccac | 660 |
| aaaccgactc atggctcagt attcgtaact gaggtgccca actcgtccag accatcccac | 720 |
| ggtcagtagt tcgttccacg aacccgtctg gcaactccac cgagtctgac tcggtggaac | 780 |
| ctgcgggttt tctaagaacc caaaagaatg gcaacccgga gagctcgaga cccagagcta | 840 |
| actcagccag ctcgctttgg ctcatcgtac cttcacttcc aaatgccacg tacaccacat | 900 |
| gccctattgg ttgaccatcg agccacttct tgattgtcac ccatgggtct ccggtgctgg | 960 |
| tgggtggttc gggtggcaat aatcccacgg gaaccactgg taggtgatgc agctttttcta | 1020 |
| aaagggttag ccattggggt tcgaactcat ggcaatgtct tataaacata caatctgatc | 1080 |
| cctttataac cattccagca cgatatatat ctgaaacccc agaagaatta atagaaaaat | 1140 |
| tatcagcaaa tatcgaattg gcctcatgct tccggtagca tactttgctt ggaaacggaa | 1200 |
| cccacttcgg cggtgtcata aaattctcaa ccctcgttcg atgatcataa ccggaaccac | 1260 |

```
ttatcaagtc gtcagccgac gctccgagaa aagcaatgaa ccatgcgtta aaattcgagt    1320
aaaaggctcg cgaggtccgt agtccagctg cgacggacgg caaccaatac              1370

<210> SEQ ID NO 87
<211> LENGTH: 1205
<212> TYPE: DNA
<213> ORGANISM: Stevia rebaudiana

<400> SEQUENCE: 87
tagtgaatgt atataacata aatgatatgt ttcaacctaa caaacggtta tttcatacac     60
ggaaaacaaa aatttatgat tattcaaaga aacatttgat catctagcta gacaaaccca    120
ataacacata tattcttcat acgatcaaag ctcatgctca atagcaacca cacgaccttt    180
ttgttccaaa tagtctataa aagggtttat atacttattt tccggcttac tatccccgaa    240
tcgttgactc aactccatcg ccttcgcctt gtagatcttc ccttcatcat cgactaaaac    300
caacctcaat gatctggcca ccgactcctt ggtgaatgaa ccatcttcgt catttcttgg    360
tatctcaatt cccacctgat tatccgccat tactcgagca tttagacctt gatccaccga    420
aagcggtagc attatcaaag ggtgaccgaa catcatcgct tccacaaatg aactccaacc    480
acaatgagtc aagaaaccac aaaccgactc atggctcagt attcgtaact gaggtgccca    540
actcgtccag accaacccac ggtcacgagt tcgttccacg aacccgtctg gcaactccac    600
cgagttacca gagccaaccg gttttctaag aacccaaaag aatggcaacc cggagagctc    660
gaggcccaga gctaactcag ccagctcgct ttggctcatc gtaccttcac ttccaaatgc    720
cacgtacacc acatgcccta ttggttgacc atcgagccac ttcttgattg tcacccatgg    780
gtctccggtg ctggtgggtg gttcgggtgg caataatccc acgggaacca ctggtaggtg    840
atgcagcttt tctaaaaggg ttagccattg gggttcgaac tcatggcaat gtcttataaa    900
catacaatct gatcccttta taaccattcc agcacgatat atatctgaaa ccccagaaga    960
attaatagaa aaattatcag caaatatcga attggcctca tgcttccggt agcatacttt   1020
gcttggaaac ggaacccact tcggcggtgt caagaaatcg tcgggtgttt tccgattgtc   1080
tgtaccgttt atcatgttat cggaagacga tccgataaaa gagacggtcc atgcgttata   1140
gattgagaaa aaacctcgtg aaattccaag gctagtggct accgccggca accaataggg   1200
agcaa                                                               1205

<210> SEQ ID NO 88
<211> LENGTH: 1266
<212> TYPE: DNA
<213> ORGANISM: Stevia rebaudiana

<400> SEQUENCE: 88 ttttttttt tttacggctg gaatcaattg ctttattcat cacataattt ggctttaaat     60
agccttacaa taacaactta ttaatatagt agcttaaaac aattaactag gacacctcct    120
aagactcgat cgattctacc aacatatttt gcaattccaa catttcattt gaatctttcc    180
aaaagaaacc caacaactca cacatacttg atgatatagt taactctcat gatcgatggc    240
aaccgcacgc gcattctttt ccaaatagtc tacgaattgg cttacatatt cttttttcaac   300 cttagtgtcg ttatagattt tactcagctc cctcgcgttc gccttgtaga tctcccttc     360 tttttccaca acaacggacc tcagtgatct agcaaccgac tccttggtca agcaaccatc    420
ttcctcattt cttggtatct cgattcccac ctgtttgtcc tccagtaatc gagcattcag    480
```

| | |
|---|---|
| aggttggtcc ccaaaaatcg gtagcatgat tagagggtga ccaaacatta gcccttccac | 540 |
| aattgatcca gaaccacaat gagtcaagaa accacaaacc gactcatggc tcagtattcg | 600 |
| taactgaggt gcccaactcg tccagaccaa cccacggtca cgagttcgtt ccacgaaccc | 660 |
| gtctggcaac tccaccgagt taccagagcc aaccggtttt ctaagaaccc aaaagaatgg | 720 |
| caacccggag agctcgagac ccaaagctaa ctcagccagc tcgctttggc tcatcgtacc | 780 |
| ttcacttcca atgccacgt acaccacatg gcctattggt tgaccatcga gccacttctt | 840 |
| gattgtcacc catgggtctc cggtgctggt gggtggttcg ggtggcaata atcccacggg | 900 |
| aaccaccggt aggtgatgca gcttttctaa aagggttagc cattggggtt cgacctcata | 960 |
| acaacttctt ataaacagac aatcagattc cttcaaaacc gtcatcattc tgtgctttag | 1020 |
| acctgaaatc acaggattat tagcagcaga catcttgcgc acaaactcat gcttccggta | 1080 |
| gcatactttg ctcggaaacg gaatccactt gggcggtgtc atgaaatcct caactgtcgt | 1140 |
| tcgactctcg aaactatttt tcatgtcatc gggtaacggt cccacgtgcg ccatgaacca | 1200 |
| tggtgaggca gtgataaaaa aggctcgcga gatcccaagg tccgccgcga cggatggcaa | 1260 |
| ccagtg | 1266 |

<210> SEQ ID NO 89
<211> LENGTH: 1292
<212> TYPE: DNA
<213> ORGANISM: Stevia rebaudiana

<400> SEQUENCE: 89

| | |
|---|---|
| cacaatacta ctctttagtt accaatatac cataaccaaa attgtttgat agataagatt | 60 |
| atcctatatt aaaattgatg aaacccagtc gatttatcaa taaaagaaat agatcaatga | 120 |
| aattatctag tttgtgaatt ttatcacatt gatgtttcta ccttatttca aacaaaccag | 180 |
| atacttcaat taattcaagc aacatttgat catgaagaca aacccaacaa cgcacattct | 240 |
| tcatacggtt aacgtacgtc gtgtcttctc caaataatct atgaaatggt ttatatactt | 300 |
| ctttcccatc ttagtgtctc cgaacaatct acttaactcc atcgcatttt ccttgtaaat | 360 |
| cttcccttca tcatcagcta caactgcccg cactgatctt gcgactgact ccttgttgaa | 420 |
| ggagccatct tcgtcatttc ttggtatctc aattcccacc tgattatccg ccattactcg | 480 |
| agcatttaga cctttgatcca ccgaaagcgg tagcattatc aaagggtgac cgaacatcat | 540 |
| cgcttccaca aatgaactcc aaccacaatg agtcaagaaa ccacaaaccg actcatggct | 600 |
| cagtattcgt aactgaggtg cccaactcgt ccagaccaac ccacggtcac gagttcgttc | 660 |
| cacgaaaccg tctggcaact ccaccgagtt accagagcca accggttttc taagaaccca | 720 |
| aaagaatggc aacccggaga gctcgaggcc cagagctaac tcagccagct cgctttggct | 780 |
| catcgtacct tcacttccaa atgccacgta caccacatgc cctattggtt gaccatcgag | 840 |
| ccacttcttg attgacaccc atgtttcatc tttctcgtct ccgtgtattt caggtggcat | 900 |
| taatcccacc ggaaccaccg gtatatggtg tagcttctcc aaaagggtta gccattgggg | 960 |
| ttcgaactca tggcaatgtc ttataaacat acaatctgat cccttttataa ccattccagc | 1020 |
| acgatatata tctgaaaccc cagaagaatt aatagaaaaa ttatcagcaa atatcgaatt | 1080 |
| ggcctcatgc ttccggtagc atactttgct tgggaacgga acccacttcg gcggtgtcaa | 1140 |
| gaaatcgtcg ggtgttttcc gattgtctgt accgtttatc atgttatcgg aagacgatcc | 1200 |
| gataaaagag acggtccatg cgttatagat tgagaaaaaa cctcgtgaaa ttccaaggct | 1260 |
| agtggctacc gccggcaacc aatagggagc aa | 1292 |

<210> SEQ ID NO 90
<211> LENGTH: 1213
<212> TYPE: DNA
<213> ORGANISM: Stevia rebaudiana

<400> SEQUENCE: 90

| | | | | | |
|---|---|---|---|---|---|
| tagtgaatgt | atataacata | aatgatatgt | ttcaacctaa | caaacggtta | tttcatacac | 60 |
| ggaaaacaaa | aatttatgat | tattcaaaga | aacatttgat | catctagcta | gacaaaccca | 120 |
| ataacacata | tattcttcat | acgatcaaag | ctcatgctca | atagcaacca | cacgaccttt | 180 |
| ttgttccaaa | tagtctataa | aagggtttat | atacttattt | tccggcttac | tatccccgaa | 240 |
| tcgttgactc | aactccatcg | ccttcgcctt | gtagatcttc | ccttcatcat | cgactaaaac | 300 |
| caacctcaat | gatctggcca | ccgactcctt | ggtgaatgaa | ccatcttcgt | catttcttgg | 360 |
| tatctcaatt | cccacctgat | tatccgccat | tactcgagca | tttagacctt | gatccaccga | 420 |
| aagcggtagc | attatcaaag | ggtgaccgaa | catcatcgct | tccacaaatg | aactccaacc | 480 |
| acaatgagtc | aagaaaccac | aaaccgactc | atggctcagt | attcgtaact | gaggtgccca | 540 |
| actcgtccag | accaacccac | ggtcacgagt | tcgttccacg | aacccgtctg | gcaactccac | 600 |
| cgagttacca | gagccaaccg | gttttctaag | aacccaaaag | aatggcaacc | cggagagctc | 660 |
| gaggcccaga | gctaactcag | ccagctcgct | ttggctcatc | gtaccttcac | ttccaaatgc | 720 |
| cacgtacacc | acatgcccta | ttggttgacc | atcgagccac | ttcttgactg | tgtcacacgt | 780 |
| cttatcattc | ccgtcttcga | tgttggtggg | ttttctggt | ggcaataatc | cgacaggaac | 840 |
| caccggtagg | tgatggagct | tctctaaaag | ggttaaccat | tgaggttcga | actcataact | 900 |
| atgtcttata | aacatacagt | cagatccttt | caaaatcatt | cccacacgat | acacacttga | 960 |
| tattccagaa | gcattagccg | aagtattccc | taccatccga | accgcctcat | acttccggta | 1020 |
| gcacacgttt | gtcggaaacg | gaacccactt | cggcggtgtc | ataaaattct | caaccctcgt | 1080 |
| tcgatgatca | taaccggaac | cacttatcaa | gtcgtcagcc | gacgctccga | gaaaagcaat | 1140 |
| gaaccatgcg | ttaaaattcg | agtaaaaggc | tcgcgaggtc | cgtagtccag | ctgcgacgga | 1200 |
| cggcaaccaa tac | | | | | 1213 |

<210> SEQ ID NO 91
<211> LENGTH: 1280
<212> TYPE: DNA
<213> ORGANISM: Stevia rebaudiana

<400> SEQUENCE: 91

| | | | | | |
|---|---|---|---|---|---|
| tttttttttt | tttacggctg | gaatcaattg | ctttattcat | cacataattt | ggctttaaat | 60 |
| agccttacaa | taacaactta | ttaatatagt | agcttaaaac | aattaactag | gacacctcct | 120 |
| aagactcgat | cgattctacc | aacatatttta | gcaattccaa | catttcattt | gaatctttcc | 180 |
| aaaagaaacc | caacaactca | cacatacttg | atgatatagt | taactctcat | gatcgatggc | 240 |
| aaccgcacgc | gcattctttt | ccaaatagtc | tacgaattgg | cttacatatt | ctttttcaac | 300 |
| cttagtgtcg | ttatagattt | tactcagctc | cctcgcgttc | gccttgtaga | tctcccctttc | 360 |
| tttttccaca | acaacggacc | tcagtgatct | agcaaccgac | tccttggtca | agcaaccatc | 420 |
| ttcctcattt | cttggtatct | cgattcccac | ctgtttgtcc | tccagtaatc | gagcattcag | 480 |
| aggttggtcc | ccaaaaatcg | gtagcatgat | tagagggtga | ccaaacatta | gcccttccac | 540 |
| aattgatcca | gaaccacaat | gagtcaagaa | accacaaacc | gactcatggc | tcagtattcg | 600 |

| taactgaggt | gcccaactcg | tccagaccaa | cccacggtca | cgagttcgtt | ccacgaaccc | 660 |
| gtctggcaac | tccaccgagt | taccagagcc | aaccggtttt | ctaagaaccc | aaaagaatgg | 720 |
| caacccggag | agctcgagac | ccaaagctaa | ctcagccagc | tcgctttggc | tcatcgtacc | 780 |
| ttcacttcca | aatgccacgt | acaccacatg | ccctattggt | tgaccatcga | gccacttctt | 840 |
| gattgtcacc | catgggtctc | cggtgctggt | gggtggttcg | ggtggcaata | atcccacggg | 900 |
| aaccactggt | aggtgatgca | gcttttctaa | aagggttagc | cattgggggtt | cgaactcatg | 960 |
| gcaatgtctt | ataaacatac | aatctgatcc | ctttataacc | attccagcac | gatatatatc | 1020 |
| tgaaacccca | gaagaattaa | tagaaaaatt | atcagcaaat | atcgaattgg | cctcatgctt | 1080 |
| ccggtagcat | actttgcttg | gaaacggaac | ccacttcggc | ggtgtcaaga | aatcgtcggg | 1140 |
| tgttttccga | ttgtctgtac | cgtttatcat | gttatcggaa | gacgatccga | taaaagagac | 1200 |
| ggtccatgcg | ttatagattg | agaaaaaacc | tcgtgaaatt | ccaaggctag | tggctaccgc | 1260 |
| cggcaaccaa | tagggagcaa | | | | | 1280 |

<210> SEQ ID NO 92
<211> LENGTH: 1288
<212> TYPE: DNA
<213> ORGANISM: Stevia rebaudiana

<400> SEQUENCE: 92

| ttttttttt | tttacggctg | gaatcaattg | ctttattcat | cacataattt | ggctttaaat | 60 |
| agccttacaa | taacaactta | ttaatatagt | agcttaaaac | aattaactag | gacacctcct | 120 |
| aagactcgat | cgattctacc | aacatattta | gcaattccaa | catttcattt | gaatctttcc | 180 |
| aaaagaaacc | caacaactca | cacatacttg | atgatatagt | taactctcat | gatcgatggc | 240 |
| aaccgcacgc | gcattctttt | ccaaatagtc | tacgaattgg | cttacatatt | cttttcaac | 300 |
| cttagtgtcg | ttatagattt | tactcagctc | cctcgcgttc | gccttgtaga | tctccccttc | 360 |
| tttttccaca | acaacggacc | tcagtgatct | agcaaccgac | tccttggtca | agcaaccatc | 420 |
| ttcctcattt | cttggtatct | cgattcccac | ctgtttgtcc | tccagtaatc | gagcattcag | 480 |
| aggttggtcc | ccaaaaatcg | gtagcatgat | tagagggtga | ccaaacatta | gcccttccac | 540 |
| aattgatcca | gaaccacaat | gagtcaagaa | accacaaacc | gactcatggc | tcagtattcg | 600 |
| taactgaggt | gcccaactcg | tccagaccaa | cccacggtca | cgagttcgtt | ccacgaaccc | 660 |
| gtctggcaac | tccaccgagt | taccagagcc | aaccggtttt | ctaagaaccc | aaaagaatgg | 720 |
| caacccggag | agctcgagac | ccaaagctaa | ctcagccagc | tcgctttggc | tcatcgtaac | 780 |
| ttcacttcca | aatgccacgt | acaccacatg | gttaacttgt | tgaccatcga | gccacttctt | 840 |
| gactgtgtcc | cacgtctcat | cattcccgtc | ttcgatgttg | gtgggttttt | ctggtggcaa | 900 |
| taatccgaca | ggaaccaccg | gtaggtgatg | gagcttctct | aaaagggtta | accattgagg | 960 |
| ttcgaactca | taactatgtc | ttataaacat | acagtcagat | cctttcaaaa | tcattcccac | 1020 |
| acgatacaca | cttgatattc | cagaagcatt | agccgaagta | ttccctacca | tccgaaccgc | 1080 |
| ctcatacttc | cggtagcaca | cgtttgtcgg | aaacggaacc | cacttcggcg | gtgtcataaa | 1140 |
| attctcaacc | ctcgttcgat | gatcataacc | ggaaccactt | atcaagtcgt | cagccgacgc | 1200 |
| tccgagaaaa | gcaatgaacc | atgcgttaaa | attcgagtaa | aaggctcgcg | aggtccgtag | 1260 |
| tccagctgcg | acggacggca | accaatac | | | | 1288 |

<210> SEQ ID NO 93
<211> LENGTH: 1283

```
<212> TYPE: DNA
<213> ORGANISM: Stevia rebaudiana

<400> SEQUENCE: 93
tttttttttt ttacggctg gaatcaattg ctttattcat cacataattt ggctttaaat      60
agccttacaa taacaactta ttaatatagt agcttaaaac aattaactag gacacctcct    120
aagactcgat cgattctacc aacatattta gcaattccaa catttcattt gaatctttcc    180
aaaagaaacc caacaactca cacatacttg atgatatagt taactctcat gatcgatggc    240
aaccgcacgc gcattctttt ccaaatagtc tacgaattgg cttacatatt cttttcaac     300
cttagtgtcg ttatagattt tactcagctc cctcgcgttc gccttgtaga tctcccttc     360
ttttccaca acaacggacc tcagtgatct agcaaccgac tccttggtca agcaaccatc     420
ttcctcattt cttggtatct cgattcccac ctgtttgtcc tccagtaatc gagcattcag    480
aggttggtcc ccaaaaatcg gtagcatgat tagagggtga ccaaacatta gcccttccac    540
aattgatcca gaaccacaat gagtcaagaa accacaaacc gactcatggc tcagtattcg    600
taactgaggt gcccaactcg tccagaccaa cccacggtca cgagttcgtt ccacgaaccc    660
gtctggcaac tccaccgagt taccagagcc aaccggtttt ctaagaaccc aaaagaatgg    720
caacccggag agctcgaggc ccagagctaa ctcagccagc tcgctttggc tcatcgtacc    780
ttcacttcca aatgccacgt acaccacatg ccctattggt tgaccatcga gccacttctt    840
gattgacacc catgtttcat cttctcgtc tccgtgtgtt tcaggtggca ttaatcccac     900
cggaaccacc ggtatatggt gtagcttttc caaaagggtt agccattggg gttcgaactc    960
atggcaatgt cttataaaca tacaatctga tccctttata accattccag cacgatatat   1020
atctgaaacc ccagaagaat taatagaaaa attatcagca aatatcgaat tggcctcatg   1080
cttccggtag catactttac ttggaaacgg aacccacttc ggcggtgtca agaaatcgtc   1140
gggtgttttc cgattgtctg taccgtttat catgttatcg gaagacgatc cgataaaaga   1200
gacggtccat gcgttataga ttgagaaaaa acctcgtgaa attccaaggc tagtggctac   1260
cgccggcaac caatagggag caa                                           1283

<210> SEQ ID NO 94
<211> LENGTH: 1379
<212> TYPE: DNA
<213> ORGANISM: Stevia rebaudiana

<400> SEQUENCE: 94
ggctggagtc aattgttttt atacaataca taatatagcg ttaaatggct ttataataac      60
gacggaaaag ttaatgactc gattctacca acgacttagc aattccaaca tgtgattaaa    120
aaagaagtgt aacaaggaca atcataacat catatgaatc attccaaaga aacccaacaa    180
ctaacttact tatagtctgt gaaacgactt atatattctt tttggttaac tctcatggtt    240
gttggcaacc acacgtacgt tcttttccat atagtctgtg aaacgactta tatattcttt    300
ttggttaact ctcatggttg ttggcaacca cacgtacgtt cttttccata tagtctgtga    360
aacgacttat atattccttt tgcagcttag tgtcgctgaa tattttactc atctctctcg    420
cattcgcctt gtagatctcc ccttcttttt ccacaacaac ggacctcagt gatctagcaa    480
ccgactcctt ggtcaagcaa ccatcttcct catttcttgg tatctcgatt cccacctgtt    540
tgtcctccag taatcgagca ttcagaggtt ggtccccgaa aatcggtagc atgattagag    600
ggtgaccaaa cattagccct tccacaactg atccagaacc acaatgagtc aagaaaccac    660
```

| aaaccgactc atggctcagt attcgtaact gaggtgccca actcgtccag accatcccac | 720 |
| ggttacgagt tcgttccacg aacccgtttg gcaactccac cgagtctgac tcggtggaac | 780 |
| ctgcgggttt tctaagaacc caaaagaatg gcaacccgga gagctcgaga cccagagcta | 840 |
| actcagccag ctcgctttgg ctcatcgtac cttcacttcc aaatgccacg tacaccacat | 900 |
| gccctattgg ttgaccatcg agccacttct tgactgtgtc acacgtctta tcattcccgt | 960 |
| cttcgatgtt ggtgggtttt tctggtggca ataatccgac aggaaccacc ggtaggtgat | 1020 |
| ggagcttctc taaaagggtt aaccattgag gttcgaactc ataactatgt cttataaaca | 1080 |
| tacagtcaga tcctttcaaa atcattccca cacgatacac acttgatatt ccagaagcat | 1140 |
| tagccgaagt attccctacc atccgaaccg cctcatactt ccggtagcac acgtttgtcg | 1200 |
| gaaacggaac ccacttcggc ggtgtcataa aattctcaac cctcgttcga tgatcataac | 1260 |
| cggaaccact tatcaagtcg tcagccgacg ctccgagaaa agcaatgaac catgcgttaa | 1320 |
| aattcgagta aaaggctcgc gaggtccgta gtccagctgc gacggacggc aaccaatac | 1379 |

<210> SEQ ID NO 95
<211> LENGTH: 1197
<212> TYPE: DNA
<213> ORGANISM: Stevia rebaudiana

<400> SEQUENCE: 95

| tagtgaatgt atataacata atgatatgt ttcaacctaa caaacggtta tttcatacac | 60 |
| ggaaaacaaa aatttatgat tattcaaaga acatttgat catctagcta gacaaaccca | 120 |
| ataacacata tattcttcat acgatcaaag ctcatgctca atagcaacca cacgaccttt | 180 |
| ttgttccaaa tagtctataa aagggtttat atacttattt tccggcttac tatccccgaa | 240 |
| tcgttgactc aactccatcg ccttcgcctt gtagatcttc ccttcatcat cgactaaaac | 300 |
| caacctcaat gatctggcca ccgactcctt ggtgaatgaa ccatcttcgt catttcttgg | 360 |
| tatctcaatt cccacctgat tatccgccat tactcgagca tttagacctt gatccaccga | 420 |
| aagcggtagc attatcaaag ggtgaccgaa catcatcgct tccacaaatg aactccaacc | 480 |
| acaatgagtc aagaaaccac aaaccgactc atggctcagt attcgtaact gaggtgccca | 540 |
| actcgtccag accaacccac ggtcacgagt tcgttccacg aacccgtctg gcaactccac | 600 |
| cgagttacca gagccaaccg gttttctaag aacccaaaag aatggcaacc cggagagctc | 660 |
| gaggcccaga gctaactcag ccagctcgct ttggctcatc gtaccttcac ttccaaatgc | 720 |
| cacgtacacc acatgcccta ttggttgacc atcgagccac ttcttgattg tcacccatgg | 780 |
| gtctccggtg ctggtgggtg gttcgggtgg caataatccc acgggaacca ccggtaggtg | 840 |
| atgcagcttt tctaaaaggg ttagccattg gggttcgaac tcatggcaat gtcttataaa | 900 |
| catacaatct gatcccttta taaccattcc agcacgatat atatctgaaa ccccagaaga | 960 |
| attaatagaa aaattatcag caaatatcga attggcctca tgcttccggt agcatacttt | 1020 |
| gctcggaaac ggaatccact tgggcggtgt catgaaatcc tcaactgtcg ttcgactctc | 1080 |
| gaaactattt ttcatgtcat cgggtaacgg tcccacgtgc gccatgaacc atggtgaggc | 1140 |
| agtgataaaa aaggctcgcg agatcccaag gtccgccgcg acggatggca accagtg | 1197 |

<210> SEQ ID NO 96
<211> LENGTH: 573
<212> TYPE: DNA
<213> ORGANISM: Stevia rebaudiana

<400> SEQUENCE: 96

-continued

```
cacaatacta ctctttagtt accaatatac cataaccaaa attgtttgat agataagatt    60
atcctatatt aaaattgatg aaacccagtc gatttatcaa taaaagaaat agatcaatga   120
aattatctag tttgtgaatt ttatcacatt gatgtttcta ccttatttca aacaaaccag   180
atacttcaat taattcaagc aacatttgat catgaagaca aacccaacaa cgcacattct   240
tcatacggtt aacgtacgtc gtgtcttctc caaataatct atgaaatggt ttatatactt   300
ctttcccatc ttagtgtctc cgaacaatct acttaactcc atcggtagga accaccggta   360
ggtgatggag cttctctaaa agggttaacc attgaggttc gaactcataa ctatgtctta   420
taaacataca gtcagatcct ttcaaaatca ttcccacacg atacacactt gatattccag   480
aagcattagc cgaagtattc cctaccatcc gaaccgcctc atacttccgg tagcacacgt   540
ttgtcggaaa cggaacccac ttcggcggtg tca                                573
```

<210> SEQ ID NO 97
<211> LENGTH: 1281
<212> TYPE: DNA
<213> ORGANISM: Stevia rebaudiana

<400> SEQUENCE: 97

```
cacaatacta ctctttagtt accaatatac cataaccaaa attgtttgat agataagatt    60
atcctatatt aaaattgatg aaacccagtc gatttatcaa taaaagaaat agatcaatga   120
aattatctag tttgtgaatt ttatcacatt gatgtttcta ccttatttca aacaaaccag   180
atacttcaat taattcaagc aacatttgat catgaagaca aacccaacaa cgcacattct   240
tcatacggtt aacgtacgtc gtgtcttctc caaataatct atgaaatggt ttatatactt   300
ctttcccatc ttagtgtctc cgaacaatct acttaactcc atcgatttt ccttgtaaat   360
cttcccttca tcatcagcta caactgcccg cactgatctt gcgactgact ccttgttgaa   420
ggagccatct tcgtcatttc ttggtatctc aattcccacc tgattatccg ccattactcg   480
agcatttaga ccttgatcca ccgaaagcgg tagcattatc aaagggtgac cgaacatcat   540
cgcttccaca aatgaactcc aaccagaatg agtcaagaaa ccacaaaccg actcatggct   600
cagtattcgt aactgaggtg cccaactcgt ccagaccaac ccacggtcac gagttcgttc   660
cacgaacccg tctggcaact ccaccgagtt accagagcca accggttttc taagaaccca   720
aaagaatggc aacccggaga gctcgaggcc cagagctaac tcagccagct cgctttggct   780
catcgtacct tcacttccaa atgccacgta caccacatgc cctattggtt gaccatcgag   840
ccacttcttg attgtcaccc atgggtctcc ggtgctggtg ggtggttcgg gtggcaataa   900
tcccacggga accactggta ggtgatgcag cttttctaaa agggttagcc attggggttc   960
gaactcatgg caatgtctta taaacataca atctgatccc tttataacca ttccagcacg  1020
atatatatct gaaaccccag aagaattaat agaaaaatta tcagcaaata tcgaattggc  1080
ctcatgcttc cggtagcata ctttgctcgg aaacggaatc cacttgggcg gtgtcatgaa  1140
atcctcaact gtcgttcgac tctcgaaact attttttcatg tcatcgggta acggtcccac  1200
gtgcgccatg aaccatggtg aggcagtgat aaaaaaggct cgcgagatcc caaggtccgc  1260
cgcgacggat ggcaaccagt g                                            1281
```

<210> SEQ ID NO 98
<211> LENGTH: 1275
<212> TYPE: DNA
<213> ORGANISM: Stevia rebaudiana

```
<400> SEQUENCE: 98
tttttttttt ttacggctg gaatcaattg ctttattcat cacataattt ggctttaaat      60
agccttacaa taacaactta ttaatatagt agcttaaaac aattaactag gacacctcct    120
aagactcgat cgattctacc aacatattta gcaattccaa catttcattt gaatctttcc    180
aaaagaaacc caacaactca cacatacttg atgatatagt taactctcat gatcgatggc    240
aaccgcacgc gcattctttt ccaaatagtc tacgaattgg cttacatatt cttttcaac     300 cttagtgtcg ttatagattt tactcagctc cctcgcgttc gccttgtaga tctcccctc     360 tttttccaca acaacggacc tcagtgatct agcaaccgac tccttggtca agcaaccatc    420
ttcctcattt cttggtatct cgattcccac ctgtttgtcc tccagtaatc gagcattcag    480
aggttggtcc ccaaaaatcg gtagcatgat tagagggtga ccaaacatta gcccttccac    540
aattgatcca gaaccacaat gagtcaagaa accacaaacc gactcatggc tcagtattcg    600
taactgaggt gcccaactcg tccacaccaa cccacggtca cgagttcgtt ccacgaaccc    660
gtctggcaac tccaccgagt taccagagcc aaccggtttt ctaagaaccc aaaagaatgg    720
caacccggag agctcgaggc ccagagctaa ctcagccagc tcgctttggc tcatcgtacc    780
ttcacttcca aatgccacgt acaccacatg ccctattggt tgaccatcga gccacttctt    840
gattgtcacc catgtttcat cttcctcgtc tccgtgtgtt tcaggtggca ttaatcccac    900
cggaaccacc ggtatatggt gtagcttctc caaaagggtt agccattggg gttcgaactc    960
atggcaatgt cttataaaca tacaatctga tcccttata accattccag cacgatatat    1020
atctgaaacc ccagaagaat taatagaaaa attatcagca aatatcgaat ggcctcatg    1080 cttccggtag catactttgc ttggaaacgg aatccacttg ggcggtgtca tgaaatcctc    1140
aactgtcgtt cgactctcga aactatttt catgtcatcg ggtaacggtc ccacgtgcgc    1200
catgaaccat ggtgaggcag tgataaaaaa ggctcgcgag atcccaaggt ccgccgcgac    1260
ggatggcaac cagtg                                                     1275

<210> SEQ ID NO 99
<211> LENGTH: 1307
<212> TYPE: DNA
<213> ORGANISM: Stevia rebaudiana

<400> SEQUENCE: 99
tttttttttt ttacggctg gaatcaattg ctttattcat cacataattt ggctttaaat      60
agccttacaa taacaactta ttaatatagt agcttaaaac aattaactag gacacctcct    120
aagactcgat cgattctacc aacatattta gcaattccaa catttcattt gaatctttcc    180
aaaagaaacc caacaactca cacatacttg atgatatagt taactctcat gatcgatggc    240
aaccgcacgc gcattctttt ccaaatagtc tacgaattgg cttacatatt cttttcaac     300 cttagtgtcg ttatagattt tactcagctc cctcgcgttc gccttgtaga tctcccctc     360 tttttccaca acaacggacc tcagtgatct agcaaccgac tccttggtca agcaaccatc    420
ttcctcattt cttggtatct cgattcccac ctgtttgtcc tccagtaatc gagcattcag    480
aggttggtcc ccaaaaatcg gtagcatgat tagagggtga ccaaacatta gcccttccac    540
aattgatcca gaaccacaat gagtcaagaa accacaaacc gactcatggc tcagtattcg    600
taactgaggt gcccaactcg tccagaccaa cccacggtca cgagttcgtt ccacgaaccc    660
gtctggcaac tccaccgagt ctgacttcgc gggaccttt ggttttctat aagcccaaac     720
aaatggcaac ccagaaagct cgagacccaa tgctaactca acaacctcgg tttggctcac    780
```

| | |
|---|---|
| caaaacctcg cttcctaatg caacgtacac cacactgcct ttttgtttac catcgagcca | 840 |
| tttcttgatt gacacccatg tttcatcttt ctcgtctccg ggtatttccg gtggcagtaa | 900 |
| tcccaccgga accaccggta cttggtgtag tgtctccaaa agaggtagcc attgagttcc | 960 |
| aaactcatgg taacatttgg aaagcaaaca atcagatccc ttaagaacca gccccatacg | 1020 |
| gtatccatca gatatccccg gagctttgta aggcaccagt cgggcaagat catgcttccg | 1080 |
| ccagcatact ttggtcggaa agggaaacca cttgggcggt gtcgtgagat cctcaaccgt | 1140 |
| ggttcgacca tctgaaccat ttatcatggc gtcagctgag ggtcccatat aagcaatggc | 1200 |
| ccatggagtg gtgacggaga gtgggctcg tgagataccg aggctagccg cgatggatgg | 1260 |
| caaccagtag tgagtataat cataaataat ccagtccgga gactctt | 1307 |

<210> SEQ ID NO 100
<211> LENGTH: 1208
<212> TYPE: DNA
<213> ORGANISM: Stevia rebaudiana

<400> SEQUENCE: 100

| | |
|---|---|
| tagtgaatgt atataacata aatgatatgt ttcaacctaa caaacggtta tttcatacac | 60 |
| ggaaaacaaa aatttatgat tattcaaaga aacatttgat catctagcta gacaaaccca | 120 |
| ataacacata tattcttcat acgatcaaag ctcatgctca atagcaacca cacgaccttt | 180 |
| ttgttccaaa tagtctataa aagggtttat atacttattt tccggcttac tatccccgaa | 240 |
| tcgttgactc aactccatcg ccttcgcctt gtagatcttc ccttcatcat cgactaaaac | 300 |
| caacctcaat gatctggcca ccgactcctt ggtgaatgaa ccatcttcgt catttcttgg | 360 |
| tatctcaatt cccacctgat tatccgccat tactcgagca tttagacctt gatccaccga | 420 |
| aagcggtagc attatcaaag ggtgaccgaa catcatcgct tccacaaatg aactccaacc | 480 |
| acaatgagtc aagaaaccac aaaccgactc atggctcagt attcgtaact gaggtgccca | 540 |
| actcgtccag accaacccac ggtcacgagt tcgttccacg aacccgtctg caactccac | 600 |
| cgagttacca gagccaaccg gttttctaag aacccaaaag aatggcaacc cggagagctc | 660 |
| gaggcccaga gctaactcag ccagctcgct ttggctcatc gtaccttcac ttccaaatgc | 720 |
| cacgtacacc acatgcccta ttggttgacc atcgagccac ttcttgattg acacccatgt | 780 |
| ttcatctttc tcgtctccgt gtgtttcagg tggcattaat cccaccggaa ccaccggtat | 840 |
| atggtgtagc ttctccaaaa gggttagcca ttggggttcg aactcatggc aatgtcttat | 900 |
| aaacatacaa tctgatccct ttataaccat tccagcacga tatatatctg aaaccccaga | 960 |
| agaattaata gaaaaattat cagcaaatat cgaattggcc tcatgcttcc ggtagcatac | 1020 |
| tttgcttgga aacggaaccc acttcggcgg tgtcaagaaa tcgtcgggtg ttttccgatt | 1080 |
| gtctgtaccg tttatcatgt tatcggaaga cgatccgata aaagagacgg tccatgcgtt | 1140 |
| atagattgag aaaaaacctc gtgaaattcc aaggctagtg gctaccgccg gcaaccaata | 1200 |
| gggagcaa | 1208 |

<210> SEQ ID NO 101
<211> LENGTH: 1341
<212> TYPE: DNA
<213> ORGANISM: Stevia rebaudiana

<400> SEQUENCE: 101

| | |
|---|---|
| tttataataa cgacggaaaa gtagcgcacc acttaatgac tcgattctac caacgactta | 60 |

| | |
|---|---|
| gcaattccaa catgtgatta aaaagaagt gtaacaagga caatcataac atcatatgaa | 120 |
| tcattccaaa gaaacccaac aactaactta cttatagtct gtgaaacgac ttatatattc | 180 |
| tttttggtta actctcatgg ttgttggcaa ccacacgtac gttctttttcc atatagtctg | 240 |
| tgaaacgact tatatattct ttttggttaa ctctcatggt tgttggcaac cacacgtacg | 300 |
| ttctttttcca tatagtctgt gaacgactt atatattcct tttgcagctt agtgtcgctg | 360 |
| aatattttac tcatctctct cgcattcgcc ttgtagatct ccccttcttt ttccacaaca | 420 |
| acggacctca gtgatctagc aaccgactcc ttggtcaagc aaccatcttc ctcatttctt | 480 |
| ggtatctcga ttcccacctg tttgtcctcc agtaatcgag cattcagagg ttggtcccca | 540 |
| aaaatcggta gcatgattag agggtgacca acattagcc cttccacaat tgatccagaa | 600 |
| ccacaatgag tcaagaaacc acaaaccgac tcatggctca gtattcgtaa ctgaggtgcc | 660 |
| caactcgtcc aaaccaaccc acggtcacga gttcgttcca cgaacccgtc tggcaactcc | 720 |
| accgagtctg actcggtgga acctaccggt tttctaagaa cccaaaagaa tggcaacccg | 780 |
| gagagctcga gacccagagc taactcagcc agctcgcttt ggctcatcgt accttcactt | 840 |
| ccaaatgcca cgtacaccac atgccctatt ggttgaccat cgagccactt cttgactgtg | 900 |
| tcacgcgtct tatcattccc gtcttcgatg ttggtgggtt tttctggtgg caataatccg | 960 |
| acaggaacca ccgtaggtg atggagcttc tctaaaaggg ttaaccattg aggttcgaac | 1020 |
| tcataactat gtcttataaa catacagtca gatcctttca aaatcattcc cacacgatac | 1080 |
| acacttgata ttccagaagc attagccgaa gtattcccta ccatccgaac cgcctcatac | 1140 |
| ttccggtagc acacgtttgt cggaaacgga acccacttcg cgcgtgtcat aaaattctca | 1200 |
| accctcgttc gatgatcata accggaacca cttatcaagt cgtcagccga cgctccgaga | 1260 |
| aaagcaatga accatgcgtt aaaattcgag taaaaggctc gcgaggtccg tagtccagct | 1320 |
| gcgacggacg gcaaccaata c | 1341 |

<210> SEQ ID NO 102
<211> LENGTH: 1289
<212> TYPE: DNA
<213> ORGANISM: Stevia rebaudiana

<400> SEQUENCE: 102

| | |
|---|---|
| cacaatacta ctctttagtt accaatatac cataaccaaa attgtttgat agataagatt | 60 |
| atcctatatt aaaattgatg aaacccagtc gatttatcaa taaagaaat agatcaatga | 120 |
| aattatctag tttgtgaatt ttatcacatt gatgtttcta ccttatttca aacaaaccag | 180 |
| atacttcaat taattcaagc aacatttgat catgaagaca aacccaacaa cgcacattct | 240 |
| tcatacggtt aacgtacgtc gtgtcttctc caaataatct atgaaatggt ttatatactt | 300 |
| ctttcccatc ttagtgtctc cgaacaatct acttaactcc atcgcatttt ccttgtaaat | 360 |
| cttcccttca tcatcagcta caactgcccg cactgatctt cgactgact ccttgttgaa | 420 |
| ggagccatct tcgtcatttc ttggtatctc aattcccacc tgattatccg ccattactcg | 480 |
| agcatttaga ccttgatcca ccgaaagcgg tagcattatc aaagggtgac cgaacatcat | 540 |
| cgcttccaca aatgaactcc aaccacaatg agtcaagaaa ccacacaccg actcatggct | 600 |
| cagtattcgt aactgaggtg cccaactcgt ccagaccaac ccacggtcac gagttcgttc | 660 |
| cacgaacccg tctggcaact ccaccgagtt accagagcca accggttttc taagaaccca | 720 |
| aaagaatggc aacccggaga gctcgaggcc cagagctaac tcagccagct cgctttggct | 780 |
| catcgtacct tcacttccaa atgccacgta caccacatgc cctattggtt gaccatcgag | 840 |

```
ccacttcttg attgtcaccc atgggtctcc ggtgctggtg ggtggttcgg gtggcaataa    900
tcccacggga accactggta ggtgatgcag cttttctaaa agggttagcc attggggttc    960
gaactcatgg caatgtctta taaacataca atctgatccc tttataacca ttccagcacg   1020
atatatatct gaaccccag aagaattaat agaaaaatta tcagcaaata tcgaattggc    1080
ctcatgcttc cggtagcata ctttgcttgg aaacggaacc cacttcggcg tgtcaagaa    1140 atcgtcgggt gttttccgat tgtctgtacc gtttatcatg ttatcggaag acgatccgat   1200
aaaagagacg gtccatgcgt tatagattga gaaaaaacct cgtgaaattc caaggctagt   1260
ggctaccgcc ggcaaccaat agggagcaa                                     1289
```

<210> SEQ ID NO 103
<211> LENGTH: 1279
<212> TYPE: DNA
<213> ORGANISM: Stevia rebaudiana

<400> SEQUENCE: 103

```
tttttttttt tttacggctg gaatcaattg ctttattcat cacataattt ggctttaaat     60
agccttacaa taacaactta ttaatatagt agcttaaaac aattaactag gacacctcct    120
aagactcgat cgattctacc aacatattta gcaattccaa catttcattt gaatctttcc    180
aaaagaaacc caacaactca cacatacttg atgatatagt taactctcat gatcgatggc    240
aaccgcacgc gcattctttt ccaaatagtc tacgaattgg cttacatatt cttttcaac    300 cttagtgtcg ttatagattt tactcagctc cctcgcgttc gccttgtaga tctcccttc    360 tttttccaca acaacggacc tcagtgatct agcaaccgac tccttggtca agcaaccatc    420
ttcctcattt cttggtatct cgattccac ctgtttgtcc tccagtaatc gagcattcag    480
aggttggtcc ccaaaaatcg gtagcatgat tagagggtga ccaaacatta gcccttccac    540
aattgatcca gaaccacaat gagtcaagaa accacaaacc gactcatggc tcagtattcg    600
taactgaggt gcccaactcg tccagaccaa cccacggtca cgagttcgtt ccacgaaccc    660
gtctggcaac tccaccgagt taccagagcc aacggttttt ctaagaaccc aaaagaatgg    720
caacccggag agctcgaggc ccagagctaa ctcagccagc tcgctttggc tcatcgtacc    780
ttcacttcca aatgccacgt acaccacatg ccctattggt tgaccatcga gccacttctt    840
gattgtcacc catgggtctc cggtgctggt gggtggttcg ggtggcaata atcccacggg    900
aaccactggt aggtgatgca gcttttctaa aagggttagc cattggggtt cgaactcatg    960
gcaatgtctt ataaacatac aatctgatcc ctttataacc attccagcac gatatatatc   1020
tgaaccccca gaagaattaa tagaaaaatt atcagcaaat atcgaattgg cctcatgctt   1080
ccggtagcat actttgcttg gaaacggaac ccacttcggc ggtgtcataa aattctcaac   1140
cctcgttcga tgatcataac cggaaccact tatcaagtcg tcagccgacg ctccgagaaa   1200
agcaatgaac catgcgttaa aattcgagta aaaggctcgc gaggtccgta gtccagctgc   1260
gacggacggc aaccaatac                                                1279
```

<210> SEQ ID NO 104
<211> LENGTH: 1322
<212> TYPE: DNA
<213> ORGANISM: Stevia rebaudiana

<400> SEQUENCE: 104

```
tttataataa cgacggaaaa gtagcgcacc acttaatgac tcgattctac caacgactta     60
```

```
gcaattccaa catgtgatta aaaagaagt gtaacaagga caatcataac atcatatgaa    120
tcattccaaa gaaacccaac aactaactta cttatagtct gtgaaacgac ttatatattc   180
tttttggtta actctcatgg ttgttggcaa ccacacgtac gttcttttcc atatagtctg   240
tgaaacgact tatatattct tttggttaa ctctcatggt tgttggcaac cacacgtacg    300
ttcttttcca tatagtctgt gaaacgactt atatattcct tttgcagctt agtgtcgctg   360
aatattttac tcatctctct cgcattcgcc ttgtagatct ccccttcttt ttccacaaca   420
acggacctca gtgatctagc aaccgactcc ttggtcaagc aaccatcttc ctcatttctt   480
ggtatctcga ttcccacctg tttgtcctcc agtaatcgag cattcagagg ttggtcccca   540
aaaatcggta gcatgattag agggtgacca acattagcc cttccacaat tgatccagaa    600
ccacaatgag tcaagaaacc acaaaccgac tcatggctca gtattcgtaa ctgaggtgcc   660
caactcgtcc agaccatccc acggttacga gttcgttcca cgaacccgtc tggcaactcc   720
accgagtctg actcggcgga acctgctggt tttctgagaa cccacaaaaa tggcaaccca   780
gagagctcga gacctaacgc taactcagcc agctcgcttt ggtcaccgt aacctcactt    840 cctaatgcaa cgtacaccac atggcctatt tgttgaccat cgagccactt cttgattgac   900
acccatgttt catctttctc gtctccgtat gtttcaggtg cattaatcc caccggaacc    960 accggtatat ggtgtagctt ctccaaaagg gttagccatt ggggttcgac ctcataacaa  1020
cttcttataa acagacaatc agattccttc aaaaccgtca tcattctgtg ctttagacct  1080
gaaatcacag gattattagc agcagacatc ttgcgcacaa actcatgctt ccggtagcat  1140
actttgctcg gaaacggaat ccacttgggc ggtgtcatga atcctcaac tgtcgttcga   1200 ctctcgaaac tatttttcat gtcatcgggt aacggtccca cgtgcgccat gaaccatggt  1260
gaggcagtga taaaaaggc tcgcgagatc ccaaggtccg ccgcgacgga tggcaaccag  1320
tg                                                                 1322

<210> SEQ ID NO 105
<211> LENGTH: 674
<212> TYPE: DNA
<213> ORGANISM: Stevia rebaudiana

<400> SEQUENCE: 105
tcctcatttc ttggtatctc gattcccacc tgtttgtccg ctaatagtcg agcattcaga    60
cattggtccc cgaaaatcgg tagcatgatt agagggtgac caaacattaa cccttccaca   120
attgatccag aaccacaatg agtcaagaaa ccacaaaccg actcatggct cagtattcgt   180
aactgaggtg cccaactcgt ccaaaccaac ccacggtcac gagttcgttc cacgaacccg   240
tctggcaact ccaccgagtc tgactcggtg gaacctaccg gttttctaag aacccaaaag   300
aatggcaacc cggagagctc gagacccaga gctaactcag ccagctcgct ttggctcatc   360
gtaccttcac ttccaaatgc cacgtacacc acatgcccta ttggttgacc atcgagccac   420
ttcttgattg tcacccatgg gtctccggtg ctggtgggtg gttcgggtgg caataatccc   480
acgggaacca ctggtaggtg atgcagcttt ctaaaaggg ttagccattg gggttcgacc   540
tcataacaac ttcttataaa cagacaatca gattccttca aaaccgtcat cattctgtgc   600
tttagacctg aaatcacagg attattagca gcagacatct tgcgcacaaa ctcatgcttc   660
cggtagcata cttt                                                    674

<210> SEQ ID NO 106
<211> LENGTH: 1360
```

<212> TYPE: DNA
<213> ORGANISM: Stevia rebaudiana

<400> SEQUENCE: 106

```
ggctggagtc aattgttttt atacaataca taatatagcg ttaaatggct ttataataac    60
gacggaaaag ttaatgactc gattctacca acgacttagc aattccaaca tgtgattaaa   120
aaagaagtgt aacaaggaca atcataacat catatgaatc attccaaaga aacccaacaa   180
ctaacttact tatagtctgt gaaacgactt atatattctt tttggttaac tctcatggtt   240
gttggcaacc acacgtacgt tcttttccat atagtctgtg aaacgactta tatattcttt   300
ttggttaact ctcatggttg ttggcaacca cacgtacgtt cttttccata tagtctgtga   360
aacgacttat atattccttt tgcagcttag tgtcgctgaa tattttactc atctctctcg   420
cattcgcctt gtagatctcc ccttcttttt ccacaacaac ggacctcagt gatctagcaa   480
ccgactcctt ggtcaagcaa ccatcttcct catttcttgg tatctcgatt cccacctgtt   540
tgtcctccag tagtcgagca ttcagaggtt ggtcccaaa  aatcggtagc atgattagag   600
ggtgaccaaa cattagccct tccacaattg atccagaacc acaatgagtc aagaaaccac   660
aaaccgactc atggctcagt attcgtaact gaggtgccca actcgtccag accaacccac   720
ggtcacgagt tcgttccacg aacccgtctg caactccac  cgagtctgac tcggcggaac   780
cttctggttt tctgagaacc cacaaaaatg caacccaga  gagctcgaga cctaacgcta   840
actcagccag ctcgcttttg gtcaccgtaa cctcgcttcc taatgcaacg tacaccacat   900
ggcctatttg ttgaccatcg agccatttct tgattgacac ccatgtttca tctttctcgt   960
ctccgtatgt ttcaggtggc attaatccca ccggaaccac cggtatatgg tgtagcttcc  1020
ccaaagggt  tagccattgg ggttcgacct cataacaact tcttataaac agacaatcag  1080
attccttcaa aaccgtcatc attctgtgct ttagacctga aatcacagga ttattagcag  1140
cagacatctt gcgcacaaac tcatgcttcc ggtagcatac tttgctcgga aacggaatcc  1200
acttgggcgg tgtcatgaaa tcctcaactg tcgttcgact ctcgaaacta tttttcatgt  1260
catcgggtaa cggtcccacg tgcgccatga accatggtga ggcagtgata aaaaaggctc  1320
gcgagatccc aaggtccgcc gcgacggatg gcaaccagtg                        1360
```

<210> SEQ ID NO 107
<211> LENGTH: 539
<212> TYPE: DNA
<213> ORGANISM: Stevia rebaudiana

<400> SEQUENCE: 107

```
actgaactcc aaccacaatg agttaagaaa ccacacaccg actcatggct cagtattcgt    60
aactgaggtg cccaactcgt ccagaccaac ccacggtcac gagttcgttc cacgaacccg   120
tctggcaact ccaccgagtc tgactcggcg gaacctaccg ttttctaag  aacccaaaag   180
aatggcaacc cggagagctc gagacccaga gctaactcag ccagctcgct ttggctcatc   240
gtaccttcac ttccaaatgc cacgtacacc acatgcccta ttggttgacc atcgagccac   300
ttcttgattg acacccatgt ttcatctttc tcgtctccgt gtgtttcagg tggcattaat   360
cccaccggaa ccaccggtat atggtgtagc ttttccaaaa gggttagcca ttggggttcg   420
aactcatggc aatgtcttat aaacatacaa tctgatccct ttataaccat tccagcacga   480
tatatatctg aaaccccaga agaattaata gaaaaattat cagcaaatat cgaattggc   539
```

<210> SEQ ID NO 108

```
<211> LENGTH: 1332
<212> TYPE: DNA
<213> ORGANISM: Stevia rebaudiana

<400> SEQUENCE: 108
tttataataa cgacggaaaa gtagcgcacc acttaatgac tcgattctac caacgactta      60
gcaattccaa catgtgatta aaaagaagt gtaacaagga caatcataac atcatatgaa      120
tcattccaaa gaaacccaac aactaactta cttatagtct gtgaaacgac ttatatattc     180
tttttggtta actctcatgg ttgttggcaa ccacacgtac gttcttttcc atatagtctg     240
tgaaacgact tatatattct ttttggttaa ctctcatggt tgttggcaac cacacgtacg     300
ttcttttcca tatagtctgt gaaacgactt atatattcct tttgcagctt agtgtcgctg     360
aatattttac tcatctctct cgcattcgcc ttgtagatct ccccttcttt ttccacaaca     420
acggacctca gtgatctagc aaccgactcc ttggtcaagc aaccatcttc ctcatttctt     480
ggtatctcga ttcccacctg tttgtcctcc agtaatcgag cattcagagg ttggtcccca     540
aaaatcggta gcatgattag agggtgacca acattagcc cttccacaat tgatccagaa      600
ccacaatgag tcaagaaacc acaaaccgac tcatggctca gtattcgtaa ctgaggtgcc     660
caactcgtcc agaccatccc acggttagga gttcgttcca cgaacccgtt tggcaactcc     720
accgagtctg actcggtgga acctgcgggt tttctaagaa cccaaaagaa tggcaacccg     780
gagagctcga gacccagagc taactcagcc agctcgcttt ggctcatcgt accttcactt     840
ccaaatgcca cgtacaccac atgccctatt ggttgaccat cgagccactt cttgattgtc     900
acccatgggt ctccggtgct ggtgggtggt tcggtggca ataatcccac gggaaccact     960
ggtaggtgat gcagcttttc taaaagggtt agccattggg gttcgaactc atggcaatgt    1020
cttataaaca tacaatctga tcccttata accattccag cacgatatat atctgaaacc    1080
ccagaagaat taatagaaaa attatcagca aatatcgaat tggcctcatg cttccggtag    1140
catactttgc ttggaaacgg aacccacttc ggcggtgtca taaaattctc aaccctcgtt    1200
cgatgatcat aaccggaacc acttatcaag tcgtcagccg acgctccgag aaaagcaatg    1260
aaccatgcgt taaaattcga gtaaaaggct cgcgaggtcc gtagtccagc tgcgacggac    1320
ggcaaccaat ac                                                         1332

<210> SEQ ID NO 109
<211> LENGTH: 1284
<212> TYPE: DNA
<213> ORGANISM: Stevia rebaudiana

<400> SEQUENCE: 109
cacaatacta ctctttagtt accaatatac cataaccaaa attgtttgat agataagatt       60
atcctatatt aaaattgatg aaacccagtc gatttatcaa taaaagaaat agatcaatga     120
aattatctag tttgtgaatt ttatcacatt gatgtttcta ccttatttca aacaaaccag     180
atacttcaat taattcaagc aacatttgat catgaagaca aacccaacaa cgcacattct     240
tcatacggtt aacgtacgtc gtgtcttctc caaataatct atgaaatggt ttatatactt     300
ctttcccatc ttagtgtctc cgaacaatct acttaactcc atcgcatttt ccttgtaaat     360
cttcccttca tcatcagcta caactgcccg cactgatctt gcgactgact ccttgttgaa     420
ggaaccatct tcgtcatttc ttggtatctc aattcccacc tgattatccg ccattactcg     480
agcatttaga ccttgatcca ccgaaagcgg tagcattatc aaagggtgac cgaacatcat     540
cgcttccaca aatgaactcc aaccagaatg agtcaagaaa ccacacaccg actcatggct     600
```

```
cagtattcgt aactgaggtg cccaactcgt ccagaccaac ccacggtcac gagttcgttc    660
cacgaacccg tctggcaact ccaccgagtt accagagcca accggttttc taagaaccca    720
aaagaatggc aacccggaga gctcgaggcc cagagctaac tcagccagct cgctttggct    780
catcgtacct tcacttccaa atgccacgta caccacatgc cctattggtt gaccatcgag    840
ccacttcttg attgtcaccc atgtttcatc tttctcgtct ccgtgtattt caggtggcat    900
taatcccacc ggaaccaccg gtatatggtg tagcttctct aaagggtta gccattgggg    960 ttcgaactca tggcaatgtc ttataaacat acaatctgat ccctttataa ccattccagc   1020
acgatatata tctgaaaccc cagaagaatt aatagaaaaa ttatcagcaa atatcgaatt   1080
ggcctcatgc ttccggtagc atactttgct tggaaacgga atccacttgg gcggtgtcat   1140
gaaatcctca actgtcgttc gactctcgaa actatttttc atgtcatcgg gtaacggtcc   1200
cacgtgcgcc atgaaccatg gtgaggcagt gataaaaaag gctcgcgaga tcccaaggtc   1260
cgccgcgacg gatggcaacc agtg                                         1284
```

<210> SEQ ID NO 110
<211> LENGTH: 1297
<212> TYPE: DNA
<213> ORGANISM: Stevia rebaudiana

<400> SEQUENCE: 110

```
cacaatacta ctctttagtt accaatatac cataaccaaa attgtttgat agataagatt     60
atcctatatt aaaattgatg aaacccagtc gatttatcaa taaagaaat agatcaatga    120 aattatctag tttgtgaatt ttatcacatt gatgtttcta ccttatttca aacaaaccag    180
atacttcaat taattcaagc aacatttgat catgaagaca aacccaacaa cgcacattct    240
tcatacggtt aacgtacgtc gtgtcttctc caaataatct atgaaatggt ttatatactt    300
cttccccatc ttagtgtctc cgaacaatct acttaactcc atcgcatttt ccttgtaaat    360
cttcccttca tcatcagcta caactgcccg cactgatctt gcgactgact ccttgttgaa    420
ggagccatct tcgtcatttc ttggtatctc aattcccacc tgattatccg ccattactcg    480
agcatttaga ccttgatcca ccgaaagcgg tagcattatc aaagggtgac cgaacatcat    540
cgcttccaca aatgaactcc aaccacaatg agtcaagaaa ccacaaaccg actcatggct    600
cagtattcgt aactgaggtg cccaactcgt ccagaccaac ccacggtcac gagttcgttc    660
cacgaacccg tctggcaact ccaccgagtt accagagcca accggttttc taagaaccca    720
aaagaatggc aacccggaga gctcgaggcc cagagctaac tcagccagct cgctttggct    780
catcgtacct tcacttccaa atgccacgta caccacatgc cctattggtt gaccatcgag    840
ccacttcttg actgtgtcac acgtcttatc attcccgtct tcgatgttgg tgggttttc    900 tggtggcaat aatccgacag gaaccaccgg taggtgatgg agcttctcta aaagggttaa    960
ccattgaggt tcgaactcat aactatgtct tataaacata cagtcagatc ctttcaaaat   1020
cattcccaca cgatacacac ttgatattcc agaagcatta gccgaagtat tccctaccat   1080
ccgaaccgcc tcatacttcc ggtagcacac gtttgtcgga aacggaaccc acttcggcgg   1140
tgtcataaaa ttctcaaccc tcgttcgatg atcataaccg gaaccactta tcaagtcgtc   1200
agccgacgct ccgagaaaag caatgaacca tgcgttaaaa ttcgagtaaa aggctcgcga   1260
ggtccgtagt ccagctgcga cggacggcaa ccaatac                            1297
```

<210> SEQ ID NO 111

```
<211> LENGTH: 1194
<212> TYPE: DNA
<213> ORGANISM: Stevia rebaudiana

<400> SEQUENCE: 111
tagtgaatgt atataacata aatgatatgt ttcaacctaa caaacggtta tttcatacac      60
ggaaaacaaa aatttatgat tattcaaaga aacatttgat catctagcta gacaaaccca     120
ataacacata tattcttcat acgatcaaag ctcatgctca atagcaacca cacgaccttt     180
ttgttccaaa tagtctataa aagggtttat atacttattt tccggcttac tatccccgaa     240
tcgttgactc aactccatcg ccttcgcctt gtagatcttc ccttcatcat cgactaaaac     300
caacctcaat gatctggcca ccgactcctt ggtgaatgaa ccatcttcgt catttcttgg     360
tatctcaatt cccacctgat tatccgccat tactcgagca tttagacctt gatccaccga     420
aagcggtagc attatcaaag ggtgaccgaa catcatcgct tccacaaatg aactccaacc     480
acaatgagtc aagaaaccac aaaccgactc atggctcagt attcgtaact gaggtgccca     540
actcgtccag accaacccac ggtcacgagt tcgttccacg aacccgtctg caactccac     600
cgagttacca gagccaaccg gttttctaag aacccaaaag aatggcaacc cggagagctc     660
gaggcccaga gctaactcag ccagctcgct ttggctcatc gtaccttcac ttccaaatgc     720
cacgtacacc acatgcccta ttggttgacc atcgagccac ttcttgattg acacccatgt     780
ttcatctttc tcgtctccgt gtatttcagg tggcattaat cccaccggaa ccaccggtat     840
atggtgtagc ttccccaaaa gggttagcca ttggggttcg acctcataac aacttcttat     900
aaacagacaa tcagattcct tcaaaaccgt catcattctg tgctttagac ctgaaatcac     960
aggattatta gcagcagaca tcttgcgcac aaactcatgc ttccggtagc atactttgct    1020
cggaaacgga atccacttgg gcggtgtcat gaaatcctca actgtcgttc gactctcgaa    1080
actatttttc atgtcatcgg gtaacggtcc cacgtgcgcc atgaaccatg gtgaggcagt    1140
gataaaaaag gctcgcgaga tcccaaggtc cgccgcgacg gatggcaacc agtg          1194

<210> SEQ ID NO 112
<211> LENGTH: 575
<212> TYPE: DNA
<213> ORGANISM: Stevia rebaudiana

<400> SEQUENCE: 112
ggtagcatga ttagagggtg accaaacatt agcccttcca caattgatcc cgaaccacaa      60
tgagtcaaga aaccacaaac cgactcatgg ctcagtattc gtaactgagg tgcccaactc     120
gtccagacca acccacggtc acgagttcgt tccacgaacc cgtctggcaa ctccaccgag     180
ttaccagagc caaccggttt tctaagaacc caaaagaatg caacccgga gagctcgaga     240
cccaaagcta actcagccag ctcgctttgg ctcaccgtaa cttcacttcc aaatgcaacg     300
tacaccacat ggcctatttg ttgaccatcg agccacttct tgattgacac ccatgtttca     360
tctttctcgt ctccgtatgt ttcaggtggc attaatccca ccggaaccac cggtatatgg     420
tgtagcttct ccaaaagggt tagccattgg ggttcgaact catggcaatg tcttataaac     480
atacaatctg atcccttat aaccattcca gcacgtatata tatctgaaac cccagaagaa     540
ttaatagaaa aattatcagc aaatatcgaa ttggc                                575

<210> SEQ ID NO 113
<211> LENGTH: 1232
<212> TYPE: DNA
<213> ORGANISM: Stevia rebaudiana
```

<400> SEQUENCE: 113

```
tagtgaatgt atataacata aatgatatgt ttcaacctaa caaacggtta tttcatacac    60
ggaaaacaaa aatttatgat tattcaaaga acatttgat catctagcta gacaaaccca   120
ataacacata tattcttcat acgatcaaag ctcatgctca atagcaacca cacgaccttt   180
ttgttccaaa tagtctataa aagggtttat atacttattt tccggcttac tatccccgaa   240
tcgttgactc aactccatcg ccttcgcctt gtagatcttc ccttcatcat cgactaaaac   300
caacctcaat gatctggcca ccgactcctt ggtgaatgaa ccatcttcgt catttcttgg   360
tatctcaatt cccacctgat tatccgccat tactcgagca tttagacctt gatccaccga   420
aagcggtagc attatcaaag ggtgaccgaa catcatcgct tccacaaatg aactccaacc   480
acaatgagtc aagaaaccac acaccgactc atggctcagt attcgtaact gaggtgccca   540
actcgtccag accaacccac ggtcacgagt cgttccacg aacccgtctg caactccac    600
cgagtctgac ttcgcgggac cttttggttt tctataagcc caaacaaatg caacccaga    660
aagctcgaga cccaatgcta actcaacaac ctcggtttgg ctcaccaaaa cctcgcttcc   720
taatgcaacg tacaccacac tgccttttg tttaccatcg agccattct tgattgacac    780
ccatgtttca tctttctcgt ctccgggtat ttccggtggc agtaatccca ccggaaccac   840
cggtacttgg tgtagtgtct ccaaaagagg tagccattga gttccaaact catggtaaca   900
tttggaaagc aaacaatcag atcccttaag aaccagcccc atacggtatc catcagatat   960
ccccggagct ttgtaaggca ccagtcgggc aagatcatgc ttccgccagc atactttggt  1020
cggaaaggga aaccacttgg gcggtgtcgt gagatcctca accgtggttc gaccatctga  1080
accatttatc atggcgtcag ctgagggtcc catataagca atggcccatg gagtggtgac  1140
ggagaagtgg gctcgtgaga taccgaggct agccgcgatg gatggcaacc agtagtgagt  1200
ataatcataa ataatccagt ccggagactc tt                                1232
```

<210> SEQ ID NO 114
<211> LENGTH: 1310
<212> TYPE: DNA
<213> ORGANISM: Stevia rebaudiana

<400> SEQUENCE: 114

```
ggctggagtc aattgttttt atacaataca taatatagcg ttaaatggct ttataataac    60
gacggaaaag ttaatgactc gattctacca acgacttagc aattccaaca tgtgattaaa   120
aaagaagtgt aacaaggaca atcataacat catatgaatc attccaaaga aacccaacaa   180
ctaacttact tatagtctgt gaaacgactt atatattctt tttggttaac tctcatggtt   240
gttggcaacc acacgtacgt tcttttccat atagtctgtg aaacgactta tatattcttt   300
ttggttaact ctcatggttg ttggcaacca cacgtacgtt cttttccata tagtctgtga   360
aacgacttat atattccttt tgcagcttag tgtcgctgaa tattactc atctctctcg     420
cattcgcctt gtagatctcc ccttcttttt ccacaacaac ggacctcagt gatctagcaa   480
ccgactcctt ggtcaagcaa ccatcttcct catttcttgg tatctcgatt cccacctgtt   540
tgtcctccag tagtcgagca ttcagaggtt ggtccccgaa atcggtagc atgattagag    600
ggtgaccaaa cattagccct tccacaattg atccagaacc acaatgagtc aagaaaccac   660
aaaccgactc atggctcagt attcgtaact gaggtgccca actcgtccaa ccatcccac    720
ggtcacgagt tcgttccacg aacccgtctg caactccac cgagtctgac ttcgtgggac    780
```

```
ctgcgggttt tctgagaacc cacaaaaatg gcaacccaga gagctcgaga cctaacgcta    840
actcagccag ctcgcttttg gtcaccgtaa cttcgcttcc taatgcaacg tacaccacat    900
ggcctatttg ttgaccatcg agccacttct tgattgacac ccatgtttca tctttctcgt    960
ctccgtatgt ttcaggtggc attaatccca ccggaaccac cggtatatgg tgtagcttct   1020
ccaaaagggt tagccattgg ggttcgaact catggcaatg tcttataaac atacaatctg   1080 atcccttat aaccattcca gcacgatata tatctgaaac cccagaagaa ttaatagaaa    1140
aattatcagc aaatatcgaa ttggcctcat gcttccggta gcatactttg cttggaaacg   1200
gaacccactt cggcggtgtc aagaaatcgt cgggtgtttt ccgattgtct gtaccgttta   1260
tcatgttatc ggaagacgat ccgataaaag agacggtcca tgcgttatag              1310
```

<210> SEQ ID NO 115
<211> LENGTH: 1316
<212> TYPE: DNA
<213> ORGANISM: Stevia rebaudiana

<400> SEQUENCE: 115

```
cacaatacta ctctttagtt accaatatac cataaccaaa attgtttgat agataagatt     60
atcctatatt aaaattgatg aaacccagtc gatttatcaa taaaagaaat agatcaatga    120
aattatctag tttgtgaatt ttatcacatt gatgtttcta ccttatttca aacaaaccag    180
atacttcaat taattcaagc aacatttgat catgaagaca aacccaacaa cgcacattct    240
tcatacggtt aacgtacgtc gtgtcttctc caaataatct atgaaatggt ttatatactt    300
ctttcccatc ttagtgtctc cgaacaatct acttaactcc atcgcatttt ccttgtaaat    360
cttcccttca tcatcagcta caactgcccg cactgatctt gcgactgact ccttgttgaa    420
ggagccatct tcgtcatttc ttggtatctc aattcccacc tgattatccg ccattactcg    480
agcatttaga ccttgatcca ccgaaagcgg tagcattatc aaagggtgac cgaacatcat    540
cgcttccaca aatgaactcc aaccacaatg agtcaagaaa ccacaaaccg actcatggct    600
cagtattcgt aactgaggtg cccaactcgt ccagaccaac ccacggtcac gagttcgttc    660
cacgaacccg tctggcaact ccaccgagtc tgacttcgcg ggaccttttg gttttctata    720
agcccaaaca aatggcaacc cagaaagctc gagacccaat gctaactcaa caacctcggt    780
ttggctcacc aaaacctcgc ttcctaatgc aacgtacacc acactgcctt tttgtttacc    840
atcgagccat ttcttgattg acacccatgt ttcatctttc tcgtctccgg gtatttccgg    900
tggcagtaat cccaccggaa ccaccggtac ttggtgtagt gtctccaaaa gaggtagcca    960
ttgagttcca aactcatggt aacatttgga aagcaaacaa tcagatccct taagaaccag   1020
ccccatacgg tatccatcag atatccccgg agctttgtaa ggcaccagtc gggcaagatc   1080
atgcttccgc cagcatactt tggtcggaaa gggaaaccac ttgggcggtg tcgtgagatc   1140
ctcaaccgtg gttcgaccat ctgaaccatt tatcatggcg tcagctgagg gtcccatata   1200
agcaatggcc catggagtgg tgacggagaa gtgggctcgt gagataccga ggctagccgc   1260
gatggatggc aaccagtagt gagtataatc ataaataatc cagtccggag actctt       1316
```

<210> SEQ ID NO 116
<211> LENGTH: 1272
<212> TYPE: DNA
<213> ORGANISM: Stevia rebaudiana

<400> SEQUENCE: 116

```
tttataataa cgacggaaaa gtagcgcacc acttaatgac tcgattctac caacgactta     60
```

```
gcaattccaa catgtgatta aaaaagaagt gtaacaagga caatcataac atcatatgaa    120
tcattccaaa gaaacccaac aactaactta cttatagtct gtgaaacgac ttatatattc    180
tttttggtta actctcatgg ttgttggcaa ccacacgtac gttcttttcc atatagtctg    240
tgaaacgact tatatattct ttttggttaa ctctcatggt tgttggcaac cacacgtacg    300
ttcttttcca tatagtctgt gaaacgactt atatattcct tttgcagctt agtgtcgctg    360
aatattttac tcatctctct cgcattcgcc ttgtagatct ccccttcttt ttccacaaca    420
acggacctca gtgatctagc aaccgactcc ttggtcaagc aaccatcttc ctcatttctt    480
ggtatctcga ttcccacctg tttgtcctcc agtagtcgag cattcagagg ttggtcccca    540
aaaatcggta gcatgattag agggtgacca acattagcc cttccacaat gaaccagaa      600 ccacaatgag tcaagaaacc acaaaccgac tcatggctca gtattcgtaa ctgaggtgcc    660
caactcgtcc agaccatccc acggttacga gttcgttcca cgaacccgtc tggcaactcc    720
accgagtctg actccgcgga acctgcgggt tttctgagaa cccacaaaaa tggcaaccca    780
gagagctcga gacctaacgc taactcagcc agctcgcttt tggtcaccgt aacttcactt    840
cctaatgcaa cgtacaccac atggcctatt tgttgaccat cgagccactt cttgattgac    900
acccatgttt catctttctc gtctccgtat gtttcaggtg cattaatcc caccggaacc     960 accggtatat ggtgtagctt ttccaaaagg gttagccatt ggggttcgaa ctcatggcaa   1020
tgtcttataa acatacaatc tgatcccttt ataaccattc cagcacgata tatatctgaa   1080
accccagaag aattaataga aaaattatca gcaaatatcg aattggcctc atgcttccgg   1140
tagcatactt tgcttggaaa cggaacccac ttcggcggtg tcaagaaatc gtcgggtgtt   1200
ttccgattgt ctgtaccgtt tatcatgtta tcggaagacg atccgataaa agagacggtc   1260
catgcgttat ag                                                       1272

<210> SEQ ID NO 117
<211> LENGTH: 21
<212> TYPE: DNA
<213> ORGANISM: Stevia rebaudiana

<400> SEQUENCE: 117
tcagccacct ttctatcttg c                                               21

<210> SEQ ID NO 118
<211> LENGTH: 22
<212> TYPE: DNA
<213> ORGANISM: Stevia rebaudiana

<400> SEQUENCE: 118
actgcaatgt gttagttaga gg                                              22

<210> SEQ ID NO 119
<211> LENGTH: 21
<212> TYPE: DNA
<213> ORGANISM: Stevia rebaudiana

<400> SEQUENCE: 119
tcgtatactg ctttgggttg c                                               21

<210> SEQ ID NO 120
<211> LENGTH: 20
<212> TYPE: DNA
<213> ORGANISM: Stevia rebaudiana
```

<400> SEQUENCE: 120
tggtcaagaa cagggtcaca                                         20

<210> SEQ ID NO 121
<211> LENGTH: 26
<212> TYPE: DNA
<213> ORGANISM: Stevia rebaudiana

<400> SEQUENCE: 121
ttacatttca ttttgataca caaaca                                  26

<210> SEQ ID NO 122
<211> LENGTH: 24
<212> TYPE: DNA
<213> ORGANISM: Stevia rebaudiana

<400> SEQUENCE: 122
agattcctag ttatttggaa cgtg                                    24

<210> SEQ ID NO 123
<211> LENGTH: 20
<212> TYPE: DNA
<213> ORGANISM: Stevia rebaudiana

<400> SEQUENCE: 123
ctttctttga gtcggcggag                                         20

<210> SEQ ID NO 124
<211> LENGTH: 21
<212> TYPE: DNA
<213> ORGANISM: Stevia rebaudiana

<400> SEQUENCE: 124
ggggtttact acgtacgttg c                                       21

<210> SEQ ID NO 125
<211> LENGTH: 22
<212> TYPE: DNA
<213> ORGANISM: Stevia rebaudiana

<400> SEQUENCE: 125 tcgcaccta caaaaacaaa ga                                       22

<210> SEQ ID NO 126
<211> LENGTH: 20
<212> TYPE: DNA
<213> ORGANISM: Stevia rebaudiana

<400> SEQUENCE: 126
caattcatca ccggactcct                                         20

<210> SEQ ID NO 127
<211> LENGTH: 20
<212> TYPE: DNA
<213> ORGANISM: Stevia rebaudiana

<400> SEQUENCE: 127
tttggatgga cttggtttga                                         20

<210> SEQ ID NO 128
<211> LENGTH: 20
<212> TYPE: DNA
<213> ORGANISM: Stevia rebaudiana

```
<400> SEQUENCE: 128
aggttgtttg gtggagcttg                                          20

<210> SEQ ID NO 129
<211> LENGTH: 20
<212> TYPE: DNA
<213> ORGANISM: Stevia rebaudiana

<400> SEQUENCE: 129
aacctgtctc aatgggacct                                          20

<210> SEQ ID NO 130
<211> LENGTH: 20
<212> TYPE: DNA
<213> ORGANISM: Stevia rebaudiana

<400> SEQUENCE: 130
atattgctag ccatgccacg                                          20

<210> SEQ ID NO 131
<211> LENGTH: 20
<212> TYPE: DNA
<213> ORGANISM: Stevia rebaudiana

<400> SEQUENCE: 131
tggggaattg tgttgactgt                                          20

<210> SEQ ID NO 132
<211> LENGTH: 23
<212> TYPE: DNA
<213> ORGANISM: Stevia rebaudiana

<400> SEQUENCE: 132
aagcttcgga aaataacttg tgt                                      23

<210> SEQ ID NO 133
<211> LENGTH: 19
<212> TYPE: DNA
<213> ORGANISM: Stevia rebaudiana

<400> SEQUENCE: 133
ctttctttga gtcggcgga                                           19

<210> SEQ ID NO 134
<211> LENGTH: 20
<212> TYPE: DNA
<213> ORGANISM: Stevia rebaudiana

<400> SEQUENCE: 134
gggtttacta cgtacgttgc                                          20

<210> SEQ ID NO 135
<211> LENGTH: 19
<212> TYPE: DNA
<213> ORGANISM: Stevia rebaudiana

<400> SEQUENCE: 135
tgacgcgatg gaagatgaa                                           19

<210> SEQ ID NO 136
<211> LENGTH: 25
<212> TYPE: DNA
```

```
<213> ORGANISM: Stevia rebaudiana

<400> SEQUENCE: 136
ccctaagtat caaatcagtg caata                                    25

<210> SEQ ID NO 137
<211> LENGTH: 19
<212> TYPE: DNA
<213> ORGANISM: Stevia rebaudiana

<400> SEQUENCE: 137
gagctttgcc tggcttaat                                           19

<210> SEQ ID NO 138
<211> LENGTH: 19
<212> TYPE: DNA
<213> ORGANISM: Stevia rebaudiana

<400> SEQUENCE: 138
ccgccaagtc aaacaagaa                                           19
```